United States Patent [19]
Goldstein et al.

[11] Patent Number: 5,891,631
[45] Date of Patent: Apr. 6, 1999

[54] METHODS RELATING TOSTEROL REGULATORY ELEMENT BINDING PROTEINS

[75] Inventors: Joseph L. Goldstein; Michael S. Brown, both of Dallas, Tex.; Michael R. Briggs, San Diego, Calif.; Xiaodong Wang, Dallas, Tex.

[73] Assignee: Board of Regents, The University of Texas System, Austin, Tex.

[21] Appl. No.: 668,123

[22] Filed: Jun. 14, 1996

Related U.S. Application Data

[60] Division of Ser. No. 131,365, Oct. 1, 1993, Pat. No. 5,527,690, which is a continuation-in-part of Ser. No. 61,697, May 13, 1993, Pat. No. 5,498,696.

[51] Int. Cl.$^6$ .............................. C12Q 1/68; G01N 33/53
[52] U.S. Cl. ................................ 435/6; 435/7.1; 435/367; 435/369
[58] Field of Search ................................ 435/6, 7.1, 367, 435/369, 366

[56] References Cited

U.S. PATENT DOCUMENTS

| | | | |
|---|---|---|---|
| 4,935,363 | 6/1990 | Brown et al. | 435/172.3 |
| 5,215,910 | 6/1993 | Brown et al. | 435/350 |
| 5,256,545 | 10/1993 | Brown et al. | 435/69.1 |
| 5,498,696 | 3/1996 | Briggs et al. | 530/350 |
| 5,527,690 | 6/1996 | Goldstein et al. | 435/69.1 |

FOREIGN PATENT DOCUMENTS

WO 88/07579  10/1988  WIPO .

OTHER PUBLICATIONS

Ayer et al., "Mad: A Heterodimeric Partner for Max That Antagonizes Myc Transcriptional Activity," *Cell,* 72:211–222, 1993.

Gil et al., "Purification of a Protein Doublet that Binds to Six TGG–Containing Sequences in the Promoter for Hamster 3–Hydroxy–3–Methylglutaryl–Coenzyme A Reductase," *J. Biol. Chem.,* 263(35):19009–19019, 1988.

Gil et al., "Multiple Genes Encode Nuclear Factor 1–Like Proteins that Bind to the Promoter for 3–Hydroxy–3–Methylglutaryl–Coenzyme A Reductase," *Proc. Natl. Acad. Sci. USA,* 85:8963–8967, 1988.

Rajavashisth et al., "Identification of a Zinc Finger Protein that Binds to the Sterol Regulatory Element," *Science,* 245:640–643, 1989.

Stark et al., Common Double– and Single–Stranded DNA Binding actor for a Sterol Regulatory Element, *Proc. Natl. Acad. Sci. USA,* 89:2180–2184, 1992.

Briggs et al., "Nuclear Protein That Binds Sterol Regulatory Element of Low Density Lipoprotein Receptor Promoter," *J. Biol. Chem.,* 268(19):14490–14496, 1993.

Hua et al., "SREBP–2, a Second Basic–Helix–Loop–Helix–Leucine Zipper Protein that Stimulates Transcription by Binding to a Sterol Regulatory Element," *Proc. Natl. Acad. Sci. USA,* 90:11603–1167, 1993.

Osborne, "Single Nucleotide Resolution of Sterol Regulatory Region in Promoter for 3–Hydroxy–3–Methylglutaryl Coenzyme A Reductase," *J. Biol. Chem.,* 266(21): 13947–13951, 1991.

Wang et al., "Nuclear Protein That Binds Sterol Regulatory Element of LowDensity Lipoprotein Receptor Promoter," *J. Biol. Chem.,* 268(19):14497–14504, 1993.

Yokoyama et al., "SREBP–1, a Basic–Helix–Loop–Helix–Leucine Zipper Protein That Controls Transcription of the Low Density Lipoprotein Receptor Gene," *Cell,* 75:187–197, 1993.

PCT Search Report, dated Nov. 28, 1994.

Agnani et al., "Antipeptide antibody against the human low–density–lipoprotein receptor," *Biochem. J.,* 263:753–760, 1989.

Briggs et al., "Purufication and Biochemical Characterization of the Promoter–Specific Transcription Factor, Sp1," *Science,* 234:47–52, 1986.

Brown and Goldstein,"A Receptor–Mediated Pathway for Cholesterol Homeostasis," *Science,* 232:34–47, 1986.

Smith et al., "Identification of Nucleotides Responsible for Enhancer Activity of Sterol Regulatory Element in Low Density Lipoprotein Receptor Gene," *The Journal of Biological Chemistry,* 265(4):2306–2310, 1990.

*Primary Examiner*—David Guzo
*Attorney, Agent, or Firm*—Arnold, White & Durkee

[57] ABSTRACT

A sterol regulatory element (SRE) binding protein (SREBP) which activates transcription from SREs, such as SRE-1 of the low intensity lipoprotein (LDL) receptor gene, is disclosed, as are DNA segments encoding SREBPs such as an SREBP-1 or SREBP-2. Also described are methods for using SREBP to promote SRE-mediated transcription and LDL receptor production in the presence of sterols, and screening assay for the identification of further agents with such properties. The SREBP and other agents may be used to reduce plasma cholesterol levels and to treat various medical problems associated with hypercholesterolemia.

30 Claims, 68 Drawing Sheets

| 2 |   5´ AAAATCACCCCACTGC 3´

| 3 |   5´ AAACTCCTCCCCTGC 3´

| 2 | 3 |   5´ AAAATCACCCCACTGCAAACTCCTCCCCTGC 3´

| 2*| 3 |   5´ AAAAgaACCCtaTGCAAACTCCTCCCCTGC 3´

FIG. 1A

5´ TGAAGCTTGCATGCCTGCAGGTCGA↓CTCGACTCTAGAGGG

TATATAATGGATCCCCGGGTACCGAGCTCGAATTCATCAGCTTGG

CGAGATTTTCAGGAGCTAAHHAHCTAAAATG 3´

FIG. 1B

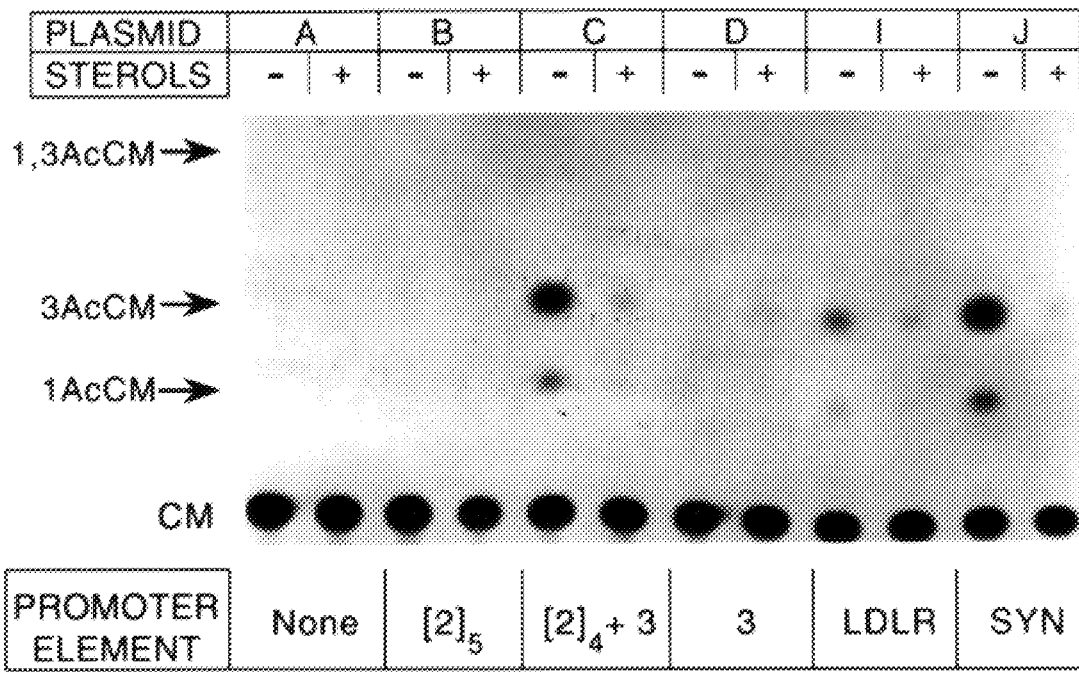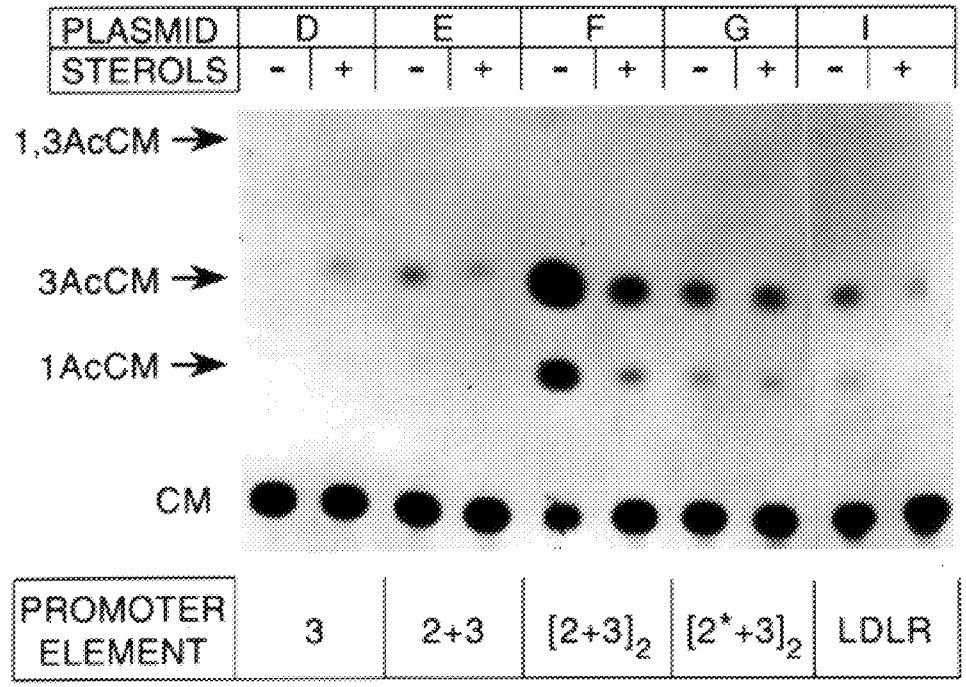
FIG. 2

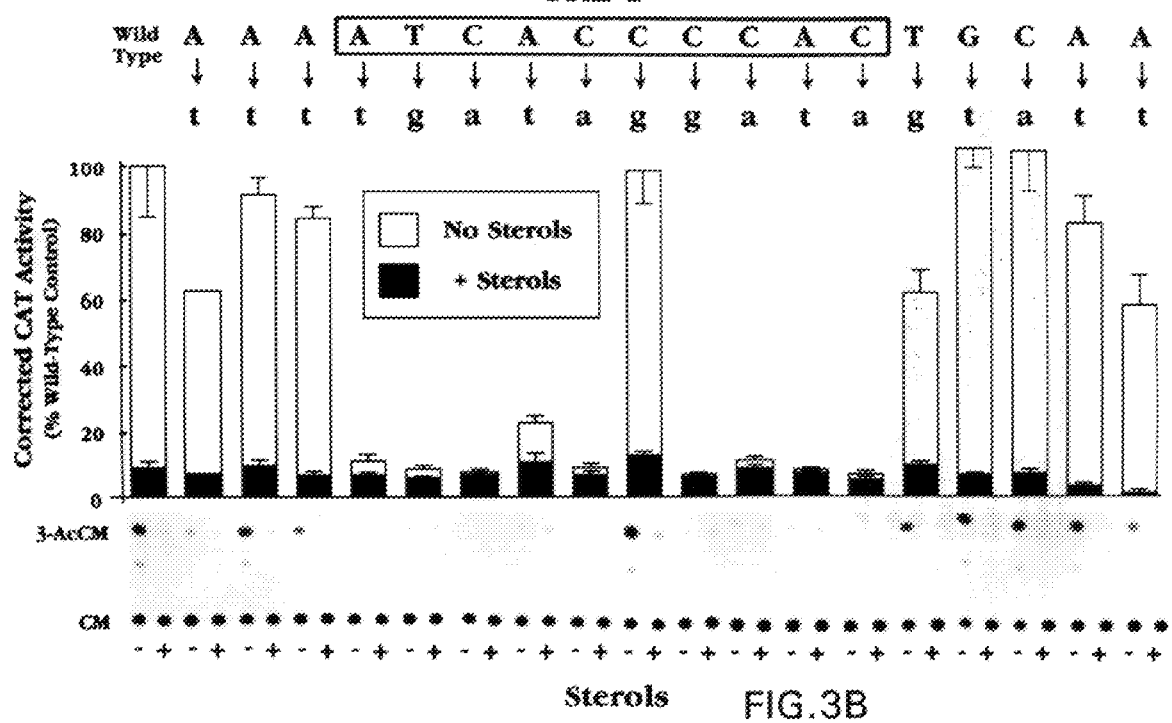

FIG.6A
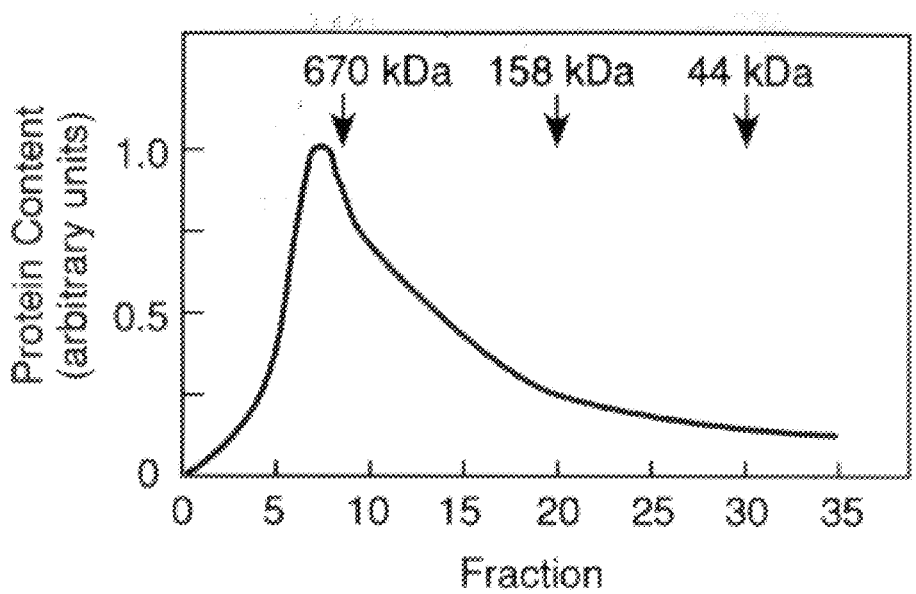
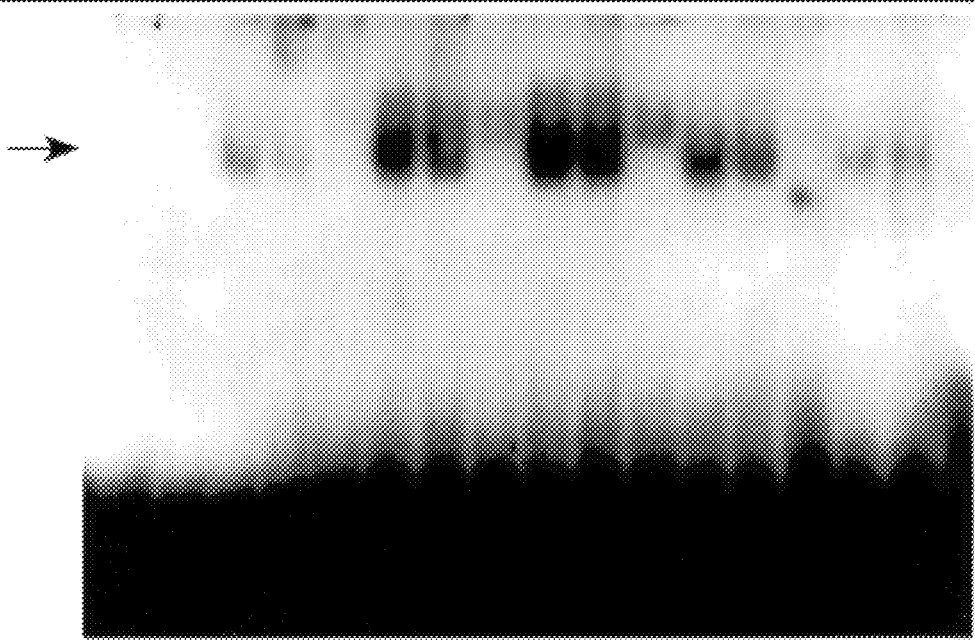
FIG.6B

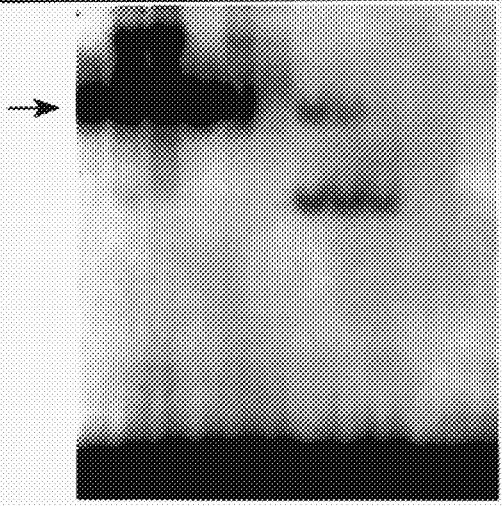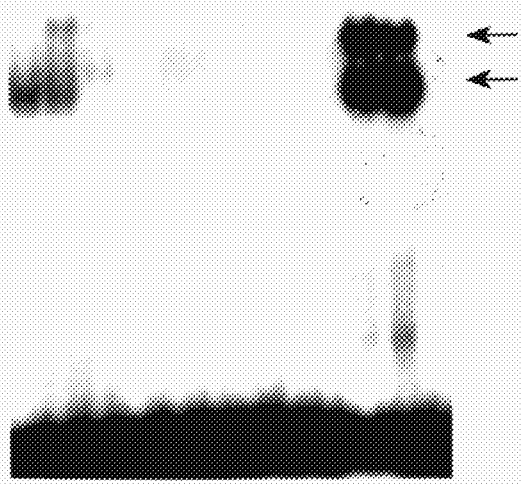

FIG. 15B

5' Sequences pCY5

```
5'  TAACGAGGAA CTTTTCCCCG GGGCCGGGCC GCCTCTGAGG CCAGGGCAGG ACACGAACGC      60
    GCCGAGCGGC GGCGGGGACT GAGAGCCCGG GCCGGGGGGG CCTTCCCTAG GAAGGGCCGT     120
    ACGAGGGCGC GGGCCCGGCG GGCCTCCCCG AGGAGGCGGC TGCGCC ATG GAC GAG        175
                                                    Met Asp Glu
                                                    1

CCA CCC TTC AGC GAG GCG GCT TTG GAG CAG GCG CTG GCG GAG CCG TGC      223
    Pro Pro Phe Ser Glu Ala Ala Leu Glu Gln Ala Leu Ala Glu Pro Cys
    4

GAT CTG GAC GCG GCG CTG CTG ACC GAC ATC                              253
    Asp Leu Asp Ala Ala Leu Leu Thr Asp Ile
    20
``` pCY22

```
5'  GG AGG GGT AGG GCC AAC GGC CTG GAC GCC CCA AGG GCG GGC GCA GAT       47
       Arg Gly Arg Ala Asn Gly Leu Asp Ala Pro Arg Ala Gly Ala Asp
```

FIG. 15C

```
                                          CGC GGA GCC ATG GAT TGC ACT TTC      71
                                          Arg Gly Ala Met Asp Cys Thr Phe

3' Sequences pCY21
        GTG TTC CTA CAT GAG GCC ACG GCC CGG                                    3295
   1035 Val Phe Leu His Glu Ala Thr Ala Arg CTG ATG GCG GGG GCC AGC CCC ACA CGG ACA CAC CAG CTC CTC GAC CGC        3343
   1044 Leu Met Ala Gly Ala Ser Pro Thr Arg Thr His Gln Leu Leu Asp Arg AGT CTG AGG CGG GCA GGC CGG CCC GGT GGC AAA GGA GGC GCG GTG GCG        3391
   1060 Ser Leu Arg Arg Ala Gly Arg Pro Gly Gly Lys Gly Gly Ala Val Ala GAG CTG GAG CCG CGG CCC ACG CGG CCC GAG CAC GCC GAG GCC TTG CTG        3439
   1076 Glu Leu Glu Pro Arg Pro Thr Arg Pro Glu His Ala Glu Ala Leu Leu CTG GCC TCC TGC TAC CTG CCC GGC TTC CTG TCG GCG CCC GGG CAG            3487
   1092 Leu Ala Ser Cys Tyr Leu Pro Gly Phe Leu Ser Ala Pro Gly Gln
```

FIG. 15D

```
     CGC GTG GGC ATG CTG GCT GAG GCG GCG ACA CTC GAG AAG CTT GGC          3535
1108 Arg Val Gly Met Leu Ala Glu Ala Ala Arg Thr Leu Glu Lys Leu Gly

GAT CGC CGG CTG CTG CAC GAC TGT CAG CAG ATG CTC ATG CGC CTG GGC      3583
1124 Asp Arg Arg Leu Leu His Asp Cys Gln Gln Met Leu Met Arg Leu Gly

GGT GGG ACC ACT GTC ACT TCC AGC TAGACCCGT GTCCCGGCC TCAGCACCC        3637
1140 Gly Gly Thr Thr Val Thr Ser Ser *

TGTCTCTAGC CACTTTGGTC CCGTGCAGCT TCTGTCCTGC GTCGAAGCTT TGAAGGCGA     3697

AGGCAGTGCA AGAGACTCTG GCCTCCACAG TTCGACCTGC GGCTGCTGTG TGCCTTCGCG    3757

GTGGAAGGCC CGAGGGGGC GATCTTGACC CTAAGACCGG CGGCCATGAT GGTGCTGACC    3817

TCTGTGGCC GATCGGGCA CTGCAGGGGC CGAGCCATTT TGGGGGCC CCTCCTTGC        3877

TCTGCAGGCA CCTTAGTGGC TTTTTCCTC CTGTGTACAG GGAAGAGAGG GGTACATTTC     3937

CCTGTGCTGA CGGAAGCCAA CTTGGCTTTC CCGGACTGCA AGCAGGGCTC TGCCCCAGAG    3997

GCCTCTCTCT CCGTCGTGGG AGAGACGT GTACATAGTG TAGGTCAGCG TGCTTAGCCT      4057
```

FIG. 15E

```
CCTGACCTGA GGCTCCTGTG CTACTTTGCC TTTTGCAAAC TTTATTTTCA TAGATTGAGA   4117

AGTTTGTAC AGAGAATTAA AAATGAAATT ATTATA 3'                          4154
                                 pCY22

CTG ATG GAT GTG CTG ACT AGT GAG AGT GCT TGG GCC CTC CCC CAG CAC
Leu Met Asp Val Leu Thr Ser Glu Ser Ala Trp Ala Leu Pro Gln His

CTA GGC AAA GGC TTC CCC TCC CCC TCC GGA CAC AAG GTC CCT GGG TGG
Leu Gly Lys Gly Phe Pro Ser Pro Ser Gly His Lys Val Pro Gly Trp

CAC GGG AGG ATG GAC TGACTTCCAG GACCTGTTGT GTGACAGGAG CTACAGCTTG
His Gly Arg Met Asp *

GGTCTCCCTG CAAGAAGTCT GGCACGTCTC ACCTCCCCCA TCCCGGCCCC TGGTCATTTC

ACAGCAAAGA AGCCTCCTCC CTCCCGACCT GCCGCCACAC TGGAGAGGGG GCACAGGGGC

GGGGAGGTT TCCTGTTCTG TGAAAGCCG ACTCCCTGAC TCCATTCATG CCCCCCCCC

CAGCCCCTCC CTTCATTCCC ATTCCCCAAC CTAAAGCCTG GCCCGGCTCC CAGCTGAATC
```

FIG. 15F

TGGTCGGAAT CCACGGGCTG CAGATTTTCC AAAACAATCG TTGTATCTTT ATTGACTTT
TTTTTTTTT TTTCTGAATG CAATGACTGT TTTTTACTCT TAAGGAAAAT AAACATCTTT
TAGAAACAAA AAAAAAAAAA AAAAAAAAAA AAAAAA 3'

FIG. 16A

```
5'  TAACGAGGAA CTTTTCGCCG GCGCCGGGCC GCCTCTGAGG CCAGGCAGG ACAGAACGC   60

GCGGAGCGGC GGCGGCGACT GAGAGCCCGG GCCGCGGCCG CGCTCCCTAG GAAGGGCCGT  120

ACGAGCCGGC GGGCCCGGCG GGCCTCCCCG AGGAGCCGGC TGCGCC ATG GAC GAG     175
                                                      Met Asp Glu
1

CCA CCC TTC AGC GAG GCG GCT TTG GAG CAG GCG CTG GGC GAG CCG TGC   223
    Pro Pro Phe Ser Glu Ala Ala Leu Glu Gln Ala Leu Gly Glu Pro Cys
4                                                    →

GAT CTG GAC GCG GCG CTG CTG ACC GAC ATC GAA GAC ATG CTT CAG CTT   271
    Asp Leu Asp Ala Ala Leu Leu Thr Asp Ile Glu Asp Met Leu Gln Leu
20

ATC AAC AAC CAA GAC AGT GAC TTC CCT GGC CTA TTT GAC CCA CCC TAT   319
    Ile Asn Asn Gln Asp Ser Asp Phe Pro Gly Leu Phe Asp Pro Pro Tyr
36

GCT GGG AGT GGG GCA GGG GCA GAC CCT GCC AGC CCC GAT ACC AGC       367
    Ala Gly Ser Gly Ala Gly Ala Asp Pro Ala Ser Pro Asp Thr Ser
52

TCC CCA GGC AGC TTG TCT CCA CCT CCT CCT GCC ACA TTG AGC TCC TCT CTT 415
    Ser Pro Gly Ser Leu Ser Pro Pro Pro Pro Ala Thr Leu Ser Ser Ser Leu
68
```

FIG. 16B

```
 84 GAA GCC TTC CTG AGC GGG CCG CAG GCA GCG CCC TCA CCC CTG TCC CCT 463
    Glu Ala Phe Leu Ser Gly Pro Gln Ala Ala Pro Ser Pro Leu Ser Pro

100 CCC CAG CCT GCA CCC ACT CCA TTG AAG ATG TAC CCG TCC ATG CCC GCT 511
    Pro Gln Pro Ala Pro Thr Pro Leu Lys Met Tyr Pro Ser Met Pro Ala

116 TTC TCC CCT GGG CCT GGT ATC AAG GAA GAG TCA GTG CCA CTG AGC ATC 559
    Phe Ser Pro Gly Pro Gly Ile Lys Glu Glu Ser Val Pro Leu Ser Ile

132 CTG CAG ACC CCC ACC CCA CAG CCC CTG CCA GGG GCC CTC CTG CCA CAG 607
    Leu Gln Thr Pro Thr Pro Gln Pro Leu Pro Gly Ala Leu Leu Pro Gln

148 AGC TTC CCA GCC CCA GCC CCA CCG CAG TTC AGC TCC ACC CCT GTG TTA 655
    Ser Phe Pro Ala Pro Ala Pro Pro Gln Phe Ser Ser Thr Pro Val Leu

164 GGC TAC CCC AGC CCT CCG GGA GGC TTC TCT ACA GGA AGC CCT CCC GGG 703
    Gly Tyr Pro Ser Pro Pro Gly Gly Phe Ser Thr Gly Ser Pro Pro Gly

180 AAC ACC CAG CAG CCG CTG CCT GGC CTG CCA CTG GCT TCC CCG CCA GGG 751
    Asn Thr Gln Gln Pro Leu Pro Gly Leu Pro Leu Ala Ser Pro Pro Gly
```

FIG. 16C

```
      GTC CCG CCC GTC TCC TTG CAC ACC CAG GTC CAG AGT GTG GTC CCC CAG   799
196   Val Pro Pro Val Ser Leu His Thr Gln Val Gln Ser Val Val Pro Gln

CAG CTA CTG ACA GTC ACA GCT GCC CCC ACG GCA GCC CCT GTA ACG ACC   847
212   Gln Leu Leu Thr Val Thr Ala Ala Pro Thr Ala Ala Pro Val Thr Thr

ACT GTG ACC TCG CAG ATC CAG CAG GTC CCG GTC CTG CAG CCC CAC       895
228   Thr Val Thr Ser Gln Ile Gln Gln Val Pro Val Leu Leu Gln Pro His

TTC ATC AAG GCA GAC TCG CTG CTT CTG ACA GCC ATG AAG ACA GAC GGA   943
244   Phe Ile Lys Ala Asp Ser Leu Leu Leu Thr Ala Met Lys Thr Asp Gly

GCC ACT GTG AAG GCG GCA GGT CTC AGT CCC CTG GTC TCT GGC ACC ACT   991
260   Ala Thr Val Lys Ala Ala Gly Leu Ser Pro Leu Val Ser Gly Thr Thr

GTG CAG ACA GGG CCT TTG CCG ACC CTG GTG AGT GGC GGA ACC ATC TTG  1039
276   Val Gln Thr Gly Pro Leu Pro Thr Leu Val Ser Gly Gly Thr Ile Leu

GCA ACA GTC CCA CTG GTC GTA GAT GCG GAG AAG CTG CCT ATC AAC CGG  1087
292   Ala Thr Val Pro Leu Val Val Asp Ala Glu Lys Leu Pro Ile Asn Arg
```

FIG. 16D

```
         CTC GCA GCT GGC AGC AAG GCC CCG GCC TCT GCC CAG AGC CGT GGA GAG   1135
         Leu Ala Ala Gly Ser Lys Ala Pro Ala Ser Ala Gln Ser Arg Gly Glu
308

AAG CGC ACA GCC CAC AAC GCC ATT GAG AAG CGC TAC CGC TCC TCC ATC   1183
         Lys Arg Thr Ala His Asn Ala Ile Glu Lys Arg Tyr Arg Ser Ser Ile
324

AAT GAC AAA ATC ATT GAG CTC AAG GAT CTC GTG GTG GGC ACT GAG GCA   1231
         Asn Asp Lys Ile Ile Glu Leu Lys Asp Leu Val Val Gly Thr Glu Ala
340

AAG CTG AAT AAA TCT GCT GTC TTG CGC AAG ATC GAC TAC ATT CGC       1279
         Lys Leu Asn Lys Ser Ala Val Leu Arg Lys Ala Ile Asp Tyr Ile Arg
356

TTT CTG CAA CAC AGC AAC CAG AAA CTC AAG CAG GAG AAC CTA AGT CTG   1327
         Phe Leu Gln His Ser Asn Gln Lys Leu Lys Gln Glu Asn Leu Ser Leu
372

CGC ACT GCT GTC CAC AAA AGC AAA TCT CTG AAG GAT CTG AAG GAC TCG GCC   1375
         Arg Thr Ala Val His Lys Ser Lys Ser Leu Lys Asp Leu Lys Val Ser Ala
388

TGT GGC AGT GGA GGG AAC ACA GAC GTC CTC ATG GAG GGC GTG AAG ACT   1423
         Cys Gly Ser Gly Gly Asn Thr Asp Val Leu Met Glu Gly Val Lys Thr
404
```

FIG. 16E

```
                GAG GTG GAG GAC ACA CTG ACC CCA CCC CCC TCG GAT GCT GGC TCA CCT    1471
                Glu Val Glu Asp Thr Leu Thr Pro Pro Pro Ser Asp Ala Gly Ser Pro
        420

TTC CAG AGC AGC CCC TTG TCC CTT GGC AGC AGG GGC AGT GGC AGC GGT    1519
                Phe Gln Ser Ser Pro Leu Ser Leu Gly Ser Arg Gly Ser Gly Ser Gly
        436

GGC AGT GGC AGT GAC TCG GAG CCT GAC AGC CCA GTC TTT GAG GAC AGC    1567
                Gly Ser Gly Ser Asp Ser Glu Pro Asp Ser Pro Val Phe Glu Asp Ser
        452

AAG GCA AAG CCA GAG CAG CGG CCG TCT CTG CAC AGC CGG GGC ATG CTG    1615
                Lys Ala Lys Pro Glu Gln Arg Pro Ser Leu His Ser Arg Gly Met Leu
        468

GAC CGC TCC CGC CTG GCC CTG TGC ACG CTC TTC CTC GTC TTC CTG TCC    1663
                Asp Arg Ser Arg Leu Ala Leu Cys Thr Leu Phe Leu Val Phe Leu Ser
        484

TGC AAC CCC TTG TCC TCC TTG CTG GGG GCC CGG GGG CTT CCC AGC CCC    1711
                Cys Asn Pro Leu Ser Ser Leu Leu Gly Ala Arg Gly Leu Pro Ser Pro
        500

TCA GAT ACC ACC AGC GTC TAC CAT AGC CCT GGG CGC AAC GTG CTG GGC    1759
                Ser Asp Thr Thr Ser Val Tyr His Ser Pro Gly Arg Asn Val Leu Gly
        516
```

FIG. 16F

```
      ACC GAG AGC AGA GAT GGC CCT GGC TGG GCC CAG TGG CTG CCC CCA   1807
532   Thr Glu Ser Arg Asp Gly Pro Gly Trp Ala Gln Trp Leu Pro Pro

GTG GTC TGG CTG CTC AAT GGG CTG TTG CTC GTC TCC TTG GTG CTT   1855
548   Val Val Trp Leu Leu Asn Gly Leu Leu Val Leu Val Ser Leu Val Leu

CTC TTT GTC TAC GGT GAG CCA GTC ACA CGG CCC CAC TCA GGC CCC GCC   1903
564   Leu Phe Val Tyr Gly Glu Pro Val Thr Arg Pro His Ser Gly Pro Ala

GTG TAC TTC TGG AGG CAT CGC AAG CAG GCT GAC CTG GAC CTG GCC CGG   1951
580   Val Tyr Phe Trp Arg His Arg Lys Gln Ala Asp Leu Asp Leu Ala Arg

GGA GAC TTT GCC CAG GCT GCC CAG CAG CTG TGG CTG GCC CTG CGG GCA   1999
596   Gly Asp Phe Ala Gln Ala Ala Gln Gln Leu Trp Leu Ala Leu Arg Ala

CTG GGC CGG CCC CTG CCC ACC TCC CAC CTG GAC CTG GCT TGT AGC CTC   2047
612   Leu Gly Arg Pro Leu Pro Thr Ser His Leu Asp Leu Ala Cys Ser Leu

CTC TGG AAC CTC CGT CAC CTG CTG CAG CGT CTC TGG GTG GGC CGC   2095
628   Leu Trp Asn Leu Arg His Leu Leu Gln Arg Leu Trp Val Gly Arg
```

FIG. 16G

```
     TGG CTG GCA GGC CGG GCA GGG GGC CTG CAG CAG GAC TGT GCT CTG CGA   2143
644  Trp Leu Ala Gly Arg Ala Gly Gly Leu Gln Gln Asp Cys Ala Leu Arg

GTG GAT GCT AGC GCC AGC GCC CGA GAC GCA GCC CTG GTC TAC CAT AAG   2191
660  Val Asp Ala Ser Ala Ser Ala Arg Asp Ala Ala Leu Val Tyr His Lys

CTG CAC CAG CTG CAC ACC ATG GGG AAG CAC ACA GGC GGG CAC CTC ACT   2239
676  Leu His Gln Leu His Thr Met Gly Lys His Thr Gly Gly His Leu Thr

GCC ACC AAC CTG GCG CTG AGT GCC CTG AAC CTG GCA GAG TGT GCA GGG   2287
692  Ala Thr Asn Leu Ala Leu Ser Ala Leu Asn Leu Ala Glu Cys Ala Gly

GAT GCC GTG TCT GTG GCG ACG CTG GCC GAG ATC TAT GTG GCG GCT GCA   2335
708  Asp Ala Val Ser Val Ala Thr Leu Ala Glu Ile Tyr Val Ala Ala Ala

TTG AGA GTG AAG ACC AGT CTC CCA CGG GCC TTG CAT TTT CTG ACA CGC   2383
724  Leu Arg Val Lys Thr Ser Leu Pro Arg Ala Leu His Phe Leu Thr Arg

TTC TTC CTG AGC AGT GCC CGC CAG GCC TGC CTG GCA CAG AGT GGC TCA   2431
740  Phe Phe Leu Ser Ser Ala Arg Gln Ala Cys Leu Ala Gln Ser Gly Ser
```

FIG. 16H

```
     GTG CCT CCT GCC ATG CAG TGG CTC TGC CAC CCC GTG GGC CAC CGT TTC    2479
756  Val Pro Pro Ala Met Gln Trp Leu Cys His Pro Val Gly His Arg Phe

TTC GTG GAT GGG GAC TGG TCC GTG CTC CCA AGT ACC CCA TGG GAG AGC CTG  2527
772  Phe Val Asp Gly Asp Trp Ser Val Leu Ser Thr Pro Trp Glu Ser Leu

TAC AGC TTG GCC GGG AAC CCA GTG GAC CCC CTG GCC CAG GTG ACT CAG    2575
788  Tyr Ser Leu Ala Gly Asn Pro Val Asp Pro Leu Ala Gln Val Thr Gln

CTA TTC CGG GAA CAT CTC TTA GAG CGA GCA CTG AAC TGT GTG ACC CAG    2623
804  Leu Phe Arg Glu His Leu Leu Glu Arg Ala Leu Asn Cys Val Thr Gln

CCC AAC CCC AGC CCT GGG TCA GCT GAT GGG GAC AAG GAA TTC TCG GAT    2671
820  Pro Asn Pro Ser Pro Gly Ser Ala Asp Gly Asp Lys Glu Phe Ser Asp

GCC CTC GGG TAC CTG CAG CTG CTG AAC AGC TGT TCT GAT GCT GCG GGG    2719
836  Ala Leu Gly Tyr Leu Gln Leu Leu Asn Ser Cys Ser Asp Ala Ala Gly

GCT CCT GCC TAC AGC TTC TCC ATC AGT TCC AGC ATG GCC ACC ACC ACC    2767
852  Ala Pro Ala Tyr Ser Phe Ser Ile Ser Ser Ser Met Ala Thr Thr Thr
```

FIG. 16I

```
     GGC GTA GAC CCG GTG GCC AAG TGG TGG GCC TCT CTG ACA GCT GTG GTG    2815
868  Gly Val Asp Pro Val Ala Lys Trp Trp Ala Ser Leu Thr Ala Val Val

ATC CAC TGG CTG CGG CGG GAT GAG GAG GCG GCT GAG CGG CTG TGC CCG    2863
884  Ile His Trp Leu Arg Arg Asp Glu Glu Ala Ala Glu Arg Leu Cys Pro

CTG GAG CAC CTG CCC CGG GTG CTG CAG GAG TCT GAG AGA CCC CTG        2911
900  Leu Val Glu His Leu Pro Arg Val Leu Gln Glu Ser Glu Arg Pro Leu

CCC AGG GCA GCT CTG CAC TCC TTC AAG GCT GCC CGG GCC CTG CTG GGC    2959
916  Pro Arg Ala Ala Leu His Ser Phe Lys Ala Ala Arg Ala Leu Leu Gly

TGT GCC AAG GCA GAG TCT GGT CCA GCC AGC CTG GCT ACC ATC TGT GAG AAG    3007
932  Cys Ala Lys Ala Glu Ser Gly Pro Ala Ser Leu Ala Thr Ile Cys Glu Lys

GCC AGT GGG TAC CTG CAG GAC AGC CTG GCT ACC ACA CCA GCC AGC AGC    3055
948  Ala Ser Gly Tyr Leu Gln Asp Ser Leu Ala Thr Thr Pro Ala Ser Ser

TCC ATT GAC AAG GCC GTG CAG CTG TTC CTG TGT GAC CTG CTT CTT GTG    3103
964  Ser Ile Asp Lys Ala Val Gln Leu Phe Leu Cys Asp Leu Leu Leu Val
```

FIG. 16J

```
 980  GTG CGC ACC AGC CTG TGG CGG CAG CAG CCC GCC CCG GCC CCA  3151
      Val Arg Thr Ser Leu Trp Arg Gln Gln Pro Pro Pro Ala Pro

996  GCA GCC CAG GGC ACC AGC AGG CCC CAG GCT TCC GCC CTT GAG CTG  3199
      Ala Ala Gln Gly Thr Ser Arg Pro Gln Ala Ser Ala Leu Glu Leu

1012  CGT GGC TTC CAA CGG GAC CTG AGC AGC CTG GCA CAG AGC  3247
      Arg Gly Phe Gln Arg Asp Leu Ser Ser Leu Arg Arg Ala Gln Ser

1028  TTC CGG CCC GCC ATG CGG AGG GTG TTC CTA CAT GAG GCC ACG CGG  3295
      Phe Arg Pro Ala Met Arg Arg Val Phe Leu His Glu Ala Thr Arg

1044  CTG ATG GCG GGG GCC AGC CCC ACA CAC CAG CTC CTC GAC CGC  3343
      Leu Met Ala Gly Ala Ser Pro Thr His Gln Leu Leu Asp Arg

1060  AGT CTG AGG CGG CGG GCA GGC CCC GGT GGC AAA GGA GGC GCG GTG GCG  3391
      Ser Leu Arg Arg Arg Ala Gly Pro Gly Gly Lys Gly Gly Ala Val Ala

1076  GAG CTG GAG CCG CGG CCC ACG CGG CGG GAG CAC GAG GCC TTG CTG  3439
      Glu Leu Glu Pro Arg Pro Thr Arg Arg Glu His Glu Ala Leu Leu
```

FIG. 16K

```
      CTG GCC TCC TGC TAC CTG CCC CCC GGC TTC CTG TCG GCG CCC GGG CAG   3487
1092  Leu Ala Ser Cys Tyr Leu Pro Pro Gly Phe Leu Ser Ala Pro Gly Gln

CGC GTG GGC ATG CTG GCT GAG GCG GCG CGC ACA CTC GAG AAG CTT GGC   3535
1108  Arg Val Gly Met Leu Ala Glu Ala Ala Arg Thr Leu Glu Lys Leu Gly

GAT CGC CGG CTG CTG CAC GAC TGT CAG CAG ATG CTC ATG CGC CTG GGC   3583
1124  Asp Arg Arg Leu Leu His Asp Cys Gln Gln Met Leu Met Arg Leu Gly

GGT GGG ACC ACT GTC ACT TCC AGC TAGACCCCGT GTCCCCGGCC TCAGCACCCC   3637
1140  Gly Gly Thr Thr Val Thr Ser Ser

TGTCTCTAGC CACTTTGGTC CCGTGCAGCT TCTGTCCTGC GTCGAAGCTT TGAAGGCCGA   3697

AGGCAGTGCA AGAGACTCTG GCCTCCACAG TTCGACCTGC GGCTGCTGTG TGCCTTCGCG   3757

GTGGAAGGCC CGAGGGGCGC GATCTTGACC CTAAGACCGG CGGCCATGAT GGTGCTGACC   3817

TCTGGTGGCC GATCGGGGCA CTGCAGGGGC CGAGCCATTT TGGGGGGCCC CCCTCCTTGC   3877

TCTGCAGGCA CCTTAGTGGC TTTTTCCTTC CTGTGTACAG GGAAGAGAGG GGTACATTTC   3937
```

FIG. 16L

```
CCTGTGCTGA CGGAAGCCAA CTTGGCTTTC CCGGACTGCA AGCAGGGCTC TGCCCCAGAG  3997
GCCTCTCT CCGTCGTGGG AGAGAGACGT GTACATAGTG TAGGTCAGCG TGCTTAGCCT  4057
CCTGACCTGA GGCTCCTGTG CTACTTTGCC TTTTGCAAAC TTTATTTTCA TAGATTGAGA  4117
AGTTTGTAC AGAGAATTAA AAATGAAATT ATTTATA 3'                        4154 b.p.
```

359 KSAVLRKAIDYIRFLQHSNQKLKQENLSLRTAVHKSKSLKDLV 401
HELIX 2

```
SREBP-2   MDS..GFLGGFFMEILTEIGFLTLGDIEMLQFVSNQVEFPDLFSEQLCSSFGSGSGSSSGSSGGSSGABDPSBQRSFTQVLLP     98
SREBP-1a  --EPPFS-AALFQALGFPD-DAA-..T--ED---LIN--DSD--G--DPPAG--GA--GIDPA--FDT--FG--L--PPPATL--...LEAFL....--GP-AAPS    95

SREBP-2   SFSPSAASFQA.......PTLQMKVSPISVPTIPRATPILQRPRQPQPQIQLQQQ.TMITPTFSITFQIRTLQQPLIYQNAAISFQVLQP.QXQSLVTSS    192
SREBP-1a  PL--FQPAPTPLKMY--SMPAFSPGFGIKEESVPLS---T.--T---L-GAL--P--SFPAPAP--Q--S--VLGYPSP--CGFSIGSPPGNIQ---LPGLP-ASPP   194

SREBP-2   QXQPVTLQQQMQIVQAQRVLIQIANGII.QIT.APATVQIVAAPQMQQVPVLMQPQIKIDSMVLTTLKIDGSPMAAVQNEALTALTTPIQIAALQVPTLV    292
SREBP-1a  G--P--SLHT----SWP--QL--V--AP-.....A-P-T--IVIS--I-----L--HF--A---L--AM----AT-K----GLS--LMSG...TV--GP-...----   285

SREBP-2   GSSGTILTTMPVMMQQEKVPTKQVEGGVKQLEPPKE. GFRRTTHNIEKYRSSINKLIEI KDLMGIDAKMHKSGVLRKAIDYIKVLQQMNHKLRQEN391
SREBP-1a  .--G----A-V--LMDA--L--NFLAA--S--APASAQSR---K--A----A---------------------V--E--LIN---A---------RF--HSNQ---K-----   384

SREBP-2   MVLKLANQKNKLLKGHLGSLMVNEMLKIELFNQWL.LMSPPASDSGSQAGFSPYST...........DSEFGSPLLDAKKDEPDSPPVALGVMD    478
SREBP-1a  LS--RT--VH--S--S---DLMSACGSGGNI--VLM--GVKIE--EDILT--P--A--PFQS--L--LGSRGGGGGSS----D--VFE--S--A--P--QRFSLHSR--L---   484

SREBP-2   RSRIILCVLIFLCLSFNPLTISLL..QMGGAHDSDQHP.HESGGERSVLSFES.GSGGMFDMVMPTLHMMNGVIVLSVFVKLIMGEPVIRHSRSSVIFW    575
SREBP-1a  ---IA--T--V------C-----A-----GAR--LPSP---TTSVMHSP--N--GT---RDGP--AQ--LL--P..VV---L--LL---VSL--L--F--Y------T-----GPA-Y---    583

SREBP-2   RHFRKQADILARGIFAAAAANLQICLAVLGRALPLTSRLDLACSLSMVVIRYSLQKLRLVMLKKVFQCRRATPATFAGFLFAKISARDAALAYHRLHQ   675
SREBP-1a  -----------------Q---QQ--WLA--RA---P------H------L--L--HL--R--WMG----......AG--AGELQQDCALRVD--SAS----------V--K-----   678

SREBP-2   LHITIGKLPAGSACSDVGMALCAVNLAECAFEKTPPSILMFIHLTAAMGLKIRCCGKLGFLASYFLSRAQSLCGFEHSAVPLSLRMCHPLGQKFMERSW    775
SREBP-1a  --TM--HIG--HLTA..TNL--S--L-------GDAVSVA--A---YVA--LRV--SLPRA--H---TRF----S--RQA--LAWSGS---PAVQ-------V--HR--VLGD---    777
```

FIG. 25Aii

```
SREB-2    SVKSAAKESLYCAQRNPADPIAQVGQAFCKNLLERATESLMKPQAKKAGLQFFESCEFSSALEMLKLTHSFVDSFVMSPPLSRSSVLKSALGPDIICR  875
SREBP-1a  --L-TPR----SLAG-V--L--T-L-REH------INCVIQ-NPSPGSA-GDK....--D--G--Q--N-CS-AA-APAVSF--I---SMATTT-V-PVAK  874

SREBP-2   WMISATTVAISMLQGDDAAVRSHFTKVERIPKALEVIESPLMKATFHACRAMHASLP.GKADQQSSFCHCERASGHLMSSINMSGGHISDPAINHMQLL  974
SREBP-1a  --A--LTA-V-H--RR--EE-AFRICPL--HL-RV-QES-R---RR-AL-SFK-AR-L-GCA--ESFGA-LTI--K---Y-QD--ATTPAS-..SIDKA---F  972

SREBP-2   TQDILISLRIALWKQ.....ASASQAVGEIYASGAEIAGFQRDLGSIRRLAHSFRPAYRKVELHEATVRLMAGGSPIRIHQLIEHSLRRRITQSIKHG  1069
SREBP-1a  L----W--S--RQ-QPPAP-P-A-GISSRPQ--AL--R-----S-----Q-----M-R-----A-----A-----DR------AGPGG-G--  1072

SREBP-2   .....EMDAWPQQRERATATLLACRHLPLSFLSSPGQRAVLLAFAARTLEKVGRRSONDCQMVKLGGGIAIAAS  1141
SREBP-1a  AVA-LEPR--IR--H-E-L---SCY--PG---A---VGM--------L---LIH------IMR------TVIS--
```

```
                      *        *           *
SREBP-2   331  RRTTHNI IEKRYRSS INDKI IELKDLVMGTDAK MHKSGVLRKA IDYIKYLQ 381
SREBP-1a  324  KRTAHNA IEKRYRSS INDKI IELKDLVVGTEAK LNKSAVLRKA IDYIRFLQ 374

CONSENSUS      KR---N--EK-R---IN-F-EL--------K--K---IL--A--YI--L-
               RK      T   R        A              K  R  V     V
                 BASIS            HELIX 1              HELIX 2
```

FIG. 25B

METHODS RELATING TO STEROL REGULATORY ELEMENT BINDING PROTEINS

The present application is a divisional application of application Ser. No. 08/131,365, filed Oct. 1, 1993 now issued as U.S. Pat. No. 5,527,690; which was a continuation-in-part of application Ser. No. 08/061,697, filed May 13, 1993, now issued as U.S. Pat. No. 5,498,696.

BACKGROUND OF THE INVENTION

1. Field of the Invention

The present invention relates generally to transcriptional activator proteins and to methods for altering gene expression, cellular function and metabolism. In particular, this invention concerns sterol regulatory element (SRE) binding proteins (SREBPs) and DNA segments encoding such proteins. Methods for using SREBP-1 to stimulate SRE-1-mediated gene transcription in the presence of sterols are also disclosed, which are contemplated for use in reducing plasma cholesterol levels and in controlling hypercholesterolemia and its associated diseases.

2. Description of the Related Art

There is currently relatively little knowledge concerning feedback suppression mechanisms involved in eukaryotic gene regulation. In animal cells, most attention has focused on positively-regulated systems in which hormones, metabolic inducers, and developmental factors increase transcription of genes. These inducing agents are generally thought to activate or form complexes with proteins that stimulate transcription by binding to short sequences of 10 to 20 base pairs (bp) in the 5'-flanking region of the target gene. Such elements, termed GRE, MRE, and IRE have been reported for glucocorticoid, metal and interferon regulatory elements, respectively (Yamamoto, 1985; Stuart et al., 1984; Goodbourn et al., 1986).

Important advances have been made recently concerning other DNA segments which are capable of conferring control capability to known genes in eukaryotic systems. For example, transcription of the gene for the low density lipoprotein (LDL) receptor is regulated by a 10 base pair (bp) element in the 5' flanking region designated sterol regulatory element-1 (SRE-1; Goldstein and Brown, 1990; U.S. Pat. No. 4,935,363). The receptor provides cholesterol to cells by binding and internalizing LDL, a plasma cholesterol transport protein. When cellular cholesterol demands are high, as when cells are grown in the absence of sterols, this element is transcriptionally active, the cells produce large numbers of LDL receptors and LDL is internalized rapidly. On the other hand, when sterols accumulate within cells, the SRE-1 is silenced, and cells reduce the number of LDL receptors, thereby preventing cholesterol over accumulation. This feedback regulatory system controls not only the cholesterol content of cells, but also that of plasma (Brown and Goldstein, 1986). When hepatic LDL receptors are repressed by intracellular accumulation of dietary cholesterol, LDL is not taken up into the liver at a normal rate, and the lipoprotein builds up to high levels in the blood.

The 10 bp SRE-1 lies within a 16-base pair (bp) sequence, designated Repeat 2, that is 53 bp upstream of the transcription start site of the LDL receptor gene (Smith et al., 1990). This sequence is the central member of a series of three imperfect repeats in the 5' flanking region, all of which are required for high level transcription (Goldstein and Brown, 1990; Smith et al., 1990; Sudhof et al., 1987). Repeats 1 and 3 bind Sp1, a constitutive transcription factor. Mutations in any of the three repeat sequences abolish high-level transcription in sterol-deprived cells (Smith et al., 1990; Südhof et al., 1987; Dawson et al., 1988).

The activity of Repeats 1 and 3, although necessary, is not sufficient for high level transcription. An additional positive contribution is required from Repeat 2, which does not bind Sp1 (Smith et al., 1990; Südhof et al., 1987; Dawson et al., 1988). Mutational analysis suggests that Repeat 2 binds a conditionally positive transcription factor that is active only under conditions of sterol deprivation (Smith et al., 1990). When sterols are added to cells, the contribution of Repeat 2 is abolished, and the rate of transcription falls.

The nucleotides within Repeat 2 that are necessary for its transcriptional activity have been delineated partially through in vitro mutagenesis and expression studies in permanently transfected CHO cells. The relevant nucleotides include the SRE-1 10 bp stretch which has the sequence ATCACCCCAC, SEQ ID NO:27 (Smith et al., 1990). The essential elements of this sequence have been shown to be conserved in evolution as far back as the last common ancestor of humans and frogs (Mehta et al., 1991).

Unfortunately, despite the elucidation of the SRE-1 DNA sequence, the nature of the putative transcription factor that binds to SRE-1 remained unknown. Two candidates have been proposed (Rajayashibth et al., 1989; Stark et al., 1992), but the proteins in these reports did not show specific binding which precisely correlated with the transcriptional activity of modified SRE-1 elements, and purification of the putative binding proteins was not reported.

The identification of a protein that binds to the SRE-1 sequence and promotes transcription would be advantageous, particularly if DNA segments encoding such a protein were available so that it could be produced in large quantities. A purified SRE transcriptional activator that could be used to promote SRE-1-mediated gene transcription in the presence of sterols would be even more useful. The availability of such a protein would represent a medical breakthrough as it could be used to promote LDL receptor gene transcription, which is normally downregulated by sterols, and to reduce plasma LDL cholesterol levels.

SUMMARY OF THE INVENTION

The present invention seeks to overcome these and other drawbacks inherent in the prior art through the identification, partial purification, and cloning of a family of proteins that are shown to be involved in the cellular homeostatic mechanism of cholesterol metabolism. This family of regulatory proteins, termed Sterol Regulatory Element Binding Proteins (SREBPs), are shown to be involved in the regulation of genes involved in cholesterol metabolism that are under the control of an associated Sterol Regulatory Element-1 (SRE-1). Two distinct families of SREBPs have been identified to date, the SREBP-1 and SREBP-2 families, but it is likely that additional, related families exist. The present invention discloses a variety of useful SREBP gene sequences, as well as methods of using a member of the SREBP family to promote SRE-1-mediated gene transcription, e.g., low density lipoprotein (LDL) receptor production in the presence of sterols. Also disclosed are methods for identifying candidate substances capable of modulating (e.g., inhibiting or promoting) this function, e.g., through the use of SRE-1 binding domains of SREBP. SREBP proteins or gene sequences, as well as other positive candidate substances, are proposed for use as cholesterol-lowering agents to control hypercholesterolemia and the various disease states associated with this condition.

The sterol regulatory element (SRE-1) binding proteins of the present invention, termed SREBPs, are DNA binding proteins that promote transcription from SRE-1 sequences. In the present text, the terms "SREBPs", SRE-1 binding proteins and DNA binding proteins are used interchangeably and each refer to a proteinaceous composition that is isolatable from mammalian cell nuclei and capable of binding to DNA segments which include the sterol regulatory element SRE-1 (see, e.g., SEQ ID NO:27). SREBPs are called binding "proteins" for simplicity. However, it is important to bear in mind that shorter subfragments of SREBP can be obtained from, e.g., natural sources, that are found to include the SRE-1 binding domain, i.e., a bHLH-Zip sequence. Thus, although purified, full length recombinant SREBP proteins are encompassed by the invention, it will be understood that the term SREBP is not necessarily limited to a full length proteins. The term includes useful polypeptides isolated from natural sources, as well as SRE-1-binding activity present within a composition, which may result from certain domains of a polypeptide, the combined actions of one or more polypeptides, combinations of polypeptides and known transcription factors and/or multienzyme complexes, and the like.

In the present context, SRE-1 is used to refer to a "functional SRE-1 sequence". Such functional sequences are those which are capable of promoting transcription and expression of sterol-responsive genes. These may be native SRE-1 sequences, such as the sequence found upstream of any mammalian LDL-receptor gene, or may be mutant SRE-1 sequences which are nonetheless capable of promoting sterol-responsive gene transcription. An SRE-1 element "capable of promoting sterol-responsive gene transcription" refers to an element which, when located upstream (i.e., 5') from and proximal to a transcription initiation site of a structural gene, serves to confer a sterol-responsive transcriptional capability to the gene. This means that gene transcription is promoted in the absence of sterols, but that little or no transcription is allowed in the presence of sterols. The identification, preparation and use of SRE-1 sequences is described herein, as well as in detail in U.S. Pat. Nos. 4,953,363 and 5,215,910, and application Ser. No. 33,081, filed Mar. 30, 1987, now U.S. Pat. No. 5,378,603, and Ser. No. 425,852, filed Oct. 20, 1989, now U.S. Pat. No. 5,256, 545 each of the foregoing being incorporated herein by reference.

Purified SREBP Compositions

Important aspects of the present invention concern purified protein compositions, free from the environment in which they may naturally occur in intact cells, comprising one or more DNA binding proteins which are isolatable from mammalian cell nuclei, or from recombinant sources, that are capable of binding to a DNA segment comprising the sterol regulatory element SRE-1 (SEQ ID NO:27). In certain embodiments, the invention concerns substantially purified SREBP compositions comprised of an SREBP family member, such as SREBP-1 or SREBP-2, or an SRE-1-binding subdomain thereof. Intact SREBP-1 and SREBP-2 proteins exhibit a molecular weight of approximately 130 kDa upon SDS-PAGE. However, the protein compositions may be further defined as including one or more polypeptides or DNA binding domains having an apparent molecular weight on SDS/PAGE of between about 59 kD and about 68 kD. This is based upon the inventors' observation that DNA binding polypeptides having these molecular weights, and found to be derived from the corresponding full-length SREBP protein, can be crosslinked-to SRE sequences and, as described in the examples below, are believed to be derived from larger proteins, perhaps by proteolytic cleavage, and may in themselves represent the DNA binding domains, and transcriptionally functional domains, of larger protein(s).

In particular aspects, the inventors disclose the isolation and cloning of two separate families of SREBP proteins, designated SREBP-1 and SREBP-2, that each have the ability to bind to SRE sequences and modulate SRE-mediated transcription. Both proteins are members of a family of basic-helix-loop-helix-leucine zipper (bHLH-Zip) transcription factor that recognize sterol regulatory element-1. SRE-1, a conditional enhancer in the promoters for the low density lipoprotein receptor and 3-hydroxy-3-methylglutaryl coenzyme A synthase genes, increases transcription in the absence of sterols and is inactivated when sterols accumulate. Human SREBP-2 contains 1141 amino acids and is 47% identity to one of the various SREBP-1 family members that has been characterized, SREBP-1a, the first recognized member of this family. SREBP-1a contains 1147 amino acids. The resemblance between SREBP-1a and SREBP-2 includes an acidic $NH_2$-terminus, a highly conserved bHLH-Zip motif (71% identical), and an unusually long extension of 740 amino acids on the COOH-terminal side of the bHLH-Zip region.

SREBP-2 possesses one feature lacking in SREBP-1a, namely, a glutamine-rich region (27% glutamine over 121 residues). In vitro SREBP-2 bound SRE-1 with the same specificity as SREBP-1a. In vivo it mimicked SREBP-1a in activating transcription of reporter genes containing SRE-1. As with SREBP-1a, activation by SREBP-2 occurred in the absence and presence of sterols, abolishing regulation. Cotransfection of low amounts of pSREBP-1a and pSREBP-2 into human 293 cells stimulates transcription of promoters containing SRE-1 in an additive fashion. At high levels transcription reaches a maximum, and the effects are no longer additive.

The term "purified" as used herein, is intended to refer to a DNA binding protein composition wherein the SREBP or SREBPs are purified to any degree relative to their naturally-obtainable state, such as, relative to the purity within a partially purified nuclear extract that is enriched in terms of SREBP content or activity. Generally, "purified" will refer to a native or recombinant SREBP composition which has been subjected to fractionation to remove various non-SREBP components, and which composition substantially retains its SRE-1 binding and/or transcription promoting activity. Where the term "substantially purified" is used in terms of native or recombinant SREBPs, this will refer to a composition in which SREBP or SREBPs form the major component of the composition, such as constituting about 50% of the proteins in the composition or more.

"Native SREBP" refers to SREBP compositions purified from sources such as mammalian cell nuclei. "Recombinant SREBP" refers to SREBP compositions, including truncated SREBPs, SREBP fusion proteins and engineered forms of SREBP, which are obtained using a recombinant DNA molecule which encodes a SREBP or a portion thereof. In terms of purified recombinant SREBP compositions, "subjecting to fractionation" will often be satisfied by collecting the recombinant SREBP from its production source, such as from a recombinant host cell or from an in vitro translation system. In substantially purified recombinant SREBP compositions, the SREBP polypeptide will generally constitute about 50% of the protein, such as 50% of the protein in a recombinant host cell extract, and may approach up to essentially pure compositions of the protein, defined as being free of substances, e.g., other proteins, that interfere with the particular use contemplated.

Although preferred for use in certain embodiments, there is no general requirement What SREBPs always be provided in their most purified state. It is contemplated that less substantially purified SREBP compositions, which nonetheless have some assayable SREBP activity, will have utility in certain embodiments. These include, for example, use as a positive control in gel-shift assays. Partially purified SREBPs may be obtained by subjecting a nuclear extract to one or a combination of the steps described below. SREBPs without significant biological activity will also have utility, such as, for example, in antibody generation protocols.

Protein Purification and Assays

Various methods for quantifying the degree of purification of an SREBP composition will be known to those of skill in the art in light of the present disclosure. These include, for example, determining the ability of an active fraction to retard the mobility of oligonucleotides containing functional SRE-1 sequences when such 'oligos' are subjected to electrophoresis, or even, assessing the number of polypeptides within a fraction by SDS/PAGE analysis. A preferred method for assessing the purity of an SREBP fraction is to calculate the specific activity of the fraction, to compare it to the specific activity of the first fraction in which activity is measurable, and to calculate a degree of purity which may be presented as a "-fold purification number".

The actual units used to represent the amount of binding activity will, of course, be dependent upon the particular assay technique chosen to follow the purification. The present inventors prefer to use a "gel-shift" assay in which the mobility of radioactively-labelled oligonucleotides containing wild-type and mutant SRE-1 sequences is determined in the presence and absence of the protein fractions. In this system, one unit of activity corresponds to 1000 cpm of shifted probe (from 6 fmol of $^{32}$P-labelled at 40,000 cpm). However, using other assays, or even other probe preparations, the definition of a unit of activity would naturally vary.

As is generally known in the art, to determine the specific activity, one would calculate the number of units of activity per milligram of total protein. The specific activity of each purified SREBP fraction may be compared to the specific activity of the first fraction in which activity was measurable, and the "-fold purification" calculated. In preferred embodiments, the SREBPs of the present invention may be purified from natural sources, such as hamster or rat liver or even adrenal tissue, or more preferably, from human HeLa cell nuclei, to between about 200-fold and greater than 38,000-fold, and most preferably, will be provided in at least an equal to or greater than a 38,000-fold purified state.

To prepare a substantially purified DNA binding protein or SREBP composition in accordance with certain aspects of the present invention one may prepare an extract from mammalian cells, and preferably, a nuclear extract from HeLa cells, subject the extract to any of the fractionation procedures known to those of skill in the art, and assay the fractions to identify those containing SREBP. One may also perform such fractionation and assay steps to isolate and purify a recombinant SREBP from a recombinant host cell which expresses an SREBP, such as one of the SREBP-1 or SREBP-2 family members. Fractionation steps such as ammonium sulfate precipitation, ultracentrifugation and various chromatographic procedures are preferred. Particularly advantageous fractionation steps are contemplated to include ion exchange chromatography, gel filtration chromatography, and most preferably, DNA affinity chromatography, particularly using affinity columns containing the oligonucleotide probes disclosed herein (SEQ ID NOS:31–36).

To assay SREBP binding activity, the present inventors prefer to use a "gel-shift" assay in which the mobility of radioactively-labelled oligonucleotides containing wild-type and mutant SRE-1 sequences is determined in the presence and absence of the protein fractions. SREBP within a fraction will bind to functional SRE-1 sequences, but not to non-functional sequences, and will reduce or "shift" the mobility of only the oligos containing functional SRE-1. In this system, one unit of activity corresponds to 1000 cpm of shifted probe.

The present invention encompasses a significant advance over the prior art in that it advantageously provides 9 mutant, but transcriptionally-functional, SRE-1 promoters which have been shown to be positive for sterol-regulated transcription (SEQ ID NOS:2–4, 10, 15–19, respectively), and 9 non-functional mutants which have been shown to abolish transcription (SEQ ID NOS:5–9, 11–14, respectively). The invention includes both reporter gene plasmids and oligonucleotide probes containing these 18 promoter sequences (SEQ ID NOS:2–19), which may be used for transfection and reporter gene expression studies and for gel-shift assays, respectively, to enable the unambiguous identification of SREBP or even in a system for controlling gene expression.

The most preferred plasmids are those containing two copies of Repeat 2+3 (SEQ ID NO:24) (with the transcriptionally-functional or non-functional sequences), operatively linked to a TATA box and the reporter gene CAT. The most preferred radiolabeled probes are 94 bp in length and contain two copies of Repeat 2+3 (SEQ ID NO:24) (with the transcriptionally-functional or non-functional sequences), flanked by restriction sites. However, the precise nature of the plasmids and oligonucleotide probes is not critical so long as they contain a functional or non-functional SRE-1 sequence as defined herein.

Now that the functional and non-functional SRE-1 sequences have been defined by the present inventors, such sequences, e.g., any of the 18 specific probes disclosed herein (SEQ ID NOS:2–19) may be straightforwardly used in gel-shift assays to identify SREBPs, which have the capacity to discriminate between the functional and non-functional sequences. In purifying SREBPs from mammalian cell nuclei or recombinant host cells, one would generally employ at least one probe to which SREBPs specifically bind and at least one non-functional SRE-1 probe which SREBPs do not significantly bind. Most preferably, the use of a panel of three probes, termed H, M and *, is preferred as the inventors discovered these to be the most suitable for routinely assaying SREBP activity and for discriminating between SREBPs and other nuclear DNA binding proteins. Probe H includes a human repeat 2+3 sequence (SEQ ID NO:24) and is transcriptionally functional; probe M includes a mouse repeat 2+human repeat 3 sequence (SEQ ID NO:21+SEQ ID NO:23) and is also transcriptionally functional; whereas probe * includes a mutation in repeat 2 that renders it transcriptionally non-functional (SEQ ID NO:14).

The purification method disclosed hereinbelow contains several steps and represents the best method presently known by the inventors to prepare a substantially purified DNA binding protein or SREBP composition from a natural, i.e., non-recombinant source. This method is currently preferred as it results in the substantial purification of SREBP, as assessed by SRE-1 binding which precisely correlates with SRE-1 functionality, in yields sufficient for further characterization and use. This preferred mode of SREBP purification involves the execution of certain purification steps in the order described hereinbelow. However, as is generally known in the art, it is believed that the order of conducting the various purification steps may be changed, or that certain steps may be omitted or other steps added, and still result in a suitable method for the preparation of a substantially purified DNA binding protein or SREBP composition.

Other methods for preparing SREBP are also contemplated and fall within the scope of the present invention. One method involves preparing polyclonal or monoclonal antibodies having binding affinity for SREBP and using such antibodies in immunoabsorbent protocols to purify SREBP, for example, using an antibody affinity column. Anti-SREBP antibodies may be raised using a variety of components as immunogens, as disclosed herein and known to those of skill in the art, including SREBP proteins, such as recombinant SREBP-1, purified functional domains, such as the active polypeptides with apparent $M_r$s on SDS/PAGE of between about 59 kD and about 68 kD, and also synthetic peptides produced from a knowledge of SREBP DNA and/or amino acid sequences.

Molecular Cloning and DNA Segments Encoding SREBP

A particularly advantageous method for preparing SREBP compositions involves obtaining a DNA segment which encodes an SREBP and using the DNA to produce a "recombinant" version of SREBP. This may be performed by using the DNA as an insert in an expression vector and introducing the expression vector into a recombinant host cell so that the host cell expresses an SREBP. Also, the DNA segment may be used in conjunction with an in vitro translation system, such as a reticulocyte lysate system, including those commercially available, e.g., from Promega.

The process of obtaining a DNA segment which encodes an SRE binding protein is generally referred to as the molecular cloning (or simply cloning) of an SREBP. Various techniques for molecular cloning are available, are described in the literature and are well known to those of skill in the art. A particular preferred method for cloning an SREBP is disclosed herein (see Example 3), which was successfully used to obtain a DNA segment encoding an SRE binding protein termed SREBP-1.

To clone an SREBP, one may generally follow the procedure described in detail in Example 3. In this method, SREBP was first purified from pooled extracts of HeLa cell nuclei and the entire active fraction was subjected to tryptic digestion, the resultant peptides were fractionated by HPLC and sequenced. Degenerate oligonucleotides corresponding to a portion of one of the peptides were designed, synthesised and used to prime polymerase chain reactions (PCR) with a HeLa cell cDNA library as template. The unique DNA sequence thus generated was used to probe two HeLa cDNA libraries and to obtain SREBP-encoding cDNAs.

In that the sequence of SREBP-1 and SREBP-2 are now disclosed herein, obtaining SREBP cDNA or genomic sequences or other related sequences will be a routine matter for those of skill in the art. Suitable hybridization screening methods and PCR technology are well known in the field, e.g., as exemplified by Sambrook et al., 1989. Antibodies may also be employed in the expression cloning of SREBPs by using methods such as those described by Young et al., 1988.

Isolated DNA segments and recombinant vectors encoding SREBPs, methods of using such DNA segments and the creation and use of SREBP-expressing recombinant host cells all form important aspects of this invention. As used herein, the term "DNA segment" refers to a DNA molecule which has been isolated free of total genomic DNA of a particular species. Therefore, a DNA segment encoding a SREBP refers to a DNA segment which contains SREBP coding sequences yet is isolated away from, or purified free from, total genomic DNA of the species from which the DNA segment is obtained, such as free from human genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified SREBP gene refers to a DNA segment including SREBP coding sequences isolated substantially away from other naturally occuring genes or protein encoding sequences. In this respect, the term "gene" is used for simplicity to refer to a functional protein or peptide encoding unit. As will be understood by those in the art, this functional term includes both genomic sequences and cDNA sequences. "Isolated substantially away from other coding sequences" means that the gene of interest, in this case an SREBP gene, forms the significant part of the coding region of the DNA segment, and that the DNA segment does not contain large portions of naturally-occuring coding DNA, such as large chromosomal fragments or other functional genes or cDNA coding regions. Of course, this refers to the DNA segment as originally isolated, and does not exclude genes or coding regions later added to the segment by the hand of man.

In certain embodiments, the invention concerns isolated DNA segments and vectors which encode an SREBP that includes within its sequence an amino acid sequence essentially as set forth in SEQ ID NO:38 or 54. The term "a sequence essentially as set forth in SEQ ID NO:38 or 54" means the sequence substantially corresponds to a portion of SEQ ID NO:38 or 54 and has relatively few amino acids which are not identical to, or a biologically functional equivalent of, those in SEQ ID NO:38 or 54. The term "biologically functional equivalent" is well understood in the art and is further defined in detail herein. Accordingly, sequences which have between about 70% and about 100%; or more preferably, between about 80% and about 100%; or even more preferably, between about 90% and about 100%; of amino acids which are identical or functionally equivalent to the amino acids of SEQ ID NO:38 or 54 will be sequences which are "essentially as set forth in SEQ ID NO:38".

In certain other embodiments, the invention concerns isolated DNA segments and recombinant vectors that include within their sequence a nucleic acid sequence essentially as set forth in SEQ ID NO:37 or 53. The term "essentially as set forth in SEQ ID NO:37 or 53" is used in the same sense as described above and means that the nucleic acid sequence substantially corresponds to a portion of SEQ ID NO:37 or 53 and has relatively few codons which are not identical, or functionally equivalent, to the codons of SEQ ID NO:37 or 53. The term "functionally equivalent codon" herein refers to codons that encode the same amino acid and to codons that encode biologically equivalent amino acids.

It will also be understood that amino acid and nucleic acid sequences may include additional residues, such as additional N- or C-terminal amino acids, and yet still be essentially as set forth in one of the sequences disclosed herein, so long as the sequence meets the criteria set forth above. This particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 70% and about 100%; or more preferably, between about 80% and about 100%; or even more preferably, between about 90% and about 1009%; of nucleotides which are identical to the nucleotides of SEQ ID NO:37 or 53 will be sequences which are "essentially as set forth in SEQ ID NO:37 or 53".

Sequences which are essentially the same as those set forth in SEQ ID NO:37 may also be functionally defined as sequences which are capable of hybridising to a nucelic acid segment containing the complement of SEQ ID NO:37 or 53 under relatively stringent conditions. Suitable relatively stringent hybridization conditions will be well known to those of skill in the art in light of the present disclosure. By way of example, suitable hybridization conditions disclosed herein include those in Method 5 of Example 3 and FIG. 18A, wherein hybridization is conducted using 5×SSPE buffer containing 50% formamide for 16 hours at 42° C., followed by washing once with 1×SSC and 0.05% SDS for 30 minutes at room temperature and twice with 0.1×SSC and 0.1% SDS for 20 minutes at 50° C.

Naturally, the present invention also encompasses DNA segments which are complementary, or essentially complementary, to the sequence set forth in SEQ ID NO:37 or 53. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridising to the nucleic acid segment of SEQ ID NO:37 or 53 under relatively stringent conditions, such as those described herein, e.g., in Method 5 of Example 3.

Nucleic Acid Hybridization

In connection with expression embodiments to prepare recombinant SREBP proteins and peptides, it is contemplated that longer DNA segments will most often be used, with DNA segments encoding SREBP-1 functional domains or the entire SREBP-1 protein being most preferred. However, it will be appreciated that the use of shorter DNA segments to direct the expression of SREBP peptides or epitopic core regions, such as may be used to generate anti-SREBP antibodies, also falls within the scope of the invention.

In addition to their use in directing the expression of SREBP proteins, the nucleic acid sequences disclosed herein also have a variety of other uses. For example, they also have utility as probes or primers in nucleic acid hybridization embodiments. As such, it is contemplated that oligonucleotide fragments corresponding to the sequence of SEQ ID NO:37 or SEQ ID NO:53 for stretches of between about 10 to 15 nucleotides and about 20 to 30 nucleotides will find particular utility. Longer complementary sequences, e.g., those of about 40, 50, 100, 200, 500, 1000, and even up to full length sequences of about 4154 nucleotides in length, will also be of use in certain embodiments.

The ability of such nucleic acid probes to specifically hybridize to SREBP-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having stretches of 10, 20, 30, 50, or even of 100 nucleotides or so, complementary to SEQ ID NO:37 or SEQ ID NO:53 are particularly contemplated as hybridization probes for use in, e.g., Southern and Northern blotting. This would allow SREBP structural or regulatory genes to be analysed, both in diverse cell types and also in various other mammalian species. The total size of fragment, as well as the size of the complementary stretch (es), will ultimately depend on the intended use or application of the particular nucleic acid segment. Smaller fragments will generally find use in hybridization embodiments, wherein the length of the complementary region may be varied, such as between about 10 and about 100 nucleotides, but larger complementarty stretches-of up to about 4154 nucleotides may be used, according to the length complementary sequences one wishes to detect.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:37 or 53, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

It will also be understood that this invention is not limited to the particular nucleic acid and amino acid sequences of SEQ ID NOS:37, 38, 53 and 54. Recombinant vectors and isolated DNA segments may therefore variously include SREBP coding regions themselves, coding regions bearing selected alterations or modifications in the basic coding region, or they may encode larger polypeptides which nevertheless include SREBP coding regions or may encode biologically functional equivalent proteins or peptides which have variant amino acids sequences.

The DNA segments of the present invention encompass biologically functional equivalent SREBP proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the DNA binding of the protein or to test point or deletion mutants in order to examine SREBP activity and regulation at the molecular level.

If desired, one may also prepare fusion proteins and peptides, e.g., where the SREBP coding regions are aligned within the same expression unit with other proteins or peptides having desired functions, such as for purification or immunodetection purposes (e.g., proteins which may be purified by affinity chromatography and enzyme label coding regions, respectively).

Recombinant Vectors

This invention also encompasses recombinant vectors that include SREBP DNA segments. Particularly useful recombinant vectors are contemplated to be those vectors in which the coding portion of the DNA segment is positioned under the control of a promoter. The promoter may be in the form of the promoter which is naturally associated with SREBP gene(s) in mammalian cells, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with an SREBP gene in its natural environment. Such promoters may include other sterol-responsive promoters normally associated with other genes and also promoters isolated from any other bacterial, viral, eukaryotic, or mammalian cell. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al. (1989).

The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression in bacterial cells, such as $E.$ $coli$, include the β-galactosidase system with IPTG as an inducer, the T7 RNA polymerase promoter system described by Tabor & Richardson (1985) and the maltose binding protein-fusion protein system (Guan et al., 1987; Nagai & Thogersen, 1987).

A variety of vectors are available for expression of SREBP in cultured animal cells, any one of which may be employed in accordance herewith. The vectors preferred by the present inventors are those based upon pCMV7, a modified version of pCMV5 (Andersson et al., 1989) that contains a hybrid adenovirus/immunoglobulin intron. For therapeutic applications of SREBP coding sequences, one will, of course, employ a vector that is not incompatible with human therapy and capable of delivering the gene to appropriate target cells, such as liver cells. Examples of suitable vectors in this regard include adenoviruses, retroviruses, ect. (see, e.g., U.S. Ser. No. 07/968,861, incorporated herein by reference). However, a DNA segment encoding SREBP may be ligated into virtually any vector using techniques which are now very routine in the art. All that is requried is to digest the vector with a restriction enzyme and to ligate a DNA segment containing appropriately matched termini into the vector.

Depending upon the use envisionsed, recombinant vectors and isolated segments may variously include the SREBP coding regions themselves, coding regions bearing selected alterations or modifications in the basic coding region or may encode larger polypeptides which nevertheless include SREBP sequences and which, preferably, function to promote SRE-1-mediated gene expression when over-expressed.

It will be understood that this aspect of the invention is not limited to the particular nucleic acid and amino acid sequences of SEQ ID NOS:37, 38, 53 and 54. Accordingly, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. A full description of biologically functional equivalent amino acids is presented herein.

Uses of SREBP

It is shown herein that SREBP proteins activate transcription of reporter genes with artificial promoters that contain multiple copies of SRE-1 as well as natural promoters, such as those containing the 5 flanking region of the LDL receptor gene and the HMG CoA synthase gene. When overproduced in animal cells, SREBPs stimulate transcription from the SRE-1, and also abolish sterol-mediated suppression of transcription. The inventors set forth various theories to explain this phenomenon in the present application. However, regardless of the underlying reason, this observation imparts a very important practical utility to SREBP proteins in that it can be used to promote transcription of the LDL receptor gene even in the presence of sterols and is therefore proposed as a cholesterol lowering agent.

Most notably and as discussed in more detail in the following section, it is contemplated that the ability of the SREBP to bind to SRE-1 sequences is a requirement or basis for its regulatory capability. Thus, the ability to screen for agents that can modify this binding will have significant utility to the pharmaceutical industry, in connection with the identification of agents having an effect on cholesterol metabolism and serum cholesterol levels. For example, agents that would promote the expression of SREBP or its interaction with the SRE binding site will tend to promote serum cholesterol lowering (by abolishing sterol-mediated suppression of, e.g., LDL receptor expression). Thus, the inventors contemplate screening for compounds that promote SREBP binding to SRE or agents that stimulate the transcription of SREBP, as a means of lowering serum cholesterol levels. Similarly, agents that would tend to promote the binding of SREBP or inhibit expression of SREBP would tend to decrease the cellular uptake of cholesterol. Thus, an important use of the SREBP protein and gene sequences is in the fashioning of assays for the identification of important pharmaceuticals that will affect cholesterol metabolism.

In addition to use in in vitro screening for pharmaceuticals, it is proposed that the SREBP and its gene sequences will have various utilities in vivo. One in vivo use that is contemplated involves the introduction of SREBP protein, or biologically active subfragments, into cells as a means of abolishing or reducing sterol-mediated suppression of LDL receptor gene expression. The identification of biologically active subfragments of SREBP proteins should be straightforward, in light of the sequence and biological information presented herein.

Other uses envisioned by the inventors include the use of SREBP proteins to increase the production of any recombinant protein expressed from an SRE-1-including promoter in host cells cultured with and without sterols; it may be used in antisense protocols if desired; and low levels of SREBP expression may even be used to promote gene expression in hypocholesterolemic animals or in normal animals at times of low sterol levels. For example, SREBP gene sequence(s) can be targeted to cells in need of cholesterol-lowering therapy, such as liver cells, with their introduction being achieved using an appropriate recombinant vector such as a retrovirus or adenovirus vector (see, e.g., U.S. Ser. No. 07/968,861, incorporated by reference.)

SREBPs, as well as SRE-1-binding subfragments, can also be used as the central components in screening assays to identify candidate substances capable of promoting LDL receptor expression, as described below. However, SREBPs may be employed in a variety of other embodiments, including, for example, in immunization regimens to prepare SREBP-specific antibodies, which may then be used in SREBP purification or further SREBP cloning, or to probe the structure, function, localization and mechanism of action of SREBPs.

Candidate Substance Screening Assays

Although it is shown that the expression of SREBP can itself promote SRE-1-mediated gene expression in the presence or absence of sterols, this invention also provides a variety of methods for evaluating candidate substances to identify further compounds capable of stimulating SRE-1-mediated transcription. Such compounds would be capable of promoting LDL receptor expression and, as an increase in the number of LDL receptors at the surface of a cell allows plasma LDL levels to be reduced, positive substances identified by such assays will be potential LDL-cholesterol lowering drugs.

SREBP-1 functions to bind SRE-1 DNA sequences and to promote transcription and gene expression, and high levels of SREBP-1 do this even in the presence of sterols. Therefore, the identification of an agent which promotes or increases SREBP binding to SRE DNA sequences is a first step towards developing further therapeutic products for use in treating hypercholesterolemia. Various assays are contemplated as a means to search for agents which increase SREBP binding to DNA, i.e., which increase this protein's affinity.

The basis of one such assay rests in mixing relatively purified SREBP-containing compositions, including recombinant SREBP-1, and SRE-1 DNA segments and allowing them to form a specific bound complex which may be separated from the free components. A positive candidate substance would be one that acted to increase the amount of protein:DNA complex formed, or one that increased the stability of the complex once formed. Generally, one of the unbound species, either the protein or DNA, would be specifically labeled prior to beginning the assay in order to quantitate the amount of bound complex later formed. Radioactive or enzymatic labels may be employed, or the protein portion of the complex may be detected by means of an antibody directed against the protein.

Various forms of DNA:protein binding assays suitable for use in accordance with the present invention will be known to those of skill in the art in light of the present disclosure. These include, for example, filter-binding and microtiter plate-type assays which can all be performed in an automated or semiautomated manner to enable analysis of a large number of candidate substances in a short period of time. Of course, the efficiency of such screening assays will be greatly increased now that the cDNA for SREBP-1 and recombinant forms of the protein are available.

Further candidate substance screening methods of the invention are based upon cellular assays in which candidate substances are screened for their ability to stimulate SRE-1-mediated transcription and gene expression, and particularly, reporter gene expression. The preferred cellular candidate substance screening assays comprise preparing a recombinant plasmid including a reporter gene, preferably a CAT gene or luciferase gene, under the transcriptional control of a functional SRE-1 sequence and introducing the plasmid into a recombinant host cell, such as a monkey CV-1 cell. The host cell is then cultured under conditions effective to allow expression of the reporter gene, which expression is measured, and then the cell is contacted with the candidate substance and the new level of reporter gene expression is measured. An increase in reporter gene expression in the presence of the candidate substance is indicative of a candidate substance capable of stimulating SRE-1-mediated transcription.

Still further embodiments of the invention concern methods to assay for candidate substances capable of stimulating SRE-1-mediated gene transcription even in the presence of sterols. These assays may be employed as a first screen, or a second screen to further analyze the properties of candidate substances which tested positive in earlier DNA binding or cellular assays. The sterol-responsive cellular screening method involves culturing the host cell in the presence of sterols and then adding the candidate substance, wherein an increase in reporter gene expression is indicative of a substance capable of stimulating SRE-1-mediated transcription even in the presence of sterols. As a practical manner, it is generally preferred to first measure gene expression without sterols, then to add sterols and to measure the "sterol-suppressed expression" and then to add the candidate substance and to test for increased reporter gene expression relative to the sterol-suppressed expression levels.

Other assays contemplated by the inventors involve the co-introduction of SRE-1-mediated reporter genes along with SREBP encoding genes into host cells. These recombinant host contructs are then employed to screen for agents that will act to modulate expression of the reporter gene and/or SREBP gene. The use of the co-introduction approach is believed to have particular advantages in terms of sensitivity, allowing a response that is readily detectable by automated detection means, such as by FACS or related technology. Moreover, a co-introduction system allows ready manipultion for the identification of selective agents that act specifically, e.g., through modulation of SREBP levels and/or through modulation of its SRE-1-binding function.

It will, of course, be understood that all the screening methods of the present invention are useful in themselves notwithstanding the fact that effective candidates may not be found, since it would be a practical utility to know that SRE-1 positive stimulators and/or sterol antagonists do not exist. The invention consists of providing methods for screening for such candidates, not in finding them.

Probes, Plasmids and Further Compositions

In addition to purified native and recombinant proteins, DNA segments and screening assays, the present invention also encompasses various other elements. For example, in certain embodiments it provides polyclonal and monoclonal antibodies having binding affinity for SREBP; affinity columns containing such antibodies; and DNA affinity columns containing transcriptionally functional or transcriptionally non-functional SRE-1 sequences.

In still further embodiments, the invention concerns oligonucleotide probes and recombinant plasmids which include transcriptionally-functional or non-functional SRE-1 sequences, and recombinant host cells, such as monkey CV-1 cells, which include such plasmids. The probes and plasmids of this aspect of the invention will include a particular SRE-1-derived sequence in combination with a functional, i.e., wild type, Repeat 3 sequence (SEQ ID NO:23) from the LDL receptor gene. The probes and plasmids may also variously include multiple copies of the SRE-1 (Repeat 2, SEQ ID NO:22) and/or Repeat 3 sequences (SEQ ID NO:23).

Transcriptionally-functional SRE-1 sequences include the wild type sequences found within mammalian LDL receptor repeat 2 sequences (for example, SEQ ID NOS:1,20,21), and also mutant promoters which remain positive for sterol-regulated transcription. Both the functional and non-functional versions have utility as they act as positive and negative elements by which to identify SREBP. The most preferred plasmids and probes are those which contain two copies of Repeat 2+3 (SEQ ID NO:24) (with the transcriptionally-functional or non-functional sequences), although the whole range of constructions described herein will have utility.

The plasmids will generally further comprise a TATA box sequence positioned downstream from the repeat 2 (SRE-1) (SEQ ID NO:22) and repeat 3 (SEQ ID NO:23) sequences and a reporter gene, preferably a CAT gene, positioned downstream from said TATA box sequence. The probes will also likely include flanking sequences which may be present due to the molecular biological methods, such as PCR, employed for their preparation. The probes will also preferably incorporate a readily-detectable label, such as a radioactive label, for example, $^{32}$p The probes termed H, M and *, are particularly preferred for use in assays during SREBP purification.

ABBREVIATIONS bHLH-Zip=basic helix-loop-helix leucine zipper
bp=base pair
CAT=chloramphenicol acetyltransferase
DNA=deoxyribonucleic acid
DTT=dithiothreitol
HMG CoA=3-hydroxy-3-methylglutaryl coenzyme A
LDL=low density lipoprotein
NP-40=Nonidet P-40
PCR=polymerase chain reaction
SDS=sodium dodecyl sulfate
SDS/PAGE=SDS polyacrylamide gel electrophoresis
SRE-1=sterol regulatory element-1
SREBP=sterol regulatory element-1 binding protein
SREBP-1=sterol regulatory element-1 binding protein-1
SREBP-2=sterol regulatory element-1 binding protein-2.

BRIEF DESCRIPTION OF THE DRAWINGS

FIG. 1A. Plasmid constructs containing SRE-1 elements (Repeat 2+3) of LDL receptor promoter inserted into E1b TATA-CAT vector; boxed sequences [2] (SEQ ID NO:22) and [3] (SEQ ID NO:23) refer to human LDL receptor gene promoter sequences -68 to -53 (repeat 2) and -52 and -37 (repeat 3) relative to the major in vivo RNA initiation site (Smith et al., 1990). The boxed sequence [2] [3] is represented as SEQ ID NO:24. The mutant sequence [2*] [3] contains the 4-bp mutation shown in lower case letters and is designated as SEQ ID NO:25.

FIG. 1B. Plasmid constructs containing SRE-1 elements (Repeat 2+3) of LDL receptor promoter inserted into E1b TATA-CAT vector; a portion of the DNA sequence of E1b TATA-CAT vector showing the SalI insertion site for LDL receptor SRE-1 promoter elements. The sequence is designated SEQ ID NO:26. The single underline denotes the SalI site; the single overline denotes the PstI cloning site; the boxed sequence denotes the adenovirus E1b TATA sequence; and the double underline denotes the initiation codon of the CAT gene.

FIG. 2. Expression of CAT activity under control of LDL receptor promoter elements in transfected CV-1 cells. CV-1 cells were transiently transfected with the E1b TATA-CAT plasmid containing the indicated LDL receptor promoter element. After incubation for 48 hours in the absence or presence of 10 μg/ml cholesterol plus 1 μg/ml 25-hydroxycholesterol, the cells were harvested for measurement of CAT activity as described hereinbelow. The acetylated forms of [$^{14}$C]chloramphenicol (1-AcCM, 3-AcCM and 1,3-AcCM) were separated from unreacted [$^{14}$C]chloramphenicol (CM) by thin layer chromatography and detected by autoradiography. The autoradiograms were exposed for three days to allow visualization of the low expression of the LDL receptor (LDLR) construct. Plasmid J, the authentic HMG CoA synthase promoter (-550 to +35) fused to CAT, is included for comparative purposes.

FIG. 3A. Single point mutation analysis of Repeat 2 of LDL receptor promoter in transfected CV-l cells; schematic diagram of the data in Table II, which represents the mean ±S.E. of 3 to 9 independent transfection studies. The sequence in upper case letters is designated SEQ ID NO:1. The mutant sequences which each contain the sequence of SEQ ID NO:1 with the exception, in each case, of the single mutation indicated by the lower case letters are designated as SEQ ID NOS:2–19, respectively. The data represent the relative CAT expression observed when cells were cultured in the absence (open bar) or presence (closed bar) of sterols.

FIG. 3B. Single point mutation analysis of Repeat 2 of LDL receptor promoter in transfected CV-1 cells; a single study in which all 19 plasmid constructs were transfected, and the CAT activity of the transfected cells cultured in the absence (-) or presence (+) of sterols was assayed by thin layer chromatography. The chromatogram was exposed for 24 hours at room temperature. The SRE-1 (sequence SEQ ID NO:27) contained within Repeat 2 is boxed.

FIG. 4A particularly shows the schematic representation of the transfection data in Table II.

FIG. 6A. Superdex 200 chromatography of SREBP. The 40% ammonium sulfate fraction (Step 3) was subjected to gel filtration on a Superdex 200 26/60 column. Aliquots of each fraction were assayed for protein content by measurement of absorbance at 280 nm. The column was calibrated with Bio-Rad molecular weight markers containing thyroglobulin (670 kDa), aldolase (158 kDa), and ovalbumin (44 kDa). Arrows denote the positions of elution of the markers.

FIG. 6B. Superdex 200 chromatography of SREBP. An aliquot (2 µl) of every other fraction was assayed for SREBP activity by the standard gel shift assay using the three $^{32}$P-probes described in FIG. 5. Arrow denotes the $^{32}$P-probe containing SREBP bound to one site. The gel was exposed for 2 hours.

FIG. 7A. Purification of SREBP by DNA affinity chromatography; active fractions from the Superdex 200 column (Step 4) were pooled and applied to a DNA affinity column containing a mutant version of Repeat 2+wild-type Repeat 3 (Column A) (SEQ ID NOS:31,32) and eluted as described hereinbelow.

FIG. 7B. Purification of SREBP by DNA affinity chromatography; the flow-through from Column A was applied directly to Column B containing tandem copies of wild-type Repeat 2 (SEQ ID NOS:33,34) and eluted as described hereinbelow. Aliquots (2 µl) of the starting material, flow-through fraction, 0.3M KCl eluate, and 1M KCl eluate from both columns were assayed for SREBP activity by the standard gel shift assay using the three $^{32}$P-probes described in FIG. 5. The gels were exposed for 2 hours. Arrows denote the $^{32}$P-probes containing SREBP bound to one or two sites.

FIG. 15B, FIG. 15C, FIG. 15D, FIG. 15E, FIG. 15F. SREBP-1 Plasmid Constructs. The 5' and 3' regions of the nucleotide and deduced amino acid sequences of pCY5, pCY21, and pCY22 that differ from each other are shown. Numbers for the nucleotide residues (right) and amino acid residues (left) refer to the numbers for pSREBP-1a (see FIG. 16); i.e., refer to SEQ ID NO:37 and SEQ ID NO:38, respectively. An inframe nonsense codon in the 5' untranslated region of pCY5 is denoted by the single underline. Putative initiator methionines in pCY5 and pCY22 are denoted by double underlines. Putative polyadenylation signals in pCY21 and pCY22 are boxed. The nucleic acid and amino acid sequences of the 5' end of pCY22 are represented by SEQ ID NO:39 and SEQ ID NO:40, respectively; and the nucleic acid and amino acid sequences of the 3' end are represented by SEQ ID NO:41 and SEQ ID NO:42, respectively.

FIG. 16A, FIG. 16B, FIG. 16C, FIG. 16D, FIG. 16E, FIG. 16F, FIG. 16G, FIG. 16H, FIG. 16I, FIG. 16J, FIG. 16K, FIG. 16L. Nucleotide (SEQ ID NO:37) and Predicted Amino Acid Sequence (SEQ ID NO:38) of cDNA Encoding Human SREBP-1a.

Amino acid residues are numbered on the left and right. Amino acid residue 1 is the putative initiator methionine. Five tryptic peptides that were found in purified SREBP (Table IV) are underlined. The amino acid sequences of pCY5 and pCY21 diverge from pCY22 after residues 28 and 1043, respectively (see FIG. 15). The cDNA sequence of SREBP-1a is deposited in GenBank (Accession No. U00968). Both strands of the CDNA were sequenced.

Figure 17A:
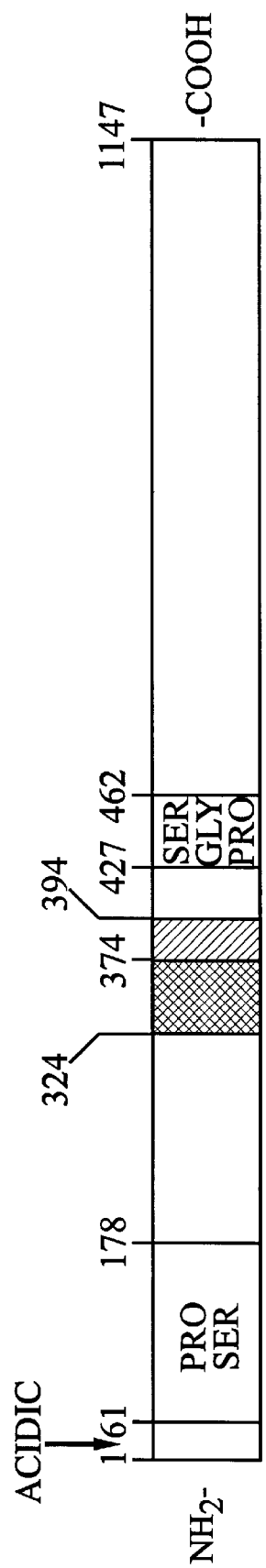

FIG. 17A. Domain Structure of SREBP-1a; schematic representation of SREBP-1a. A horizontal bar with numbers corresponding to the amino acid residues in FIG. 16. The helix-loop-helix region is denoted by the crosshatched box, the leucine zipper region by the single hatched box, and two serine/proline-rich regions by the open boxes. The NH$_2$-terminal acidic region is also indicated.

Figure 17B:
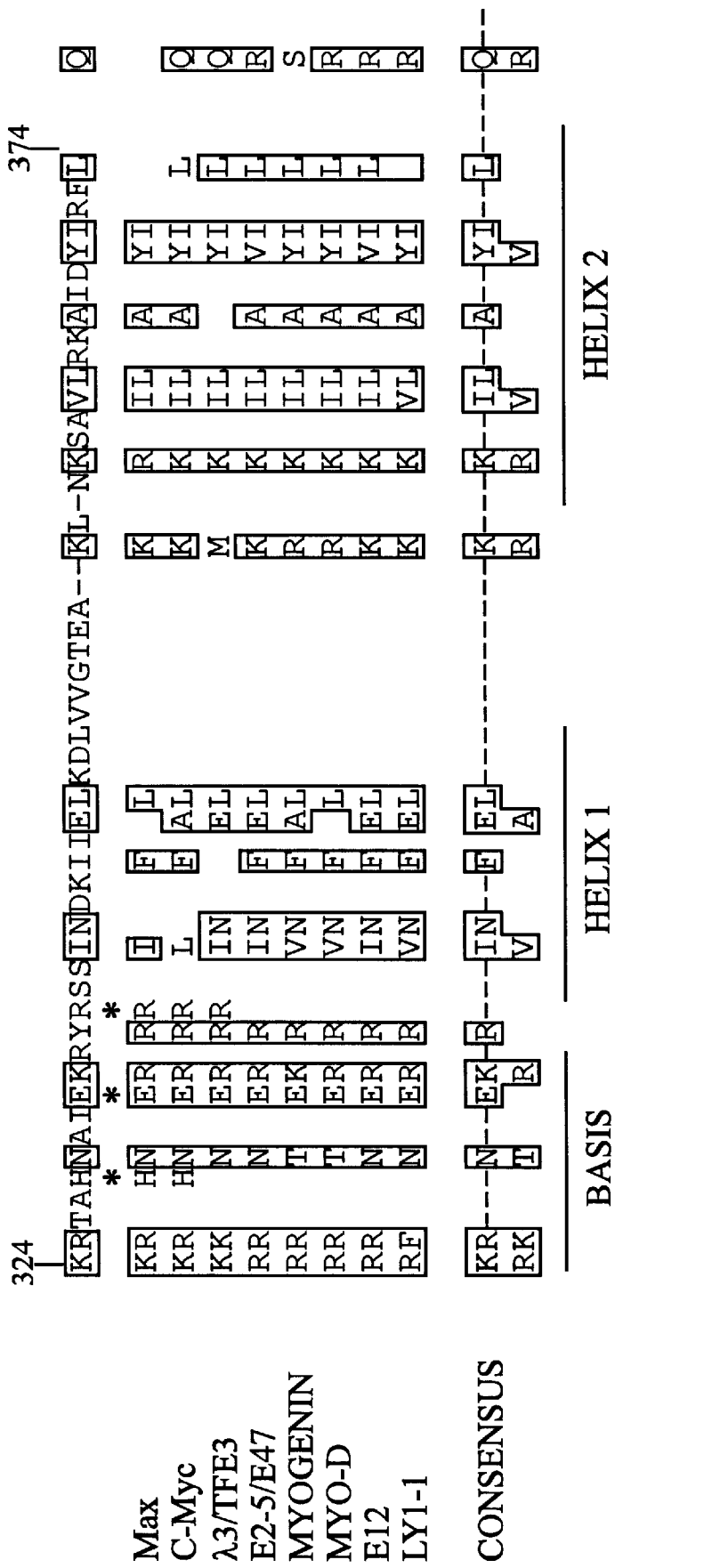

FIG. 17B. Domain Structure of SREBP-1a; the amino acid sequence of the helix-loop-helix region of SREBP-1a (residues 318 to 380 of SEQ ID NO:38) is compared to that of other helix-loop-helix family members (Beckmann et al., 1990; Prendergast et al., 1991) and residues identical to the consensus sequence are boxed. The boundaries of the basic, helix 1, and helix 2 regions are indicated below the consensus sequence. Asterisks (*) denote amino acids in Max that contact specific nucleotide bases in its DNA recognition sequence as determined by x-ray crystallography (Ferré-D'Amaré et al., 1993; see FIG. 24).

FIG. 17C. Domain Structure of SREBP-1a; the amino acid sequence of the putative leucine zipper region of SREBP-1a is shown (residues 359 to 401 of SEQ ID NO:38).

Figure 18A:
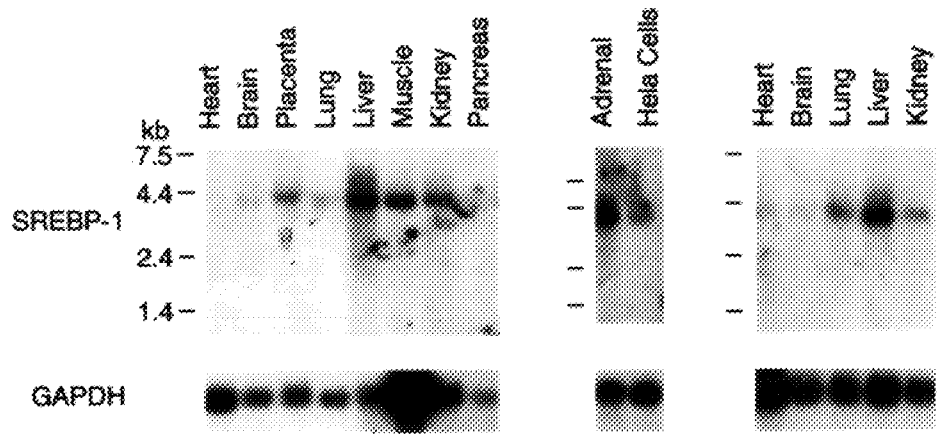

FIG. 18A. Expression of Human SREBP-1; tissue distribution of mRNA for SREBP-1. pSREBP-1c was hybridized to poly(A)$^+$ RNA from the indicated tissue (2 μg/lane in left and right panels and 2.5 μg/lane in middle panel) as described in Method 5 of Example 3. The filters were exposed to Kodak XAR-5 film with an intensifying screen at −70° C. for 16 hours. The same filters were subsequently hybridized with rat glyceraldehyde-3-phosphate dehydrogenase (GAPDH) and exposed to film for 4 hours. The samples in left and middle panels are from human adult tissues and those in right panel are from human fetal tissues.

Figure 18B:
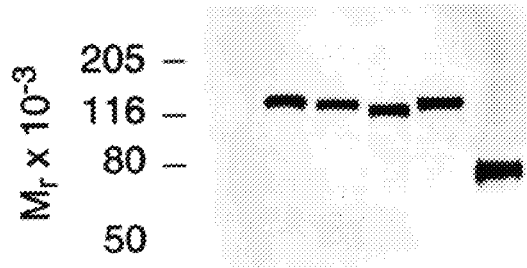

FIG. 18B. Expression of Human SREBP-1; immunoblot analysis of SREBP-1 overexpressed in transfected 293 cells. Samples (see below) were subjected to electrophoresis on a 7.5% SDS-polyacrylamide gel and transferred to nitrocellulose filters. The filters were incubated with 5 μg/ml rabbit anti-SREBP-1 IgG, followed by incubation with anti-rabbit IgG conjugated to horseradish peroxidase using the ECL Western kit. The filter was exposed to Kodak XAR-5 film for 10 seconds at room temperature. The position of migration of prestained molecular weight markers is indicated. Lanes 1–5 were loaded with 5 μg protein of total extract from 293 cells transfected with 3 μg of the following plasmids: lane 1, pCMV7; lanes 2 and 5, pSREBP-1a; lane 3, pSREBP-1b; lane 4, pSREBP-1c. Lane 6 was loaded with 0.1 μg of partially purified SREBP from HeLa cells as disclosed herein in step 6 of Example 2.

Figure 19:
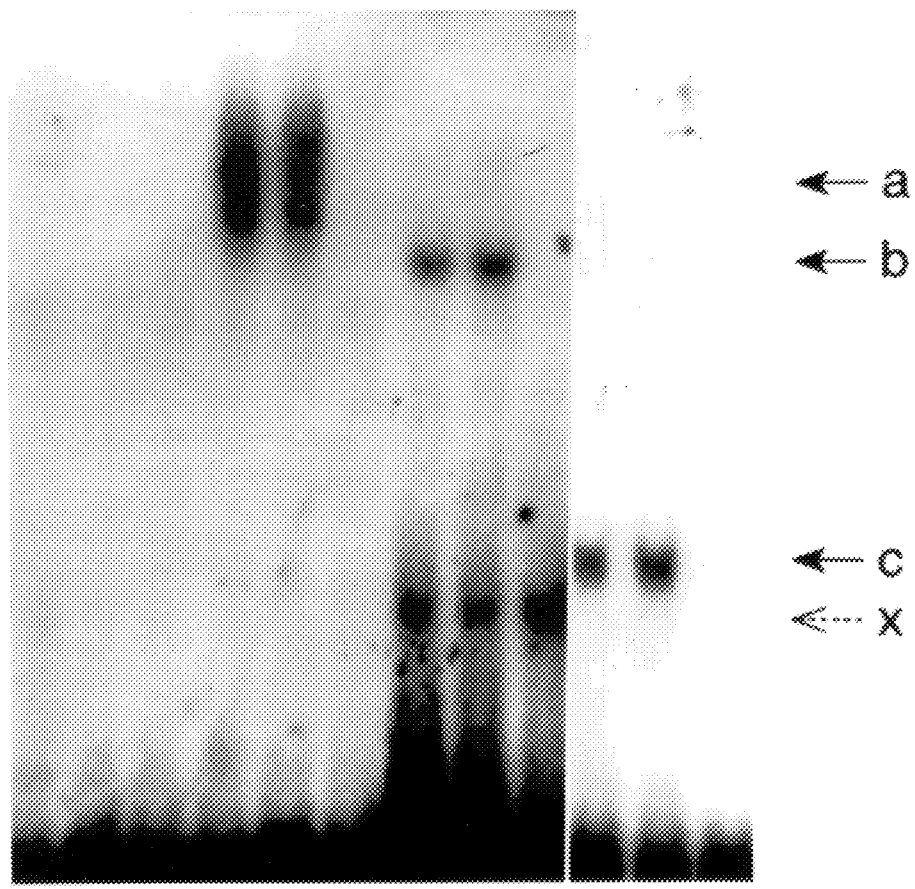

FIG. 19. Gel Mobility Shift Assays of In Vitro Translated SREBP-1c, DNA Affinity-Purified SREBP from HeLa Cells, and Recombinant bHLH-Zip Domain of SREBP-1.

Aliquots of the indicated proteins (see below) were incubated in the standard gel shift assay (final volume of 20 μl) for 20 minutes at room temperature with the indicated $^{32}$P-labeled, PCR-derived DNA probe (94 bp). Each probe (~4×10$^4$ cpm/reaction) contained two tandem copies of Repeats 2+3 with the following versions of Repeat 2: Probe H, wild-type human SRE-1; Probe M, wild-type mouse SRE-1, which differs by one bp (C→T) from the human sequence at position 10 in SRE-1 (see FIG. 21); and Probe *, mutant version of human SRE-1 containing a substitution of A for C at the same position, which abolishes transcriptional activity. The following proteins were used in the assays: lanes 1 to 3, 3 μl of in vitro transcription/translation mixture lacking plasmid pSREBP-1c; lanes 4 to 6, 3 μl of in vitro transcription/translation mixture with pSREBP-1c; lanes 7 to 9, 0.1 μg of partially purified SREBP from HeLa cells; lanes 10 to 12, 0.1 μg of purified recombinant bHLH-Zip domain of SREBP-1. Arrow a denotes SRE-1 bound to full length SREBP-1c; arrow b denotes SRE-1 bound to purified SREBP; arrow c denotes SRE-1 bound to the recombinant bHLH-Zip domain; arrow X denotes a contaminating protein that binds the mutant probe as well as the two wild-type probes. After electrophoresis, lanes 1 to 9 were exposed to Kodak XAR film for 6 hours at −80° C. with intensifying screen; lanes 10 to 12 were exposed for 2 hours with intensifying screen at −80° C.

Figure 20:
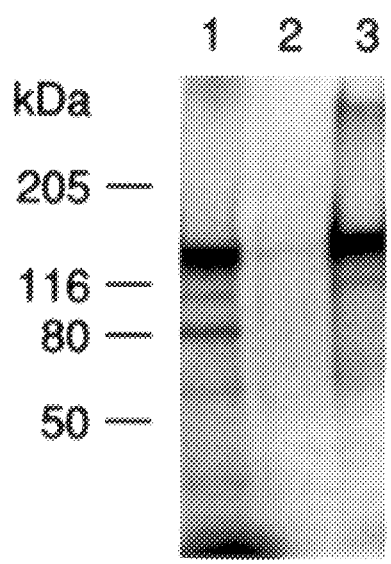

FIG. 20. SDS Polyacrylamide Gel Electrophoresis of In Vitro Translated $^{32}$S-Labeled SREBP-1c Purified by Binding to Biotinylated SRE-1.

Aliquots (10 μl) of in vitro translated $^{32}$S-labeled SREBP-1c (lanes 2 and 3) were incubated in a final volume of 100 μl containing 0.5 μg of a 5'-biotin-labeled SRE-1 oligonucleotide probe, the same concentration of components used in the standard gel mobility shift assay, and a 5'-fold excess of either unlabeled wild-type (lane 2) or mutant (lane 3) oligonucleotide competitor as described herein in Example 3, Materials and Methods. After incubation for 20 minutes at room temperature, 10 μl of Streptavidin-agarose (Gibco-BRL) equilibrated in Buffer A was added to each tube and rotated at 4° C. for 6 hours. The pellets were collected by centrifugation in a microcentrifuge and washed twice with 1 ml Buffer A containing 0.3M KCl and 0.1% (v/v) Nonidet P-40. Each pellet was then mixed with 30 μl of SDS sample buffer, boiled for 3 minutes, and spun in a microfuge for 2 minutes. The supernatant was loaded onto a 4–15% gradient gel. Lane 1, 1 μl of in vitro translated $^{32}$S-labeled SREBP-1c loaded directly onto the gel; lane 2, Streptavidin-agarose pellet from reaction that contained wild-type oligonucleotde competitor; lane 3, Streptavidin-agarose pellet from reaction that contained mutant oligonucleotide competitor. After electrophoresis, the gel was exposed to Kodak XAR film for 16 hours at −80° C. with intensifying screen.

Figure 21:
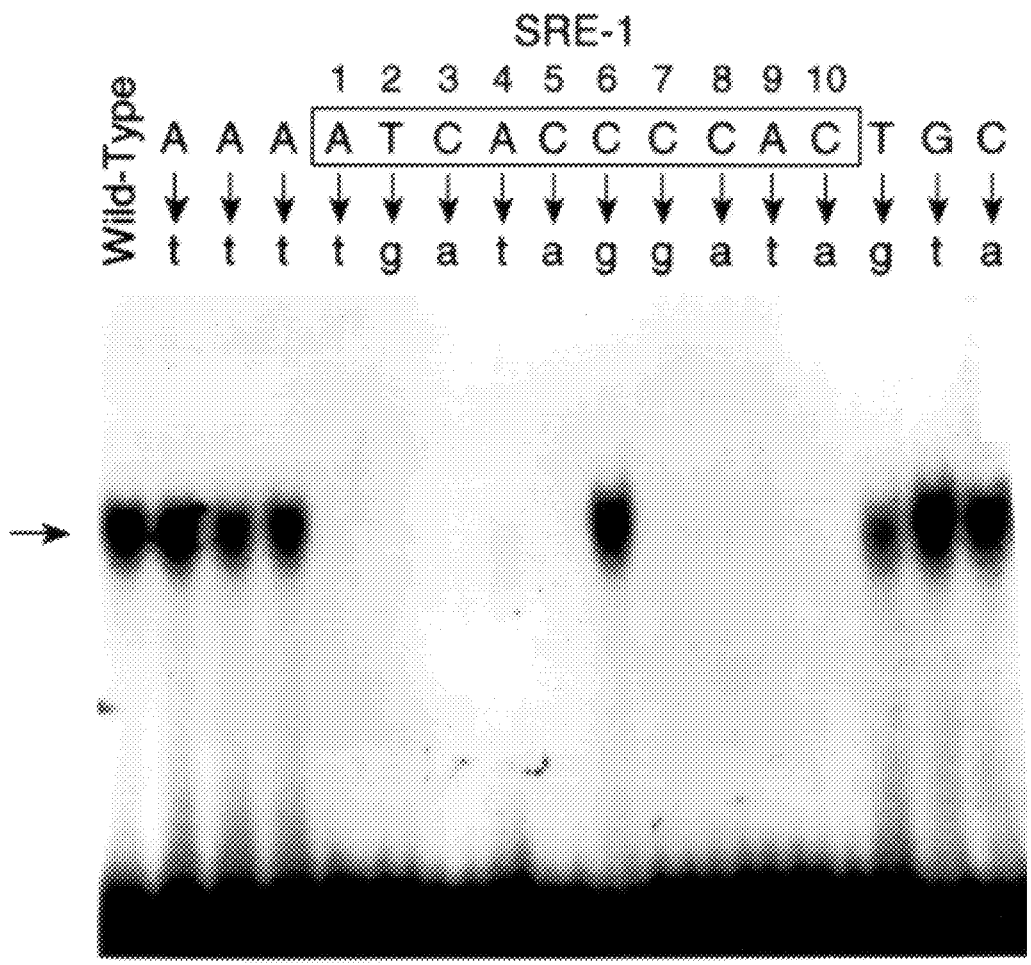

FIG. 21. Binding of Recombinant bHLH-Zip Domain of SREBP-1 to Wild-type and Mutant Forms of Repeat 2.

Aliquots of the purified recombinant bHLH-Zip domain of SREBP-1 (0.2 Ag) were incubated in the standard gel shift assay (final volume of 20 μl) for 20 minutes at room temperature with the indicated wild-type or mutant $^{32}$P-labeled, PCR-derived DNA probe (45 bp). Each $^{32}$P-probe (4×10$^4$ cpm/reaction) contained one copy of Repeat 2+3 with the indicated point mutation in Repeat 2. After electrophoresis, the gel was exposed to Kodak XAR film for 2 hours at −80° C. with an intensifying screen. The SRE-1 sequence contained within Repeat 2 is boxed.

Figure 22A:
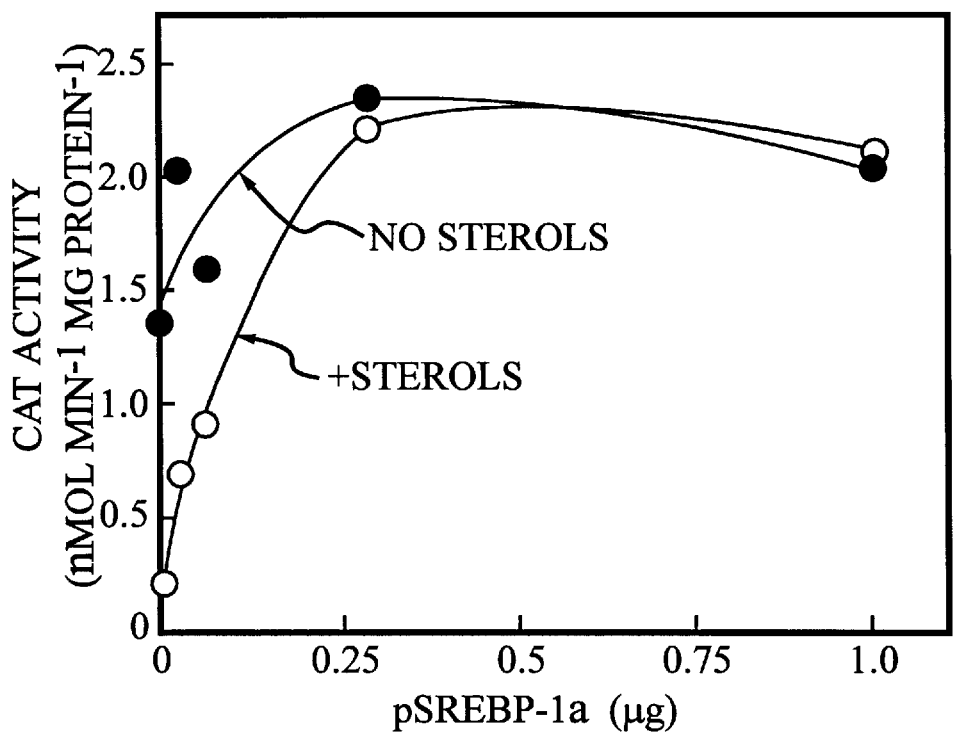

FIG. 22A. Effect of SREBP-1a on Expression of CAT Activity Under Control of Synthetic LDL Receptor Promoter Elements in Transfected Simian CV-1 Cells. Cells were transiently cotransfected with a synthetic LDL receptor promoter-CAT gene driven by two tandem copies of Repeats 2+3 (Plasmid K, 10 μg) and the indicated amounts of pSREBP-1a as described herein in Example 3. After incubation for 48 hours in the absence (•) or presence (O) of 10 μg/ml cholesterol plus 1 μg/ml 25-hydroxycholesterol, triplicate dishes of cells were harvested for measurement of CAT activity.

Figure 22B:
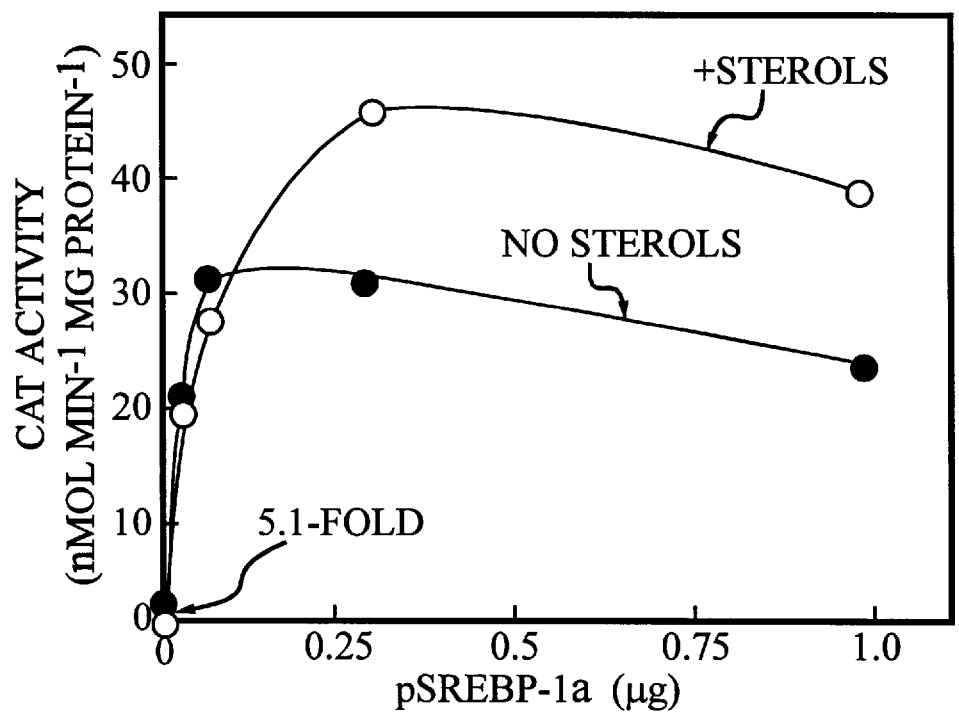

FIG. 22B. Effect of SREBP-1a on Expression of CAT Activity Under Control of Synthetic LDL Receptor Promoter Elements in Transfected Human 293 Cells. Cells were transiently cotransfected with a synthetic LDL receptor promoter-CAT gene driven by two tandem copies of Repeats 2+3 (Plasmid K, 1 μg) and the indicated amounts of pSREBP-1a as described herein in Example 3. After incubation for 40 hours in the absence (•) or presence (O) of 10 μg/ml cholesterol plus 1 μg/ml 25-hydroxycholesterol, triplicate dishes of cells were harvested for measurement of CAT activity. The -fold value refers to the difference in CAT activity in cells incubated with or without sterols in the absence of pSREBP-1a.

Figure 23A:
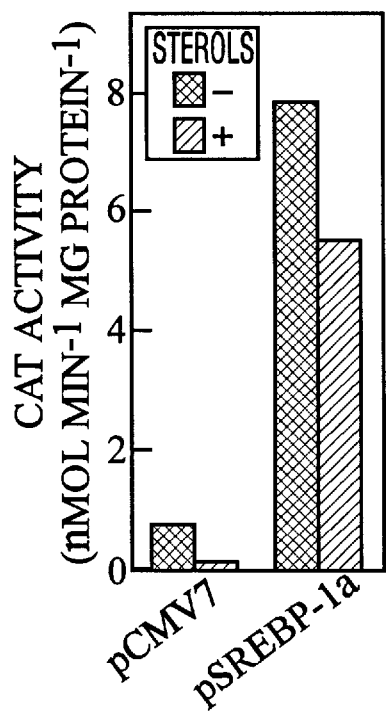

FIG. 23A. Effect of SREBP-1a on Expression of CAT Activity Under Control of Synthetic Promoter Elements Containing Wild-type and Mutant SRE-1 Sequences in Transfected 293 Cells. 293 cells were transiently cotransfected with 0.2 μg of either pCMV or pSREBP-1a as indicated and 1 μg of a reporter CAT gene driven by the synthetic wild-type SRE-1 sequence containing two tandem copies of Repeats 2+3 (Plasmid K). After incubation for 40 hours in the absence (crosshatched bars) or presence (single hatch bars) of 10 μg/ml cholesterol plus 1 μg/ml 25-hydroxycholesterol, triplicate dishes of cells were harvested for measurement of CAT activity. The data are from two separate transfection studies.

Figure 23B:
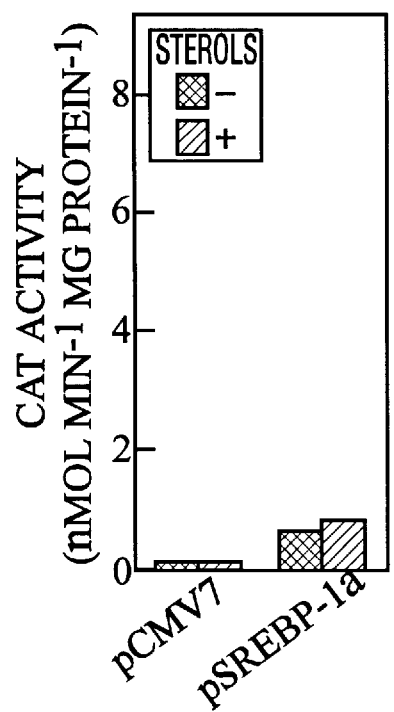

FIG. 23B. Effect of SREBP-1a on Expression of CAT Activity Under Control of Synthetic Promoter Elements Containing Wild-type and Mutant SRE-1 Sequences in Transfected 293 Cells. 293 cells were transiently cotransfected with 0.2 μg of either pCMV or pSREBP-1a as indicated and 1 μg of a reporter CAT gene driven by the mutant SRE-1 sequence containing two tandem copies of Repeats 2+3 with point mutation in Repeat 2 (Plasmid Q). After incubation for 40 h in the absence (crosshatched bars) or presence (single hatch bars) of 10 μg/ml cholesterol plus 1 μg/ml 25-hydroxycholesterol, triplicate dishes of cells were harvested for measurement of CAT activity. The data are from two separate transfection studies.

Figure 23C:
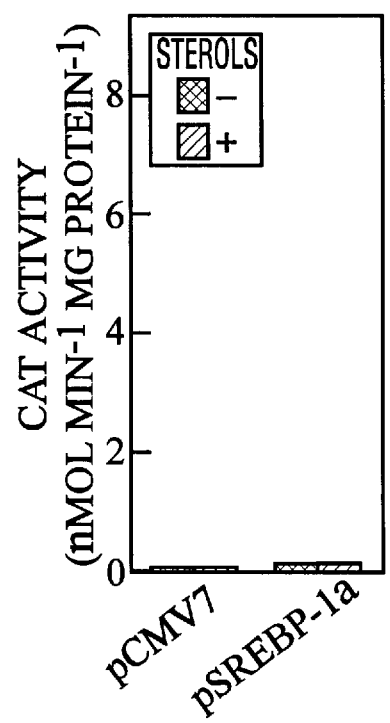

FIG. 23C. Effect of SREBP-1a on Expression of CAT Activity Under Control of Synthetic Promoter Elements Containing Wild-type and Mutant SRE-1 Sequences in Transfected 293 Cells. 293 cells were transiently cotransfected with 0.2 μg of either pCMV or pSREBP-1a as indicated and 1 μg of a reporter CAT gene driven by the mutant SRE-1 sequence containing two tandem copies of Repeat 2+3 with point mutation in Repeat 2 (Plasmid X). After incubation for 40 hours in the absence (crosshatched bars) or presence (single hatched bars) of 10 μg/ml cholesterol plus 1 μg/ml 25-hydroxycholesterol, triplicate dishes of cells were harvested for measurement of CAT activity. The data are from two separate transfection studies.

Figure 23D:
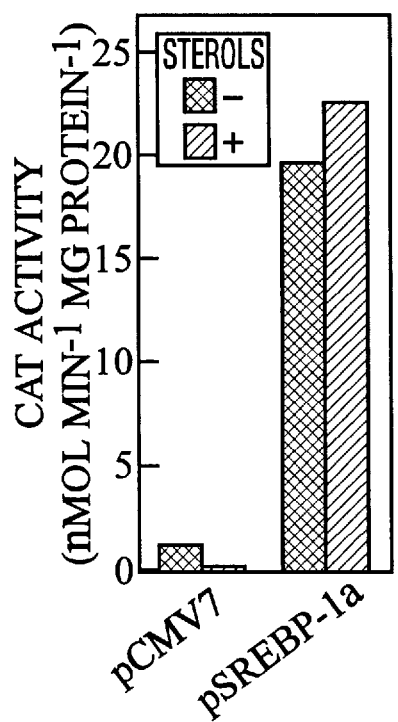

FIG. 23D. Effect of SREBP-1a on Expression of CAT Activity Under Control of Synthetic Promoter Elements Containing Native Promoter Elements from Three Sterol-Regulated Genes in Transfected 293 Cells. 293 cells were transiently cotransfected with 0.2 μg of either pCMV or pSREBP-1a as indicated and 1 μg of a reporter CAT gene driven by the the synthetic wild-type SRE-1 sequence containing two tandem copies of Repeats 2+3 (Plasmid K). After incubation for 40 hours in the absence (crosshatched bars) or presence (single hatched bars) of 10 μg/ml cholesterol plus 1 μg/ml 25-hydroxycholesterol, triplicate dishes of cells were harvested for measurement of CAT activity. The data are from two separate transfection studies.

Figure 23E:
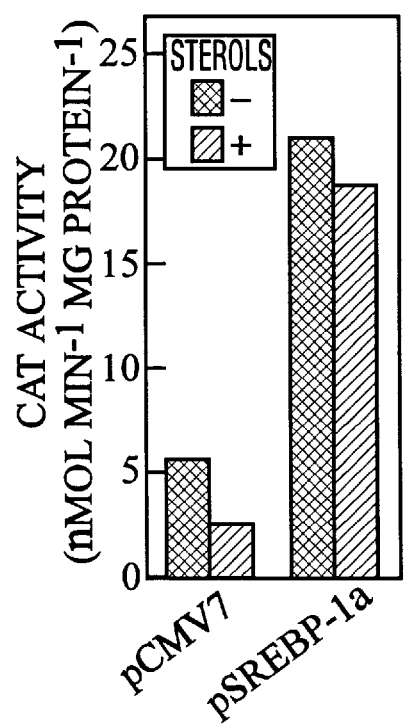

FIG. 23E. Effect of SREBP-1a on Expression of CAT Activity Under Control of Synthetic Promoter Elements Containing Native Promoter Elements from Three Sterol-Regulated Genes in Transfected 293 Cells. 293 cells were transiently cotransfected with 0.2 μg of either pCMV or pSREBP-1a as indicated and 1 μg of a reporter CAT gene driven by the native HMG CoA synthase promoter, nucleotides −527 to +39 (Plasmid J). After incubation for 40 h in the absence (crosshatched bars) or presence (single hatched bars) of 10 μg/ml cholesterol plus 1 μg/ml 25-hydroxycholesterol, triplicate dishes of cells were harvested for measurement of CAT activity. The data are from two separate transfection studies.

Figure 23F:
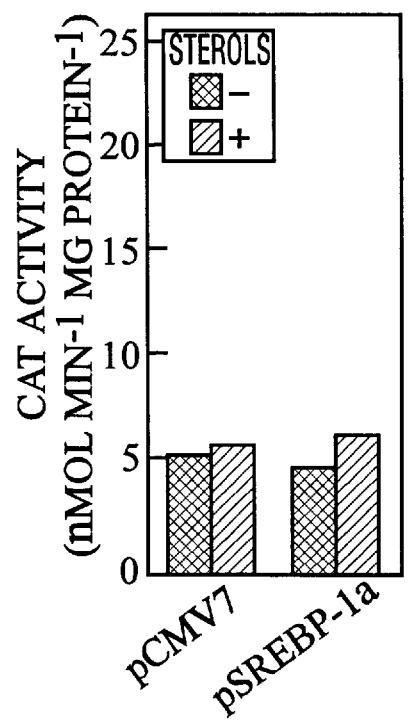

FIG. 23F. Effect of SREBP-1a on Expression of CAT Activity Under Control of Synthetic Promoter Elements Containing Native Promoter Elements from Three Sterol-Regulated Genes in Transfected 293 Cells. 293 cells were transiently cotransfected with 0.2 μg of either pCMV or pSREBP-1a as indicated and 1 μg of a reporter CAT gene driven by the native HMG CoA reductase promter, nucleotides −277 to +231 (pRedCAT-1). After incubation for 40 hours in the absence (crosshatched bars) or presence (stripped bars) of 10 μg/ml cholesterol plus 1 μg/ml 25-hydroxycholesterol, triplicate dishes of cells were harvested for measurement of CAT activity. The data are from two separate transfection studies.

Figure 23G:
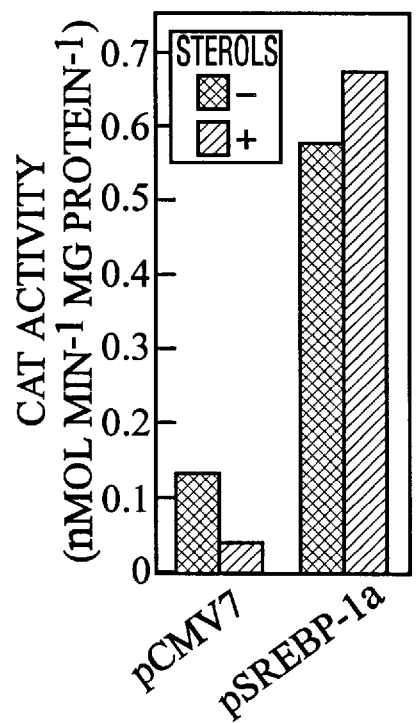

FIG. 23G. Effect of SREBP-1a on Expression of CAT Activity Under. Control of Synthetic Promoter Elements Containing Native Promoter Elements from Three Sterol-Regulated Genes in Transfected 293 Cells. 293 cells were transiently cotransfected with 0.2 μg of either pCMV or pSREBP-1a as indicated and 1 μg of a reporter CAT gene driven by the native LDL receptor promter, nucleotides −1471 to +36 (p1471). After incubation for 40 hours in the absence (crosshatched bars) or presence (single hatched bars) of 10 μg/ml cholesterol plus 1 μg/ml 25-hydroxycholesterol, triplicate dishes of cells were harvested for measurement of CAT activity. The data are from two separate transfection studies.

Figure 24A:
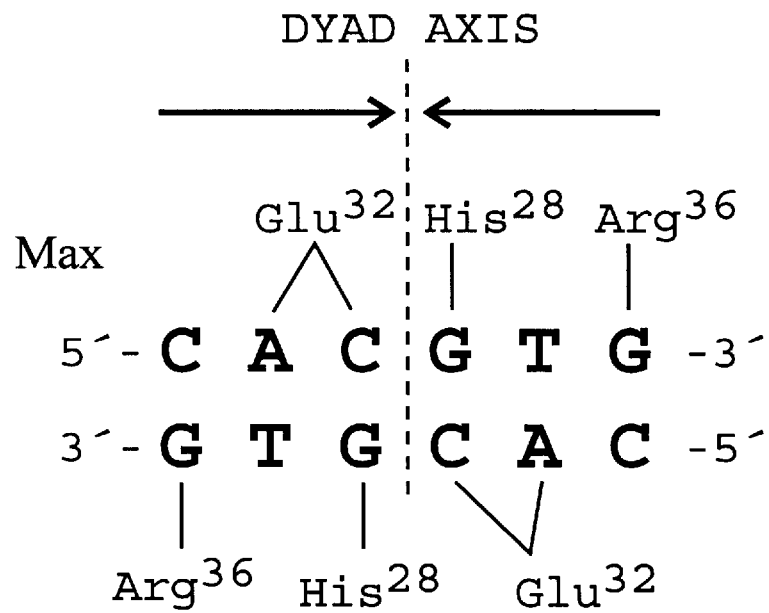
Figure 24B:
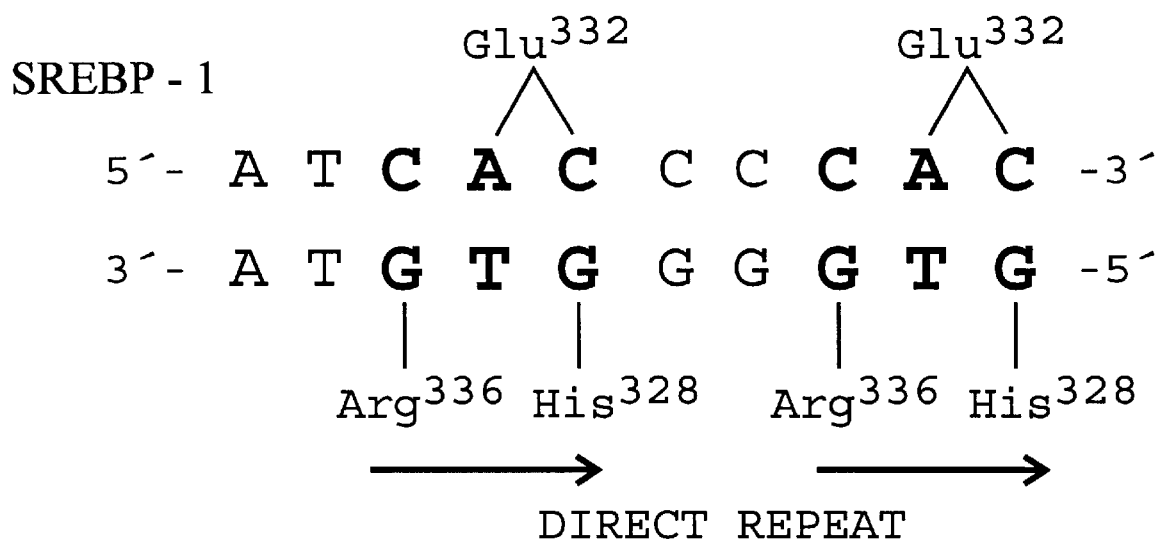

FIG. 24, Top Panel. Schematic Diagram of Contacts Between Amino Acids of bHLH-Zip Proteins and Nucleotide Bases of Their Target DNA; contacts between Max homodimer and its palindromic recognition sequence as determined by x-ray crystallography (Ferré-D'Amaré et al., 1993).

FIG. 24, Bottom Panel. Schematic Diagram of Contacts Between Amino Acids of bHLH-Zip Proteins and Nucleotide Bases of Their Target DNA; possible contacts between analogous amino acids of SREBP-1 and its direct repeat recognition sequence. The top sequence in the bottom panel is SEQ ID NO:27, and the bottom sequence is SEQ ID NO:43.

FIG. 25Ai and FIG. 25Aii. Comparison of the amino acid sequences and domain structures of human SREBP-2 (SEQ ID NO:54) and SREBP-1a (SEQ ID NO:3), in which the dashed line denotes residues in SREBP-1a that are identical to SREBP-2. The overline denotes the bHLH-Zip region.

FIG. 25B, Comparison of the bHLH region of SREBP-2 (amino acid residues 331–381 of SEQ ID NO:54 and 1a (amino acid residues 324–374 of SEQ ID NO:38) with the consensus sequence of other bHLH proteins (Ferre-D'Amare et al., 1993). Asterisks (*) denote amino acids in Max that contact specific nucleotides in its recognition sequence as determined by X-ray crystallography (Ferre-D'Amare et al., 1993).

Figure 25C:
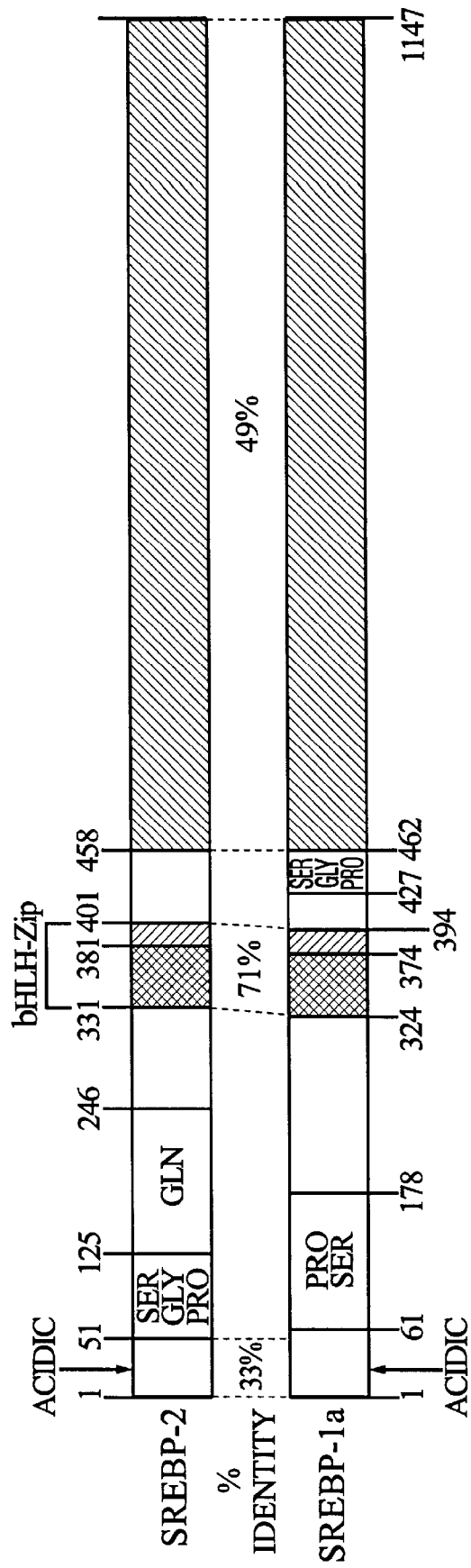

FIG. 25C, Domain structure of SREBP-2 and 1a with number corresponding to the amino acid residues. The basic-helix-loop-helix region is denoted by the crosshatched box, the leucine zipper region by the right hatched box, and the COOH-terminal domain by the left hatched box. Regions rich in particular amino acids are indicated. The % identities in the three most homologous regions are indicated. The full-length nucleotide sequences of pSREBP-1a and 2 are deposited in GenBank (U00968 and U02031, respectively).

Figure 26A:
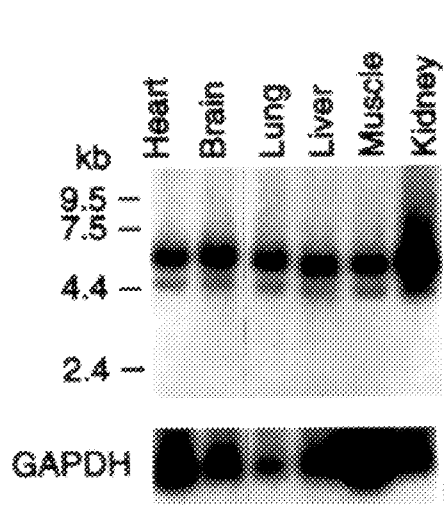

FIG. 26A. Tissue distribution of mRNA Human SREBP-2. $^{32}$P-Labeled oligonucleotide probes were hybridized to poly(A)$^+$ RNA from the indicated human tissue as described in Example 4 (2 μg/lane in left and right panels and 2.5 μg/lane in middle panel). The filters were exposed to Kodak XAR-5 film with an intensifying screen at −70° C. for 16 hours. The same filters were subsequently hybridized with a rat glyceraldehyde-3-phosphate dehydrogenase (GAPDH) probe and exposed for 2 hours. The samples in the left and middle panels are from adult tissues and those in the right panel are from fetal tissues.

Figure 26B:
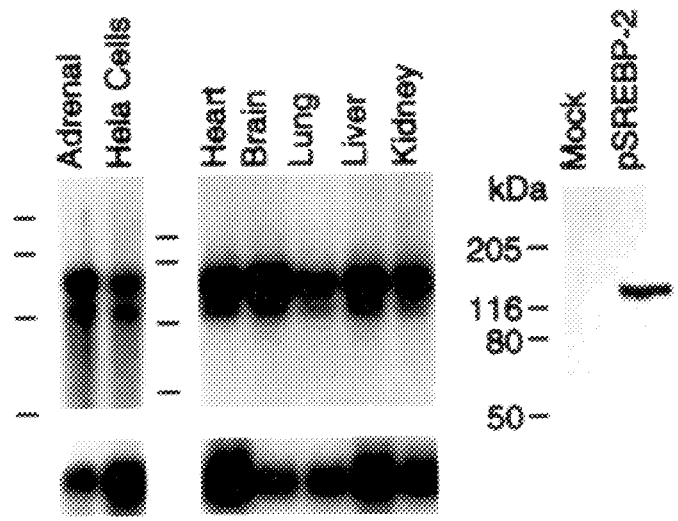

FIG. 26B. Immunoblot analysis in transfected 293 cells. A cDNA encoding human SREBP-2 driven by the CMV promoter was introduced into 293 cells by transfection. After 40 hours in medium containing no sterols, cell extracts were subjected to electrophoresis on a 7.5% SDS-polyacrylamide gel, transferred to nitrocellulose filters, and incubated with 5 μg/ml rabbit anti-SREBP-2 IgG, followed by anti-rabbit IgG conjugated to horseradish peroxidase (ECL Western Kit). The filter was exposed to Kodak XAR-5 film for 5 sec at room temperature. The positions of molecular weight markers are indicated. Left lane, 10 μg protein from cells transfected with 3 μg pCMV7 (control). Right lane, 5 μg protein from cells transfected with 3 μg pSREBP-2.

Figure 27:
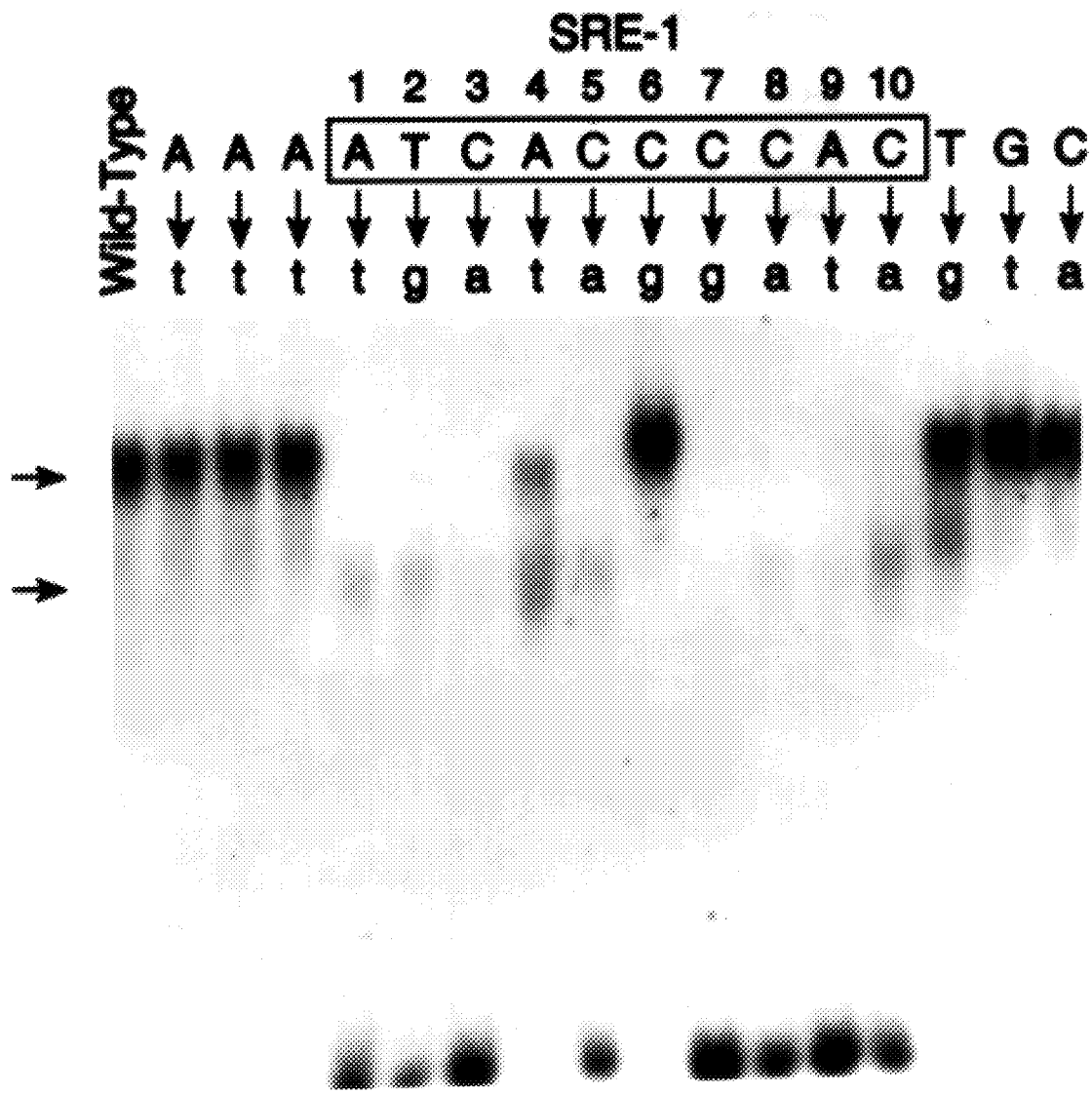

FIG. 27. DNA binding activity of recombinant bHLH-Zip domain (nucleotides 1–16 of SEQ ID NO:1) of SREBP-2. Aliquots (2 μg) of the purified recombinant bHLH-ZIP domain of SREBP-2 were incubated in a gel shift mobility assay (see Example 4) for 20 minutes at room temperature with the indicated wild-type or mutant $^{32}$P-labeled, PCR-derived DNA probe (94 bp). Each $^{32}$P-probe (4×10$^4$ cpm/reaction) contained two copies of Repeat 2+3 with the indicated point mutation in each copy of Repeat 2 (Wang et al., 1993). After electrophoresis, the gel was exposed to Kodak XAR film for 1 hour at −80° C. with an intensifying screen. The SRE-1 sequence within Repeat 2 is boxed. Lower and upper arrows denote protein bound to one or two copies of SRE-1 in the probe, respectively (Wang et al., 1993).

Figure 28A:
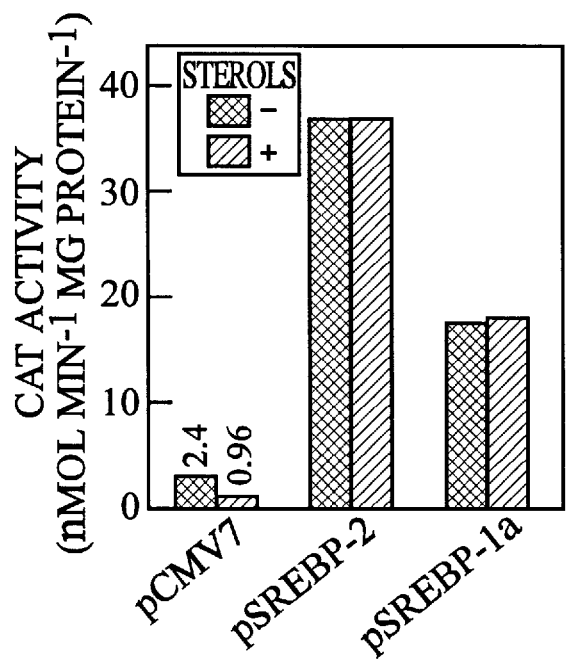

FIG. 28A. Effect of SREBP-2 and 1a on transcription using CAT reporter assays in transfected 293 cells. Cells were cotransfected with 0.3 μg of the indicated plasmid and 1 μg of a reporter CAT gene driven by a synthetic sequence containing two tandem copies of Repeats 2+3 with wild-type SRE-1 (Plasmid K). After incubation for 40 hours in the absence (crosshatched bars) or presence (stipped bars) of 10 μg/ml cholesterol plus 1 μg/ml 25-hydroxycholesterol, triplicate dishes of cells were harvested for measurement of CAT activity. The absolute values for the control pCMV7-transfected cells in FIG. 28A through 28D are shown above the bars. The data in all Figures are from the same transfection study.

Figure 28B:
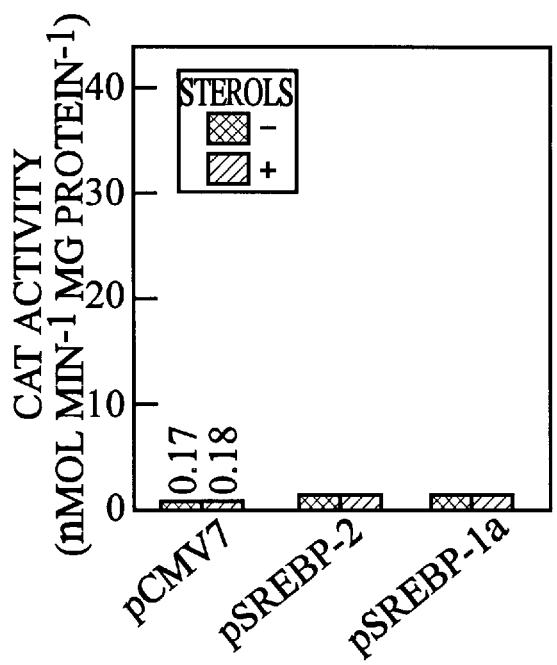

FIG. 28B. Effect of SREBP-2 and 1a on transcription in which the CAT gene was driven by a mutant sequence containing two tandem copies of Repeat 2+3 with point mutation in each SRE-1 (Plasmid X).

Figure 28C:
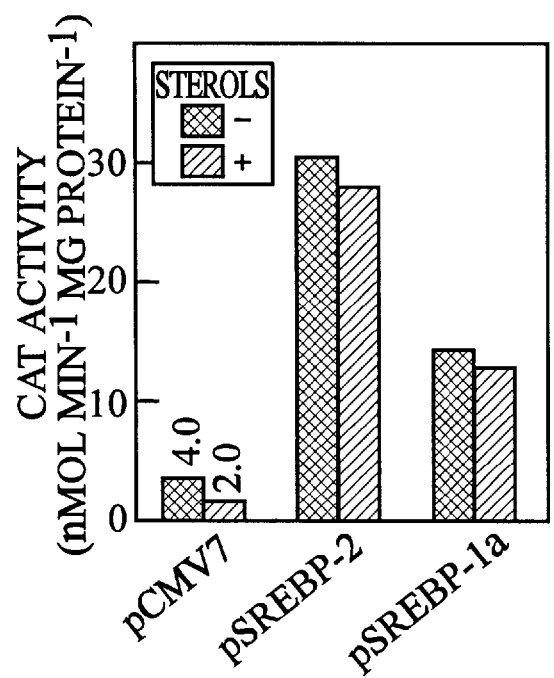

FIG. 28C. Effect of SREBP-2 and 1a on transcription in which the CAT gene was driven by native HMG CoA synthase, nucleotides −527 to +39 (Plasmid J).

Figure 28D:
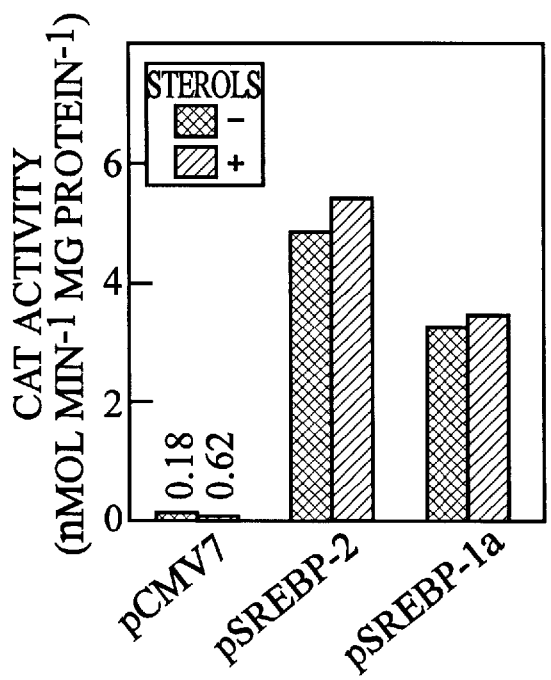

FIG. 28D. Effect of SREBP-2 and 1a on transcription in which the CAT gene was driven by native LDL receptor, −1471 to +36 (p1471).

Figure 28E:
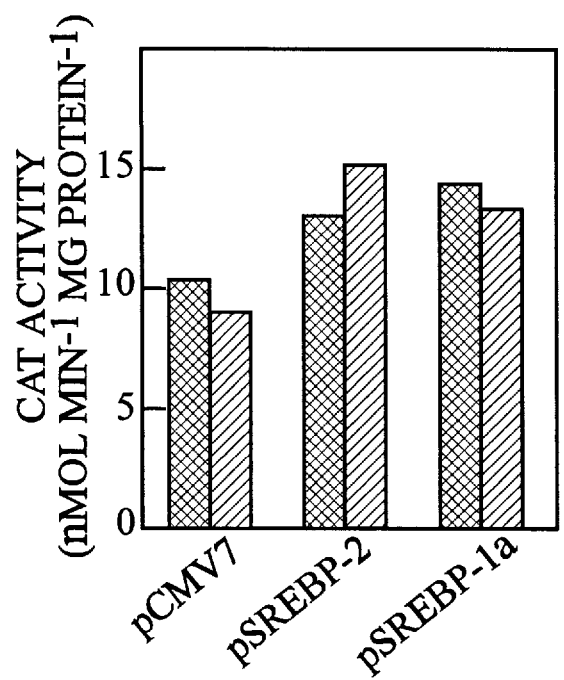

FIG. 28E. Effect of SREBP-2 and 1a on transcription in which the CAT gene was driven by native HMG CoA reductase, −277 to +231 (pRedCAT-1).

Figure 29A:
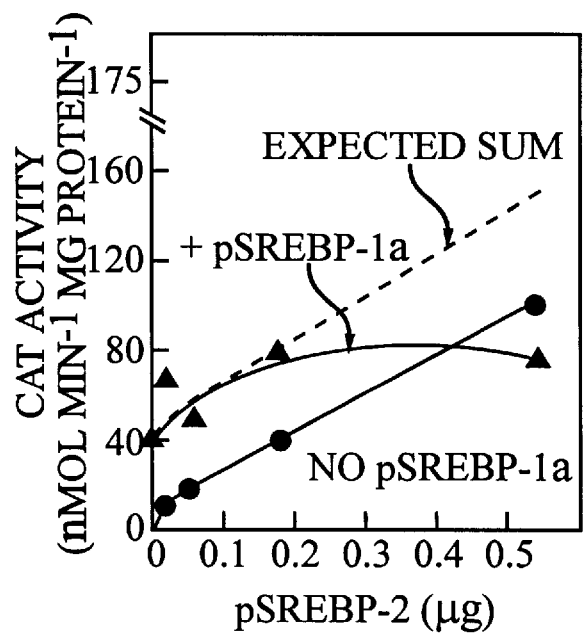

FIG. 29A. Additivity of pSREBP-2 and 1a on transcription of LDL receptor promoter-CAT reporter gene in transfected 293 cells in the absence of cholesterol and 25-hydroxycholesterol. Cells were cotransfected with the indicated amount of pSREBP-2 in the absence (•) or presence (Δ) of 0.02 gg pSREBP-1a and 1 μg of a reporter CAT gene containing tow tandem copies of Repeats 2+3 (Plasmid K). After incubation for 40 hours in the absence of 10 μg/ml cholesterol plus 1 μg/ml 25-hydroxycholesterol, duplicate dishes of cells were harvested for measurement of CAT activity. Assays were carried out under conditions (0.25 μg extract protein; 12 min at 37° C.) in which less than 20% of the [$^{14}$C]chloramphenicol had been converted to butyrylated products. A blank value from cells cotransfected with the reporter CAT gene and pCMV (vector control) was subtracted from each value (9.7 nmol·min$^{-1}$·mg protein$^{-1}$). The dotted line denotes the expected sum of CAT activity generated by pSREBP-2 plus pSREBP-1a.

FIG. 29A. Additivity of pSREBP-2 and 1a on transcription of LDL receptor promoter-CAT reporter gene in transfected 293 cells in the presence of cholesterol and 25-hydroxycholesterol. Cells were cotransfected with the indicated amount of pSREBP-2 in the absence (•) or presence (Δ) of 0.02 μg pSREBP-1a and 1 μg of a reporter CAT gene containing tow tandem copies of Repeats 2+3 (Plasmid K). After incubation for 40 hours in the presence of 10 μg/ml cholesterol plus 1 μg/ml 25-hydroxycholesterol, duplicate dishes of cells were harvested for measurement of CAT activity. Assays were carried out under conditions (0.25 μg extract protein; 12 min at 37° C.) in which less than 20% of the [$^{14}$C]chloramphenicol had been converted to butyrylated products. A blank value from cells cotransfected with the reporter CAT gene and pCMV (vector control) was subtracted from each value (2.6 nmol·min$^{-1}$·mg protein$^{-1}$). The dotted line denotes the expected sum of CAT activity generated by pSREBP-2 plus pSREBP-1a.

DETAILED DESCRIPTION OF THE PREFERRED EMBODIMENTS

A. Genetic Control Systems

In the 32 years since Jacob and Monod first proposed the lac operon model and the concept of messenger RNA (Jacob et al., 1961), the structure and function of a number of prokaryotic operons has been elucidated in elegant detail. For example, it has been shown that transcriptional control of structural genes in various operons reside in upstream (i.e., 5' with respect to the structural genes) regulatory regions. In the lac operon, a regulatory gene produces a protein repressor that interacts with an "operator" to prevent transcription initiation of the structural gene. Metabolic inducers bind to the repressor and thereby induce transcription by preventing the binding of the repressor to the operator. Additionally, there is a promoter site P, upstream of the operator and downstream of the regulatory gene, which serves as an RNA polymerase binding site.

Studies on the lac operon further have led to the discovery and elucidation of the mechanism of prokaryotic catabolic suppression. In E. coli it is found that the presence of glucose in the growth medium serves to prevent expression of gluconeogenic pathways, including the lac operon and its associated structural genes.

In contrast to prokaryotic systems, much less is presently known about control mechanisms, and particularly feedback suppression, in eukaryotic systems. Positively-regulated systems in which hormones, metabolic inducers, and developmental factors increase transcription of genes are somewhat better understood. In these systems, positive inducing agents are thought to activate or form complexes with proteins that stimulate transcription by binding to short sequences of 10 to 20 base pairs (bp) in the 5'-flanking region of the target gene. The sequences for the glucocorticoid, metal and interferon regulatory elements (GRE, MRE, and IRE, respectively) have been reported (Yamamoto, 1985; Stuart et al., 1984; Goodbourn et al., 1986).

More recently, other DNA segments which are capable of conferring control capability to known genes in eukaryotic systems have been identified, including the sterol regulatory element-1 (SRE-1) associated with the low density lipoprotein (LDL) receptor. Although this represents a significant advance, the protein factor which binds to SRE-1 and stimulates transcription has yet to be identified.

The identification of the SRE-1 binding protein would be an important step towards elucidating the mechanisms of eukaryotic gene control, and would also provide biomedical science with a powerful tool by which to regulate specific gene expression. Such a development would lead to numerous useful applications in the pharmaceutical and biotechnological industries. Although many applications are envisioned, one particularly useful application would be as the central component in screening assays to identify new classes of pharmacologically active substances which may be employed to manipulate, and particularly, to promote, the transcription of structural genes such as the LDL receptor gene.

An SRE-1 binding protein or transcription factor would thus be of great use in identifying agents to combat hypercholesterolemia. A cholesterol-lowering agent would act to promote the cellular production of LDL receptors, which would in turn serve to lower plasma LDL-cholesterol levels by increasing the cellular uptake of LDL.

B. Cholesterol Metabolism

Animal cells regulate their cholesterol content-through the integration of two pathways that govern the supply of exogenous and endogenous cholesterol. Both pathways are controlled by end-product repression. Cells may obtain cholesterol through the receptor-mediated endocytosis and lysosomal hydrolysis of plasma low density lipoprotein. Cells may also increase their endogenous cholesterol production by increasing the amount of two enzymes involved in de novo cholesterol biosynthesis, namely, 3-hydroxy-3-methylglutaryl coenzyme A (HMG CoA) synthase and HMG CoA reductase.

The LDL receptor gene is the structural gene which provides for the production of the LDL receptor protein, the receptor protein responsible for the facilitated uptake of cholesterol by mammalian cells. Upstream of the coding sequences for the LDL receptor gene is the SRE-1 sequence, which provides for sterol-mediated regulation of LDL receptor gene transcription. In the relative absence of sterols within the cell, transcription of the LDL receptor gene is promoted, whereas in the presence of cholesterol, transcription is suppressed. The transcription of HMG-CoA synthase and reductase of the cholesterol biosynthetic pathway is also reduced when sterols accumulate within the cell. When sterols are depleted, transcription increases and both the uptake and synthesis of cholesterol is promoted.

Currently, there are few cholesterol-lowering drugs that are both safe and efficacious, and no drugs which are known to operate at the genetic control level, as described above. For example, aside from agents that function by sequestering bile salts in the gut and thereby increase cholesterol excretion, the principal therapeutic agent available for cholesterol lowering is Lovastatin, a drug manufactured by Merck, Co. that acts indirectly to stimulate production of LDL receptors.

Lovastatin, and other drugs in this class (Simvastatin, Pravastatin), act by inhibiting the activity of HMG CoA reductase, the rate-limiting enzyme of endogenous cholesterol synthesis. These drugs contain side chains that resemble the native substrate for HMG CoA reductase and thus competitively inhibit the activity of the enzyme. Eventually this lowers the endogenous synthesis of cholesterol and, by normal homeostatic mechanisms, plasma cholesterol is taken up by increased LDL receptor populations in order to restore the intracellular cholesterol balance.

Conceptually, HMG CoA reductase inhibitors are acting at the penultimate stage of cellular mechanisms for cholesterol metabolism. It would be most desirable if the synthesis of LDL receptor could be directly up regulated at the gene level. The up regulation of LDL receptor synthesis at the gene level offers the promise of resetting the level of blood cholesterol at a lower and clinically more desirable level (Brown et al., 1984) However, no methods exist for conveniently assaying the ability of a candidate composition to exert such an effect on the transcription of the LDL receptor gene.

C. SRE-1 Sequences and Heterologous Gene Expression

The identification, preparation and use of SRE-1 sequences is described in detail herein (see, e.g., SEQ ID NOS:2–4, 10, 15–19), and more generally in U.S. patent applications Ser, Nos. 07/033,302 (U.S. Pat. No. 4,935,363), 07/425,852 (now U.S. Pat. No. 5,256,545), 07/532,318 (now U.S. Pat. No. 5,215,910), 07/033,081 (now U.S. Pat. No. 5,378,603), 07/032,134 (abandoned) and 07/032,130 (abandoned), each incorporated herein by reference. SRE-1 sequences may be employed as novel control units to direct sterol-mediated expression. Placing such sequences upstream of and sufficiently proximal to a transcription initiation site of a given gene will impart a sterol-regulated transcriptional control capability to the gene. LDL receptor gene repeat 2 and repeat 3 sequences may be advantageously used, and may be employed as multiple units, in numerous various combinations and organizations, in forward or reverse orientations, but preferably, would be located within from 0–20 nucleotides of each other.

SRE-1 control sequences may be employed to direct expression of heterologous structural genes. The precise location of the SRE-1 sequences is not particularly crucial and they may be located up to about 300 nucleotides or more from a transcription initiation site, with distances of 150, 100 and 50 nucleotides being preferred. In general, the closer the control sequences are to transcription initiation, the more pronounced and effective the control obtained.

To employ the sterol regulatory elements in the context of heterologous gene expression, one simply obtains the structural gene and attaches one or more of such control sequences upstream of a transcription initiation site. Additionally, as is known in the art, it is generally desirable to include TATA-box sequences upstream of and proximal to a transcription initiation site of the heterologous structural gene. Such sequences may be synthesized and inserted in the same manner as the novel control sequences. Alternatively, one may desire to simply employ the TATA sequences normally associated with the heterologous gene. In any event, TATA sequences are most desirably located between about 20 and 30 nucleotides upstream of transcription initiation.

Numerous methods are known in the art for precisely locating selected sequences at selected points within larger sequences. Most conveniently, the desired control sequence or sequences, or combinations of sequences, are synthesized and restriction site linker fragments added to the control sequence termini. This allows for ready insertion of control sequences into compatible restriction sites within upstream regions. Alternatively, synthesized control sequences may be ligated directly to selected regions. Moreover, site specific mutagenesis may be employed to fashion restriction sites into which control sequences may be inserted in the case where no convenient restriction sites are found at a desired insertion site.

D. SRE-1 Sequence Mutant Analyses

An important aspect of the present invention is the delineation of the essential nucleotides within the SRE-1 sequence and the identification of a family of nuclear proteins that bind to this newly-defined target nucleotide sequence.

In order to identify and purify the physiologically relevant SRE-1 binding proteins, the inventors designed and created a series of oligonucleotide probes with point mutations that either inactivated the SRE-1 or retained transcriptional activity. It was then possible to characterize the transcriptional activity of the mutant sequences in transient transfection assays. This is an advantage over previous studies of the LDL receptor promoter, using permanently transfected cell lines, which proved cumbersome for the analysis of multiple mutations (Smith et al., 1990; Sudhof et al., 1987; Dawson et al., 1988). As with other transcriptional regulatory systems (Klein-Hitpass et al., 1990; Pascal et al., 1991; Freedman et al., 1989), the activity of promoter elements in transient assays was increased by the creation of artificial promoters with multiple copies of the transcriptional element combined with novel TATA boxes.

The present inventors created an artificial sterol-dependent promoter by oligomerizing multiple copies of Repeat 2+3 in tandem and inserting them upstream of a TATA box derived from the adenovirus E1b gene (Lillie et al., 1989). The resulting vectors produced high levels of transcription in sterol-deprived cells after transient transfection. Transcription was repressed by sterols to a degree that is greater than observed with the native LDL receptor. This system allowed the inventors to define the precise nucleotides required for sterol-dependent regulation through point mutational analysis of Repeat 2. It was found that a segment of 10 nucleotides within the 16-bp Repeat 2 element is required for high level sterol-sensitive transcription activity and that mutation of any one of 9 nucleotides within this sequence markedly reduced the transcriptional activity of the SRE-1. The sole exception was the nucleotide at position 6 (the second C in the CCCC tetramer).

This information was used to design a series of oligonucleotides with point mutations that either permit or disrupt sterol-regulated transcription for use in specific gel shift assays. Using this system, a nuclear protein from HeLa cells or rat liver nuclei was identified that bound to the SRE-1 sequence in a fashion that was dependent on each of the 9 nucleotides that were required for transcription. Strikingly, the binding of this protein did not depend on a C nucleotide at the 6th position, which was also not necessary for transcriptional activity. In light of the precision of this correlation, the inventors propose that this protein, designated sterol regulatory element-1 binding protein (SREBP), is the protein required for sterol-sensitive transcription.

E. SRE-1 Binding Proteins, SREBPs

Another important aspect of the invention is the purification and characterization of a family of polypeptides with SRE binding activity. This proved particularly difficult as SREBPs are present in trace amounts and as several abundant nuclear proteins also bind to the SRE-1 sequence and obscure the binding of SREBPs. The inventors were required to identify the most discriminatory oligonucleotides, herein termed M and *, for use in the SREBP assay, and to overcome many obstacles during the initial preparation.

An SREBP composition was purified more than 38,000-fold from nuclear extracts of human HeLa cells by ion exchange, gel filtration, and DNA affinity chromatography. SDS polyacrylamide gel electrophoresis of the purified preparation revealed a cluster of bands at 59–68 kDa, which may represent multiple modifications of a single protein or several related proteins. Each of the 59–68 kDa polypeptides have the ability to bind to the SRE-1 element, as revealed by crosslinking studies, suggesting that all are able to bind specifically to SRE-containing DNA either independently or through formation of a protein complex. The later recombinant cloning of the SREBP proteins have indicated that these 59–68 kD species are in fact polypeptides derived from the full-length SREBPs, that include amino terminal SRE-1 binding domains (pHLH-Zip). Moreover, these polypeptide bands represent different, but apparently related, proteins falling broadly into various SREBP families, designated SREBP-1 and SREBP-2. These families share some sequence similarities and homologies, and members of each family appear to have the same or similar biological characteristics in terms of binding to SRE-1 and the reversal of sterol-mediated suppression of SRE-1-mediated genes.

Binding of SREBP proteins correlated perfectly with transcriptional activity in a series of 16 sterol regulatory elements with point mutations. In the LDL receptor promoter the 10-base pair SRE-1 (SEQ ID NO:27) is embedded in a 16-base pair sequence designated Repeat 2 (SEQ ID NO:22), which is adjacent to Repeat 3 (SEQ ID NO:23), a binding site for nuclear factor Sp1. Oligonucleotides containing Repeat 2+3 (SEQ ID NO:24) bound SREBP and Sp1 as revealed by mobility shift assays. SREBP produced a DNase I footprint over the SRE-1 sequence, which was immediately adjacent to the footprint produced by Sp1. The current data are consistent with the inventors' concept that SREBP acts in concert with Sp1 to achieve high level, sterol-suppressible transcription of the gene for the LDL receptor and that SREBPs mediate the final regulatory step that controls LDL receptor gene expression.

F. Cloning and Analysis of SREBP

Also disclosed herein is the cloning of a human CDNA which encodes an SREBP-1 (Example 3) and/or an SREBP-2 (Example 4). Cloning of SREBP-1 was achieved by using peptide sequence information derived from the 59–68 kDa polypeptides described above to design oligonucleotides for use in PCR and HeLa cell cDNA library screening. The SREBP protein whose cloning is set forth in Example 3, termed SREBP-1, contains a basic helix-loop-helix leucine zipper (bHLH-Zip) motif and is therefore a member of the bHLH-Zip family of transcription factors which includes the oncogenic protein, Myc, and its modulators Max, Mad, and Mxi1 (Ferré-D'Amaré et al., 1993; Zervos et al., 1993; Ayer et al., 1993).

Human SREBP-2 contains 1141 amino acids and shows 47% identity to human SREBP-1a, the first recognized member of this family. SREBP-1a contains 1147 amino acids. The resemblance includes an acidic $NH_2$-terminus, a highly conserved bHLH-Zip motif (71% identical), and an unusually long extension of 740 amino acids on the COOH-terminal side of the bHLH-Zip region. SREBP-2 possesses one feature lacking in SREBP-1a, namely, a glutamine-rich region (27% glutamine over 121 residues). In vitro SREBP-2 bound SRE-1 with the same specificity as SREBP-1a. In vivo it mimicked SREBP-1a in activating transcription of reporter genes containing SRE-1. As with SREBP-1a, activation by SREBP-2 occurred in the absence and presence of sterols, abolishing regulation. Cotransfection of low amounts of pSREBP-1a and pSREBP-2 into human 293 cells stimulates transcription of promoters containing SRE-1 in an additive fashion. At high levels transcription reaches a maximum, and the effects are no longer additive. The reason for the existence of two SREBPs and the mechanism by which they are regulated by sterols remains to be determined.

It is known that recombinant proteins may differ from their naturally-produced counterparts in certain ways. For example, the degree of post-translational modifications, such as glycosylation and phosphorylation, may be different between recombinant proteins and proteins obtained following purification from natural sources. In the case of SREBP-1a, cloning confirmed the inventors earlier proposal that SREBPs are composed of more than one functional domain. The cloned SREBP-1a is a protein of 1147 amino acids in length (corresponding to its approximate size on SDS gels of about 130 kDa). The functional 59–68 kDa SREBP polypeptides initially purified are therefore likely to be SRE-1 DNA binding domain polypeptides that have been separated by proteolytic cleavage. This separation into distinct domains that maintain their activity may be the result of a physiological process or the result of proteolysis during purification—in an manner similar to that reported by Gil et al. (1988a; 1988b).

Although in the bHLH-Zip family, SREBP-1a differs from other bHLH-Zip proteins as it is larger (1147 vs 160–536 amino acids) and has a distinct target sequence. Classic bHLH-Zip proteins form homodimers and heterodimers that recognize palindromic sequences containing the so-called E box (CANNTG). However, the SRE-1 target contains a direct repeat of CAC instead of an inverted repeat like the E box. Despite this, it is proposed that an SREBP-1 monomer can bind to a single CAC/GTG of its target in a fashion similar to that previously described for Max binding. The inventors also propose that SREBP-1 can form higher order multimers through nonsymmetrical interactions which will allow a second SREBP-1 monomer to bind and interact with the SRE-1 DNA.

SREBPs are also envisioned to be capable of forming multiprotein complexes with other distinct SREBP polypeptides, or even with other known, or as yet unidentified proteins, such as other bHLH-Zip proteins. For example, it is contemplated that SREBPs may interact with another one of the purified SREBP polypeptides of 59–68 kDa, particularly as the inventors have preliminary evidence that an SREBP peptide sequence not present in the cDNAs disclosed herein is derived from a separate protein of the bHLH-Zip family that copurifies with SREBP.

As shown in herein in Example 3, the overexpression of SREBP-1a in 293 cells activates transcription of reporter genes containing SRE-1 in the absence (15-fold) and presence (90-fold) of sterols, thus abolishing sterol regulation. The inventors propose that, in the natural cellular environment, SREBP-1 is normally regulated by an, as yet, unknown regulatory mechanism and that this normal mechanism is overwhelmed when SREBP-1 is overexpressed. Although very interesting scientifically, the mechanism by which SREBP-1 is normally regulated is not important to those aspects of the ivnention which concern the overexpression of SREBP-1 and the consequent stimulation of SRE-1-meduiated transcription which results from this. SREBP-2 shows a virtually identical pattern of regulation as does SREBP-1a.

The inventors propose that one possible explanation for the de-regulation observed on overexpression is that SREBP-1 or SREBP-2 (FIG. 28) may be controlled by homo- and hetero-oligomerization and that overexpression of an SREBP could force the formation of homo-oligomers which are constitutively active, as opposed to hetero-oligomers (e.g., with another bHLH-Zip protein) which are active only in the absence of sterols. Alternatively, the entry or retention of SREBP(s) in the nucleus may be regulated by a sterol-mediated process that becomes overwhelmed when SREBP is overexpressed. In this regard, regulated nuclear entry or retention may be a property of the long COOH-terminal half of SREBP, which does not have a counterpart in other bHLH-Zip proteins.

In any event, understanding the regulation of SREBPs is considered to be important for understanding the control of plasma cholesterol levels in normal and abnormal states. The cDNA for the SREBP family members provided by the present invention is, therefore, a long-sought-for tool for use in elucidating the signal transduction pathway by which cellular cholesterol derived from the receptor-mediated endocytosis of LDL regulates gene expression. In the meantime, the over-expression of SREBPs will continue to provide a means by which the transcription of genes under the control of sterol regulatory elements, such as the LDL receptor gene under the control of SRE, may be increased. Therefore, SREBPs are in themselves particularly useful proteins which have direct utility irrespective of further elucidating the regulatory mechanisms of which it may be part.

The gene sequences and SREBP proteins of the invention afford the opportunity, for the first time, to investigate the structure-function relationship of SREBPs. The inventors contemplate conducting various studies such as, e.g., treating SREBP with various agents, such as phosphatases, kinases and proteases, to determine how such agents affect its action. Expressing SREBP in cultured cells, such as CV-1 cells and 293 cells, is also now possible and will allow SREBP regulation to be investigated using full-length SREBP, truncated SREBP and various genetically engineered forms of SREBP. For example, the mutation of potential phosphorylation sites and/or the modification or deletion of certain SREBP domains is contemplated. The interaction of many components of intracellular cholesterol metabolism may also be determined using cellular systems in which SREBP(s) is expressed.

G. Biological Functional Equivalents and Epitopic Core Regions

As is known in the art, modification and changes may be made in the structure of proteins such as SREBPs and still obtain molecules having like or otherwise desirable characteristics. For example, certain amino acids may be substituted for other amino acids in a protein structure without appreciable loss of interactive binding capacity with structures such as, for example, antibodies, receptors and substrates. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even counterveiling properties (e.g., antagonistic v. agonistic). It is thus contemplated by the inventors that various changes may be made in the sequence of SREBP proteins or peptides (or underlying DNA) without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristsics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); praline (−1.6); histidine (−3.2); glutamate (−3.5); glutamine (−3.5); aspartate (−3.5); asparagine (−3.5); lysine (−3.9); and arginine (−4.5).

To obtain a biological functionally equivalent protein by making amino acids changes based upon a similar hydropathic index or score, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been asssigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (-0.4); praline (-0.5±1); alanine (-0.5); histidine (-0.5); cysteine (-1.0); methionine (-1.3); valine (-1.5); leucine (-1.8); isoleucine (-1.8); tyrosine (-2.3); phenylalanine (-2.5); tryptophan (-3.4).

To obtain a biological functionally equivalent protein by making amino acids changes based upon a similar hydrophilicity value, the substitution of amino acids whose hydrophilicity values are within ±2 is preferred, those which are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

U.S. Pat. No. 4,554,101 (Hopp, incorporated herein by reference) also teaches the identification and preparation of epitopes from primary amino acid sequences on the basis of hydrophilicity. Through the methods disclosed in Hopp one of skill in the art would be able to identify epitopes from within an amino acid sequence such as the SREBP-1 sequence disclosed herein (SEQ ID NO:38). These regions are also referred to as "eptiopic core regions".

Numerous scientific publications have been devoted to the prediction of secondary structure, and to the identification of epitopes, from analyses of amino acid sequences (Chou & Fasman, 1974a,b; 1978a,b, 1979). Any of these may be used, if desired, to supplement the teachings of Hopp in U.S. Pat. No. 4,554,101. Moreover, computer programs are currently available to assist with predicting antigenic portions and eptiopic core regions of proteins. Examples include those programs based upon the Jameson-Wolf analysis (Jameson & Wolf, 1998; Wolf et al., 1988), the program PepPlot® (Brutlag et al., 1990; Weinberger et al., 1985), and other new programs for potein tertiary structure prediction (Fetrow & Bryant, 1993).

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. The exchange of codons for other equivalent codons is discussed in the following section and a table of codons for reference in such matters is also provided.

H. Nucleic Acid Hybridization

As mentioned above, the present invention involves the use of nucleic acid segments in various hybridization embodiments. The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired.

Hybridization probes may be selected from any portion of any of the sequences disclosed herein. All that is required is to review the sequence set forth in SEQ ID NO:37 or 53 and to select any continuous portion of the sequence, from about 10 nucleotides in length up to and including the full length sequence, that one wishes to utilise as a probe or primer. The choice of probe and primer sequences may be governed by various factors, such as, by way of example only, one may which to employ primers from towards the termini of the total sequence, or from the ends of the functional domain-encoding sequences, in order to amplify further DNA; or one may employ probes corresponding to the entire DNA, or to particular DNA binding motif regions, to clone SREBP-type genes from other species or to clone further SREBP-like or homologous human genes.

The process of selecting and preparing a nucleic acid segment which includes a sequence from within SEQ ID NO:37 or SEQ ID NO:53 may alternatively be described as preparing a nucleic acid fragment. Of course, fragments may also be obtained by other techniques such as, e.g., by mechanical shearing or by restriction enzyme digestion. Small nucelic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR technology of U.S. Pat. No. 4,603,102 (incorporated herein by reference), by introducing selected sequences into recombinant vectors for recombinant production, and by ohter recombinant DNA techniques generally known to those of skill in the art of molecular biology.

Accordingly, the nucleotide sequences of the invention may be used for their ability to selectively form duplex molecules with complementary stretches of SREBP genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt andor high temperature conditions, such as provided by 0.02M–0.15M NaCl at temperatures of 50° C. to 70° C. Such selective conditions tolerate little, if any, mismatch between the probe and the template or target strand, and would be particularly suitable for isolating SREBP genes.

Of course, for some applications, for example, where one desires to prepare mutants employing a mutant primer strand hybridized to an underlying template or where one seeks to isolate SREBP-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

In these embodiments, DNA segments may be employed which include SREBP sequences which are essentially, although not exactly, as set forth in SEQ ID NO:37 or 53. Essentially means that the nucleic acid sequence substantially corresponds to a portion of SEQ ID NO:37 or 53 and has relatively few codons which are not identical, or functionally equivalent, to the codons of SEQ ID NO:37 or 53. As is known in the art, codons are groups of three nucleotides which, in the terms of the coding exons, encode a particular amino acid. The term "functionally equivalent codon" is used herein to refer to codons that encode the same amino acid, such as the six codons for arginine or serine, and also refers to codons that encode biologically equivalent amino acids. One may refer to the following table in selecting different codons for use in the nucleic acis segments of the present invention.

TABLE OF AMINO ACIDS AND THEIR CODONS

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | J | AUA | AUC | AUU | |
| Lysine | Lys | K | AAA | AAG | | |

TABLE OF AMINO ACIDS AND THEIR CODONS -continued

| Amino Acids | | | Codons | | | | | |
|---|---|---|---|---|---|---|---|---|
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

I. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, e.g., to analyse the function and regulation of various domains and individual residues within SREBP-1, by introducing one or more nucleotide sequence changes into the DNA.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which B0 includes within its sequence a DNA sequence which encodes the SREBP. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of SREBP cDNAs or genes using site-directed mutagenesis is provided as a means of producing potentially useful SREBP species and is not meant to be limiting as there are other ways in which sequence variants of SREBP may be obtained. For example, recombinant vectors encoding the desired SREBP cDNA or gene may be treated with mutagenic agents to obtain sequence variants (see, e.g., a method described by Eichenlaub, 1979) for the mutagenesis of plasmid DNA using hydroxylamine.

J. Recombinant Host Cells and Recombinant Expression

Once a suitable SREBP clone has been obtained, whether cDNA based or genomic, one may proceed to prepare an expression system for the recombinant preparation of SREBPs. The engineering of DNA segment(s) for expression in a prokaryotic or eukaryotic system may be performed by techniques generally known to those of skill in recombinant expression. It is believed that virtually any expression system may be employed in the expression of SREBP.

One may choose to follow the methods set forth in Examples 3 or 4, where the expression of SREBP-1 or SREBP-2 in both eukaryotic and procaryotic cells is described, with each leading to the production of active SREBP. In general, for the preparation of large amounts of SREBP, bacterial expression systems may be preferred. A cDNA for SREBP alone may be separately expressed in bacterial systems, or may be expressed as a fusion protein in conjunction with, e.g., β-galactosidase, ubiquitin, *Schistosoma japonicum* glutathione S-transferase, and the like. It is believed that bacterial expression will have advantages over eukaryotic expression in certain embodiments in terms of ease of use and quantity of materials obtained thereby.

It is proposed that transformation of host cells with DNA segments encoding SREBPs, such as SREBP-1, will provide a convenient means for obtaining active enzyme. Both cDNA and genomic sequences are suitable for eukaryotic expression, as the host cell will, of course, process the genomic transcripts to yield functional mRNA for translation into protein. Genomic sequences for SREBP-1 fall within the scope of the present invention.

It is similarly believed that almost any eukaryotic expression system may be utilized for the expression of SREBP, e.g., baculovirus-based, glutamine synthase-based or dihydrofolate reductase-based systems could be employed. However, in preferred embodiments, it is contemplated that plasmid vectors incorporating an origin of replication and an efficient eukaryotic promoter, as exemplified by the eukaryotic vectors of the pCMV series, such as pCMV5 and pCMV7, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit recombinantly introduced exogenous DNA segment or gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

K. Antibodies directed against SREBP

Antibodies, both polyclonal and monoclonal, specific for the SREBP of the present invention may be prepared using conventional immunization techniques, as will be generally known to those of skill in the art. A composition containing antigenic epitopes of the SREBP can be used to immunize one or more experimental animals, such as a rabbit or mouse, which will then proceed to produce specific antibodies against the SREBP. Polyclonal antisera may be obtained, after allowing time for antibody generation, simply by bleeding the animal and preparing serum samples from the whole blood. A particular example of polyclonal antibody generation is disclosed herein in method 10 of Example 3. In this method, synthetic peptides from the SREBP-1 sequence were coupled to a carrier protein and used to immunize rabbits. which includes the enzyme, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that virtually any of the commonly employed host cells can be used in connection with the expression of SREBPs in accordance herewith. Examples include cell lines typically employed for eukaryotic expression such as 239, CV-1, VERO, HeLa, CHO, WI 38, BHK, COS-7, RIN and MDCK cell lines. Preferred lines for use in eukaryotic expression embodiments of the present invention are simian CV-1 cells and human 293 cells.

SREBP may be "overexpressed", i.e., expressed in increased levels relative to natural expression in the cells of the human body. As SREBPs are naturally expressed in very low levels, the over-expression of SREBP is not thought to pose a problem. If desired, overexpression may be assessed by a variety of methods, including functional assays as described in Example 3, radio-labelling and/or protein purification. Simple and direct methods, such as SDS/PAGE and protein staining or Western blotting and, if desired, quantitative densitometric scanning of the resultant gel or blot, are contemplated. A specific increase in the level of the recombinant protein or peptide in comparison to the level in natural cells is indicative of overexpression, as is a relative abundance of the specific protein in relation to the other proteins produced by the host cell and, e.g., visible on a gel.

As used herein, the term "engineered" or "recombinant" cell is intended to refer to a cell into which an exogenous DNA segment or gene, such as a cDNA or gene encoding a SREBP-1 has been introduced. Therefore, engineered cells are distinguishable from naturally occurring cells which do not contain a To obtain monoclonal antibodies, one would also initially immunize an experimental animal, often preferably a mouse, with an SREBP composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to SREBP.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against SREBP. Hybridomas which produce monoclonal antibodies to the selected antigens are identified using standard techniques, such as ELISA and Western blot methods. Hybridoma clones thus identified can then be cultured in liquid media and the culture supernatants purified to provide the SREBP-specific monoclonal antibodies.

In general, both poly- and monoclonal antibodies against SREBP may be used in a variety of embodiments. For example, they may be employed in antibody cloning protocols to obtain cDNAs or genes encoding SREBP or related proteins. They may also be used in inhibition studies to analyze the effects of SREBP, or certain domains of SREBP, in cells or animals. Anti SREBP antibodies will also be useful in immunolocalization studies to analyze the distribution of SREBP during various cellular events, for example, to determine the nuclear and/or cellular distribution during the presence or absence of sterols. A particularly useful application of such antibodies is in immunoabsorbent protocols such as may be employed to purify native or recombinant SREBP, for example, using an antibody affinity column. The operation of all such immunological techniques will be known to those of skill in the art in light of the present disclosure.

L. In vitro Screening Assays for Candidate Substances

Further aspects of this invention concern methods for conveniently evaluating candidate substances to identify compounds capable of stimulating SRE-1-mediated transcription. Such compounds will be capable of promoting LDL receptor expression, and thus can be said to have receptor up regulating activity. In as much as increased LDL receptor expression in the body functions to reduce plasma LDL concentrations (Brown and Goldstein, 1986), any positive substances identified by the assays of the present invention will be potential cholesterol-lowering agents or anti-hypercholesterolemic drugs. Before human administration, such compounds would be rigorously tested using conventional animal models known to those of skill in the art.

Successful candidate substances may function in the absence of added sterols, in which case the candidate compound may be termed a "positive stimulator" of SRE-1. Alternatively, such compounds may stimulate transcription in the presence of sterols, i.e., function to oppose sterol-mediated suppression, and thus may be termed "a sterol antagonist". Compounds may even be discovered which combine both of these actions, as does SREBP-1, depending on the level at which it is present. Although the antagonist class of compounds may ultimately seem to be the most desirable, compounds of either class will likely be useful therapeutic agents for use in stimulating LDL receptor production and lowering blood cholesterol in human subjects.

As SREBP is herein shown to bind to functional SRE-1 DNA sequences, one method by which to identify a candidate substance capable of stimulating SRE-1-mediated transcription is based upon specific protein:DNA binding. Accordingly, to conduct such an assay, one may prepare an SREBP-1 protein composition, such as recombinant SREBP-1, and determine the ability of a candidate substance to increase SREBP binding to a DNA segment including a functional SRE-1 sequence, i.e., to increase the amount or the binding affinity of a protein:DNA complex.

This would generally be achieved using two parallel assays, one which contains SREBP-1 and the specific DNA alone and one which contains SREBP-1, DNA and the candidate substance composition. One would perform each assay under conditions, and for a period of time, effective to allow the formation of protein:DNA complexes, and one would then separate the bound protein:DNA complexes from any unbound protein or DNA and measure the amount of the protein:DNA complexes. An increase in the amount of the bound protein:DNA complex formed in the presence of the candidate substance would be indicative of a candidate substance capable of promoting SREBP-1 binding, and thus, capable of stimulating SRE-1-mediated transcription.

In such binding assays, the amount of the protein:DNA complex may be measured, after the removal of unbound species, by detecting a label, such as a radioactive or enzymatic label, which was incorporated into the original SREBP-1 composition or recombinant protein or SRE-1-containing DNA segment. Alternatively, one could detect the protein portion of the complex by means of an antibody directed against the protein, such as those disclosed-herein.

Preferred binding assays are those in which either the SREBP recombinant protein or purified composition or the SRE-1-containing DNA segment is bound to a solid support and contacted with the other component to allow complex formation. Unbound protein or DNA components are then separated from the protein:DNA complexes by washing and the amount of the remaining bound complex quantitated by detecting the label or with antibodies. Such DNA binding assays form the basis of filter-binding and microtiter plate-type assays and can be performed in a semi-automated manner to enable analysis of a large number of candidate substances in a short period of time. Electrophoretic methods, such as the gel-shift assay disclosed herein, could also be employed to separate unbound protein or DNA from bound protein:DNA complexes, but such labor-intensive methods are not preferred.

Assays such as those described above are initially directed to identifying positive stimulator candidate substances and do not, by themselves, address the activity of the substance in the presence of sterols. However, such positive regulators may also prove to act as sterol antagonists, and in any event, would likely have utility in transcriptional promotion, either in vitro or in vivo. Positive regulators would likely be further evaluated to assess the effects of sterols on their action, for example, by employing a cellular reporter gene assay such as those described hereinbelow.

Virtually any candidate substance may be analyzed by these methods, including compounds which may interact with SREBP, SRE-1 or protein:DNA complexes, and also substances such as enzymes which may act by physically altering one of the structures present. Examples of the former substances include sterols and sterol derivatives, and an example of the latter include phosphatase or kinase enzymes which may regulate SREBP activity. Of course, any compound isolated from natural sources such as plants, animals or even marine, forest or soil samples, may be assayed, as may any synthetic chemical or recombinant protein.

Another potential method for stimulating SRE-1-mediated transcription is to prepare a SREBP composition and to modify the protein composition in a manner effective to increase SREBP binding to a DNA segment including the sterol regulatory element SRE-1. The binding assays would be performed in parallel, similar to those described above, allowing the native and modified SREBP to be compared. In addition to phosphatases and kinases, other agents, including proteases and chemical agents, could be employed to modify SREBP. The present invention, with the cloning of SREBP-1 cDNA, also opens the way for genetically engineering SREBP to promote LDL receptor transcription that is not suppressible by sterols. In this regard, the mutation of potential phosphorylation sites and/or the modification or deletion of other domains is contemplated.

M. Reporter Genes and Cell-Based Screening Assays

Cellular assays are also available for screening candidate substances to identify those capable of stimulating SRE-1-mediated transcription and gene expression. In these assays, the increased expression of any natural or heterologous gene under the control of a functional SRE-1 element may be employed as a measure of stimulatory activity, although the use of reporter genes is preferred. A reporter gene is a gene that confers on its recombinant host cell a readily detectable phenotype that emerges only under specific conditions. In the present case, the reporter gene, being under the control of a functional SRE-1 element, will generally be expressed under conditions of sterol deprivation and will generally be repressed in the presence of sterols.

Reporter genes are genes which encode a polypeptide not otherwise produced by the host cell which is detectable by analysis of the cell culture, e.g., by fluorometric, radioisotopic or spectrophotometric analysis of the cell culture. Exemplary enzymes include luciferases, transferases, esterases, phosphatases, proteases (tissue plasminogen activator or urokinase), and other enzymes capable of being detected by their physical presence or functional activity. The reporter gene currently preferred is chloramphenicol acetyltransferase (CAT; Osborne et al., 1985) which may be employed with a radiolabeled substrate, or luciferase, which is measured fluorometrically.

Another class of reporter genes which confer detectable characteristics on a host cell are those which encode polypeptides, generally enzymes, which render their transformants resistant against toxins, e.g., the neo gene which protects host cells against toxic levels of the antibiotic G418, and genes encoding dihydrofolate reductase, which confers resistance to methotrexate. Genes of this class are not generally preferred since the phenotype (resistance) does not provide a convenient or rapid quantitative output. Resistance to antibiotic or toxin requires days of culture to confirm, or complex assay procedures if other than a biological determination is to be made.

Other genes of potential for use in screening assays are those capable of transforming hosts to express unique cell surface antigens, e.g., viral env proteins such as HIV gp120 or herpes gD, which are readily detectable by immunoassays. However, antigenic reporters are not preferred because, unlike enzymes, they are not catalytic and thus do not amplify their signals.

The polypeptide products of the reporter gene are secreted, intracellular or, as noted above, membrane bound polypeptides. If the polypeptide is not ordinarily secreted it is fused to a heterologous signal sequence for processing and secretion. In other circumstance the signal is modified in order to remove sequences that interdict secretion. For example, the herpes gD coat protein has been modified by site directed deletion of its transmembrane binding domain, thereby facilitating its secretion (EP 139,417A). This truncated form of the herpes gD protein is detectable in the culture medium by conventional immunoassays. Preferably, however, the products of the reporter gene are lodged in the intracellular or membrane compartments. Then they can be fixed to the culture container, e.g., microtiter wells, in which they are grown, followed by addition of a detectable signal generating substance such as a chromogenic substrate for reporter enzymes.

The transcriptional promotion process which, in its entirety, leads to enhanced transcription is termed "activation." The mechanism by which a successful candidate substance acts is not material since the objective is to promote LDL receptor expression, or even, to promote LDL receptor expression in the presence of sterols, by whatever means will function to do so.

To create an appropriate vector or plasmid for use in such assays one would ligate the SRE-1-containing promoter, whether a hybrid or the native LDL receptor promoter, to a DNA segment encoding the reporter gene by conventional methods. The SRE may be obtained by in vitro synthesis or recovered from genomic DNA and should be ligated upstream of the start codon of the reporter gene. An AT-rich TATA box region should also be employed and should be located between the SRE-1 sequence and the reporter gene start codon. The region 3' to the coding sequence for the reporter gene will ideally contain a transcription termination and polyadenylation site. The promoter and reporter gene may be inserted into a replicable vector and transfected into a cloning host such as E. coli, the host cultured and the replicated vector recovered in order to prepare sufficient quantities of the construction for later transfection into a suitable eukaryotic host.

Host cells for use in the screening assays of the present invention will generally be mammalian cells, and are preferably cell lines which may be used in connection with transient transfection studies. Cell lines should be relatively easy to grow in large scale culture. Also, they should contain as little native background as possible considering the nature of the reporter polypeptide. Examples include the Hep G2, VERO, HeLa, human embryonic kidney, 293, CHO, W138, BHK, COS-7, and MDCK cell lines, with monkey CV-1 cells being particularly preferred.

The screening assay typically is conducted by growing recombinant host cells in the presence and absence of candidate substances and determining the amount or the activity of the reporter gene. To assay for candidate substances capable of exerting their effects in the presence of sterols, one would make serial molar proportions of cholesterol and/or other sterols that suppress SRE-1-mediated expression to the cells. One would ideally measure the reporter signal level after an incubation period that is sufficient to demonstrate sterol-mediated repression of signal expression in controls incubated solely with sterols, for example with 10 micrograms cholesterol/ml and 1 microgram 25-hydroxy-cholesterol/ml. Cells containing varying proportions of candidate substances would then be evaluated for signal activation in comparison to the suppressed levels.

Candidates that demonstrate dose related enhancement of reporter gene transcription or expression are then selected for further evaluation as clinical therapeutic agents. The stimulation of transcription may be observed in the absence of added sterols, in which case the candidate compound might be a positive stimulator of the SRE. Alternatively, the candidate compound might only give a stimulation in the presence of sterols, which would indicate that it functions to oppose the sterol-mediated suppression of the SRE. Candidate compounds of either class might be useful therapeutic agents that would stimulate production of LDL receptors and thereby lower blood cholesterol in patients.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Identification of Sterol Regulatory Element-1 Binding Protein (SREBP) and Delineation of its Target Nucleotide Sequence The present example reports the identification of a protein in rat liver nuclei that binds to the sterol regulatory element (SRE-1), as exemplified by SRE-1 in the promoter of the gene for the low density lipoprotein (LDL) receptor (SEQ ID NO:27).

The 10-base pair SRE-1 (SEQ ID NO:27) is embedded within a 16-base pair sequence designated Repeat 2 (SEQ ID NO:22) located immediately upstream of a related sequence designated Repeat 3 (SEQ ID NO:23). To confirm that DNA recognition by the SRE-1 binding protein (SREBP) correlates with sterol-regulated transcription, an artificial promoter was synthesized that contains two copies of wild-type or mutant Repeat 2+3 sequences immediately upstream of a TATA box from adenovirus. The synthetic promoters were inserted upstream of a reporter gene and tested for transcriptional activity in the absence and presence of sterols after transient transfection into monkey CV-1 cells.

The reporter gene with two copies of the wild-type Repeat 2+3 sequence (SEQ ID NO:25) was transcribed actively in sterol-deprived cells and was repressed by more than 80% when sterols were present. Binding of SREBP to the SRE-1 sequence, assessed by gel mobility shift assays, correlated precisely on a nucleotide-by-nucleotide basis with the transcriptional activity of each of 18 synthetic promoters with point mutations in Repeat 2 (SEQ ID NOS:2–19, respectively). The SREBP bound to the 9 mutant promoters that were positive for sterol-regulated transcription (SEQ ID NOS:2–4,10,15–19, respectively), and it did not bind to any of the 9 point mutants that abolished transcription (SEQ ID NOS:5–9,11–14, respectively).

A. Materials and Methods

1. Materials. Enzymes used in plasmid constructions were obtained from Pharmacia LKB Biotechnology, Inc. and Life Technologies, Inc.; chromatography supplies and the FPLC system from Pharmacia LKB; Dulbecco's modified Eagle medium, high glucose formulation (DMEM), from JRH Biomedicals, Inc.; sterols from Steraloids, Inc.; protease and phosphatase inhibitors from Sigma Chemical Co. and Boehringer Mannheim; [$^{14}$C]chloramphenicol (55 mCi/mmol) from Amersham; and [$\alpha$-$^{32}$p]dCTP (3000 Ci/mmol) from Dupont-New England Nuclear. Newborn calf lipoprotein-deficient serum (d>1.215 g/ml) was prepared by ultracentrifugation (Goldstein, et al., 1983).

Figure 4A:
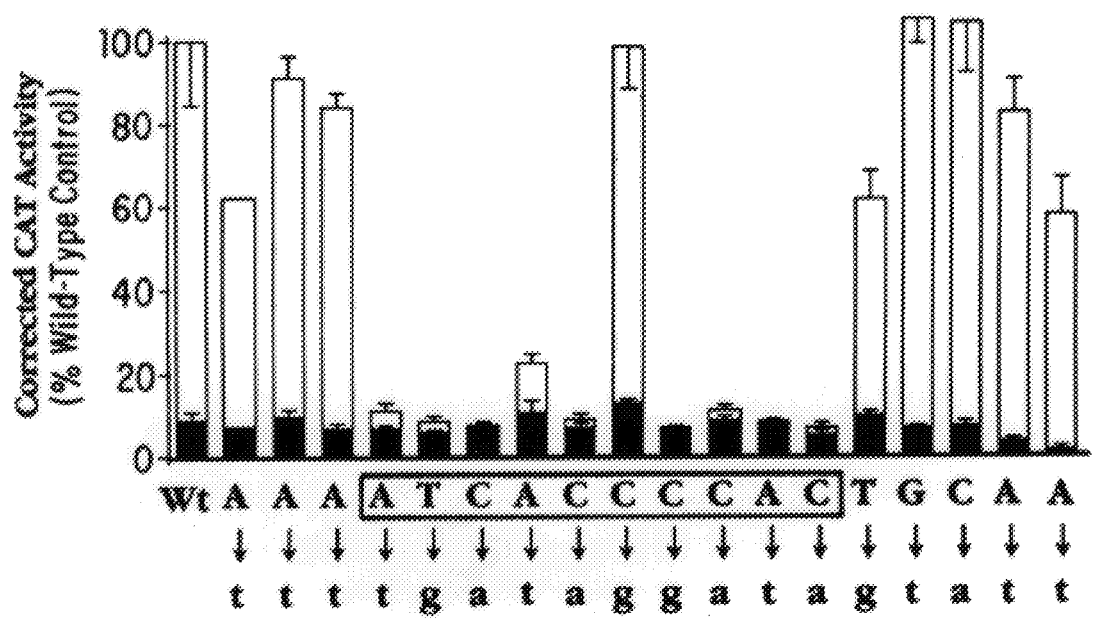
FIG. 4A. Single point mutation analysis of Repeat 2 of LDL receptor promoter. The point mutation analysis of Repeat 2 is assessed in vitro by gel mobility shift assay as shown in FIG. 4A,; and in vivo by transient transfection in CV-1 cells as shown in FIG. 4B,. As indicated in the description of FIG. 3, the sequence in upper case letters is designated SEQ ID NO:1. The mutant sequences which each contain the sequence of SEQ ID NO:1 with the exception, in each case, of a single mutation indicated by the lower case letters are designated as SEQ ID NO:2–19, respectively.

2. Plasmid Constructions. Plasmid pCMV-βGAL (β-galactosidase under control of the human cytomegalovirus promoter) was obtained from Karl Normington (University of Texas Southwestern Medical Center at Dallas). Plasmids were constructed by standard methods (Sambrook et al., 1989) using annealed complementary deoxyoligonucleotides cloned into an E1b TATA-CAT vector (Lillie et al., 1989) digested with either SalI (FIG. 2 and Table I) or PstI-SalI (FIGS. 3 and 4 and Table II). Oligonucleotides were synthesized on an Applied Biosystems 380B DNA synthesizer. Plasmids were purified on Qiagen-tip 2500 columns. DNA sequences of all constructs were determined with a $^{32}$P-labeled SP6 primer using a Sequenase Version 2.0 sequencing kit from United States Biochemicals, Inc. according to the supplier's instructions.

3. DNA Transfection. All cells were grown in an 8% $CO_2$ incubator at 37° C. African green monkey kidney CV-1 cells (obtained from American Type Culture Collection, No. CCL70) were grown in monolayers in medium A (DMEM with 100 U/ml penicillin and 100 μg/ml streptomycin sulfate) containing 10% (v/v) fetal calf serum.

On day 0, the CV-1 cells were plated at $5\times10^5$ cells per 90-mm petri dish and incubated for 24 hours. On day 1, each dish received 10 ml of fresh medium A containing 10% fetal calf serum and were then transfected with calcium phosphate-precipitated DNA (Sambrook et al., 1989). Briefly, 12.5 or 25 μg of test plasmid DNA and 7.5 or 15 μg of pCMV-βGAL in 0.44 ml of 10 mM Tris-HCl/1 mM EDTA at pH 8.0 were added to 0.11 ml of 2.5M $CaCl_2$ and mixed with 0.55 ml of 2X Hanks' buffered saline solution (Sambrook et al., 1989). The precipitate was allowed to form for 45 minutes at room temperature, after which 1 ml was added dropwise to each monolayer. The cells were incubated for 14 hours with the DNA, and then washed twice with 6 ml of warm Dulbecco's phosphate-buffered saline, and re-fed with 8 ml of medium A containing 10% calf lipoprotein-deficient serum in the presence or absence of sterols (10 μg/ml cholesterol plus 1 μg/ml 25-hydroxycholesterol added in 16 μl ethanol). After incubation for 48 hours (day 4), the cells were harvested for measurement of CAT and β-galactosidase activity.

4. CAT Assay. Transfected cells were washed three times with phosphate-buffered saline, scraped into 1 ml of 40 mM Tris-HCl/1 mM EDTA/150 mM NaCl at pH 7.4, lysed by shearing through a 25-gauge needle ten times, and centrifuged at 14,000 g for 2 minutes at 4° C. An aliquot of the supernatant (15–25 μg protein) was incubated for 1–2 hours at 37° C. in a standard CAT assay (Gorman et al., 1982) in a final volume of 0.15 ml containing 0.9 nmol [$^{14}$C] chloramphenicol (50 nCi) and either 0.53 mM acetyl CoA or 0.53 mM butyryl CoA (Pothier et al., 1992). All assays were linear with respect to time of incubation and concentration of extract protein.

The reaction products were quantified by either of two methods. In one method (Table I), the ethyl acetate-solubilized reaction products were chromatographed on Merck 5748 silica gel plates developed in a chloroform/methanol (95/5, v/v) solvent system. The plates were dried and exposed at room temperature to Kodak X-OMAT XAR film for the indicated time. The radioactive spots were cut out and counted in a scintillation counter.

In the second method (Table II), the reaction products were extracted with 0.5 ml xylenes (Seed et al., 1988). The xylene phase was back-washed twice with 0.2 ml of 0.25M Tris-HCl, pH 8, after which a 350-μl aliquot of the xylenes phase was counted in a scintillation counter. The protein content of cell extracts was measured by the Lowry method (Lowry et al., 1951).

5. β-Galactosidase Assay. An aliquot of the 14,000 g supernatant from the lysed transfected cellls (15–25 μg protein) was incubated at 28° C. for 15–60 minutes with 0.67 mg/ml o-nitrophenyl-β-D-galactopyranoside in a final volume of 1.2 ml (Lee et al., 1984). Reactions were stopped with 0.5 ml 1M $Na_2CO_3$, and the amount of o-nitrophenol formed was measured spectrophotometrically at 420 nm.

6. Partial Purification of Rat Liver SRE-1 Binding Protein (SREBP). An extract of rat liver nuclei was prepared by the method of Lichtsteiner, et al. (Lichtsteiner et al., 1987). Livers from 100 rats rinsed with cold Dulbecco's phosphate-buffered saline (JRH Biosciences) containing protease inhibitors (1 mM benzamidine, 0.5 mM phenylmethylsulfonyl fluoride, 10 μg/ml leupeptin, 5 μg/ml pepstatin, 28 milli-trypsin inhibitory units of aprotinin) and phosphatase inhibitors (1 mM EDTA, 1 mM EGTA, 1 mM β-glycerophosphate, 5 mM sodium fluoride, 1 mM sodium molybdate) were homogenized at 4° C. for 30 sec in a specially designed Waring blender (circular design with cap to exclude air) (Lichtsteiner et al., 1987) in 4 volumes of Buffer A (10 mM Hepes-KOH, pH 7.6, 2M sucrose, 25 mM potassium chloride, 0.15 mM spermine, 0.5 mM spermidine, 1 mM EDTA, 1 mM DTT, protease inhibitors, and phosphatase inhibitors).

After filtration through 4 layers of cheesecloth, 30 ml of homogenate were layered over 10 ml of Buffer A in AH629 tubes and centrifuged at 103,600 g at 4° C. for 30 minutes. The nuclear pellets were suspended in nuclear lysis buffer (10 mM Hepes-KOH, pH 7.6, 100 mM potassium chloride, 3 mM magnesium chloride, 1 mM DTT, 10% [v/v] glycerol, protease and phosphatase inhibitors) using the B pestle of a Dounce homogenizer and adjusted to a final concentration of 15 $A^{260}$ units/ml. Twenty-eight ml of the nuclear suspension were dispensed into high-speed centrifugation tubes to which 2.8 ml of 4M ammonium sulfate, pH 7.9 (0.36M final concentration) was added and mixed by gentle inversion. The extract was rocked gently for 30 minutes at 0° C. After centrifugation at 244,300 g at 4° C. for 1 hour, the supernatant (nuclear extract) was dialyzed against a 100-fold excess of Buffer B (25 mM Hepes-KOH, pH 7.6, 12 mM magnesium chloride, 10% glycerol, 0.5 mM DTT, protease and phosphatase inhibitors) at 4° C. for 2–3 hours. The dialysis was stopped when the conductivity of the nuclear extract became equivalent to that of Buffer B containing 100 mM KCl. Insoluble material was removed by centrifugation at 24,000 g for 15 minutes at 4° C.

The supernatant (425 mg protein) was applied to an S-Sepharose (SP Sepharose, Pharmacia) column (20-ml bed volume) equilibrated with Buffer B containing 100 mM KCl. The column was washed with 2 column volumes of Buffer B containing 100 mM KCl, and the fraction containing the SREBP activity was eluted with Buffer B containing 300 mM KCl. Solid ammonium sulfate was added to the eluate (40 ml), and the pellet obtained at 500 saturation was dissolved in 6 ml and clarified by centrifugation. The resulting solution (88 mg protein in 6 ml) was applied to an FPLC HiLoad™ 16/60 Superdex 200 column equilibrated in Buffer B containing 100 mM KCl. Fractions were assayed for SREBP activity, and the active fractions were pooled and stored at −80° C.

7. PCR Probes for Gel Mobility Shift Assay. Each PCR probe was synthesized in a 100-μl reaction containing 10 mM Tris-HCl, pH 9.0 (at 25° C.), 50 mM KCl, 0.1% [v/v] Triton X-100, 50 pM dGTP, 50 μM DATP, 50 μM dTTP, and 5 μM dCTP, 10 μl [α-$^{32}$p]dCTP (3000 Ci/mmol), 100 ng of the corresponding plasmid used for the transfection studies (see above), and 1 nmol each of two PCR oligonucleotides designed to hybridize to the flanking sequences of the two copies of Repeat 2+3 of the LDL receptor promoter in Plasmid K (5' oligo GACACTATAGAACTCGAGCAGCTGAAGCTTGCATGC (SEQ ID NO:28); 3 ' oligo GGTACCCGGGGATCCATTATATACC (SEQ ID NO:29). The reaction was initiated by adding 2 U of Taq DNA Polymerase (Promega), and the tubes were incubated at 94° C. for 30 s, 55° C. for 1.5 minutes, 72° C. for 1 minute, for 15 cycles.

The PCR products were subsequently digested with XbaI and Hind III, and the $^{32}$P-labeled 94-bp double-stranded fragment with a 5' overhang of 4 nucleotides was purified on a 6% polyacrylamide gel. This $^{32}$P-fragment contains two copies of Repeat 2+3 from the LDL receptor promoter region linked by a SalI site (70 bp) surrounded by 16 bp of 5'-flanking sequence (HindIII site) and 7 bp of 3'-flanking sequence (XbaI site).

8. Gel Mobility Shift Assay. The binding activity of SREBP was assayed in a 20-μl reaction containing 12.5 mM Hepes-KOH (pH 7.5), 6 mM $MgCl_2$, 5.5 mM EDTA, 50 mM KCl, 0.5 mM DTT, 0.25 mg/ml non-fat dry milk (Kroger brand), 50 μg/ml sodium polyd(I-C)·polyd(I-C) (Pharmacia; average length, 1332 bp), 5% (v/v) glycerol, 25 μg/ml of a double-stranded oligonucleotide containing one copy of a 9-bp scrambled (underlined below) mutant version of Repeat 2 followed by one copy of a wild-type Repeat 3 sequence (5' TCGACAAAAGATAAGATGTGCAAACTCCTCCCCCTGCG-3', SEQ ID NO:30), 2.2 μg partially purified rat liver SREBP, and 6 fmol of the indicated $^{32}$P-labeled PCR-generated probe (40,000 cpm). Each reaction mixture was incubated at room temperature for 20 minutes and then loaded directly onto a 4% polyacrylamide gel in 0.5× TBE buffer (1× TBE buffer contains 90 mM Tris-borate/2 mM EDTA). The gel was run at constant current of 22 mA at room temperature for 90 minutes and exposed wet to Kodak XAR film overnight at −80° C.

B. Results

Figure 1C:
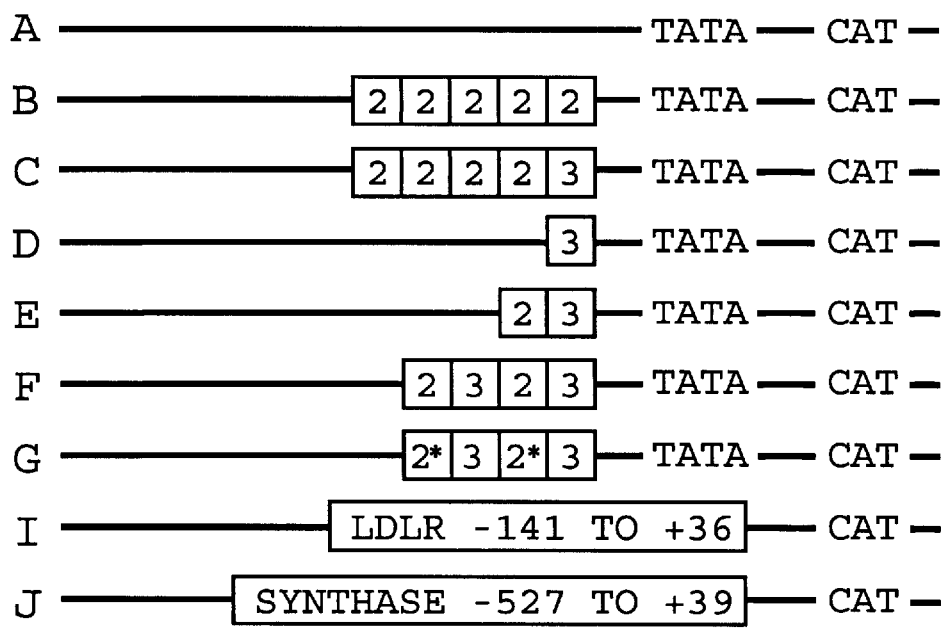
FIG. 1C. Plasmid constructs containing SRE-1 elements (Repeat 2+3) of LDL receptor promoter inserted into E1b TATA-CAT vector; plasmids B and C were constructed by inserting annealed complementary oligonucleotides consisting of five contiguous elements with SalI cloning sites at both ends. Plasmids D to G were made by ligating the indicated oligonucleotides in SalI-digested, phosphatase-treated E1b TATA-CAT vector and sequenced to confirm orientation. LDL receptor (LDLR) and HMG CoA synthase constructs refer to plasmids pLDLR-CAT-234 (Südhof et al., 1987) and pSyn-CAT-1 (Smith et al., 1988), described in the indicated references.
Figure 1D:
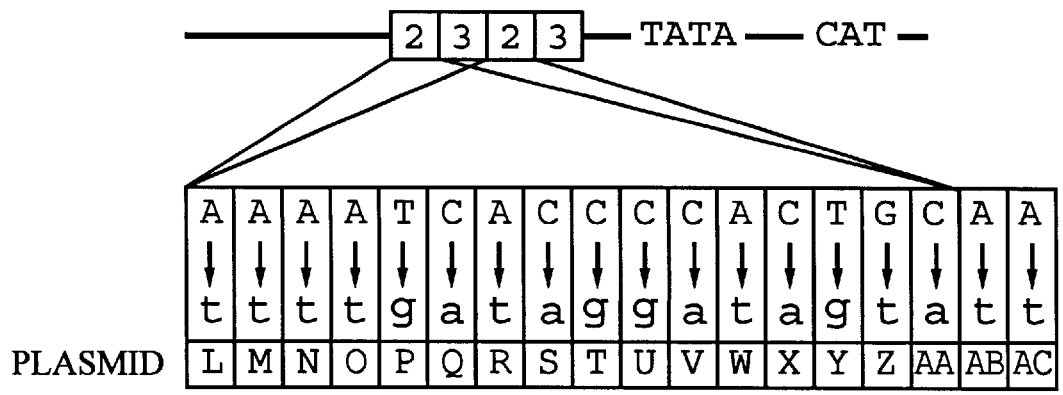
FIG. 1D. Plasmid constructs containing SRE-1 elements (Repeat 2+3) of LDL receptor promoter inserted into E1b TATA-CAT vector; the wild-type nucleotide sequence of LDL receptor Repeat 2 plus two adjacent base pairs of Repeat 3 (Plasmid K) is shown in capital letters (SEQ ID NO:1). The corresponding single base changes in mutant plasmids L to Z and AA to AE are shown in lower case letters. These plasmids contain the sequences designated as SEQ ID NOS:2–19, respectively. Each of the 18 plasmids contained two copies of the mutant Repeat 2+3 construct in tandem upstream of the TATA box in the PstI-SalI-digested vector.

FIG. 1 shows the DNA sequences of Repeats 2 (SEQ ID NO:22) and 3 (SEQ ID NO:23), which are immediately contiguous in the native LDL receptor promoter (Südhof et al., 1987). Plasmid constructs were prepared that contain multiple copies of a Repeat 2+3 oligonucleotide (SEQ ID NO:24) inserted 15 bp upstream of a TATA box sequence derived from the adenovirus E1b promoter. These synthetic promoters were cloned upstream of a reporter gene encoding bacterial chloramphenicol acetyltransferase (CAT) and introduced into monkey CV-1 cells in transient expression assays.

FIG. 2 shows the CAT activity in CV-1 cells that were transiently transfected with the various promoter constructs and incubated for 48 hours either in the absence or presence of sterols. When no LDL receptor promoter elements were present in the vector, no CAT activity was obtained (Plasmid A). Five copies of Repeat 2 (SEQ ID NO:22) also showed no activity (B). A single copy of Repeat 3 (SEQ ID NO:23) gave only low levels of non-regulated transcription (D). However, when the construct contained four copies of Repeat 2 (SEQ ID NO:22) plus a single copy of Repeat 3 (SEQ ID NO:23), transcription was observed in the absence of sterols and was repressed when sterols were present (C). A single copy of the Repeat 2+3 element (SEQ ID NO:24) gave low level transcription that was sterol-regulated (E) similar to that of the native LDL receptor (I). A much higher level of regulated transcription was observed when the Repeat 2+3 element (SEQ ID NO:24) was repeated twice (F). The induced level of transcription of this plasmid was much higher than was seen with the native LDL receptor promoter under the same conditions (I).

In a vector that contained two copies of the Repeat 2+3 sequence (SEQ ID NO:25), a 4-bp mutation in both copies of Repeat 2 reduced transcription to a low level that was similar in the absence and presence of sterols (G), indicating that sterol responsiveness had been abolished. This mutation contains two nucleotide substitutions that were previously shown to obliterate SRE-1 function in the native LDL receptor promoter (Smith et al., 1990).

Table I presents a quantitative analysis of the above expression data. As an internal control for transfection efficiency, in each study a control plasmid was included that encodes β-galactosidase under the direction of the CMV promoter. The observed CAT activity was normalized for the amount of β-galactosidase activity in the same cells, and the results are expressed as corrected CAT activity. The ratio of corrected CAT activities in the absence and presence of sterols,is the fold regulation. Table I shows the mean results from 4 to 8 independent studies for each plasmid. In the absence of sterols, the CAT activity in CV-1 cells rose from 5.2 to 62% [$^{14}$C]chloramphenicol conversion when the number of copies of the Repeat 2+3 element (SEQ ID NO:24) was increased from 1 to 2. The dependence of transcription on sterol deprivation also increased from 2.5 to 5.3-fold when the Repeat 2+3 sequence (SEQ ID NO:24) was duplicated. The fold regulation by sterols was highest (14-fold) when four copies of Repeat 2 (SEQ ID NO:22) were placed adjacent to one copy of Repeat 3, SEQ ID NO:23 (Plasmid C).

in detail in Table II. For this purpose, construct K was used, which contains two copies of the wild-type Repeat 2+3 (SEQ ID NO:24) element cloned into the E1b CAT vector as a PstI-SalI insert. In this synthetic promoter, the point mutations gave essentially all-or-none results. This allowed the identification of a sequence of 10 nucleotides, SEQ ID NO:27, within Repeat 2, SEQ ID NO:22, of which 9 were essential for high level transcription in the absence of sterols. The only exception was the sixth nucleotide within this sequence, namely, the second C in the CCCC tetramer. Replacement of this C with a G did not affect transcription. This nucleotide is an A in the wild-type hamster Repeat 2 element, SEQ ID NO:20 (Bishop, 1992), which is fully active in transcription (Plasmid AD, Table II). With this sole exception, mutation of any single nucleotide within the SRE-1 severely reduced transcription in the absence of

TABLE I

Sterol-Mediated Regulation of E1b TATA-CAT Genes Containing
LDL Receptor Promoter Elements in Transfected CV-1 and HeLa Cells

| Plasm. | Promoter Element | Transfected Cell Type | β-Galactosidase Activity | | Corrected CAT Activity | | Fold Regulation of CAT$ |
|---|---|---|---|---|---|---|---|
| | | | − Sterols | + Sterols | − Sterols | + Sterols | |
| | | | nmol/min/mg protein | | % conversion | | |
| A | None | CV-1 (n = 4)‡ | 341 ± 11¶ | 490 ± 6.6 | 0.17 ± 0.02¶ | 0.16 ± 0.01¶ | 1.1 |
| I | LDL Receptor (−141 to +36) | CV-1 (n = 8) | 118 ± 11 | 193 ± 21 | 6.8 ± 0.9 | 1.9 ± 0.3 | 3.6 |
| J | HMG CoA Synthase (−527 to +39) | CV-1 (n = 6) | 124 ± 13 | 135 ± 21 | 32 ± 6.9 | 6.1 ± 0.6 | 5.2 |
| B | [2]$_5$ | CV-1 (n = 4) | 323 ± 15 | 374 ± 6.4 | 0.42 ± 0.1 | 0.17 ± 0.02 | 2.5 |
| C | [2]$_4$ + 3 | CV-1 (n = 4) | 242 ± 4.7 | 380 ± 3.2 | 15 ± 0.9 | 1.1 ± 0.1 | 14 |
| D | 3 | CV-1 (n = 8) | 273 ± 23 | 324 ± 23 | 0.81 ± 0.14 | 0.88 ± 0.17 | 0 |
| E | 2 + 3 | CV-1 (n = 6) | 223 ± 3.4 | 292 ± 15 | 5.2 ± 0.3 | 2.1 ± 0.1 | 2.5 |
| F | [2 + 3]$_2$ | CV-1 (n = 4) | 277 ± 46 | 298 ± 49 | 62 ± 6.0 | 11.8 ± 2.1 | 5.3 |
| G | [2* + 3]$_2$ | CV-1 (n = 4) | 241 ± 41 | 310 ± 38 | 5.2 ± 0.3 | 5.5 ± 0.4 | 0 |

The indicated cell type was transiently transfected with 25 µg of the E1b TATA-CAT vector containing the indicated LDL receptor promoter element together with 15 µg of pCMV-βGAL. After incubation for 48 hours in the absence or presence of 10 µg/ml cholesterol plus 1 µg/ml 25-hydroxycholesterol, the cells were harvested for duplicate measurement of CAT and β-galactosidase activities as described in the "Materials and Methods". CAT activity in an individual study was corrected for variation in transfection efficiency by normalizing the value to the β-galactosidase activity in the same extract. In each study, the first β-galactosidase value assayed was assigned an arbitrary value of 1 and all other β-galactosidase values were expressed as fractional equivalents of this value. Plasmid J, the authentic HMG CoA synthase promoter fused to CAT, is included for comparative purposes. In the promoter element column, 2 designates SEQ ID NO:22, 3 designates SEQ ID NO:23 and 2* + 3 designates SEQ ID NO:25.
$Fold reguiation is the ratio of corrected CAT activity in the absence of sterols divided by corrected activity in the presence of sterols.
‡Number in parenthesis denotes the number of independent transfection studies.
¶Mean ± S.E. of the indicated number of independent transfection studies.

A nucleotide-by-nucleotide mutational analysis of Repeat 2 is shown graphically in FIG. 3, and the data are provided sterols, but did not affect constitutive transcription in the presence of sterols.

TABLE II

Sterol-mediated Regulation of E1b TATA-CAT Genes Containing Single Point Mutations
in Repeat 2 of LDL Receptor Promoter in Transfected CV-1 Cells

| | | | | | | | | | | | | | | | | Corrected CAT Activity | | | |
|---|---|---|---|---|---|---|---|---|---|---|---|---|---|---|---|---|---|---|---|
| | | | | | | | | | | | | | | | | (−) Sterols | (+) Sterols | | Fold |
| Plasmid | Repeat 2 Mutants | | | | | | | | | | | | | | | % of wild-type control | | | Regulation$ |
| K | A | A | A | A | T | C | A | C | C | C | C | A | C | T | G | C | A | A | 100 ± 10.3¶ | 9.1 ± 1.2 | (n = 9)‡ | 11 |
| L | t | — | — | — | — | — | — | — | — | — | — | — | — | — | — | — | — | — | 62 | 7.4 | (n = 1) | 8.4 |
| M | — | t | — | — | — | — | — | — | — | — | — | — | — | — | — | — | — | — | 91 ± 5.6 | 9.7 ± 1.4 | (n = 3) | 9.4 |
| N | — | — | t | — | — | — | — | — | — | — | — | — | — | — | — | — | — | — | 84 ± 3.7 | 6.8 ± 1.1 | (n = 3) | 12 |
| O | — | — | — | t | — | — | — | — | — | — | — | — | — | — | — | — | — | — | 11 ± 2.1 | 6.7 ± 0.7 | (n = 3) | 1.6 |

TABLE II-continued

Sterol-mediated Regulation of E1b TATA-CAT Genes Containing Single Point Mutations
in Repeat 2 of LDL Receptor Promoter in Transfected CV-1 Cells

| Plasmid | Repeat 2 Mutants | Corrected CAT Activity | | | Fold Regulation§ |
|---|---|---|---|---|---|
| | | (−) Sterols % of wild-type control | (+) Sterols % of wild-type control | | |
| P  | — — — — g — — — — — — — — — — — — | 8.7 ± 1.3 | 6.1 ± 0.5 | (n = 3) | 1.4 |
| Q  | — — — — — a — — — — — — — — — — — | 7.8 ± 0.6 | 6.7 ± 0.6 | (n = 3) | 1.2 |
| R  | — — — — — — t — — — — — — — — — — | 22 ± 2.0 | 10 ± 2.4 | (n = 4) | 2.2 |
| S  | — — — — — — — a — — — — — — — — — | 9.0 ± 1.1 | 6.7 ± 1.0 | (n = 4) | 1.3 |
| T  | — — — — — — — — g — — — — — — — — | 99 ± 9.7 | 13 ± 1.0 | (n = 4) | 7.6 |
| U  | — — — — — — — — — g — — — — — — — | 6.9 ± 0.5 | 6.0 ± 0.4 | (n = 3) | 1.2 |
| V  | — — — — — — — — — — a — — — — — — | 11 ± 1.1 | 8.6 ± 0.9 | (n = 3) | 1.3 |
| W  | — — — — — — — — — — — t — — — — — | 8.0 ± 0.5 | 7.3 ± 0.6 | (n = 3) | 1.1 |
| X  | — — — — — — — — — — — — a — — — — | 7.0 ± 1.0 | 5.1 ± 0.9 | (n = 3) | 1.4 |
| Y  | — — — — — — — — — — — — — g — — — | 62 ± 6.8 | 9.7 ± 0.8 | (n = 3) | 6.4 |
| Z  | — — — — — — — — — — — — — — t — — | 106 ± 5.4 | 6.8 ± 0.3 | (n = 3) | 16 |
| AA | — — — — — — — — — — — — — — — a — | 105 ± 12 | 7.5 ± 0.5 | (n = 3) | 14 |
| AB | — — — — — — — — — — — — — — — — t | 83 ± 7.7 | 3.6 ± 0.2 | (n = 3) | 23 |
| AC | — — — — — — — — — — — — — — — — — t | 58 ± 7.4 | 1.4 ± 0.1 | (n = 3) | 41 |
| AD* | — — — — — — — — — — — — — — — — — | 50 | 3.6 | (n = 1) | 14 |
| AE* | — — — — — — — — — — — — — — — — — | 97 ± 7.3 | 6.6 ± 0.2 | (n = 3) | 15 |

CV-1 cells were transiently transfected with 12.5 µg of the idicated plasmid containig 2 copies of the Repeat 2 + 3 sequence, with each copy of Repeat 2 bearing the indicated point mutation, together with 7.5 µg of pCMV-βGAL. After incubation for 48 hours in the absence or presence of 10 µg/ml cholesterol plus 1 µg/ml 25-hydroxycholesterol, the cells were harvested for duplicate measurement of CAT and β-galactosidase activities as described in "Materials and Methods". Corrected CAT activities were calculated as described in the legend to Table I and expressed as "% of the wild-type control" value obtained in the same study.
§fold regulation is the ratio of corrected CAT activity in the absence of sterols divided by the corrected CAT activity in the presence of sterols.
¶Mean ± S.E. of the idicated number of transfection studies.
‡Number in parentheses indicates the number of independent transfection studies.
*Plasmids AD and AE each contain mutant Repeat 2 sequences that correspond to the wild-type Repeat 2 of the LDL receptor promoter in the hamster (Bishop, 1992) and mouse genes, respectively.
The sequences from plasmids K through AE are designated as SEQ ID NOS:1–21, respectively.

The present inventors then proceeded to identify a protein in rat liver nuclear extracts that binds SRE-1 in a fashion that is dependent upon each of the 9 nucleotides that are required for transcriptional activity. In order to obtain a clear result, the rat liver nuclear extract was subjected to ion exchange chromatography on S-Sepharose and gel filtration on Superdex, as described in detail hereinbelow (Example 2). The active fractions from the Superdex column were pooled and tested for specificity of DNA binding, using gel retardation assays.

Figure 4B:
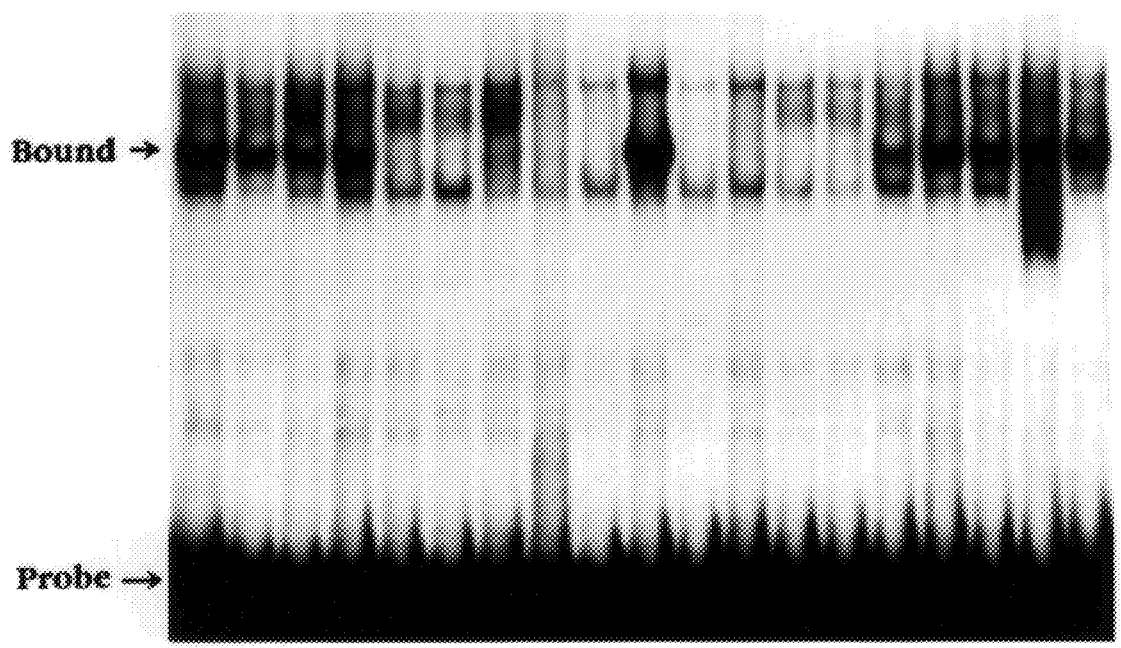
FIG. 4B. Single point mutation analysis of Repeat 2 of LDL receptor promoter. An aliquot of partially purified rat liver SREBP (2.2 µg) was incubated for 20 minutes at room temperature with the indicated wild-type or mutant $^{32}$P-labeled, PCR-derived DNA probe of 94 bp in length. Each $^{32}$P-probe (~4×10$^4$ cpm/reaction) contained two tandem copies of Repeat 2+3 with the indicated point mutation in both copies of Repeat 2. After electrophoresis, the gel was exposed to Kodak XAR film for 14 hours at −80° C. with an intensifying screen. The SRE-1 sequence (SEQ ID NO:27) contained within Repeat 2 is boxed.

FIG. 4B shows that the partially purified rat liver nuclear extract fraction contained an activity that retarded the migration of a radiolabeled oligonucleotide that consisted of two tandem copies of the Repeat 2+3 sequence (SEQ ID NO:24). Binding was reduced markedly when any of the 9 essential nucleotides within the SRE-1 were mutated. Mutation of the nucleotide at position 6 did not affect this gel shift activity. Mutation of any of the nucleotides that flanked the SRE-1 did not reduce binding appreciably. These results paralleled completely the results obtained for in vivo transcription, as shown in of FIG. 4A.

C. Discussion

In the present example, artificial promoters were constructed containing multiple copies of the repeated sequences from the LDL receptor promoter for use-in transient transfection assays to determine precisely the nucleotides that are required for high level sterol-sensitive transcription. The results indicate that a segment of 10 nucleotides within the 16-bp Repeat 2 element, SEQ ID NO:22, contains the sterol-sensitive transcription activity. Mutation of any one of 9 nucleotides within this sequence markedly reduced transcriptional activity of the SRE-1. The sole exception was the nucleotide at position 6 (the second C in the CCCC tetramer).

Repeat 2, SEQ ID NO:22, did not have any detectable transcriptional activity on its own, even when present in five copies. However, when one of these copies was replaced by a single copy of Repeat 3, SEQ ID NO:23, significant sterol-sensitive transcription appeared. A single copy of Repeat 3, SEQ ID NO:23, on its own had virtually no transcriptional activity, either in the absence or presence of sterols. These data are consistent with previous data showing that Repeat 2 synergizes with Repeat 3 in promoting transcription, but only in the absence of sterols (Smith et al., 1990; Südhof et al., 1987; Dawson et al., 1988).

In the native LDL receptor promoter, Repeats 2 and 3 are immediately adjacent to each other. When constructs were prepared that contained two copies of Repeat 2+3, SEQ ID NO:24, in tandem, sterol-sensitive transcription increased as the number of the Repeat 2 and 3 element units increased. In the mutagenesis studies, the construct that contained two copies of the Repeat 2+3 sequence was used which allowed the demonstration that sterol-dependent transcription in vivo requires every nucleotide in the 10-bp SRE-1 with the exception of one cytosine.

Using gel retardation assays, an activity in rat liver nuclear extracts was identified that bound to the SRE-1 sequence in a fashion that was dependent on each of the 9 nucleotides that were required for transcription. Strikingly, the binding of this protein did not depend on the nucleotide in the 6th position, i.e., the second C in the CCCC tetramer. This was also the only nucleotide whose replacement could be tolerated without loss of transcriptional activity. The precision of this correlation makes it highly likely that the DNA binding activity in the rat nuclear extracts is the one that is required for sterol-sensitive transcription.

The goal of this example was to generate a series of probes with single point mutations in the SRE-1 sequence that abolished sterol-regulated transcription and could be used to detect physiologically relevant nuclear binding proteins. The present inventors were not attempting to detect all possible nucleotides that might substitute for the native ones without loss of function. The results of these mutagenesis studies are completely consistent with previous studies in which point mutations were made in the native LDL receptor promoter (Smith et al., 1990). The earlier studies used CHO cells that were permanently transfected with recombinant plasmids containing the native LDL receptor promoter. Those studies delineated the same 10-bp sequence that was identified in this study. They also showed that a transversion at position 6 (C to A mutation) preserved transcriptional activity. However, the fold changes in transcription in the absence and presence of sterols were lower in the earlier study, and several mutations produced intermediate effects. These problems were avoided in the current study through the use of a synthetic construct containing two copies of the Repeat 2+3 unit, SEQ ID NO:24, and through the use of transient transfection assays that gave a larger amplitude of regulation and all-or-none effects of the mutations.

It was necessary to perform the detailed analysis of nucleotide requirements for transcriptional activity described in this Example because of the previous difficulty encountered in identifying a DNA binding protein that correlated with SRE-1-dependent transcription. Nuclear extracts contain many abundant DNA binding proteins that shift the electrophoretic mobility of oligonucleotides that contain the SRE-1 sequence (Rajavashisth et al., 1989; Stark et al., 1992). However, these proteins do not show the specificity of binding that is defined here for a true transcriptional regulator. Once the precise nucleotides were identified, it became possible to exclude other Repeat 2 binding proteins and to focus on the activity that is shown in FIG. 4.

EXAMPLE 2

The Purification of SREBP to Homogeneity from the Nuclei of Human HeLa Cells The present example describes the purification of SREBP to apparent homogeneity from the nuclei of human HeLa cells.

A. Materials and Methods

1. Materials. SP-Sepharose, CNBr-activated Sepharose 4B, pre-packed Superdex 200 26/60 gel filtration column, and the nucleotides used for PCR were obtained from Pharmacia LKB Biotechnology, Inc; molecular weight markers and Silver Stain Plus Kit were from Bio-Rad; Nonidet P-40 from Pierce Chemical Co.; 5'-bromo-dUTP and Joklik minimum essential medium from Sigma Chemical Co; DNaseI (DPFF grade) from Worthington Biochemical Corp.; micrococcal nuclease from Boehringer Mannheim; and purified human Sp1 from Promega. Other materials were obtained from sources described in Example 1.

2. Cell Culture. Human HeLa S3 cells (obtained from B. Johnson and R. Tjian, University of California, Berkeley, Calif.) were grown in spinner culture at a density of ~2.5–5× $10^5$ cells/ml in 4-liter spinner flasks in Joklik minimum essential medium containing 5% (v/v) newborn calf serum, 100 u/ml penicillin, and 100 µg/ml streptomycin sulfate. The cells were split into an equal volume of fresh complete medium every 24 hours. On the day prior to harvest, the cells were split into an equal volume of medium without serum so that the final concentration of newborn calf serum was 2.5%. Of the total HeLa cells used in the current studies, one half were purchased from the National Cell Culture Center (Minneapolis, Minn.), and the other half were grown in the present inventors' laboratory. HeLa cells obtained from the National Cell Culture Center were shipped overnight as a packed pellet on wet ice and processed within 1 hour of arrival. Pilot studies showed that the SREBP activity in these cells was similar to that in HeLa cells grown in the present inventors' laboratory.

3. Preparation of DNA Affinity Columns. DNA affinity columns were prepared using established methods (Briggs et al., 1986; Kadonaga and Tjian, 1986) in which multimerized double-stranded oligonucleotides were coupled to CNBr-activated Sepharose 4B. Column A contains a multimerized oligonucleotide, each monomer consisting of one copy of a mutant Repeat 2 with a scrambled SRE-1 sequence (underlined below) followed by one copy of a wild-type Repeat 3 (Suidhof et al., 1987). Each Repeat 2+3 element is flanked by a 4-bp linker (TCGA). The two sequences that comprise column A are designated SEQ ID NOS:31 and 32, respectively. Column B contains a multimerized oligonucleotide flanked by a TCGA linker. Each monomer consists of two tandem copies of a wild-type Repeat 2 sequence except for a single bp change (C→T) in the 3' region flanking the SRE-1 sequence (underlined below). This bp change was designed to eliminate a contaminating protein that bound to the flanking sequence. The two sequences that comprise column B are designated SEQ ID NOS:33 and 34, respectively. Column C contains a multimerized oligonucleotide, each monomer consisting only of the 10-bp SRE-1 sequence flanked by a 4-bp linker (CTAG). The sequences that comprise column C are designated SEQ ID NOS:35 and 36, respectively. The three double-stranded oligonucleotides used for multimerization have the following sequences (represented by SEQ ID NO:31 through SEQ ID NO:36, respectively):

| | |
|---|---|
| Column A | 5'-TCGACAAAAgataagatatGCAAACTCCTCCCCCTGCG-3' (31) |
| | 3'-GTTTTctattctataCGTTTGAGGAGGGGGACGCAGCT-5' (32) |
| Column B | 5'-TCGACAAAATCACCCCACTGTAAAATCACCCCACTGTG-3' (33) |
| | 3'-GTTTTAGTGGGGTGACATTTTAGTGGGGTGACACAGCT-5' (34) |
| Column C | 5'-GATCATCACCCCACTG-3' (35) |
| | 3'-TAGTGGGGTGACCTAG-5' (36) |

4. Purification of the SRE-1 Binding Protein (SREBP). A typical purification is described. All steps were carried out at 4° C.

Step 1: Nuclear Extracts—Nuclear extracts from 75–100 liters of HeLa S3 cells (4–5×$10^{10}$ cells) were prepared according to Dignam, et al. (1983) with two modifications. Firstly, the nuclei were extracted with Buffer A (20 mM Hepes-KOH, pH 7.6, 25% (v/v) glycerol, 0.5M NaCl, 1.5 mM MgCl$_2$, 1 mM sodium EDTA, 1 mM sodium EGTA, and 0.5 mM DTT) supplemented with protease and phosphatase inhibitors (0.5 mM phenylmethylsulfonyl fluoride, 5 µg/ml pepstatin A, 10 µg/ml leupeptin, 2 µg/ml aprotinin, 1 mM sodium β-glycerolphosphate, 5 mM sodium fluoride, and 1 mM sodium molybdate). Secondly, after extraction in Buffer A, the nuclear extract was centrifuged at 24,000 rpm for 3 hours in an AH 629 rotor (Du Pont Sorvall), and the $10^5$ g supernatant was used for further purification.

Step 2: SP-Sepharose Chromatography—The $1.03 \times 10^5$ g supernatant (1 g protein) was diluted with 3 volumes of Buffer B (25 mM Hepes-KOH, pH 7.5, 12 mM $MgCl_2$, 10% glycerol, 1 mM sodium EDTA, 1 mM sodium EGTA, 0.5 mM DTT) supplemented with protease and phosphatase inhibitors (see above) and applied onto an SP-Sepharose column (100-ml bed volume) equilibrated with Buffer B containing 0.1M KCl. The column was washed with 2.5 volumes of Buffer B with 0.1M KCl and eluted with 2 volumes of Buffer B with 0.3M KCl.

Steps 3 and 4: Ammonium Sulfate Fractionation and Gel Filtration Chromatography—Solid ammonium sulfate was added to the SP-Sepharose 0.3M KCl eluate (480 mg protein) to achieve 40% saturation, and the mixture was rotated for 3 hours. The ammonium sulfate precipitate was centrifuged (32,600×g for 15 minutes), resuspended in 25 ml Buffer B, and divided into two aliquots. Each aliquot was loaded onto a Superdex 200 26/60 gel filtration column (330-ml bed volume) using a Fast Protein Liquid Chromatography system (FPLC, Pharmacia Biotechnology, Inc.). The column was equilibrated and eluted in Buffer B containing 0.15M KCl. After 90 ml elution, individual fractions of 4 ml were collected. SREBP activity was typically found in fractions 9–13, which were pooled, frozen in liquid nitrogen, and stored at −80° C. for 1–7 days.

Steps 5 and 6: First DNA Affinity Chromatography—The active fractions from 12 separate Superdex preparations (representing 6 different nuclear extract preparations) were thawed and pooled (498 mg protein in 240 ml), after which sodium EDTA (5 mM) and sodium molybdate (10 mM) were added to achieve the indicated final concentration. The mixture was loaded onto a 20-ml DNA affinity column that contained a mutant version of Repeat 2+a wild-type Repeat 3 (Column A, SEQ ID NOS:31 and 32, see above). The flow-through containing SREBP activity was collected, and sodium poly(dI-dC)·poly(dI-dC) (Pharmacia; average length, 1332 bp) was added to achieve a final concentration of 40 μg/ml. After incubation on ice for 10 minutes, the mixture was divided into six aliquots, each of which was loaded onto a 1 ml DNA affinity column that contained tandem copies of Repeat 2 (Column B, SEQ ID NOS:33 and 34). The columns were each washed with 30 column volumes of Buffer B containing 0.3M KCl and 0.1% (v/v) Nonidet P-40 (NP-40) and eluted with Buffer B with 1M KCl plus 0.1% NP-40.

Steps 7 and 8: Repeat DNA Affinity Chromatography—The active fractions from the Step 6 eluate (1.7 mg protein in 18 ml) were pooled and dialyzed overnight against Buffer B containing 0.15M KCl and 0.1% NP-40. After dialysis, sodium EDTA and sodium molybdate were added to achieve final concentrations of 5 mM and 10 mM, respectively. The protein was then loaded onto two sequential 2-ml DNA affinity columns containing a mutant version of Repeat 2+a wild-type Repeat 3 (Column A, SEQ ID NOS:31 and 32). The flow-through fractions were collected and poly(dI-dC)·poly(dI-dC) was added to a final concentration of 40 μg/ml. After incubation on ice for 10 minutes, the mixture was loaded onto a 1-ml DNA affinity column that contained only the SRE-1 portion of Repeat 2 (Column C, SEQ ID NOS:35 and 36). The column was washed with 30 column volumes of Buffer B containing 0.3M KCl and 0.1' NP-40 and eluted stepwise with 1 ml aliquots of Buffer B containing 0.1% NP-40 and concentrations of NaCl that increased from 0.4M to 1.0M in increments of 0.1M.

Step 9: Glycerol Gradient Sedimentation—The active fractions from step 8 (0.5M–0.7M NaCl step elutions) were pooled, and a 0.2-ml aliquot of the 3-ml pooled fraction was loaded onto a 4.5 ml 10%–30% (v/v) glycerol gradient containing 25 mM Hepes, 12 mM $MgCl_2$, 5 mM sodium EDTA, 0.6M NaCl, 1 mM DTT, and 0.1% NP-40 at pH 7.5. The gradient was centrifuged in a SW-60 rotor (Beckman) at 55,000 rpm for 15 hours. Fractions of 0.45 ml were collected from the top.

5. Gel Mobility Shift Assay. PCR probes containing copies of wild-type and mutant Repeat 2+3 elements (SEQ ID NOS:28 and 29) were prepared and used for gel mobility shift assays as described in Example 1. Unless otherwise stated, gels were exposed to Kodak XAR film at −80 ° C. for the indicated time with intensifying screens. SREBP activity was quantified by scanning the gel for 15 minutes on the Ambis 100 Radioanalytic Imaging System. Each unit of activity corresponds to 1000 cpm of shifted probe.

6. UV Crosslinking. The general protocol described by Chodosh, et al. (1986) was followed. The $^{32}$P-labeled probes used for UV crosslinking were prepared in the same way as those used for the gel mobility shift assay except that 5'-bromo-dUTP was substituted for dTTP in the PCR reaction. The DNA binding reactions were performed in a 1.5-ml Eppendorf tube in a final volume of 0.1 ml containing 60 fmol $^{32}$P-labeled probe ($5 \times 10^5$ cpm), ~4 μg of partially purified SREBP (1M KCl eluate from Step 6 that had been dialyzed against Buffer B containing 0.15M KCl and 0.1% NP-40), and the same buffer components used in the gel mobility shift assay. The probes were prepared just prior to the reactions.

After incubation for 20 minutes at room temperature, the Ependorf tubes were placed on ice and exposed to a UV lamp (254 nM) for 1 hour, after which a 10-μl aliquot was removed for a gel mobility shift assay. In the remaining 90 μl, the concentration of $MgCl_2$ was adjusted to 10 mM, $CaCl_2$ was added to 10 mM, DNaseI was added to 736 units/ml, and micrococcal nuclease was added to 28 units/ml. Each mixture was incubated at 37° C. for 25 minutes. After nuclease digestion, the samples were precipitated with 10% (w/v) trichloroacetic acid, washed with cold acetone, resuspended in SDS-PAGE sample buffer (Laemmli, 1970), loaded onto an 8% SDS polyacrylamide minigel, and run together with molecular weight markers and purified SREBP. The gel was stained with silver, dried, and exposed to X-ray film.

7. DNase I Footprinting. DNase I footprinting was carried out as described by Briggs et al. (1986) with the following modifications. DNA binding reactions contained, in a final volume of 50 μl, 2 fmol of a single-stranded $^{32}$P-end-labeled DNA fragment ($\sim 10^4$ cpm/tube), 12.5 mM Hepes-KOH (pH 7.5), 6 mM $MgCl_2$, 5 mM sodium EDTA, 50 mM KCl, 0.25 mg/ml nonfat dry milk (Kroger brand), 20 μg/ml poly d(I-C)·poly d(I-C), 10% glycerol, 0.5 mM DTT, and the indicated protein fractions. Single 5' end-labeled, double-stranded DNA footprint probes (239 bp) encompassing Repeat 2+3 from Plasmids K and X (SEQ ID NO:24, Example 1) were prepared by sequential digestion with EcoRI, treatment with calf intestinal alkaline phosphatase and T4 polynucleotide kinase in the presence of $[\gamma^{32}p]$ ATP, digestion with NdeI, and gel purification.

8. Other Methods. SDS-polyacrylamide gel electrophoresis was carried out as described by Laemmli (1970). The gels were calibrated with high range SDS-polyacrylamide gel electrophoresis standards (Bio-Rad). All protein gels were stained with a Silver Stain Plus Kit from Bio-Rad. Gel filtration columns were calibrated with gel filtration standard markers from Bio-Rad. The protein content of all samples (except Step 8) was determined by the Lowry method (1951). The protein content of purified SREBP in Step 8 was estimated by silver staining and densitometric scanning of an 8% SDS polyacrylamide gel in which known amounts (10 ng to 1 μg) of the bovine serum albumin component of a Bio-Rad standard protein mixture were used as a reference.

B. Results

Although SREBP activity could be visualized with gel mobility shift assays in partially purified extracts of rat liver nuclei, the protein lost activity during purification, and it was not possible to isolate it from this source (Example 1). Similar difficulties were encountered with nuclei from livers of hamsters, rabbits, and cows. On the other hand, the protein from human HeLa cell nuclei was stable and was isolated from largescale cultures of these cells.

Figure 5A:
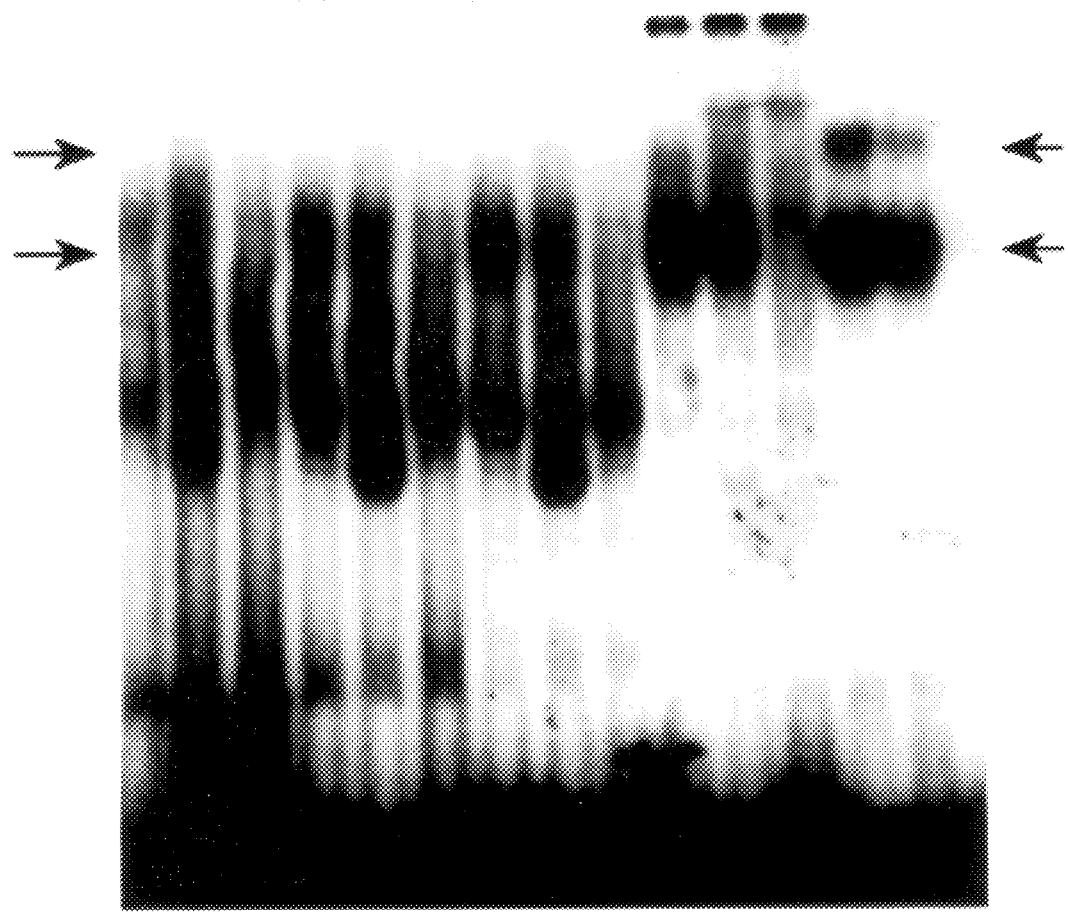
FIG. 5A. Gel mobility shift assays of HeLa cell SREEP after various steps of purification; aliquots of the indicated fractions at different stages of purification were incubated in the standard gel shift assay for 20 minutes at room temperature with the indicated $^{32}$P-labeled, PCR-derived DNA probe of 94 bp in length. Each probe (~4×10$^4$ cpm/reaction) contained two tandem copies of version of Repeats 2+3. The probes contained the following versions of Repeat 2: probe H, wild-type human SRE-1 sequence (Plasmid K in Example 1) (SEQ ID NO:1); Probe M, wild-type mouse SRE-1 sequence (SEQ ID NO:21) which differs by one bp (C→T) from the human sequence (Plasmid AE in Example 1); and Probe *, mutant version of human SRE-1 sequence that contains a substitution of A for C at the same position (SEQ ID NO:14), which abolishes the transcriptional activity of SRE-1 (Plasmid X in Example 1). Arrows denote the position of migration of SREBP bound to one (bottom arrow) or two (top arrow) copies of SRE-1 in the $^{32}$P-probe. The gel was exposed for 2 hours. The 1st DNA affinity fraction had been subjected to sequential purification on DNA affinity Columns A and B.
Figure 5B:
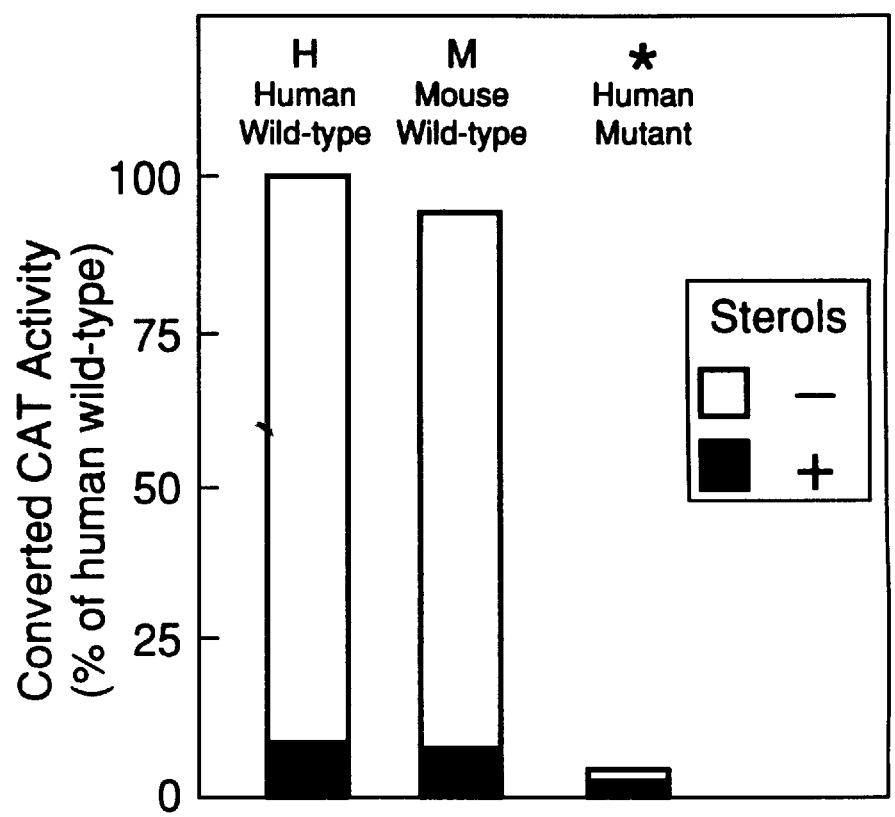
FIG. 5B. Gel mobility shift assays of HeLa cell SREBP after various steps of purification; HeLa cells growing in spinner culture were plated onto monolayers at 5×10$^5$ cells per 90-mM dish in medium A (Example 1) containing 10% fetal calf serum. After 24 hours, the cells were transiently transfected with the indicated LDL receptor promoter-CAT plasmid, incubated in the absence or presence of sterols, and processed for measurement of CAT activity as described in Example 1. The data represent the average of two independent transfection studies and are consistent with expression data in simian CV-1 cells (Table II). H, M, and * refer to Plasmids K, AE, and X, respectively.
Figure 8A:
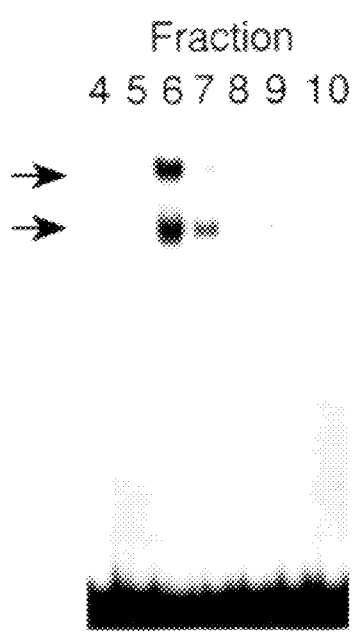
FIG. 8A. Purification of SREBP on second SRE-1 DNA affinity column. Active fractions from the 1M KCl eluate from DNA affinity Column B (Step 6) were pooled, dialyzed against Buffer B containing 150 mM KCl and 0.1' NP-40, applied to two sequential mutant DNA affinity columns (Column A, SEQ ID NOS:31,32) followed by one SRE-1 DNA affinity column (Column C, SEQ ID NOS:35,36), and eluted as described hereinbelow in Example 2. Aliquots (2 µl) of the stepwise NaCl elution from Column C were assayed for SREBP activity by the standard gel shift assay using $^{32}$P-probe H (see FIG. 5). The gel was exposed for 8 hours without intensifying screen. Arrows denote the $^{32}$P-probe containing SREBP bound to one or two sites.
Figure 8B:
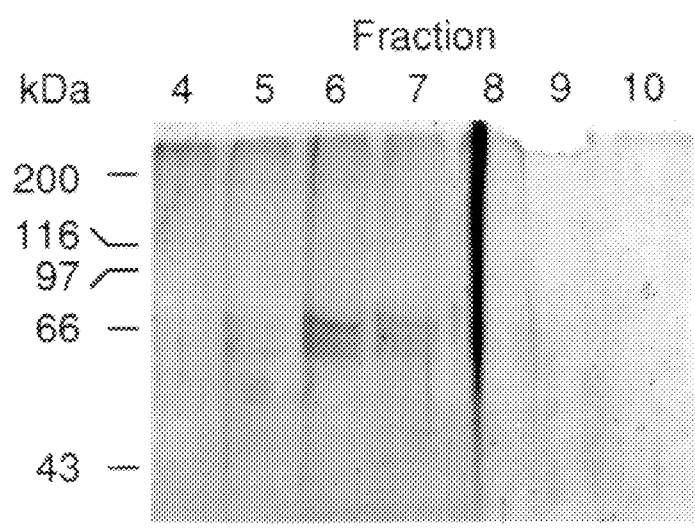
FIG. 8B. Purification of SREBP on second SRE-1 DNA affinity column; aliquots (20 µl) of the same fractions were subjected to electrophoresis on an 8% SDS-polyacrylamide minigel. The protein bands were detected by silver staining.

FIG. 5 shows the results of gel mobility shift assays of SREBP in extracts of HeLa cell nuclei that were subjected to sequential fractionation procedures. As a routine test for specificity during the purification, we used a panel of three $^{32}$P-labelled probes. Probe H consists of two tandem copies of the human Repeat 2+3 sequence, SEQ ID NO:24, and it produces regulated transcription when transfected into HeLa cells (FIG. 5B). Probes M and * also consist of two tandem copies of the Repeat 2+3 sequence, but they differ from the human sequence at one position within the SRE-1 (the most 3' C) in both copies of Repeat 2, SEQ ID NOS:14 and 21. Probe M contains a T at this position, which corresponds to the wild-type mouse LDL receptor Repeat 2 sequence and is transcriptionally active in HeLa cells (FIG. 5) and in cultured simian CV-1 cells (Example 1). In Probe *, the same 3' C is replaced by an A in both copies of Repeat 2. This mutation inactivates the function of Repeat 2 in HeLa cells (FIG. 5) and in CV-1 cells (Example 1).

In crude nuclear extracts, gel mobility shift assays failed to reveal a shifted band that appeared with Probes H and M, but not *, which was the criterion for specificity (FIG. 5A). Similarly, no such activity was found in a fraction from an SP-Sepharose anion exchange column that was subsequently shown to contain SREBP activity (FIG. 5). However, when this fraction was precipitated with 40' ammonium sulfate, a trace of specific binding activity was observed, i.e., there were two shifted bands (designated by arrows in FIG. 5) that were slightly more intense with the wild-type probes (H and M) than they were with the mutant probe *. A similar hint of specificity was observed in certain column fractions when the ammonium sulfate precipitate was subjected to Superdex gel filtration chromatography (FIG. 6). The active fractions from the Superdex column were then subjected to sequential DNA affinity chromatography on two columns. The first column contained multimerized copies of an oligonucleotide composed of a mutated, transcriptionally inactive form of Repeat 2 adjacent to wild-type Repeat 3. The flow-through fraction from this column was then adsorbed to a column containing multiple tandem copies of Repeat 2 and eluted with buffer containing 1M KCl. The eluate contained an activity that bound strongly to the H and M probes, but did not bind detectably to the mutant probe * (last 3 lanes of FIG. 5A).

FIG. 6 shows assays of SREBP as it emerged from the Superdex gel filtration column, which was the first step at which the specific binding activity could be visualized clearly. The peak fraction (number 11) was between the 670-kDa and 158-kDa markers at a position corresponding to approximately 500 kDa.

FIG. 7 shows the results of the DNA affinity chromatography steps. The starting material, which was derived from the Superdex column, contained the specific SREBP activity as well as a contaminating protein that bound the mutant * probe. The specific SREBP activity emerged in the flow-through of the first column, which contained an inactive mutant form of Repeat 2 in tandem with wild-type Repeat 3 (SEQ ID NOS:31 and 32) (FIG. 7A). When this flow-through material was applied to a column containing oligo-merized Repeat 2, the binding activity was adsorbed, and it did not appear in the 0.3M KCl eluate (SEQ ID NOS:33 and 34) (FIG. 7B). It was eluted when the concentration of KCl was raised to 1.0M. This 1.0M KCl eluate was free of the contaminating material that bound the mutant * probe. The arrows in FIG. 7B represent shifted bands containing the SREBP bound to one or both copies, respectively, of the Repeat 2 sequence in the probe.

To complete the purification of the SREBP, the 1.0M KCl eluate from the Repeat 2+3 column was applied to another column containing oligomers of the 10-bp SRE-1 flanked only by a 4-bp linker whose nucleotides differed from the flanking nucleotides in Repeat 2 (SEQ ID NOS:35 and 36). This column was eluted stepwise with aliquots of solutions containing 0.1M increments of NaCl from 0.4M to 1.0M. Mobility shift assays showed that the peak of SREBP activity was in fraction 6 (0.6M NaCl) with smaller amounts in the adjacent fractions. All of these fractions were subjected to SDS polyacrylamide gel electrophoresis and silver staining. A cluster of protein bands with molecular masses between 59 and 68 kDa co-eluted with the SREBP activity, peaking in fraction 6 (FIG. 5A).

Table III shows quantitative estimates of the results of a complete purification starting with nuclear extract from 500 liters of HeLa cells, which contained 6 g protein. As shown in FIG. 5, the SREBP activity from early fractions could not be estimated, owing to the presence of contaminating proteins that bound the mutant as well as the wild-type probe on gel mobility shift assays. After the gel filtration chromatography on Superdex 200 (Step 4), approximately 500 mg of protein were recovered, which contained approximately 114,000 units of SREBP activity. Each unit is defined as the activity that shifts 1000 cpm of the specific probe under the standard conditions of the assay. After the four DNA affinity column steps, the amount of protein was reduced by a factor of more than 100,000 (to 4 μg) with a 31% recovery of SREBP activity. The total calculated purification was approximately 38,000-fold with Step 4 as the starting point.

TABLE III

Purification of SREBP from Human HeLa Cells

| Step | Fraction | Protein* mg | Specific Activity† units/mg | Total Activity units | Purification -fold | Recovery % |
|---|---|---|---|---|---|---|
| 1 | Nuclear Extract | 6009 | — | — | — | — |
| 2 | SP-Sepharose | 2900 | — | — | — | — |

TABLE III-continued

Purification of SREBP from Human HeLa Cells

| Step | Fraction | Protein* mg | Specific Activity† units/mg | Total Activity units | Purification -fold | Recovery % |
|---|---|---|---|---|---|---|
| 3 | Ammonium Sulfate | 1382 | — | — | — | — |
| 4 | Superdex 200 | 498 | 230 | 114,540 | 1 | 100 |
| 5 | Mutant Repeat 2 DNA Affinity (Column A) | 445 | 212 | 94,340 | 0.82 | 82 |
| 6 | Specific DNA Affinity (Column B) | 1.7 | 50,405 | 85,688 | 219 | 75 |
| 7 | Mutant Repeat 2 DNA Affinity (Column A) | 0.97 | 70,230 | 68,123 | 305 | 59 |
| 8 | Specific DNA Affinity (Column C) | 0.004 | 8,784,000 | 35,136 | 38,191 | 31 |

Nuclear extracts were prepared frotn a total of ~500 liters of HeLa cells spinner culture (representing 6 different preparations) as described in the "Materials and Methods". SREBP activity of fractions was assayed by the standard gel mobility shift assay at two concentrations of protein. Activity could not be accurately measured in fractions derived from Steps 1–3. Column A contains SEQ ID NOS:31 and 32; Column B contains SEQ ID NOS:33 and 34; and Column C contains SEQ ID NOS:35 and 36.
*protein concentration of the various fractions was determined as described in "Materials and Methods".
†One unit of activity is defined as described in "Materials and Methods".

Figure 9A:
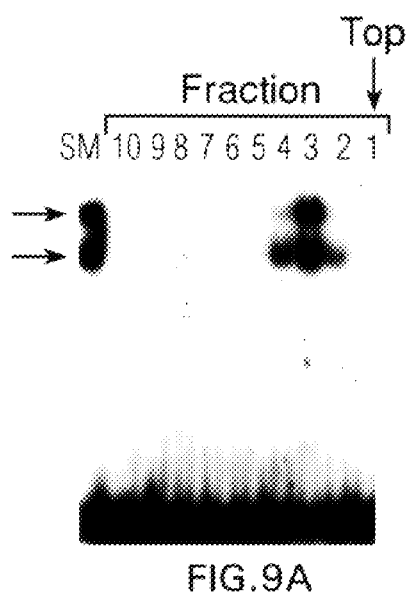
FIG. 9A. Glycerol gradient sedimentation of purified SREBP. The peak fraction from the second SRE-1 DNA affinity column (Step 8) was loaded directly on the top of a 4.5 ml 10%–30% glycerol gradient and centrifuged as described in Example 2. Aliquots (2 µl) of each fraction were assayed by the standard gel shift assay using $^{32}$P-probe H (see FIG. 5). The gel was exposed for 2 hours. Arrows denote the $^{32}$P-probe containing SREBP bound to one or two copies of SREBP.
Figure 9B:
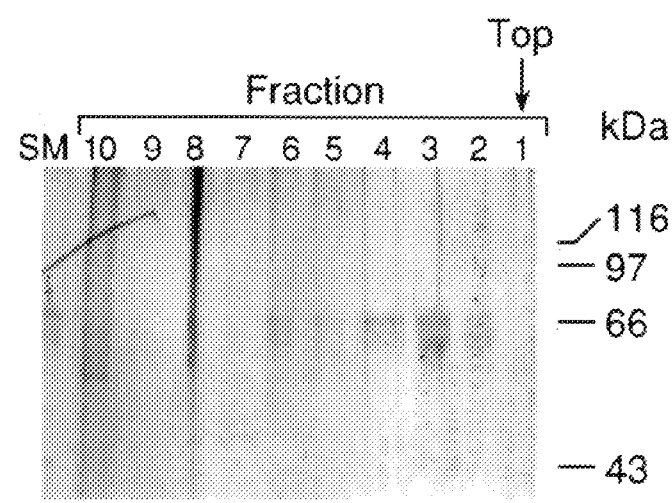
FIG. 9B. Glycerol gradient sedimentation of purified SREBP; aliquots (20 µl) of the same fractions were subjected to electrophoresis on an 8% SDS-polyacrylamide minigel, and the proteins were detected by silver staining. SM, starting material.

A series of studies were next performed to confirm that the protein bands seen in the purified preparation actually constitute SREBP. In one such study, the purified proteins were subjected to ultracentrifugation on a glycerol gradient, and fractions were assayed for SREBP activity (FIG. 9A) and for protein content by SDS polyacrylamide gel electrophoresis (FIG. 9B). The peak of SREBP activity was found in fraction 3, which also contained the cluster of proteins between 59 and 68 kDa. This position of sedimentation corresponded to a molecular mass somewhat less than that of the ovalbumin standard (44 kDa), the peak of which was found in fraction 4.

To further validate the inventors' hypothesis, a partially purified preparation of SREBP was incubated with a $^{32}$P-labeled SRE-1 sequence in which deoxythymidine was replaced with 5-bromodeoxyuridine. After exposure to ultraviolet light and digestion with nucleases, the proteins were subjected to SDS polyacrylamide gel electrophoresis. A cluster of radiolabeled bands was seen in the region of 59 to 68 kDa (FIG. 10, lane 3), which corresponded precisely with the migration of purified SREBP in the same electrophoresis system (lane 6). Labeling was also seen with the M probe (lane 5), but not with the mutant * probe (lane 4). These results suggest that each of the proteins in the 59 to 68 kDa cluster recognizes the SRE-1 element in a specific fashion.

Figure 11:
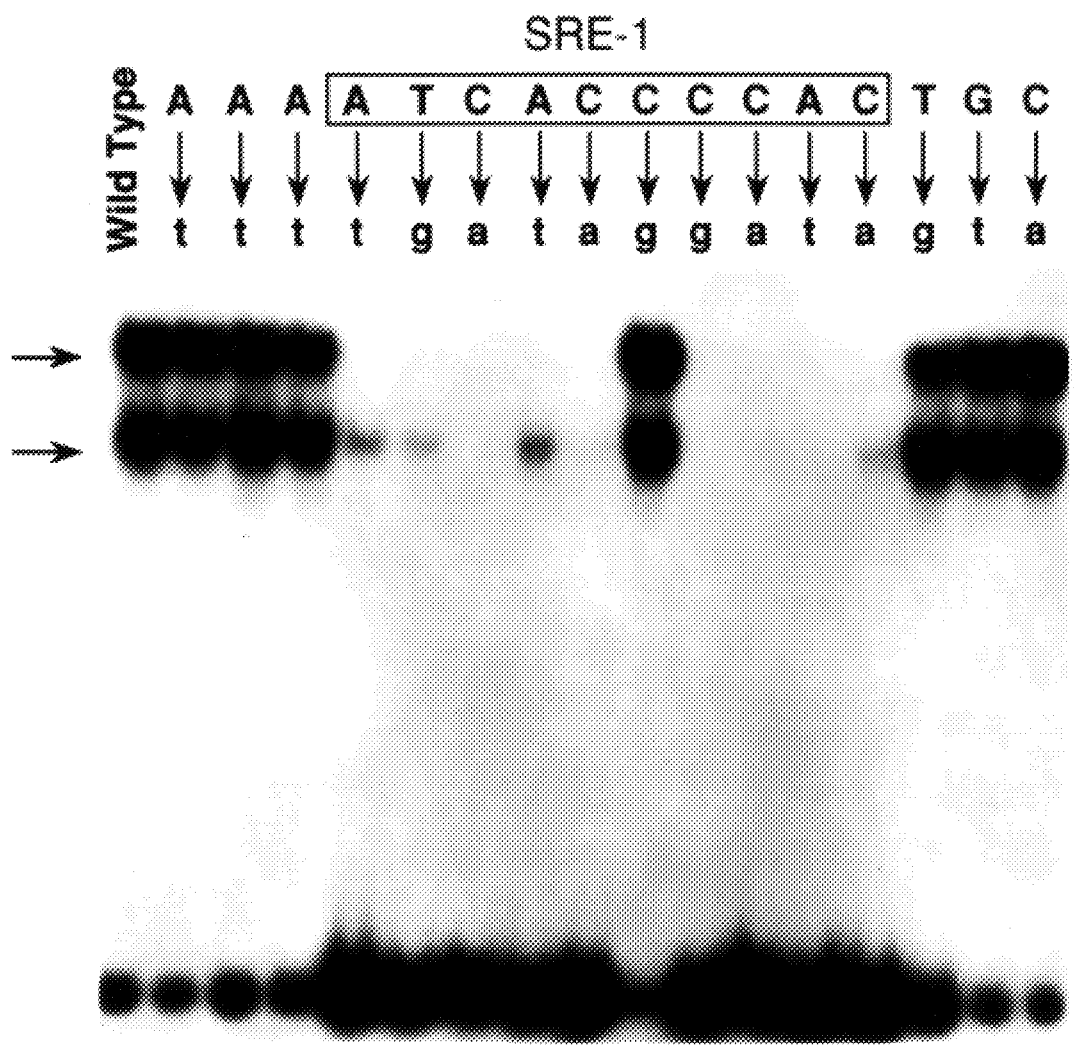
FIG. 11. Binding of purified SREBP to wild-type and mutant forms of Repeat 2. Aliquots (~1 ng) of purified SREBP (Step 8) were incubated in the standard gel shift assay with the indicated wild-type or mutant $^{32}$P-labeled, PCR-derived DNA probe of 94 bp in length. Each $^{32}$P-probe contained two tandem copies of Repeats 2+3 with the indicated point mutation in both copies of Repeat 2. Probes were prepared as described in Example 1. The sequence in upper case letters is designated SEQ ID NO:22. The mutant sequences which each contain the sequence of SEQ ID NO:22 with the exception, in each case, of a single mutation indicated by the lower case letters are designated as SEQ ID NOS:2–17, respectively. The 10-bp sequence of SRE-1 (SEQ ID NO:27) in Repeat 2 is boxed. The gel was exposed for 2 hours. Arrows denote the $^{32}$P-probe containing SREBP bound to one or two sites of Repeat 2.

To confirm the specificity of the SREPP for its DNA recognition site, the purified SREBP was subjected to gel mobility shift assays with a panel of 16 mutant probes that were characterized for transcriptional activity in Example 1 (FIG. 11). The SREBP bound only to the probes that were active in transcription, including the probe that contained a G in place of a C at position 6 of the SRE-1. This result confirms that the purified SREBP has a binding specificity that matches exactly with the transcriptional activity of the SRE-1 element (Example 1).

Figure 12:
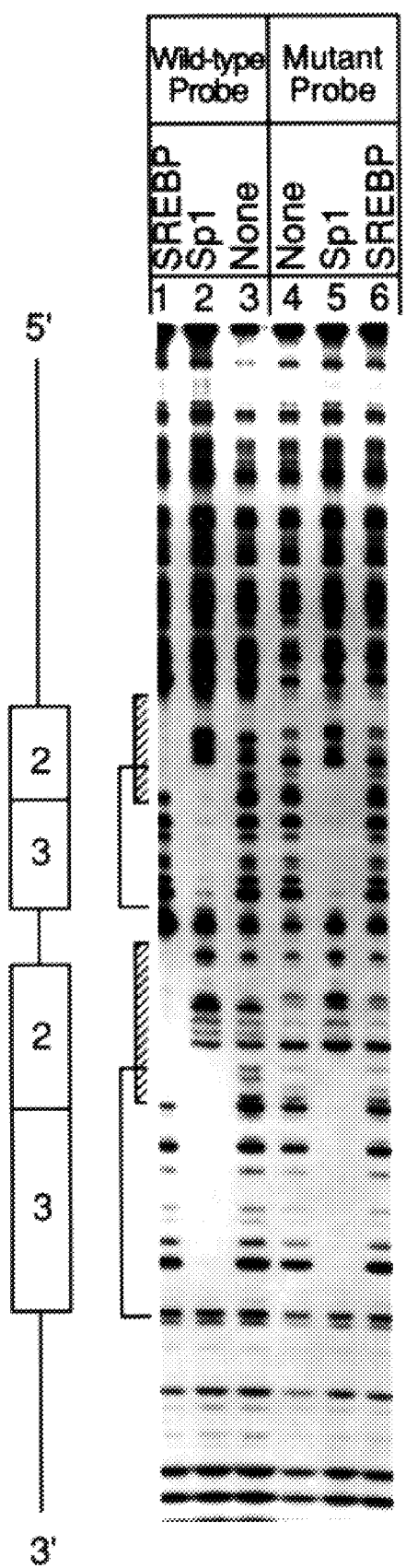
FIG. 12. DNaseI footprint of LDL receptor promoter elements by SREBP and Sp1. A 239-bp DNA fragment from Plasmid K corresponding to wild-type Probe H in gel shift studies (lanes 1–3) or Plasmid X corresponding to mutant Probe * (lanes 4–6) was end labeled with $^{32}$p on the noncoding strand as described in Example 2. The $^{32}$P-fragment (2 fmol, ~$10^4$ cpm) was incubated for 15 minutes at room temperature with one of the following proteins: none, lanes 3 and 4; 10 μg of partially purified SREBP from Step 6 (lanes 1 and 6); and 5 footprint units of purified Sp1 (lanes 2 and 5). After digestion with 40 ng DNaseI for 1 minute at room temperature (Briggs et al., 1986), each reaction mixture was stopped and subjected to electrophoresis on a 6% denaturing gel. The gel was exposed to X-ray film for 12 hours at −70° C. with intensifying screen. The locations of Repeat 2 and Repeat 3 in the $^{32}$P-DNA fragment are indicated at the left. Brackets denote the extent of the protected region (footprint) by SREBP (hatched) or Sp1 (open).

DNaseI footprinting analysis showed that SREBP bound to the SRE-1 sequence within Repeat 2, SEQ ID NO:27, whereas Sp1 bound to Repeat 3, SEQ ID NO:23 (FIG. 12, lanes 1 and 2). The two footprint regions overlapped, with the Sp1 footprint extending partially into Repeat 2. When the SRE-1 sequence was mutated, the SREBP footprint was abolished, but the Sp1 footprint was retained (FIG. 12, lanes 5 and 6).

Figure 13A:
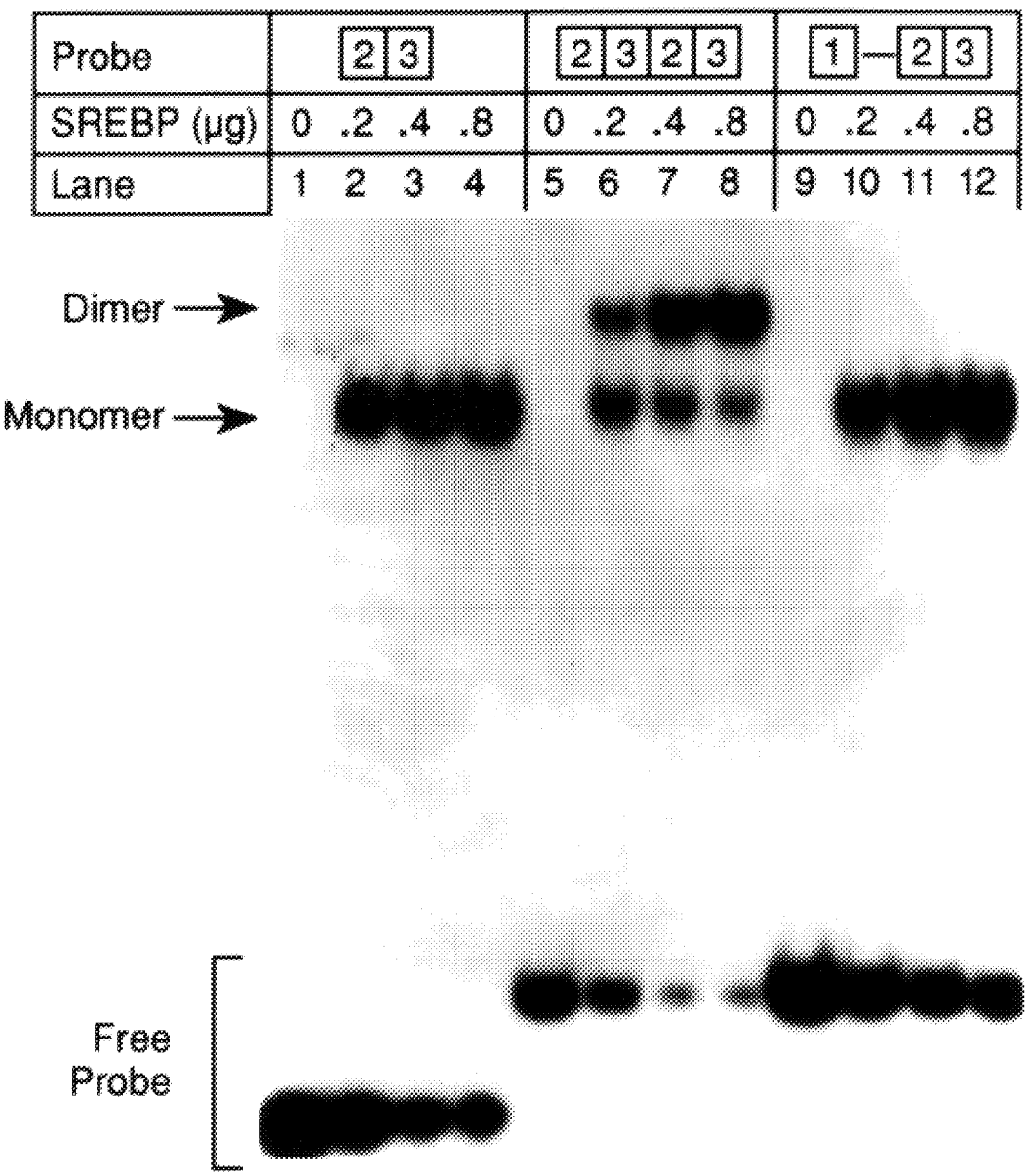
FIG. 13A. Binding of SREBP to oligonucleotides containing one or two copies of SRE-1; the indicated amount of affinity purified SREBP (Step 6) was incubated in the standard gel shift assay with one of the following $^{32}$P-probes: lanes 1–4, 12 fmol ($8\times10^4$ cpm) of $^{32}$P-probe H (see FIG. 5) digested with SalI to yield a 45-bp double-stranded fragment containing one copy of Repeat 2+3 and a 5' overhang of 4 nucleotides; lanes 5–8, 6 fmol ($4\times10^4$ cpm) of $^{32}$P-probe H containing two tandem copies of Repeat 2+3; lanes 9–12, 12 fmol ($8\times10^4$ cpm) of a PCR-generated fragment corresponding to nucleotides −103 to −38 in the human LDL receptor promoter that contains one copy of Repeat 1+2+3 (Brown & Goldstein, 1986). The gel was exposed for 1 hour. Arrows denote the $^{32}$P-probe containing SREBP bound to one or two sites.

In gel mobility shift assays, partially purified SREBP produced two shifted bands when incubated with the $^{32}$P-labeled probe that contained two tandem copies of the Repeat 2+3 sequence (FIG. 13A, lanes 5–8). When the amount of SREBP was increased, the amount of the upper band increased progressively, and the amount of the lower band decreased correspondingly. When the probe contained only a single copy of the Repeat 2+3 sequence, only the lower mobility shifted band was observed (lanes 1–4). Moreover, the lower band was the only one visualized when a probe containing all three of the repeats in the native LDL receptor promoter was used, which includes only one copy of Repeat 2 (lanes 9–12). The present inventors concluded that the lower band represents SREBP bound to one copy of Repeat 2 and that the upper band represents binding to two copies.

Figure 13B:
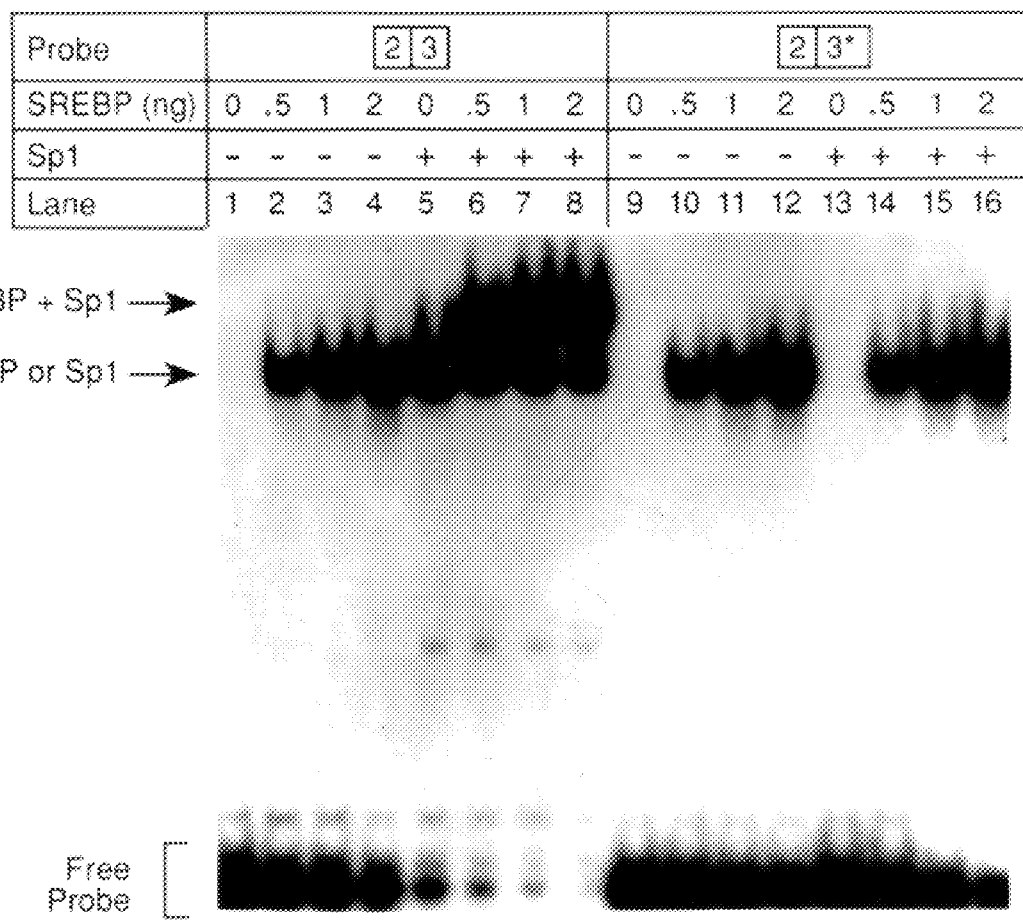
FIG. 13B. Binding of SREBP to oligonucleotides containing one or two copies of SRE-1; the indicated amount of affinity purified SREBP (Step 8) in the absence (−) or presence (+) of 1 footprint unit of purified Sp1 was incubated in the standard gel shift assay except that the oligonucleotide competitor (mutant Repeat 2+wild-type Repeat 3 sequence) was omitted. The following $^{32}$P-probes were used: lanes 1–8, 12 fmol ($8\times10^4$ cpm) of $^{32}$P-probe H (see Panel A); lanes 9–16, 12 fmol ($8\times10^4$ cpm) of a $^{32}$P-labeled, PCR-generated 45-bp double-stranded fragment containing one copy of wild-type Repeat 2 followed by one copy of a mutant Repeat 3 that bears two C→T substitutions that eliminate Sp1 binding. The gel was exposed for 40 minutes. Arrows denote the $^{32}$P-probe containing bound SREBP and/or Sp1 as indicated.

When a prgbe that contained one copy of the Repeat 2+3 sequence was used, increasing amounts of purified SREBP produced only one retarded band (FIG. 13B, lanes 1–4) as in FIG. 13A. Purified Sp1 produced a similar band (lane 5, in FIG. 13B). The addition of increasing amounts of purified SREBP in the presence of Sp1 produced increasing amounts of a second band of slower mobility (lanes 6–8), indicating that Sp1 and SREBP were both binding to the oligonucleotide. When the Repeat 3 sequence was mutated to destroy the Sp1 binding site, the probe still bound SREBP (lanes 9–12), but it did not bind Sp1 (lane 13). In the presence of both proteins, the mutant probe produced only the single retarded band that corresponded to the binding of SREBP (lanes 14–16). These data confirm that SREBP can recognize the SRE-1 sequence in Repeat 2, SEQ ID NO:27, in the absence of any contribution from Repeat 3, SEQ ID NO:23, and that the binding of Sp1 and SREBP are additive.

During the course of these studies, SREBP appeared to lose binding activity in the mobility shift assays as the protein became more highly purified. This loss was particularly dramatic after the first two DNA affinity column steps.

Figure 14:
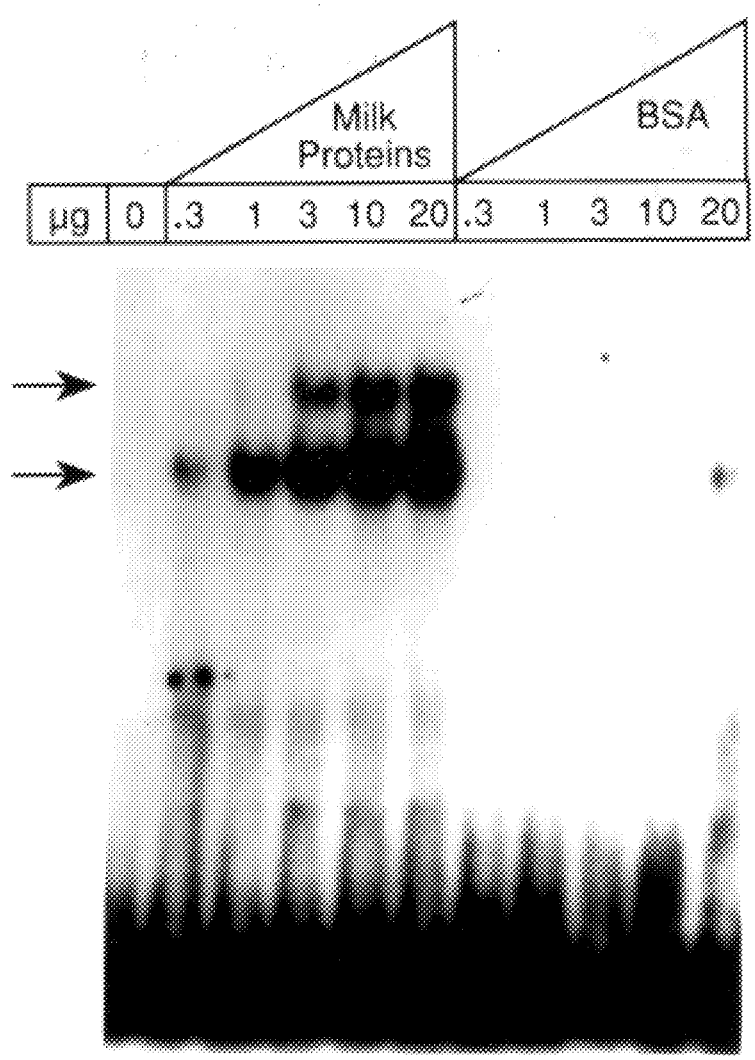
FIG. 14. Activation of SREBP by milk proteins. An aliquot (~0.14 μg) of affinity purified SREBP (Step 6) was incubated in the standard gel shift assay with $^{32}$P-labeled probe H (see FIG. 5) in the presence of the indicated amount of either milk proteins or bovine serum albumin (BSA, Fraction V; Sigma). The gel was exposed for 4 hours. Arrows denote the $^{32}$P-probe containing SREBP bound to one or two sites.

This loss could be prevented by including a variety of proteins in the assay mixture used for the mobility shift assays. The most effective agent consisted of a preparation of bovine nonfat milk proteins that is frequently used to prevent nonspecific binding on nitrocellulose protein blots. FIG. 14 shows that partially purified SREBP caused no detectable band shift activity when assayed in the absence of milk proteins. Increasing the concentration of milk proteins from 0.3 to 20 μg/tube (0.015 to 1 mg/ml) caused a progressive increase in binding activity. Milk proteins had no binding activity in the absence of SREBP. Comparable concentrations of bovine serum albumin had very little stimulatory effect on SREBP (FIG. 14).

In addition to milk proteins, several other proteins stimulated SRE4F activity when tested at 250 μg/ml. These included bovine milk casein, thyroglobulin, fetuin, asialofetuin, bovine submaxillary mucin (type I), fetal calf serum, and the lipoprotein-deficient fraction of newborn calf serum. In addition to bovine serum albumin, other proteins that lacked stimulatory activity included human IgG, bovine milk lactalbumin, and bovine milk lactoglobulin when tested at 250 μg/ml.

C. Discussion

The importance of Repeats 1, 2, and 3 in transcription was first demonstrated in 1987 through linker-scanning mutagenesis studies with the LDL receptor promoter (Südhof et al., 1987). Mutations in any of the three 16-bp sequences abolished high-level transcription in the absence of sterols. Repeats 1 and 3 were assigned functions in binding Sp1 based on their conformity with the consensus recognition sequence for this factor and their demonstrated ability to bind Sp1 in vitro (Dawson et al., 1988). Repeat 2 did not conform to this consensus and it did not bind Sp1. When inserted into heterologous promoters, Repeat 3 enhanced transcription constitutively in the absence or presence of sterols, particularly when present in multiple copies (Dawson et al., 1988). Repeat 2 had enhancer activity only when cells were incubated in the absence of sterols and only when it was present together with Repeat 3 or an Sp1 binding site provided by the heterologous promoter (Smith et al., 1990; Dawson et al., 1988). This led to the hypothesis that Repeat 2 contains a conditional enhancer that increases the activity of Repeat 3, but only in sterol-depleted cells (Goldstein and Brown, 1990; Smith et al., 1990). The nature of the putative sterol-regulated protein that recognizes Repeat 2 had not been settled, despite intensive previous efforts (Rajavashisth et al., 1989; Stark et al., 1992).

Studies of point mutants revealed that the active sequence within Repeat 2 is a 10-bp segment designated SRE-1, SEQ ID NO:27 (Smith et al., 1990; Example 1). In the present example, a protein factor has been purified, designated SREBP, that binds specifically to the SRE-1 in a fashion that correlates precisely with the nucleotide-by-nucleotide requirements for sterol-regulated transcription defined in Example 1. Based on this extensive correlation, the present inventors believe that SREBP mediates the conditional enhancer activity of SRE-1.

Identification and purification of SREBP were especially difficult because the factor is present in trace amounts and because nuclear extracts contain several abundant proteins that bind to oligonucleotides containing this sequence, obscuring the binding of SREBP (FIG. 5). These abundant proteins are not involved in regulated transcription because they bind to oligonucleotides that contain point mutations known to inactivate the SRE-1 (Smith et al., 1990; Example 1). After much trial and error, the present inventors found that the pair of mutants designated M and * were the most discriminatory. These contain a T and an A, respectively, in place of the 3'-most C in the SRE-1. The T-containing sequence, which corresponds to the native SRE-1 sequence in the mouse, is active in transcription, whereas the A-containing sequence is inactive (Example 1).

Even with this panel of three discriminatory oligonucleotides, the first steps of purification were carried out in a blind fashion, without being able to assay for specific binding. The empirical purification scheme that was finally employed was based upon lessons learned during the pursuit of several contaminating proteins that bound Repeat 2 in a fashion that did not correlate with physiological function. Now that the SREBP has been identified and purified, it should be possible to refine and streamline the purification scheme, especially after antibodies to SREBP become available. Furthermore, as detailed in Example 3, now that the present inventors have obtained the cDNA for SREBP-1 a variety of particularly efficient methods for its preparation in a recombinant form are available.

Figure 10:
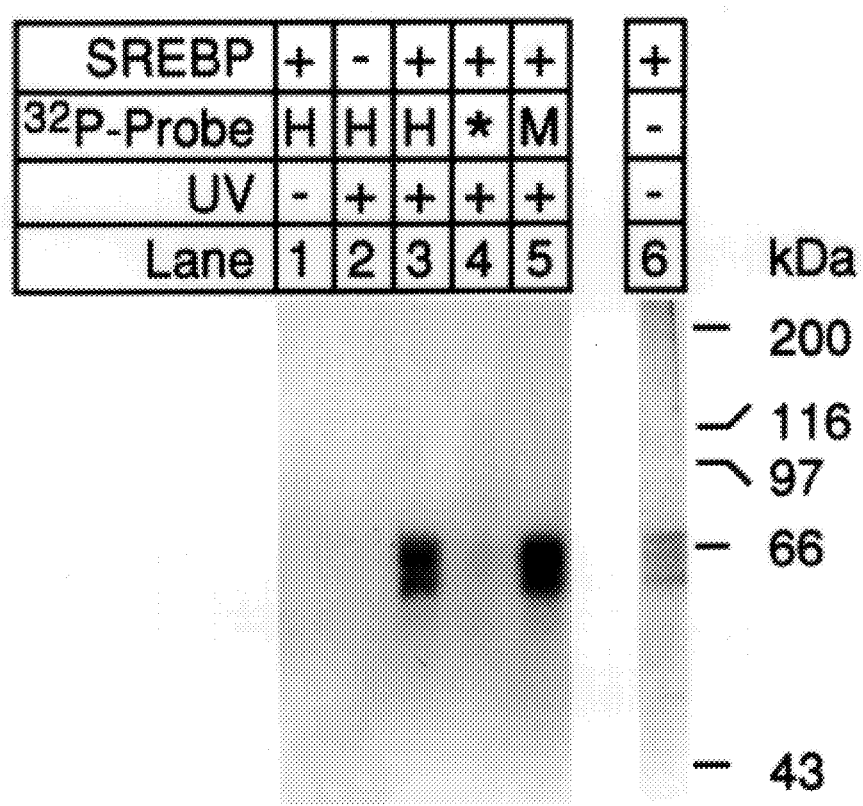
FIG. 10. Photoaffinity labeling of SREBP. Aliquots of partially purified SREBP (lanes 1–5, protein from Step 6 at 4 µg/lane) were incubated with the indicated $^{32}$P-labeled, 5'-bromo-dUTP-substituted probe and subjected to UV crosslinking as described in Example 2. After nuclease digestion, the samples were subjected to electrophoresis on an 8% SDS polyacrylamide gel. Lanes 1–5, autoradiogram of the gel after exposure to X-ray film for 48 hours at −80° C. with an intensifying screen. Lane 6, silver stain of purified SREBP (20 ng protein from Step 8) that was subjected to electrophoresis on the same gel adjacent to the samples in lanes 1–5. See FIG. 5 for description of probes H, M, and *.

The final preparation of SREBP, purified more than 38,000-fold, contains a cluster of protein bands between 59 and 68 kDa that bind the SRE-1 in a specific fashion, as indicated by the crosslinking study (FIG. 10). It is possible that all of these bands represent a single protein that is subject to either multiple covalent modifications, such as phosphorylation, or partial proteolysis. It is also possible that SREBP consists of several closely related proteins. These questions have been partially resolved with the cloning of the SREBP-1 CDNA (Example 3) and further cloning studies are ongoing which will enable these issues to be fully resolved.

When subjected to size fractionation by gel filtration early in the purification, SREBP emerged from the column at a position corresponding to a molecular mass of 500 kDa (FIG. 6). In contrast, the purified protein sedimented on glycerol gradient centrifugation at a slower rate than ovalbumin ($M_r$ 44,000) (FIG. 9). These observations may indicate that SREBP exists as a multiprotein complex which dissociates during purification, or that SREBP is an elongated molecule which behaves anomalously on gel filtration.

In the gel mobility shift assays, the activity of purified SREBP was stimulated markedly by a variety of proteins, including the components of nonfat bovine milk. This enhancing activity was originally noted in the flow-through fraction from the first Repeat 2-containing DNA affinity column. The stimulatory effect was not entirely nonspecific since proteins such as albumin and immunoglobulins failed to substitute. It is possible that a further protein may enhance SREBP activity, but SREBP is clearly active under the conditions described herein.

The availability of the SREBP protein will allow, for the first time, the means by which cells regulate SREBP activity in response to cholesterol to be investigated. Having the purified protein has also allowed both the generation of antibodies against this protein and the molecular cloning of a cDNAs encoding the SREBP protein to be achieved (Example 3). By means of the protein itself and the other biological products which can now be obtained, including the cDNA disclosed herein, the inventors propose to determine further events in the sterol-regulated transcription pathway of the LDL receptor gene. This is one of the subjects of the following example, Example 3.

In addition to the LDL receptor gene, the genes for 3-hydroxy-3-methylglutaryl CoA (HMG CoA) synthase and HMG CoA reductase are repressed by sterols (Goldstein and Brown, 1990). The 5' flanking region of the HMG CoA synthase gene contains three regions that are required for sterol-regulated transcription (Smith et al., 1988). Two of these regions contain SRE-1 sequences that may conform to the requirements for binding of SREBP. The 5' flanking region of the HMG CoA reductase gene also contains a region that is necessary for sterol-mediated regulation (Goldstein and Brown, 1990; Osborne et al., 1988). This region contains a sequence that loosely resembles the SRE-1, which led to the suggestion that the HMG CoA reductase gene might be regulated by the same protein that regulates the LDL receptor (Smith et al., 1988). More extensive mutagenesis studies (Osborne, 1991) indicate that the putative sterol regulatory element in HMG CoA reductase should not bind to SREBP as defined in the current studies (Example 1), and this has indeed proved to be the case, see FIG. 23 as discussed in Example 3. Moreover, Osborne et al. (1992) have recently identified a protein designated Red25 that recognizes the sterol-sensitive HMG CoA reductase sequence. This protein does not recognize the SRE-1 from the LDL receptor, indicating that the control mechanisms for the two genes are distinct.

EXAMPLE 3

Molecular Cloning, Sequencing and Further Analysis of SREBP-1

The present example describes the isolation and functional analysis of a cDNA encoding SREBP-1. The analysis shows that SREBP-1 is a new member of the basic helix-loop-helix leucine zipper (bHLH-Zip) family of DNA binding proteins (Murre and Baltimore, 1992; Pabo and Sauer, 1992; Ferré-D'Amaré et al., 1993). This example also demonstrates that, when expressed in animal cells by transfection, SREBP-1 activates transcription of a reporter gene driven by the SRE-1 sequence.

A. Materials and Methods

1. Materials. Standard molecular biology techniques were used (Sambrook et al., 1989). cDNA fragments were subcloned into pBluescriptII SK+ (Stratagene) or pCRII vectors (Invitrogen) and sequenced by the dideoxy chain termination method (Sanger et al., 1980) using M13 universal and reverse sequencing primers; T7, T3, and SP6 promoter primers; or specific internal primers. Sequencing reactions were performed on an Applied Biosystems Model 373A DNA Sequencer. Selected regions of the cDNA were manually sequenced with a Sequenase kit (U.S. Biochemicals). Randomly primed probes were synthesized using a random primer labeling kit (Pharmacia). p1471 (Smith et al., 1990) and pRedCAT-1 (Osborne et al., 1988) were described in the indicated references each incorporated herein by reference.

2. Amino Acid Sequence of Human SREBP. SREBP was purified from nuclear extracts prepared from 1500 liters of HeLa cells by repetitions of the procedure described herein in Example 2. About 6 µg of the purified protein, consisting of a cluster of bands at 59–68 kDa on SDS-PAGE, was precipitated with 10% (v/v) trichloroacetic acid, washed with acetone, and dissolved in a buffer containing 0.4M ammonium bicarbonate, 8M urea, and 5 mM dithiothreitol at 55° C. with vortexing. After treatment with 10 mM iodoacetamide, the protein was digested with sequencing grade trypsin (Boehringer-Mannheim) as described (Stone et al., 1989). The resulting peptides were separated by reverse-phase HPLC using a 0.1% (v/v) trifluroacetic acid and acetonitrile gradient on a 1-mm×25-cm RP-300 column (Applied Biosystems). The resolved peptides were collected and sequenced by automated Edman degradation on an Applied Biosystems Model 477A sequencer using standard chemistry, a micro-reaction cartridge, and fast cycles.

3. cDNA Cloning of Human SREBP-1. An aliquot (10 ng) of purified phage template DNA from a HeLa λgt10 CDNA library (Clontech) was amplified with 300 pmol of a degenerate oligonucleotide (primer 1; SEQ ID NO:45) from the COOH-terminal end of Peptide 3 (Table IV), 5'-TT(T/C)TC(T/C)TG(T/C)TTIAG(T/C)TT(T/C)TG-3' (SEQ ID NO:55); and 20 pmol of a λgt10 vector reverse primer, 5'-GGCTTATGAGTATTTCTTCCAGGG-3'; SEQ ID NO:46. The primers were removed by passage over a Qiagen Tip-column, and ½0th of the PCR reaction product was subjected to a second round of PCR with 160 pmol of a degenerate oligonucleotide (primer 2; SEQ ID NO:47) from the NH$_2$-terminal end of Peptide 3, 5'-TT(T/C)TG(A/G)TTIGA(A/G)TG(T/C)TG-3' (SEQ ID NO:56), and 20 pmol of the λgt10 vector reverse primer. PCR products were isolated by agarose gel electrophoresis and subcloned into the pCRII vector using a TA Cloning™ Kit (Invitrogen). The DNA sequence of the resulting 345-bp PCR product encoded Peptides 2, 5, and 6 of SREBP (Table IV). The 345-bp PCR product was randomly labeled with $^{32}$P-dCTP ($4\times10^5$ cpm/ml) and used to screen HeLa cDNA libraries as described below.

Poly(A)$^+$ RNA from HeLa S3 cells cultured in 2.5% (v/v) newborn calf serum (Example 2; Wang et al., 1993) was isolated with Oligotex-(dT)30® resin (Qiagen) and used to construct a T7-driven λEXlox® vector-based cDNA library (Novagen). First-strand synthesis was carried out with a combination of oligo(dT) and random primers. After second-strand synthesis, the double-stranded cDNA was ligated to EcoRI(NotI) Adapters containing a SalI restriction site (Gibco-BRL), inserted into XEXlox-EcoRI arms (Novagen), and packaged with Gigapack®II Packaging Extract (Stratagene).

The HeLa λgt10 and HeLa λEXlox libraries were screened by hybridizing duplicate filters with the 345-bp PCR probe (see immediately above) at 60° C. overnight in 3× SSC containing 0.1% (w/v) SDS, 5× Denhardt's, and 50 µg/ml salmon sperm DNA, and washed three times with 3× SSC/0.1% SDS at room temperature for 5 minutes and twice with 0.1× SSC/0.1% SDS at 60° C. for 20 minutes. Of $6\times10^5$ plaques screened in the λEXlox library, 7 positive clones were identified and subcloned into the NotI site of pBluescriptII SK+. The two longest clones (pCY21 and pCY22) were characterized. Of the $5\times10^5$ plaques screened in the λgt10 library, 6 positive clones were identified and subcloned into the EcoRI site of pBluescriptII SK+. The clone containing the most 5' sequence (pCY5) was characterized.

4. Construction of Expression Vectors for pSREBP-1. Vectors for expression of human SREBP-1 in cultured animal cells were constructed in pCMV7, a modified version of pCMV5 (Andersson et al., 1989) that contains a hybrid adenovirus/immunoglobulin intron (obtained from David W. Russell of the University of Texas Southwestern Medical Centre at Dallas). Plasmid pSREBP-1a was constructed by digesting pCY5 with SalI and Eco47III to obtain the vector and 5' cDNA sequences and ligating them into the 2989 bp Eco47III-SalI fragment encoding the 3' end of pCY21 (FIG. 15). This pBluescriptII SK-based vector was digested with BamHI and HincII, and the cDNA fragment (4183-bp) was cloned into a BamHI-SmaI-digested pCMV7 vector. pSREBP-1b was constructed by digesting pCY5 with XbaI and Eco47ITI (1204-bp) to obtain the 5' cDNA sequence and ligating it into a XbaI-Eco47III (5615-bp) fragment encoding the 3' end of pCY22. This cDNA was subcloned into pCMV7 as described for pSREBP-1a. pSREBP-1c was constructed by inserting the SalI fragment of pCY22 into the SalI site of pCMV7, and the orientation was confirmed by restriction mapping. All restriction sites used in the above constructions except Eco47III are present in the linker sequences.

5. Blot Hybridization of RNA. Poly(A)+ RNA from human adrenal and northern blots containing 2 μg of poly (A)+ RNA from multiple human adult and fetal tissues were purchased from Clontech. Poly(A)+ RNA from HeLa S3 cells cultured in 2.5% (v/v) newborn calf serum (Example 2; Wang et al., 1993) was prepared with Oligotex-(dT)30® beads (Qiagen). Blots were hybridized with a random primed probe synthesized from the 3.6-kb NotI fragment of pSREBP-1c. Hybridizations were performed in 5× SSPE containing 50% formamide at $2 \times 10^6$ cpm per ml for 16 hours at 42° C. After hybridization, each filter was washed once with 1× SSC and 0.05% SDS for 30 minutes at room temperature and twice with 0.1× SSC and 0.1% SDS for 20 minutes each at 50° C. After exposure to Kodak XAR-5 film for the indicated time, each filter was reprobed with a $^{32}$P-labeled cDNA (1.2 kb) for rat glyceraldehyde-3-phosphate dehydrogenase (Chen et al., 1991) at $4 \times 10^6$ cpm per ml.

6. In Vitro Translation of SREBP-1 mRNA. pSREBP-1c was cloned into the SalI site of pBluescript SK+, purified by CsCl banding, and translated in a TNT™ T7 Coupled Reticulocyte Lysate System (Promega). Each coupled transcription-translation reaction contained 1 μg plasmid DNA in a final volume of 50 μl and was incubated at 30° C. for 2 h. For radiolabeling, pSREBP-1c was translated in a methionine-free amino acid mixture supplemented with [$^3$S] methionine according to the manufacturer's instructions. An aliquot (1 μl) of the reaction was added to 20 μl of SDS sample buffer (Laeimmli, 1970) and subjected to electrophoresis on a 4–15% gradient gel. The gel was fixed in 50% (v/v) methanol and 10% (v/v) acetic acid for 20 minutes, treated with Enlightening™ enhancer solution (NEN-DuPont) for 15 minutes at room temperature, dried, and exposed to Kodak X-ray film at −80° C. for 16 h. For gel mobility shift assays, pSREBP-1c was translated with unlabeled amino acids. An aliquot (3 μl) of the reaction was assayed directly in the gel mobility shift assay.

7. Gel Mobility Shift Assays. SREBP was incubated with a PCR-generated $^{32}$P-labeled DNA probe containing one or two tandem copies of wild-type or mutant Repeat 2+3 elements of the LDL receptor promoter as described above in Examples 1 and 2 and in the bief description of the drawings. Probes were synthesized, and electrophoresis was performed as previously described in Examples 1 and 2 above (and Briggs et al., 1993; Wang et al., 1993).

The 5'-biotin-labeled, double-stranded oligonucleotide used herein (synthesized as described in Applied Biosystems User Bulletin Number 70 38X/39X) contains two tandem copies of the Repeat 2 sequence with the C at position 6 in the SRE-1 sequence changed to a G, which does not affect its in vitro binding or in vivo transcriptional activity. The wild-type and the mutant competitor oligonucleotides (double-stranded) used are the same ones used to construct DNA affinity column B and A, respectively, as described above in Example 2 and in Wang et al. (1993).

8. Production of Recombinant bHLH-Zip Domain of SREBP-1. pSREBP-1(bHLH-Zip) is a recombinant plasmid that encodes a fusion protein of 130 amino acids. The COOH-terminal 107 amino acids comprises the basic-helix-loop-helix-zipper (bHLH-Zip) domain of SREBP-1a (residues 301–407 of SEQ ID NO:38). The NH$_2$-terminal 23 amino acids includes an initiator methionine followed by three functional elements: 1) His His His His His His (SEQ ID NO:48), site for Ni$^{2+}$ binding; 2) Asp Asp Asp Asp Lys (SEQ ID NO:49), site for a specific endopeptidase (enterokinase); and 3) Arg Arg Ala Ser Val (SEQ ID NO:50), site for the catalytic domain of heart muscle kinase (Blanar and Rutter, 1992).

pSREBP-1(bHLH-Zip) was constructed by PCR with pSREBP-1c as a template and the following two primers: 5' oligonucleotide, CGCGGATCCGATGACGATGA-CAAACGTCGTGCATCTGTTGAGAAGCT-GCCTATCAACCGG (SEQ ID NO:51; corresponding 5' to 3' to the BamHI cloning site, followed by sequences for the enterokinase site, heart muscle kinase site, and SREBP-1); 3' oligonucleotide, CTAATTAAGCTTACTATCCACTGCCA-CAGGCCGACAC (SEQ ID NO:52; corresponding 3' to 5' to the HindIII cloning site and part of the SREBP-1 sequence). The amplified PCR product was digested with BamHI and HindIII and inserted into pQE-30, a bacterial expression vector that contains sequences encoding an initiator methionine and 6 consecutive histidine residues preceding a polylinker cloning site (Qiagen).

The resulting pSREBP-l(bHLH-Zip) was transformed into E. coli host strain M15[pREP4] (Qiagen), grown in 1 liter cultures at 37° C., and induced with IPTG for 5 h. The cells were collected by centrifugation; disrupted by stirring at room temperature for 1 hour in 6M guanidine-HCl, 0.1M sodium phosphate, 10 mM Tris-chloride at pH 8.0; and centrifuged at 10,000 g for 15 minutes at 4° C. The supernatant solution was subjected to Ni$^{2+}$-sepharose affinity chromatography under conditions recommended by the manufacturer (Qiagen). The bHLH-Zip fusion protein was eluted with 250 mM imidazole, 8M urea, 0.1M sodium phosphate, 10 mM Tris-chloride at pH 6.3 and then dialyzed overnight at 4° C. into Buffer A (25 mM Hepes-KOH at pH 7.5, 12 mM MgCl$_2$1 10% (v/v) glycerol, 0.5 mM phenyl-methylsulfonyl fluoride, 0.5 mM dithiothreitol, 0.1M KCl). The dialyzed fusion protein (~0.2 mg/ml) was stored in multiple aliquots at −80° C.

9. Transfection, Immunoblot Analysis, and Reporter CAT Assays. For immunoblot analysis, monolayers of human embryonic kidney 293 cells were set up ($3 \times 10^5$ cells/60-mm dish) in Dulbecco's modified Eagle's medium (DMEM) containing 10% fetal bovine serum, 100 units/ml penicillin, and 100 μg/ml streptomycin. After incubation for 24 hours, the cells were transfected with 3 μg of either the indicated pSREBP-1 or the control vector pCMV7 plus 0.3 μg of pVA (a plasmid encoding adenovirus VA RNA$_1$) (Akusjarvi et al., 1987) using the calcium-phosphate method (Sambrook et al., 1989). Four hours after transfections, the cells were washed twice with phosphate-buffered saline (PBS) and refed with fresh medium. After 40 hours, cells were washed once with ice-cold PBS and harvested in PBS. The resulting cell pellets were lysed with 0.3 ml lysis buffer containing 1 (w/v) SDS (Gil et al. 1985). Cell extracts were sheared through a 20-G needle and subjected to electrophoresis and immunoblot analysis.

For in vivo functional analysis, monolayers of human 293 cells and simian CV-1 cells were established as described above in Example 1. Varying amounts of pSREBP-1a (0 to 1 μg) were cotransfected with the indicated reporter CAT gene (Example 1; Briggs et al., 1993). In FIG. 22, the total amount of DNA was adjusted to 3.3 gg (293 cells) or 12 μg (CV-1 cells) by the addition of pCMV7. After transfection, the medium was changed to DMEM containing 10% calf lipoprotein-deficient serum in the absence or presence of sterols (10 μg/ml cholesterol plus 1 μg/ml 25-hydroxycholesterol added in 20 μl ethanol). After incubation for 40–48 h, cells were harvested, and CAT activity was measured by the xylenes extraction method. Protein concentration was determined by the method of Bradford (1976).

10. Antibodies and Immunoblotting. An antibody directed against SREBP-1 was produced by immunizing rabbits with a synthetic peptide, (C)KPEQRPSLHS, corresponding to amino acids 470 to 479 in SREBP-1a (FIG. 16A, FIG. 16B, FIG. 16C, FIG. 16D, FIG. 16E, FIG. 16F, FIG. 16G, FIG. 16H, FIG. 16I, FIG. 16J, FIG. 16K, FIG. 16L; SEQ ID NO:38). The peptide was coupled to keyhole limpet hemocyanin usinig m-maleimidobenzoic acid N-hydroxysuccinimide ester (Harlow and Lane, 1988). New Zealand White rabbits were immunized with 500 μg of coupled peptide in Freund's complete adjuvant, and IgG fractions were prepared (Harlow and Lane, 1988). Immunoblot analysis was performed with anti-rabbit horseradish peroxidase-conjugated IgG using the Enhanced Chemiluminescence (ECL) Western Blotting Detection System Kit™ (Amersham). Gels were calibrated with prestained high and low-range molecular weight markers (BioRad).

B. Results

Figure 15A:
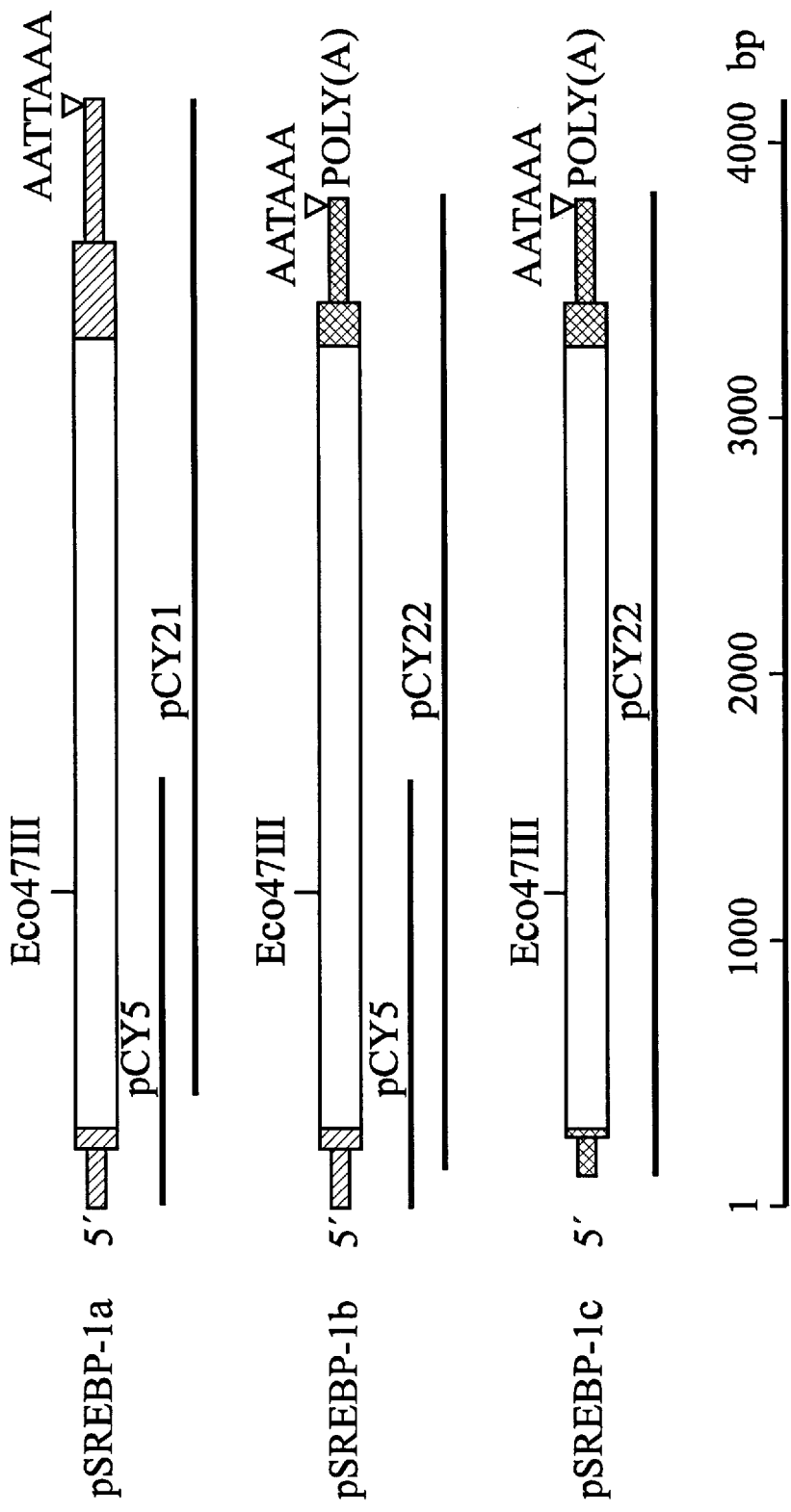
FIG. 15A. SREBP-1 Plasmid Constructs. cDNAs encoding SREBP-1 sequences (pCY5, pCY21, and pCY22) are denoted by the solid lines. To generate plasmid constructs pSREBP-1a and pSREBP-1b, the Eco47III site at nucleotide position 1167 of pSREBP-1a (FIG. 2) was used to fuse the 5' end-of pCY5 to the 3' end of either pCY21 or pCY22 as indicated. Plasmid pSREBP-1c was generated as the SalI fragment of pCY22. Identical sequences in all three plasmid constructs are denoted by the open boxes. The 5' sequences of pCY22 and pCY5 differ in the regions denoted by the crosshatched and single hatched boxes shown in the plasmid constructs (see below). The 3' sequences of pCY22 and pCY21 differ in the regions denoted by the solid and hatched boxes shown in the plasmid constructs; the sequences diverge at nucleotide position 3269 in pSREBP-1a (see below and FIG. 16).

SREBP was purified from pooled extracts of HeLa cell nuclei as previously described (Example 2; Wang et al., 1993). The final preparation showed a cluster of bands between 59 and 68 kDa on silver-stained SDS polyacrylamide gels. The entire fraction from the final DNA affinity chromatography step was subjected to tryptic digestion, and peptides were fractionated by HPLC and sequenced as described in Experimental Procedures. Six unambiguous sequences were obtained (Table IV). Degenerate oligonucleotides encoding a portion of Peptide 3 (residues 372 to 387 of SEQ ID NO:38) were used to prime polymerase chain reactions (PCR) with a HeLa cell cDNA library as template. This yielded a unique DNA sequence that was used to probe two HeLa cDNA libraries. Three overlapping partial cDNAs, designated pCY5, pCY21, and pCY22, were characterized. These three cDNAs had the identical sequence over most of the coding region (indicated by the open box in FIG. 15A), but they differed at the 5' and 3' ends, suggesting the possibility of alternative splicing or cloning artifact (FIG. 15A).

TABLE IV

| Peptide | Amino Acid Sequence | Amino Acid Position in SEQ ID NO:38 (Derived from cDNA) |
|---|---|---|
| 1 | $^A/_S$ KPEQRPSLHSR | 469–480 |
| 2 | AAGLSPLVSGTTVQTGPLPTLV$^S/_R$ | 264–286 |
| 3 | FLQHSNQKLKQENLSL | 372–387 |
| 4 | SFTQVTLPSFSPSAASPQA (SEQ ID NO:44) | Not Found |
| 5 | LAAGSKAPASAQSRGE$^K/_I{}^R$ | 308–325 |
| 6 | SSINDKIIELK | 337–347 |

Sequences were obtained from HPLC-purified tryptic peptides isolated from purified SREBP. Each peptide represents a pure species from a single HPLC peak. Amino acid sequences corresponding to 5 of the 6 peptides were found in the amino acid sequence predicted from the cDNAs for SREBP-1 (SEQ ID NO:38). The sequence corresponding to peptide 4 (SEQ ID NO:44) was not found in the cDNA (FIG. 15). Three positions of ambiguity in the amino acid sequences are noted, and the bold residue denotes the amino acid found in the cDNA-derived sequence. The solid and dotted underlines for Peptide 3 correspond to amino acids used to derive oligonucleotide primers 1 and 2, respectively, for PCR reactions in cDNA cloning, as described herein.

FIG. 15B shows the divergent sequences. The 5' end of pCY5 predicts a 5' untranslated region of 166 nt (residues 1–166 of SEQ ID NO:37) which contains an inframe stop codon (single underline in FIG. 15B). The first methionine (double underline) occurs within a good consensus for translational initiation as defined by Kozak (1984). The 5' end of pCY22 is shorter than that of pCY5, and the open reading frame continues to the 5' end. The 5' nucleic acid sequence of pCY22 is represented by SEQ ID NO:39 and the corresponding amino acid sequence by SEQ ID NO:40. At the 3' end the sequences of pCY21 and pCY22 are identical up to nucleotide 3268 of the composite sequence (FIG. 15A), after which they diverge completely. pCY21 encodes an additional 113 amino acids followed by a stop codon and a 3' untranslated region of 544 bp with a potential polyadenylation signal 16 bp from the 3' end of the clone. Both of these sequences are located within SEQ ID NOS:37 and 38. No poly(A) sequence is present. pCY22 encodes only 37 amino acids (SEQ ID NO:42) followed by a stop codon, 433 bp of 3' untranslated region, including a poly(A) sequence preceded by a potential polyadenylation signal. The 3' nucleic acid sequence of pCY22 is represented by SEQ ID NO:41.

For functional studies, the inventors produced an expressible composite cDNA encompassing the 5' end of pCY5, the invariant region, and the 3' end of pCY21 (designated pSREBP-1a in FIG. 15A). This combination was chosen on the basis of information obtained frgm two different cDNA clones isolated from two different Chinese hamster ovary cell cDNA libraries. These clones, apparently of full length, contained 5' ends that closely resembled the coding region of pCY5 and 3' ends whose coding regions resembled that of pCY21. Both hamster cDNAs encode a protein of 1133 amino acids that shows 81% identity to the predicted sequence encoded by the human pSREBP-1a. Human pSREBP-1b (5' end of pCY5 and 3' end of pCY22) and pSREBP-1c (5' and 3' ends of pCY22) were also prepared.

FIG. 16 shows the predicted amino acid sequence encoded by human pSREBP-1a, SEQ ID NOS:37 and 38 respectively. The cDNA encodes a protein of 1147 amino acids, which includes five of the six peptides whose sequences were obtained (indicated by underlines in FIG. 16). The sixth peptide (Peptide 4 in Table IV; SEQ ID NO:44) was not found in the cDNA sequence, and it is believed that it is derived from another protein in the purified SREBP preparation (see Discussion below).

A search of the GenBank, PIR, and SWISS-PROT data banks revealed only one region of SREBP-1 that showed a close match with other proteins. Amino acid residues 324–394 of SREBP-1 (i.e., of SEQ ID NO:38) conform to the consensus sequence for the basic helix-loop-helix leucine zipper (bHLH-Zip) class of DNA binding proteins (FIG. 17A). In the bHLH region, the closest overall match to SREBP-1 is a transcription factor designated TFE3 that activates the immunoglobulin μE3 motif (Beckmann et al., 1990). The sequence identity within this region was 44%. Sequence identity with other bHLH proteins was in the range of 33%. The putative leucine zipper region of pSREBP-1 consists of one alanine, three leucines, and one serine spaced at intervals of 7 residues (FIG. 17B). This sequence begins within the second helix of the HLH motif, a feature that is also observed in several other transcription factors, including AP4, CBF1, TFE3, and TFEB (Ferré-D'Amaré et al., 1993). Helical wheel analysis of this sequence confirms the segregation of hydrophobic residues on orie face, suggesting a true "leucine zipper" (Landschulz et al., 1988; Pabo and Sauer, 1992).

The protein encoded by pSREBP-1a (SEQ ID NO:38) contains several other noteworthy features. At the extreme $NH_2$-terminus there is a stretch of 42 residues that contains 12 negatively charged amino acids and no positively charged amino acids (the first positively charged residue occurs at position 108). The acidic region is predicted to be largely a-helical as determined by the method of Garnier et al. (1978). The acidic region (residues 1–42) is followed by a serine/proline rich region (28% proline and 18% serine) extending from residues 61–178. Following the bHLH-Zip region, there is a stretch of 36 amino acids (residues 427–462) that contains 33% serine, 19% glycine, and 19% proline (71% Ser +Gly +Pro).

Northern blots of human poly(A)$^+$ RNA indicate that pSREBP-1 is expressed in a wide variety of tissues and is most abundant in liver and adrenal (FIG. 18A, left and middle panels), the two tissues that express the highest concentration of LDL receptors (Brown and Goldstein, 1986). Among fetal tissues (FIG. 18A, right panel), the liver and lung showed high expression (the fetal adrenal was not tested). In all tissues there was a predominant mRNA of ~4000 nucleotides. The diffuse nature of the band raises the possibility of alternately spliced variants of similar size.

A polyclonal antibody was raised against amino acid residues 470–479 of SREBP-1a (470–479 of SEQ ID NO:38; part of Peptide 1 in Table IV), and this reacted with purified SREBP on immunoblots (FIG. 18B). The antibody also reacted with SREBP-1 that was produced in human embryonic kidney 293 cells after transfection with an expression vector containing pSREBP-1a (lanes 2 and 5), pSREBP-1b (lane 3), and pSREBP-1c (lane 4). As expected, pSREBP-1b and pSREBP-1c produced proteins that were slightly smaller than the one encoded by pSREBP-1a, owing to shorter coding regions at the 5' and 3' ends (see FIG. 15). Control cells transfected with the vector alone did not contain sufficient endogenous SREBP-1 to be recognized by this antibody (lane 1). All of the cDNA-encoded versions of SREBP-1 were considerably larger than the protein that was purified from HeLa cells (lane 6), indicating that the purified protein was proteolyzed; either by a physiologic process occurring within the cell or during the purification procedure.

To test the DNA binding activity of the protein encoded by pSREBP-1, gel retardation assays were performed (FIG. 19) with three $^{32}$P-labeled oligonucleotide probes: Probe H, which contains the wild-type human SRE-1 sequence; Probe M, which is transcriptionally active and contains a T substituted for a C at position 10 in the SRE-1 sequence (corresponding to the wild-type mouse sequence); and Probe *, which contains an A for C at position 10 and is transcriptionally inactive as disclosed herein above in Examples 1 and 2. The partially purified SREBP from HeLa cells bound to probes H and M, but not * (FIG. 19, lanes 7–9). Full-length SREBP-1c translated in a reticulocyte lysate system bound Probes H and M, but not Probe * (lanes 4–6). The retarded band migrated more slowly than the band produced by purified HeLa SREBP (lanes 7–9), which is the expected result based on the larger size of the in vitro translated product. The reticulocyte lysate mixture without pSREBP-1c gave no retarded band (lanes 1–3). In the same assay, the binding activity of a small fragment containing the bHLH-Zip domain of SREBP-1 (amino acids 301–407 of SEQ ID NO:38), that was produced by expression of a fragment of pSREBP-1c in *E. coli*, was tested. This peptide also bound Probes H and M, but not * (lanes 10–12), indicating that the bHLH-Zip domain contains the specific DNA binding activity. As expected, this retarded band showed fast mobility, owing to the small size of the bHLH-Zip fragment (107 amino acids).

When a plasmid containing pSREBP-1c was translated in a reticulocyte lysate system in the presence of [$^{35}$S] methionine, the translation product on SDS PAGE migrated as a major protein of ~130 kDa and several minor proteins of lower molecular weight (FIG. 20, lane 1). To demonstrate that the DNA binding activity detected by gel mobility shift assay in FIG. 19 was due to the full-length translated SREBP-1, aliquots of the translated mixture were incubated with a biotinylated oligonucleotide containing a wild-type SRE-1 sequence. The bound proteins were isolated by adsorption to a Streptavidin-agarose gel and analyzed by SDS PAGE. When the incubation mixture contained an excess of nonbiotinylated oligonucleotide encoding the wild-type SRE-1 sequence as a competitor, none of the SREBP-1 was bound to the Streptavidin-agarose (lane 2). When the nonbiotinylated oligonucleotide contained a mutant SRE-1 sequence that is not transcriptionally active, competition failed to occur, and the full length SREBP-1 was bound to the Streptavidin-agarose (lane 3).

Described herein above (see Example 1) are a series of 16 point mutations in the SRE-1 and flanking sequences which give clear-cut results with regard to transcriptional activity. Seven of the mutants are induced normally by sterol depletion after transfection into cultured cells, and nine are induced poorly, if at all. Purified SREBP from HeLa cells bound only to the seven mutants that were efficiently induced (Example 2). FIG. 21 shows that the same pattern of binding was found for the recombinant truncated bHLH-Zip domain of SREBP-1 that was produced in *E. coli*. The bHLH-Zip domain bound to the wild-type SRE-1 sequence and to all seven of the mutants that retained transcriptional induction, including the highly diagnostic sequence that contains a G in place of the C at position 6 of the SRE-1. On the other hand, the bHLH-Zip domain protein failed to bind to any of the oligonucleotides that had point mutations at any of the other nine positions in the SRE-1 sequence. This finding indicates that the bHLH-Zip domain, which contains only 107 amino acids, contains the structural information sufficient for specific DNA binding.

To test the functional activity of SREBP-1 in vivo, a reporter plasmid (Plasmid K) that contains two copies of the SRE-1 sequence upstream of a gene encoding bacterial chloramphenicol acetyltransferase (CAT) was employed. In the native LDL receptor promoter, the 10-bp SRE-1 sequence is contained within a 16-bp element designated Repeat 2, which is followed by a distantly related sequence designated Repeat 3. Although Repeat 3 binds transcription factor Sp1, it is insufficient to give high-level transcription on its own, and it requires a contribution from the SRE-1 element within Repeat 2 (Smith et al., 1990; Example 1 herein above). The latter element is active only when cells are deprived of sterols. Plasmid K contains two copies of the Repeat 2+3 sequence in tandem followed by a TATA box from adenovirus E1b (Example 1). When transfected into cells, this construct gives rise to high levels of CAT enzyme activity in the absence of sterols, and the activity is suppressed by sterols, owing to removal of the positive contribution of the SRE-1 sequences (Example 1).

Plasmid K was cotransfected into simian CV-1 cells (FIG. 22A) and human 293 cells (FIG. 22B) together with varying amounts of a plasmid encoding pSREBP-1a. In the absence of pSREBP-1a, the CV-1 cells produced 7-fold more CAT activity in the absence as compared with the presence of sterols. Increasing amounts of pSREBP-1a increased the amount of CAT activity under both conditions of incubation, but the relative effect in the presence of sterols was more profound. As a result, at high levels of SREBP, CAT activity was the same in the absence and presence of sterols. Similar results were obtained with the 293 cells. In the absence of SREBP, these cells also showed a 5-fold higher CAT activity when sterols were depleted. When pSREBP-1a was present, CAT activity was increased 15-fold in the absence of sterols. Again the relative stimulation was greatest in the presence of sterols (90-fold) so that at high levels of pSREBP-1a CAT activity was actually higher in the presence of sterols than in their absence.

To confirm that the transcriptional stimulation by pSREBP-1a was dependent on the SRE-1, the cotransfection study was repeated with reporter plasmids that contain inactivating mutations in both copies of the SRE-1 (FIG. 23). One of these plasmids (Q) contains an A in place of C at position 3 of the SRE-1 (the 5' C of the first CAC trimer), and the other plasmid (X) contains an A in place of C at position 10 (the 3' C of the second CAC trimer) (see FIG. 21). Transcription from the plasmid containing the wild-type SRE-1 sequence (Plasmid K) was stimulated 10-fold by co-transfection with pSREBP-1a, and sterol suppression was nearly eliminated (FIG. 23A). In contrast, transcription driven by Plasmid Q was stimulated only slightly by pSREBP-1a (B), and Plasmid X was not stimulated at all (C).

The ability of pSREBP-1a to stimulate transcription of reporter constructs containing the native promoters of three sterol-regulated genes was next determined (FIG. 23). As a positive control in this study, pSREBP-1a was cotransfected together with Plasmid K, and again a marked stimulation of transcription and an abolition of sterol suppression was observed (FIG. 23D). A similar effect was observed when transcription of the CAT gene was driven by a fragment of the native LDL receptor promoter (G), which contains Repeats 2+3 as well as Repeat 1, another weak Sp1 binding site (Dawson et al., 1988). The absolute level of CAT activity was much lower with the native promoter construct than with Plasmid K (note the different scales for D and G). The promoter for 3-hydroxy-3-methylglutaryl CoA (HMG CoA) synthase was much more active than the LDL receptor promoter in this assay, and it, too, was stimulated by pSREBP-1a with an abolition of sterol regulation (E). In contrast, the promoter for HMG CoA reductase was not affected by pSREBP-1a (F). The promoter for HMG CoA synthase, but not HMG CoA reductase, contains a sequence that fits the requirements for binding SREBP-1 (Example 2; Wang et al., 1993; Osborne et al., 1992).

C. Discussion

SREBP-1, A Regulator of Cholesterol Levels. The current example reports the cloning and functional expression of SREBP-1, a transcription factor of the bHLH-Zip family that activates transcription of the LDL receptor gene through binding to the sterol regulatory element (SRE-1). The following lines of evidence indicate that SREBP-1 is a crucial molecule in controlling LDL receptor gene expression and is thus a key element in controlling plasma cholesterol levels in humans.

First, when overproduced in animal cells by transfection, SREBP-1 activates transcription of reporter genes with artificial promoters that contain multiple copies of SRE-1 as well as natural promoters containing the 5' flanking region of the LDL receptor gene or the HMG CoA synthase gene. Second, the requirements for the activity of SREBP-1 correlate with the known requirements for transcription of the LDL receptor gene. Third, in vitro, the protein produced from pSREBP-1 bound to sequences containing the SRE-1 as determined by gel mobility shift assays. Fourth, the sequence requirements for binding matched precisely the requirements for transcriptional activation by SRE-1.

SREBP-1 is a bHLH-Zip Protein. The sequence of SREBP-1 reveals it to be a member of the bHLH-Zip family of transcription factors. This growing family includes the oncogenic protein, Myc, and its modulators Max, Mad, and Mxi1 (Ferré-D'Amaré et al., 1993; Zervos et al., 1993; Ayer et al., 1993). It includes a variety of proteins, such as TFE3, that regulate transcription of immunoglobulin genes (Beckmann et al., 1990); AP-4, which activates transcription from the SV40 enhancer (Hu et al., 1990); and certain transcription factors that regulate differentiation in mammals and insects (Murre and Baltimore, 1992). The bHLH-Zip proteins form homodimers and heterodimers through interactions between the paired helices on adjacent monomers. Dimerization is reinforced by the adjacent leucine zippers which form coiled coils. Dimerization orients the nearby basic regions of the two monomers so that they can make specific contacts with palindromic sequences in the major groove of the target DNA (Ferré-D'Amaré et al., 1993).

All of the classic bHLH-Zip proteins recognize palindromic sequences containing the so-called E box (CANNTG). These proteins can be divided into two classes, depending on the two central nucleotides of the E box (Dang et al., 1992). Class B proteins recognize CACGTC, whereas Class A proteins recognize CAGCTG. Recently, Ferré-D'Amaré et al. (1993) reported the three-dimensional structure of Max, a Class B bHLH-Zip protein, in a complex with DNA. The two basic regions form extended α-helices that straddle the DNA in a chopstick-like fashion.

Three residues from the basic region of a single monomer make specific contacts with one of the CAC trimers and its opposing GTG (FIG. 24). These residues are His 28, Glu 32, and Arg 36 (in the numbering scheme of Ferré-D'Amaré et al. (1993)). The second protein monomer is attached to the first in a symmetrical head-to-head fashion, thereby allowing it to bind to the second CAC/GTG sequence in inverted orientation.

Novel Features of SREBP-1. SREBP-1 differs from the other bHLH-Zip proteins in two crucial respects. First, SREBP-1a, which contains 1147 amino acids, is much larger than the other bHLH-Zip proteins, which contain 160 to 536 amino acids. The extra length is at the COOH-terminal end of the protein. Second, SREBP-1 does not recognize a classic E box. The SRE-1 target sequence has no dyad symmetry, but instead it contains a direct repeat of the target CAC sequence on the same DNA strand separated by two Cs (FIG. 24). The two CAC sequences are spaced 5 residues apart and thus they occur on opposite sides of the double helix. Binding of SREBP-1 requires both copies of CAC: point mutations (transversions) in either copy abolish binding as well as the transcriptional activity of SRE-1 (FIG. 21).

SREBP-1 shares with Max the three amino acids in the basic domain that contact the CAC/GTG sequence. In SREBP-1 these are His 328, Glu 332, and Arg 336 (see FIG. 17 (asterisks) and FIG. 24). It is likely therefore that a monomer of SREBP-1 binds to a single CAC/GTG in a fashion similar to that previously described for Max (FIG. 24). But the binding of SREBP-1 requires two sequential CAC sequences as well as the flanking nucleotides. How can a second SREBP-1 monomer bind to the second CAC/GTG? This would not be possible if two SREBP-1 monomers were joined in a symmetrical head-to-head dimer such as that described for Max. Perhaps two monomers of SREBP-1 bind to DNA independently and in the same orientation. More likely, SREBP-1 forms higher order multimers through nonsymmetrical interactions between helices as postulated by Farmer et al. (1992) for bHLH proteins without leucine zippers. Such a multimer might wind around the DNA so as to allow two basic regions in the same orientation to attach to two CAC sequences on the same DNA strand, but on opposite sides of the helix. The two monomers would have to make somewhat different contacts with DNA since the two half-sites have a different sequence (ATCAC and CCCAC). Moreover, the requirement for the terminal C in the second CAC is not absolute. A transition to a T is tolerated (wild-type mouse SRE-1 sequence M in FIG. 19), but a transversion to an A is not (mutant * sequence in FIG. 19). The inventors contemplate conducting a detailed physicochemical characterization of SREBP-1/DNA complexes to resolve these issues.

The predicted α-helical acidic region at the $NH_2$-terminus of SREBP-1a is likely to be a transcriptional activation domain. Acidic regions that activate transcription are found at the $NH_2$-termini of some, but not all bHLH-Zip proteins, including Myc and TFE3 (Kato et al., 1990; Beckmann et al., 1990). The proline-rich region adjacent to the acidic region of SREBP-1 may also play a role in transactivation (Mermod et al., 1989).

Alternatively Spliced Forms of SREBP-1. The significance of the pCY22 cDNA whose coding sequence differs from pCY5 and pCY21 at the $NH_2$- and COOH-termini, respectively (FIG. 15) remains to be established. The inventors believe that pCY5 and pCY21 reflect the major form of SREBP-1 because two full-length cDNAs with ends corresponding to these sequences were isolated from two different Chinese hamster cell libraries. The pCY22 sequence might be produced by alternative splicing, or it may result from a rearrangement during cloning. The present inventors have found that pSREBP-1c, which corresponds to pCY22, binds to the same SRE-1 sequence as pSREBP-1a, and it activates transcription driven by Plasmid K in transfected cells. Moreover, transcription stimulated by pSREBP-1c, like that driven by pSREBP-1a, is not suppressed by sterols. Thus, to date the inventors have found no evidence for a functional difference between pSREBP-1a and pSREBP-1c. It should be noted that the $NH_2$-terminus of the SREBP-1c protein lacks some of the acidic amino acids found in SREBP-1a. However, the $NH_2$-terminus of SREBP-1c retains an overall acidic character with seven negatively charged residues and no positives up to the residue corresponding to residue 42 of SREBP-1a.

Proposed Regulatory Role of SREBP-1 in Sterol-Mediated Regulation Overexpression of SREBP-1 stimulates transcript-ion from the SRE-1, but it abolishes sterol sensitivity. Several explanations are possible. First, SREBP-1, like other bHLH-Zip proteins, may be controlled by homo- and hetero-oligomerization. It is possible that homo-oligomers of SREBP-1 are constitutively active, whereas hetero-oligomers with another bHLH-Zip protein are active only in the absence of sterols. Overexpression of SREBP-1 may force the formation of homo-oligomers, thereby producing constitutive transcription. In this regard it is interesting that purified SREBP appears as a cluster of proteins of 59–68 kDa on SDS polyacrylamide gels (Example 2; Wang et al., 1993) and that a coding sequence in any of the pSREBP-1 cDNAs has not yet been found for one of six peptides (peptide 4; SEQ ID NO:44) sequenced from purified SREBP (Table IV). Preliminary evidence of the inventors' indicates that this sequence comes from a separate protein of the bHLH-Zip family that copurifies with SREBP.

Other mechanisms of regulation in addition to hetero-oligomerization are possible, including sterol-mediated regulation of SREBP-1 entry or retention in the nucleus by a process that becomes overwhelmed when SREBP-1 is overexpressed. Regulated nuclear entry or retention may be a property of the long COOH-terminal half of SREBP-1, which does not have a counterpart in other bHLH-Zip proteins.

EXAMPLE 4

Molecular Cloning, Sequencing and Further Analysis of SREBP-2

In the current example, the inventors disclose the isolation of a cDNA encoding a protein that contains the single peptide that was not found in SREBP-1. This new protein, designated SREBP-2, contains 1141 amino acids, shows 47% identity to SREBP-1a, and shares the bHLH-Zip motif, the acidic $NH_2$-terminal domain, and the long COOH-terminus. SREBP-2 shows the same specificity for binding SRE-1 as does SREBP-1, and it also activates transcription driven by promoters that contain SRE-1. Activation occurs in the presence and absence of sterols, abolishing sterol suppression. Thus, HeLa cells have two closely related bHLH-Zip transcription factors, each of which can activate promoters containing an SRE-1 sequence.

A. Materials and Methods

1. Molecular Biological Techniques. Standard molecular biology techniques were used (Sambrook et al., 1989). DNA sequencing was performed by the dideoxy chain termination method manually or on an Applied Biosystems Model 373A DNA sequencer. Blot hybridization of RNA was performed using three end-labeled oligonucleotides corresponding to nucleotides 598–651, 1357–1410, and 2146–2196 of human pSREBP-2 as probes. An antibody directed against SREBP-2 was produced by immunizing rabbits with a synthetic peptide, (C)SFTQVTLPSFSPS (amino acid residues 1–13 of SEQ ID NO:4, corresponding to amino acids 91 to 103 in SREBP-2 (FIG. 25Ai and FIG. 25Aii). Immunoblot analysis was performed using an ECL Western Blotting Detection Kit (Amersham). Gel mobility shift assays were carried out as described with a PCR-generated $^{32}P$-labeled DNA probe containing two copies of wild-type or mutant Repeat 2+3 elements of the LDL receptor promoter using a reporter CAT genes.

2. cDNA Cloning of Human SREBP-2. To obtain a cDNA probe corresponding to peptide 4 of purified SREBP (SFTQVTLPSFSPSAASPQA)(SEQ ID NO:44), four pools of degenerate oligonucleotides were synthesized, comprising 5'-TT(T/C)ACICA(A/G)GT(T/A/G/C)AC(T/A/G/C)(T/C)T-3' (SEQ ID NO:57) based on the $NH_2$-terminus of the peptide and three pools of degenerate oligonucleotides comprising 5'-GC(T/C)TGIGG(T/A/G/C)(G/C)(A/T)(T/A/G/C)GC-3' (SEQ ID NO:58) based on the COOH-terminus of the peptide. The 12 primer pairs were used in all combinations in a two-step PCR reaction (94° C./50° C.) to amplify template DNA purified from a HeLa λgt10 cDNA library (Clontech). One primer pair, 5'-TT(T/C)ACICA(A/G)GT(C/G)AC(T/A)(T/C)T-3' (SEQ ID NO:59) and 5'-GC(T/C)TGIGG(A/T/G/C/)GA(G/C)GC-3' (SEQ ID NO:60), yielded a 53-bp insert that was subsequently isolated from a polyacrylamide gel, reamplified, and subcloned into the pCRII vector in a TA Cloning Kit (Invitrogen). The translated nucleotide sequence matched peptide 4.

Two partially overlapping pairs of oligonucleotides based on the 53-bp insert sequence (5'-GGTCACATTACCTTCCTTCTC-3' (SEQ ID NO:61)/5'-TTCCTTCTCTCCCTCGGC-3' (SEQ ID NO:62), and 5'-GGAGGCCGCCGAGGGAG-3' (SEQ ID NO:63)/5'-CGAGGGAGAGAAGGAAGGTA-3' (SEQ ID NO:64) were used together with forward and reverse primers of λgt10 (New England Biolabs) in an anchored PCR reaction performed with a "touchdown" program (Don et al., 1991) to amplify the adjacent sequences of the insert from the HeLa λgt10 cDNA library. Fragments of 168 and 348 bp were amplified from the 5' and 3' ends of the insert, respectively. The two amplified fragments were $^{32}$P-labeled by the random primer method and used to screen a HeLa λEXlox cDNA library. Eleven positive clones were obtained from 4.2×10$^5$ plaques. One 4.2-kb clone, pXH-4, was sequenced on both strands.

To screen for longer cDNAs, the inventors generated a PCR fragment corresponding to the most 5' 258 bp of pXH-4. This 258-bp fragment was $^{32}$p-labeled by the random primer method and used to screen 5.2×10$^5$ plaques from the HeLa λEXlox cDNA library. Twenty positive clones were obtained. The longest clone, pXH-11, was ~5.2 kb in length. It did not extend past the 5' end of pXH-4. Rather, it extended further in the 3' direction. The 3' untranslated region of pXH-11 (1.1 kb) was sequenced on both strands.

3. Transfection and Reporter CAT Assays. An expression vector for SREBP-2, designated pSREBP-2, was constructed by cloning the SalI 4.2-kb insert from pXH-2 into the SalI site of pCMV7 (Andersson et al., 1989). Monolayers of human embryonic kidney 293 cells were cotransfected with 0–0.6 μg pSREBP-1 or pSREBP-2, 0.3 μg pVA, and 1 μg of the indicated reporter CAT gene as described. The total amount of cDNA was adjusted to 3 μg by addition of pCMV (vector control) and salmon sperm DNA. After 2 days the cells were harvested, and CAT activity was measured by the xylenes extraction method (Briggs et al., 1993). Protein content was measured by the method of Bradford (Bradford, 1976).

4. Production of Recombinant bHLH-Zip Domain of SREBP-2. The nucleotide sequence corresponding to amino acids 48–403 of SREBP-2 was amplified by PCR, subcloned between the BamHI/HindIII sites of a pQE-30 vector (containing 6 consecutive histidines after the initiator methionine) (Qiagen), and expressed in E. coli. The resulting fusion protein was purified by NI$^{2+}$-sepharose affinity chromatography.

B. Results

In Example 3, the sequence of 6 peptides obtained from a mixture of SREBPs isolated from HeLa cells was disclosed. DNA sequences encoding 5 of the 6 peptides were found in SREBP-1. Using a strategy based on sequential PCR applied to a HeLa cell cDNA library, the inventors isolated a cDNA encoding the single peptide (peptide 4) that was missing from SREBP-1 (see Materials and Methods). The longest of the initial clones, designated pXH-4, was 4.2 kb in length (nucleotides 1 to 4249) and encoded a protein of 1141 amino acids. This cDNA had a putative 5'-untranslated region of 117 bp; it lacked a terminator codon upstream of the first inframe methionine. To ensure that the first methionine was indeed the initiator, the library was rescreened using a probe corresponding to the 5' end of pXH-4. The longest clone isolated (pXH-11) was 5.2 kb in length and did not encode additional 5' sequence (nucleotides 88 to 5197). Rather, it extended further in the 3' direction, terminating in a poly A tract.

An expressible cDNA was constructd from pXH-4. The sequence of this cDNA, designated pSREBP-2, has been deposited in GenBank (accession number U02031). pSREBP-2 includes a 5'untranslated region of 117 bp, and open readng frame of 3423 bp, and a 3' untranslated region of 1654 bp which terminates in a poly A tract that is 18 nucleotides distal to a consensus polyadenylation signal of nucleotide 5164. The 3' untranslated region contains two other putative polyadenylation sites, one near the 3' end of pXH-4 at nucleotide 4234 and the other at nucleotide 4611. It is believed that pSREBP-2 represents a full-length cDNA because its length corresponds to the longest mRNA detected on northern blots (see below) and because the initiator methionine occurs in a position corresponding to the initiator methionine in SREBP-1a (see FIG. 25Ai and FIG. 25Aii; SEQ ID NO:53). SREBP-2 contains 1141 amino acids. Residues 91–109 correspond exactly to the sequence of peptide 4 derived from the purified SREBP preparation.

FIG. 25Ai, FIG. 25Aii, FIG. 25B and FIG. 25C compare the amino acid sequences and domain maps of SREBP-1a and SREBP-2. The two protein share 47% of their amino acids in common, and the identities extend throughout the proteins. In the bHLH-Zip region the proteins are 71% identical, and SREBP-2 shares all of the important amino acids that form the bHLH-Zip consensus. SREBP-2 also shares the histidine, glutamic acid, and arginine residues (denoted by asterisks in FIG. 25B) that are found in SREBP-1 and that have been implicated in DNA recognition by Max, another b-HLH-Zip protein (Ferre-D'Amare et al., 1993). Both proteins have a pair of negative residues immediately following the initiator methionine. Although the NH$_2$-terminal ends of the two proteins are only 33% identical, they share an extremely acidic character. The NH$_2$-terminal 51 amino acids of SREBP-2 include 14 negative residues (27s). The first basic amino acid (an arginine) does not occur until position 77. This is similar to the situation with SREBP-1a in which the first basic residue occurs at position 108. The acidic region of SREBP-2 is followed by a region in which serine, proline, and glycine comprise 60% of the residues. The corresponding region of SREBP-1a is also rich in proline and serine, but not in glycine. SREBP-2 contains one feature not present in SREBP-1, namely, a glutamine-rich region extending from residues 125–246 (27% Gln). The COOH-terminal halves of both proteins share long stretches of identity (49% identical over 684 residues).

The mRNA for SREBP-2, like that for SREBP-1, is expressed in a wide variety of human tissues as revealed by northern blots (FIG. 26A). In most tissues the predominant mRNA is 5.2 kb in length, corresponding to pXH-11. A less abundant mRNA of ~4.2 kb is also seen. It is believed by the inventors that this corresponds to pXH-4, and represents the use of an upstream polyadenylation signal. The mRNA is also expressed widely in human fetal tissues, as shown in the five lanes at the right of FIG. 26A.

The sequence of pXH-4 was inserted into an expression plasmid under control of the CMV promoter and introduced into 293 cells by transfection. Cell extracts were subjected to SDS electrophoresis and immunoblotting with an anti-peptide antibody directed against SREBP-2. FIG. 26B shows that the cells produced a protein of approximately 120 kDa, consistent with the predicted molecular weight of SREBP-2, which is 123,665.

In the LDL receptor promoter the SRE-1 is contained within a 16-bp sequence designated Repeat 2 that is immediately followed by a 16-bp sequence designated Repeat 3 (see earlier Examples and Smith et al., 1990; Goldstein et al., 1990). Repeat 3 does not bind SREBP, but rather is contains a binding site for another transcription factor, Sp1 (see earlier Examples and Dawson et al., 1988). High level transcription requires Repeats 2 and 3. To test the binding activity of SREBP-2, a portion of the cDNA encoding the bHLH-Zip region was inserted into an E. coli expression vector. The protein was produced with an NH$_2$-terminal extension of 6 histidine residues that permitted isolation on a Ni$^{2+}$-agarose column (see Materials and Methods). The purified protein gave a retarded band when incubated with a $^{32}$P-labeled oligonucleotide containing two tandem copies of Repeats 2+3 (FIG. 27). Binding was markedly reduced or abolished when any one of the nucleotides in the SRE-1 was subjected to transversion mutation with the exception of the C at position 6, which is the only one of the SRE-1 mutants that is actively transcribed in vivo. A small amount of binding was observed when the A at position 4 was mutated to a T. This sequence gives rise to low, but detectable transcription in vivo. Mutations in the Repeat 2 sequences flanking SRE-1 had no effect on SREBP-2 binding.

To test the activity of SREBP-2 on gene transcription, we used the mammalian expression vector that produces SREBP-2 driven by the CMV promoter (see FIG. 26B), and a similar vector that produces SREBP-1a (Example 3). These constructs, or a control pCMV vector, were introduced into 293 cells together with plasmids containing a CAT transcription reporter gene driven by promoters that contain SRE-1. When transfected together with pCMV, Plasmid K, which contains two tandem copies of Repeats 2+3 (Examples 2 and 3), was transcribed in the absence of sterols and repressed by sterols (FIG. 28A). Cotransfection with either pSREBP-2 or pSREBP-1a markedly enhanced transcription in the absence and presence of sterols, abolishing sterol suppression. This stimulation was not observed with Plasmid X, which contains a point mutation that inactivates the SRE-1 (FIG. 28B). The promoters for HMG CoA synthase (FIG. 28C) and the LDL receptor (FIG. 28D) were also stimulated by pSREBP-2 to a similar extent as pSREBP-1A. There was no significant stimulation of the promoter for HMG CoA reductase, which does not contain SRE-1 (FIG. 28E).

Figure 29B:
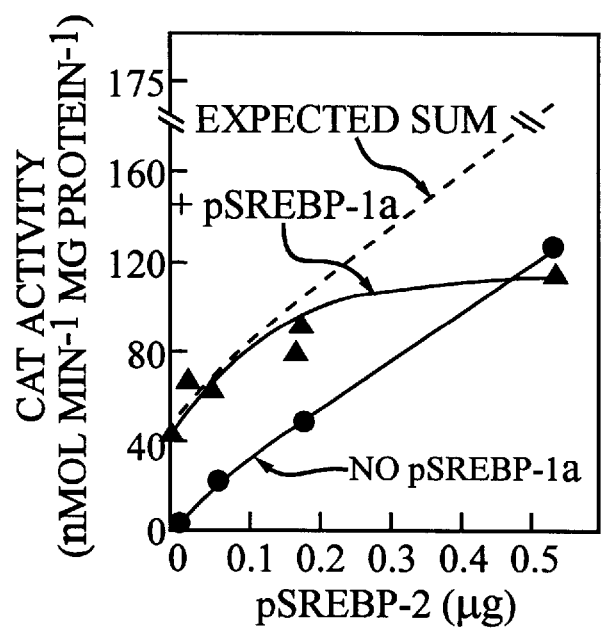

The data of FIG. 28 suggest that SREBP-2 and -1a act similarly in stimulating transcription driven by promoters that contain SRE-1. To determine whether the effects are additive, the inventors performed a titration study (FIG. 29). 293 cells were cotransfected with Plasmid K plus increasing concentrations of pSREBP-2 alone or together with a fixed amount (0.02 µg) of pSREBP-1a. As a blank value for the CAT assays, the activity observed in the absence of either SREBP was substracted, and therefore the data represent the SREBP-stimulated transcription activity. The dashed line in FIG. 29 indicates the CAT activity to be expected if the actions of SREBP-1a and 2 were additive. In the absence of sterols, increasing amounts pSREBP-2 gave a nearly linear increase of CAT activity up to 100 nmol·min$^{-1}$·mg$^{-1}$. (FIG. 29A, closed circles). pSREBP-1a by itself increased CAT activity by 40 nmol·min$^{-1}$·mg$^{-1}$. In the presence of SRERP-1a, the further addition of pSREBP-2 in amounts up to 0.2 µg gave an additive effect, reaching a plateau at 80 nmol·min$^{-1}$·mg$^{-1}$ (closed triangles). Increasing pSREBP-2 above this level did not produce a further increase in CAT activity. Similar results were obtained in the presence of sterols (FIG. 29B).

C. DISCUSSION

This example demonstrates the primary structure and activity profile of SREBP-2, the second member of a family of sterol regulatory element binding proteins. The sequence and biologic activities of this protein resemble those of SREBP-1a discussed in the foregoing example. The reason for the existence of two sterol binding proteins is not yet clear. Both proteins are likely to be expressed in the same cells as evidenced by the observation that mRNAs for SREBP-1a and 2 are present in the same tissues and both proteins were purified and their cDNAs cloned from HeLa cells.

bHLH proteins, with or without leucine zippers, usually act by forming homo- or heterodimers (Ferre-D'Amare et al., 1993). The inventors have preliminary evidence that SREBP-1a can form homodimers and higher order homo-multimers. To date, the inventors have not examined potential interactions between SREBP-1a and 2. Each is able to bind DNA independently, as revealed by gel retardation assays using recombinant proteins prepared in *E. coli* or translated in reticulocyte lysates. Moreover, each independently stimulates transcription from SRE-1-containing promoters in transfected cells. The latter conclusion must be tempered because we cannot rule out the formal possibility that the active species is a heterodimer between the protein produced by the transfected cDNA and an endogenous partner.

When transfected together at low concentrations, pSREBP-1a and 2 produce additive effects on transcription as indicated by CAT assays. At higher concentrations a plateau is reached, and additivity is no longer apparent. The simplest explanation is that each protein is capable of binding to SRE-1 and activating transcription independently, and that the SRE-1 eventually becomes saturated with one or the other SREBP, limiting any further increase. Whether transfected separately or together, SREBP-1a and SREBP-2 abolish sterol suppression.

The one striking difference between SREBP-2 and 1a is the glutamine-rich region in the former. Glutamine-rich regions are reported to activate transcription, presumably by interacting with co-activator proteins (Pugh et al., 1990). SREBP-1a and 2 both have acidic NH$_2$-termini, which are likely to be transcriptional activating domains. It is possible that the additional glutamine-rich domain in SREBP-2 allows it to interact with an additional co-activator and thereby to produce effects that are different from those of SREBP-1a.

The mechanism by which sterols reduce the activities of SREBP-1 and 2 remains obscure. The inventors hypothesize that this control is abolished in transfected cells because some component of the regulatory machinery is overwhelmed by the large amount of SREBP that is produced.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter can be made without undue experimentation.

REFERENCES

The following references, to the extent that they provide exemplary procedural or other details supplementary to those set forth herein, are specifically incorporated herein by reference.

Adelman et al., (1983) *DNA* 2:183.
Akusjarvi, G., et al. (1989) *Mol. Cell Biol.* 7, 549–551.
Andersson, S., et al. (1989). *J. Biol. Chem.* 264, 8222–8229.
Ayer et al.. (1993) *Cell*, 72:211–222.
Beckmann, H., et al. (1990). *Genes Dev.* 4, 167–179.
Bishop, R. W. (1992) *J. Lipid Res.* 33, 549–557.
Blanar, M. A. and Rutter, W. J. (1992). *Science* 256, 1014–1018.
Bradford, M. M. (1976). *Analyt. Biochem.* 72, 248–254.
Briggs, M. R., Kadonaga, J. T., Bell, S. P., and Tjian, R. (1986) *Science* 234, 47–52.
Briggs, M. R., Yokoyama, C., Wang, X., Brown, M. S., and Goldstein, J. L. (1993). *J. Biol. Chem.* 268, 14490–14496.
Brown, M. S. and Goldstein, J. L. (1986) *Science* 232, 34–47.
Brutlag, D. L. et al. (1990) *CABIOS*, 6:237–245.
Chen, W.-J., et al., (1991). *Cell* 66, 327–334.
Chodosh, L. A., Carthew, R. W., and Sharp, P. A. (1986) *Mol. Cell. Biol.* 6, 4723–4733.
Chou and Fasman, (1974a) *Biochemistry*, 13(2):222–245.
Chou and Fasman, (1974b) *Biochemistry*, 13(2):211–222.
Chou and Fasman, (1978a) *Adv. Enzymol. Relat. Areas Mol. Biol.*, 47:45–148.
Chou and Fasman, (1978b) *Ann. Rev. Biochem.*, 47:251–276.
Chou and Fasman, (1979) *Biophys. J.*, 26:367–384.
Crea et al. (1978) *Proc. Natl. Acad. Sci. U.S.A* 75:5765.
Dang, C. V., et al., (1992). *Proc. Natl. Acad. Sci. USA* 89, 599–602.
Dawson, P. A., Hofmann, S. L., van der Westhuyzen, D. R., Brown, M. S., and Goldstein, J. L. (1988) *J. Diol. Chem.* 263, 3372–3379.
Dignam, J. D., Lebovitz, R. M., and Roeder, R. G. (1983) *Nucl. Acids Res.* 11, 1475–1489.
Don, R. H., Cox, P. T., Wainwright, B. J., Baker, K and Mattick, J. S. (1991) *Nucl. Acid. Res.* 19, 4008.
Eichenlaub, (1979) *J. Bacteriol* 138:559–566.
Farmer, K., Catala, F., and Wright, W.E. (1992). *J. Biol. Chem.* 267, 5631–5636.
Ferré-D'Amaré, A. R., Prendergast, G. C., Ziff, E. B., and Burley, S. K. (1993). *Nature* 363, 38–45.
Fetrow & Bryant, (1993) *BIOTECHNOLOGY*, 11:479–483.
Freedman, L. P., Yoshinaga, S. K., Vanderbilt, J. N., and Yamamoto, K. R. (1989) *Science* 245, 298–301.
Garnier, J., Osguthorpe, D. J., and Robson, B. (1978). *J. Mol. Biol.* 120, 97–120.
Gil, G., Faust, J. R., Chin, D. J., Goldstein, J. L., and Brown, M. S. (1985). *Cell* 41, 249–258.
Gil, G., et al., (1988) *Proc. Natl. Acad. Sci. USA* 85, 8963–8967.
Gil, G., Osborne, T. F., Goldstein, J. L. and Brown, M. S. (1988) *J. Biol. Chem.* 263, 19009–19019.
Goldstein, J. L., Basu, S. K., and Brown, M. S. (1983) *Meth. Enzymol.* 98, 241–260.
Goldstein, J. L. and Brown, M. S. (1990) *Nature* 343, 425–430.
Goodbourn et al. (1986), *Cell*, 45:601–610.
Gorman, C. M., Moffat, L. F., and Howard, B. H. (1982) *Mol. Cell. Biol.* 2, 1044–1051.
Guan et al., (1987) *Gene*, 67:21–30.
D Jacob et al. (1961), *J. Mol. Biol.*, 3:318–350.
Harlow, E. and Lane, D. (1988). Antibodies: A laboratory manual (New York: Cold Spring Harbor Laboratory).
Hu, Y.-F., Luscher, B., Admon, A., Mermod, N., and Tjian, R. (1990). *Genes Dev.* 4, 1741–1752.
Hua, X., Yokoyama, C.., Wu, J., Briggs, M. R., Brown, M. S., Goldstein, J. L. and Wang, X. (1994). *Proc. Natl. Acad Sci. USA*, in press.
Jameson & Wolf, (1998) *Comput. Appl. Biosci.*, 4(1):181–186.
Kadonaga, J. T. and Tjian, R. (1986) *Proc. Natl. Acad. Sci. USA* 83, 5889–5893.
Kato, G. J., Barrett, J., Villa-Garcia, M., and Dang, C. V. (1990). *Mol. Cell. Biol.* 10, 5914–5920.
Klein-Hitpass, L., et al., (1990) *Cell* 60, 247–257.
Kozak, M. (1984). *Nucl. Acid. Res.* 12, 3873–3893.
Kyte & Doolittle, (1982) *J. Mol. Biol.*, 157(1):105–132
Laemmli, U. K. (1970) *Nature* 227, 680–685.
Landschulz, W. H., Johnson, P. F., and McKnight, S. L. (1988). *Science* 240, 1759–1764.
Lee, F., Hall, C. V., Ringold, G. M., Dodson, D. E., Luh, J., and Jacob, P. E. (1984) *Nucl. Acid. Res.* 12, 4191–4206.
Lichtsteiner, S., Wuarin, J., and Schibler, U. (1987) *Cell* 51, 963–973.
Lillie, J. W. and Green, M. R. (1989) *Nature* 338, 39–44.
Lowry, O. H., Rosebrough, N. J., Farr, A. L., and Randall, R. J. (1951) *J. Biol. Chem.* 193, 265–275.
Mehta, K. D., Brown, M. S., Bilheimer, D. W., and Goldstein, J. L. (1991) *J. Biol. Chem.* 266, 10415–10419.
Mermod, N., O'Neill, E. A., Kelly, T. J., and Tjian, R. (1989). *Cell* 58, 741–753.
Messing et al., (1981) Third Cleveland Symposium on Macromoleculesand Recombinant DNA, Editor A. Walton, Elsevier, Amsterdam.
Murre, C. and Baltimore, D. (1992). In Transcriptional Regulation. S.L. McKnight and K.R. Yamamoto, Eds. (New York: Cold Spring Harbor Laboratory Press), pp. 861–879.
S Nagai & Thogersen, (1987) *Meth. Enzymol.*, 153:461–487.
Osborne et al., *Cell*, 42:203–212 (1985).
Osborne, T. F., Gil, G., Goldstein, J. L. & Brown, M. S. (1988) *J. Biol. Chem.* 263, 3380–3387.
Osborne, T. F. (1991) *J. Biol. Chem.* 266, 13947–13951.
Osborne, T. F., Bennett, M. & Rhee, K. (1992) *J. Biol. Chem.* 267, 18973–18982.
Pabo, C. O. and Sauer, R. T. (1992). *Annu. Rev. Biochem.* 61, 1053–1095.
Pascal, E. and Tjian, R. (1991) *Genes & Dev.* 5, 1646–1656.
Pothier, F., Ouellet, M., Julien, J. P., and Guerin, S. L. (1992) *DNA Cell Biol.* 11, 83–90.
Prendergast, G. C., Lawe, D., and Ziff, E. B. (1991). *Cell* 65, 395–407.
Pugh, B. F. and Tijian, R. (1990) *Cell* 61, 1187–1197
Rajavashisth, T. B., Taylor, A. K., Andalibi, A., Svenson, K. L., and Lusis, A. J. (1989) *Science* 245, 640–643.
Sambrook, J., Fritsch, E. F., and Maniatis, T. (1989) *Molecular cloning: A laboratory manual*, Cold Spring Harbor Laboratory Press, New York.
Sanger, F., Coulson, A. R., Barrell, B. G., Smith, A. J. H., and Roe, B. A. (1980). *J. Mol. Biol.* 143, 161–178.
Seed, B. and Sheen, J. Y. (1988) *Gene* 67, 271–277.
Smith, J. R., Osborne, T. F., Brown, M. S., Goldstein, J. L., and Gil, G. (1988) *J. Biol. Chem.* 263, 18480–18487.
Smith, J. R., Osborne, T. F., Goldstein, J. L., and Brown, M. S. (1990) *J. Biol. Chem.* 265, 2306–2310.
Stark, H. C., Weinberger, O., and Weinberger, J. (1992) *Proc. Natl. Acad. Sci. USA* 89, 2180–2184.
Stone, K. L., LoPresti, M. B., Crawford, J. M., DeAngelis, R., and Williams, K. R. (1989). In A Practical Guide to Protein and Peptide Purification for Microsequencing. P. T. Matsudairia, Ed. (San Diego: Academic Press, Inc.), pp. 33–47.
Stuart et al. (1984), *Proc. Natl. Acad. Sci. USA*, 81:7318–7322.

Südhof, T. C., van der Westhuyzen, D. R., Goldstein, J. L., Brown, M. S., and Russell, D. W. (1987) *J. Biol. Chem.* 262, 10773–10779.

Tabor & Richardson (1985) *Proc. Natl. Acad. Sci.*, 82:1074–1078

Weinberger et al., (1985) *Science*, 228:740–742.

Wolf et al., (1988) *Comput. Appl. Biosci.*, 4(1):187–191.

Wang, X., Briggs, M. R., Hua, X., Yokoyama, C., Goldstein, J. L., and Brown, M. S. (1993). *J. Biol. Chem.* 268, 14497–14504.

Yamamoto (1985), *Ann. Rev. Genet.*, 19:209–252.

Yokoyama, C., Wang, X., Briggs, M. R., Admon, A., Wu, J., Hua, X., Goldstein, J. L., and Wang, X. (1994). *Cell* 75, 187–197.

Zervos, A. S., Gyuris, J., and Brent, R. (1993). *Cell* 72, 223–232.

---

What is claimed is:

1. A method for identifying a candidate substance that stimulates SRE-1-mediated transcription, comprising the steps of:

(a) preparing an SREBP composition comprising an SREBP protein that exhibits a molecular weight of between about 59 kD and about 68 kD on sodium dodecyl sulfate polyacrylamide gels and binds with sequence specificity to the sterol regulatory element SRE-1; and (b) determining the ability of a candidate substance to increase the formation of a protein:DNA complex between said SREBP protein and a DNA segment including the sterol regulatory element SRE-1, wherein an increase in said protein:DNA complex in the presence of the candidate substance is indicative of a candidate substance that stimulates SRE-1-mediated transcription.

2. The method of claim 1, wherein step (b) comprises:

(a) contacting a first sample of said SREBP composition with a first SRE-1 DNA segment under conditions effective to allow the formation of a first SREBP protein:DNA complex;

(b) contacting a second sample of said SREBP composition with a candidate substance and a second SRE-1 DNA segment under conditions effective to allow the formation of a second SREBP protein:DNA complex;

(c) separating said first and second SREBP protein:DNA complexes from unbound protein or DNA; and (d) measuring the amount of said first and second SREBP protein:DNA complexes, wherein an increased amount of the second complex relative to the first complex is indicative of a candidate substance that stimulates SRE-1-mediated transcription.

3. The method of claim 1, wherein said SREBP protein or said DNA segment includes a detectable label.

4. The method of claim 1, wherein said candidate substance is a sterol derivative.

5. The method of claim 1, wherein said candidate substance is a phosphatase or kinase.

6. The method of claim 1, wherein said SREBP composition comprises an SREBP-1 or SREBP-2 protein.

7. The method of claim 1, wherein said SREBP composition comprises a native SREBP protein obtained by purification from natural sources.

8. The method of claim 1, wherein said SREBP composition comprises an SREBP protein obtained by recombinant expression.

9. The method of claim 2, wherein said SREBP protein or said DNA segment is bound to a solid support and unbound protein or DNA is separated from said SREBP protein:DNA complexes by washing.

10. The method of claim 2, wherein said SREBP protein:DNA complex is detected by means of an antibody directed against said SREBP protein.

11. The method of claim 2, wherein unbound protein or DNA is separated from said SREBP protein:DNA complexes by electrophoresis.

12. The method of claim 3, wherein said label is a radioactive or enzymatic label.

13. A method for identifying a candidate substance that stimulates SRE-1-mediated transcription, comprising the steps of:

(a) preparing a recombinant host cell incorporating a first recombinant reporter gene under the transcriptional control of a functional SRE-1 sterol regulatory element, and a recombinant SREBP gene;

(b) culturing said host cell under conditions effective to allow expression of said reporter gene;

(c) contacting said host cell with a candidate substance; and (d) measuring the expression of said reporter gene, wherein an increase in reporter gene expression in the presence of the candidate substance is indicative of a candidate substance that stimulates SRE-1-mediated transcription.

14. The method of claim 13, wherein said host cell is cultured in the presence of sterols and wherein an increase in reporter gene expression in the presence of the candidate substance is indicative of a candidate substance that stimulates SRE-1-mediated transcription in the presence of sterols.

15. The method of claim 13, wherein said host cell is cultured in the absence of sterols.

16. The method of claim 13, wherein said SREBP gene of said host cell is a recombinant SREBP-1 or SREBP-2 gene.

17. The method of claim 13, wherein said recombinant reporter gene of said host cell is a CAT gene.

18. The method of claim 13, wherein said recombinant reporter gene of said host cell is a luciferase gene.

19. The method of claim 6, wherein said SREBP composition comprises an SREBP-1 protein.

20. The method of claim 6, wherein said SREBP composition comprises an SREBP-2 protein.

21. The method of claim 19, wherein said SREBP composition comprises an SREBP-1a protein having the amino acid sequence of SEQ ID NO:38.

22. The method of claim 20, wherein said SREBP composition comprises an SREBP-2 protein having the amino acid sequence of SEQ ID NO:54.

23. The method of claim 7, wherein said SREBP composition comprises an SREBP protein purified to between about 200-fold and about 38,000-fold relative to its natural state.

24. The method of claim 23, wherein said SREBP composition comprises an SREBP protein purified to about 38,000-fold relative to its natural state.

25. The method of claim 8, wherein said SREBP composition comprises an SREBP-1a protein obtained by recombinant expression of the SREBP-1a-encoding nucleic acid sequence of SEQ ID NO:37.

26. The method of claim 8, wherein said SREBP composition comprises an SREBP-2 protein obtained by recombinant expression of the SREBP-2-encoding nucleic acid sequence of SEQ ID NO:53.

27. The method of claim 16, wherein said SREBP gene of said host cell is a recombinant SREBP-1 gene.

28. The method of claim 16, wherein said SREBP gene of said host cell is a recombinant SREBP-2 gene.

29. The method of claim 27, wherein said SREBP gene of said host cell is a recombinant SREBP-1a gene having the nucleic acid sequence of SEQ ID NO:37.

30. The method of claim 28, wherein said SREBP gene of said host cell is a recombinant SREBP-2 gene having the nucleic acid sequence of SEQ ID NO:53.

* * * * *

UNITED STATES PATENT AND TRADEMARK OFFICE
CERTIFICATE OF CORRECTION

PATENT NO.    :   5,891,631

DATED         :   April 6, 1999

INVENTOR(S)   :   Goldstein et al

It is certified that error appears in the above-identified patent and that said Letters Patent is hereby corrected as shown below:

Title page, item [54], and col. 1, line 1, delete "TOSTEROL" and substitute therefore --TO STEROL--.

Signed and Sealed this

Twenty-eighth Day of September, 1999

*Attest:*

Q. TODD DICKINSON

*Attesting Officer*            *Acting Commissioner of Patents and Trademarks*

SEQUENCE LISTING ( 1 ) GENERAL INFORMATION:

( i i i ) NUMBER OF SEQUENCES: 64

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:1:

AAAATCACCC CACTGCAA 18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:2:

TAAATCACCC CACTGCAA 18

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:3:

ATAATCACCC CACTGCAA 18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:4:

AATATCACCC CACTGCAA                                                                                                  18

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:5:

AAATTCACCC CACTGCAA                                                                                                  18

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:6:

AAAAGCACCC CACTGCAA                                                                                                  18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:7:

AAAATAACCC CACTGCAA                                                                                                  18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:8:

AAAATCTCCC CACTGCAA                                                                                                  18

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

(x i) SEQUENCE DESCRIPTION: SEQ ID NO:9:

AAAATCAACC CACTGCAA                                                          18

(2) INFORMATION FOR SEQ ID NO:10:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "DNA"

(x i) SEQUENCE DESCRIPTION: SEQ ID NO:10:

AAAATCACGC CACTGCAA                                                          18

(2) INFORMATION FOR SEQ ID NO:11:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "DNA"

(x i) SEQUENCE DESCRIPTION: SEQ ID NO:11:

AAAATCACCG CACTGCAA                                                          18

(2) INFORMATION FOR SEQ ID NO:12:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "DNA"

(x i) SEQUENCE DESCRIPTION: SEQ ID NO:12:

AAAATCACCC AACTGCAA                                                          18

(2) INFORMATION FOR SEQ ID NO:13:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "DNA"

(x i) SEQUENCE DESCRIPTION: SEQ ID NO:13:

AAAATCACCC CTCTGCAA                                                          18

(2) INFORMATION FOR SEQ ID NO:14:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "DNA"

( x i ) SEQUENCE DESCRIPTION: SEQ ID NO:14:

AAAATCACCC CAATGCAA                                                                                  18

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:15:

AAAATCACCC CACGGCAA                                                                                  18

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:16:

AAAATCACCC CACTTCAA                                                                                  18

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:17:

AAAATCACCC CACTGAAA                                                                                  18

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:18:

AAAATCACCC CACTGCTA                                                                                  18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:19:

AAAATCACCC CACTGCAT                    18

( 2 ) INFORMATION FOR SEQ ID NO:20:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:20:

AAAATCACAC CACTGCAA                    18

( 2 ) INFORMATION FOR SEQ ID NO:21:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:21:

AAAATCACCC CATTGCAA                    18

( 2 ) INFORMATION FOR SEQ ID NO:22:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:22:

AAAATCACCC CACTGC                      16

( 2 ) INFORMATION FOR SEQ ID NO:23:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:23:

AAACTCCTCC CCCTGC                      16

( 2 ) INFORMATION FOR SEQ ID NO:24:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "DNA"

( x i ) SEQUENCE DESCRIPTION: SEQ ID NO:24:

AAAATCACCC CACTGCAAAC TCCTCCCCCT GC    32

( 2 ) INFORMATION FOR SEQ ID NO:25:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:25:

AAAAGAACCC CTATGCAAAC TCCTCCCCCT GC    32

( 2 ) INFORMATION FOR SEQ ID NO:26:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:26:

TGAAGCTTGC ATGCCTGCAG GTCGACTCGA CTCTAGAGGG TATATAATGG ATCCCGGGT    60

ACCGAGCTCG AATTCATCAG CTTGGCGAGA TTTTCAGGAG CTAAGGAAGC TAAAATG    117

( 2 ) INFORMATION FOR SEQ ID NO:27:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:27:

ATCACCCCAC    10

( 2 ) INFORMATION FOR SEQ ID NO:28:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:28:

GACACTATAG AACTCGAGCA GCTGAAGCTT GCATGC    36

( 2 ) INFORMATION FOR SEQ ID NO:29:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
    ( A ) DESCRIPTION: /desc = "DNA"

( x i ) SEQUENCE DESCRIPTION: SEQ ID NO:29:

GGTACCCGGG GATCCATTAT ATACC    25

( 2 ) INFORMATION FOR SEQ ID NO:30:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:30:

TCGACAAAAG ATAAGATGTG CAAACTCCTC CCCCTGCG    38

( 2 ) INFORMATION FOR SEQ ID NO:31:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:31:

TCGACAAAAG ATAAGATATG CAAACTCCTC CCCCTGCG    38

( 2 ) INFORMATION FOR SEQ ID NO:32:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:32:

TCGACGCAGG GGGAGGAGTT TGCATATCTT ATCTTTTG    38

( 2 ) INFORMATION FOR SEQ ID NO:33:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:33:

TCGACAAAAT CACCCCACTG TAAAATCACC CCACTGTG    38

( 2 ) INFORMATION FOR SEQ ID NO:34:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear -continued ( i i ) MOLECULE TYPE: other nucleic acid
  ( A ) DESCRIPTION: /desc = "DNA"

( x i ) SEQUENCE DESCRIPTION: SEQ ID NO:34:

```
TCGACACAGT  GGGGTGATTT  TACAGTGGGG  TGATTTTG                                    38
```

( 2 ) INFORMATION FOR SEQ ID NO:35:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:35:

```
GATCATCACC  CCACTG                                                              16
```

( 2 ) INFORMATION FOR SEQ ID NO:36:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:36:

```
GATCCAGTGG  GGTGAT                                                              16
```

( 2 ) INFORMATION FOR SEQ ID NO:37:

( i ) SEQUENCE CHARACTERISTICS:
  ( A ) LENGTH: 4154 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( i x ) FEATURE:
  ( A ) NAME/KEY: CDS
  ( B ) LOCATION: 167..3607

( x i ) SEQUENCE DESCRIPTION: SEQ ID NO:37:

```
TAACGAGGAA  CTTTTCGCCG  GCGCCGGGCC  GCCTCTGAGG  CCAGGGCAGG  ACACGAACGC          60

GCGGAGCGGC  GGCGGCGACT  GAGAGCCGGG  GCCGCGGCGG  CGCTCCCTAG  GAAGGGCCGT         120

ACGAGGCGGC  GGGCCCGGCG  GGCCTCCCGG  AGGAGGCGGC  TGCGCC ATG GAC GAG            175
                                                        Met Asp Glu
                                                         1

CCA CCC TTC AGC GAG GCG GCT TTG GAG CAG GCG CTG GGC GAG CCG TGC               223
Pro Pro Phe Ser Glu Ala Ala Leu Glu Gln Ala Leu Gly Glu Pro Cys
     5              10                  15

GAT CTG GAC GCG GCG CTG CTG ACC GAC ATC GAA GAC ATG CTT CAG CTT               271
Asp Leu Asp Ala Ala Leu Leu Thr Asp Ile Glu Asp Met Leu Gln Leu
 20              25                  30                  35

ATC AAC AAC CAA GAC AGT GAC TTC CCT GGC CTA TTT GAC CCA CCC TAT               319
Ile Asn Asn Gln Asp Ser Asp Phe Pro Gly Leu Phe Asp Pro Pro Tyr
             40                  45                  50

GCT GGG AGT GGG GCA GGG GGC ACA GAC CCT GCC AGC CCC GAT ACC AGC               367
Ala Gly Ser Gly Ala Gly Gly Thr Asp Pro Ala Ser Pro Asp Thr Ser
         55                  60                  65
```

| | | | | | | | | | | | | | | | |
|---|---|---|---|---|---|---|---|---|---|---|---|---|---|---|---|
| TCC | CCA | GGC | AGC | TTG | TCT | CCA | CCT | CCT | GCC | ACA | TTG | AGC | TCC | TCT | CTT | 415 |
| Ser | Pro | Gly | Ser | Leu | Ser | Pro | Pro | Pro | Ala | Thr | Leu | Ser | Ser | Ser | Leu | |
| | | 70 | | | | 75 | | | | | 80 | | | | | |
| GAA | GCC | TTC | CTG | AGC | GGG | CCG | CAG | GCA | GCG | CCC | TCA | CCC | CTG | TCC | CCT | 463 |
| Glu | Ala | Phe | Leu | Ser | Gly | Pro | Gln | Ala | Ala | Pro | Ser | Pro | Leu | Ser | Pro | |
| | 85 | | | | | 90 | | | | | 95 | | | | | |
| CCC | CAG | CCT | GCA | CCC | ACT | CCA | TTG | AAG | ATG | TAC | CCG | TCC | ATG | CCC | GCT | 511 |
| Pro | Gln | Pro | Ala | Pro | Thr | Pro | Leu | Lys | Met | Tyr | Pro | Ser | Met | Pro | Ala | |
| 100 | | | | | 105 | | | | | 110 | | | | | 115 | |
| TTC | TCC | CCT | GGG | CCT | GGT | ATC | AAG | GAA | GAG | TCA | GTG | CCA | CTG | AGC | ATC | 559 |
| Phe | Ser | Pro | Gly | Pro | Gly | Ile | Lys | Glu | Glu | Ser | Val | Pro | Leu | Ser | Ile | |
| | | | 120 | | | | | 125 | | | | | 130 | | | |
| CTG | CAG | ACC | CCC | ACC | CCA | CAG | CCC | CTG | CCA | GGG | GCC | CTC | CTG | CCA | CAG | 607 |
| Leu | Gln | Thr | Pro | Thr | Pro | Gln | Pro | Leu | Pro | Gly | Ala | Leu | Leu | Pro | Gln | |
| | | | 135 | | | | 140 | | | | | 145 | | | | |
| AGC | TTC | CCA | GCC | CCA | GCC | CCA | CCG | CAG | TTC | AGC | TCC | ACC | CCT | GTG | TTA | 655 |
| Ser | Phe | Pro | Ala | Pro | Ala | Pro | Pro | Gln | Phe | Ser | Ser | Thr | Pro | Val | Leu | |
| | | | 150 | | | | | 155 | | | | 160 | | | | |
| GGC | TAC | CCC | AGC | CCT | CCG | GGA | GGC | TTC | TCT | ACA | GGA | AGC | CCT | CCC | GGG | 703 |
| Gly | Tyr | Pro | Ser | Pro | Pro | Gly | Gly | Phe | Ser | Thr | Gly | Ser | Pro | Pro | Gly | |
| | 165 | | | | | 170 | | | | | 175 | | | | | |
| AAC | ACC | CAG | CAG | CCG | CTG | CCT | GGC | CTG | CCA | CTG | GCT | TCC | CCG | CCA | GGG | 751 |
| Asn | Thr | Gln | Gln | Pro | Leu | Pro | Gly | Leu | Pro | Leu | Ala | Ser | Pro | Pro | Gly | |
| 180 | | | | | 185 | | | | | 190 | | | | | 195 | |
| GTC | CCG | CCC | GTC | TCC | TTG | CAC | ACC | CAG | GTC | CAG | AGT | GTG | GTC | CCC | CAG | 799 |
| Val | Pro | Pro | Val | Ser | Leu | His | Thr | Gln | Val | Gln | Ser | Val | Val | Pro | Gln | |
| | | | | 200 | | | | | 205 | | | | | 210 | | |
| CAG | CTA | CTG | ACA | GTC | ACA | GCT | GCC | CCC | ACG | GCA | GCC | CCT | GTA | ACG | ACC | 847 |
| Gln | Leu | Leu | Thr | Val | Thr | Ala | Ala | Pro | Thr | Ala | Ala | Pro | Val | Thr | Thr | |
| | | | 215 | | | | | 220 | | | | | 225 | | | |
| ACT | GTG | ACC | TCG | CAG | ATC | CAG | CAG | GTC | CCG | GTC | CTG | CTG | CAG | CCC | CAC | 895 |
| Thr | Val | Thr | Ser | Gln | Ile | Gln | Gln | Val | Pro | Val | Leu | Leu | Gln | Pro | His | |
| | | 230 | | | | | 235 | | | | | 240 | | | | |
| TTC | ATC | AAG | GCA | GAC | TCG | CTG | CTT | CTG | ACA | GCC | ATG | AAG | ACA | GAC | GGA | 943 |
| Phe | Ile | Lys | Ala | Asp | Ser | Leu | Leu | Leu | Thr | Ala | Met | Lys | Thr | Asp | Gly | |
| | 245 | | | | | 250 | | | | | 255 | | | | | |
| GCC | ACT | GTG | AAG | GCG | GCA | GGT | CTC | AGT | CCC | CTG | GTC | TCT | GGC | ACC | ACT | 991 |
| Ala | Thr | Val | Lys | Ala | Ala | Gly | Leu | Ser | Pro | Leu | Val | Ser | Gly | Thr | Thr | |
| 260 | | | | | 265 | | | | | 270 | | | | | 275 | |
| GTG | CAG | ACA | GGG | CCT | TTG | CCG | ACC | CTG | GTG | AGT | GGC | GGA | ACC | ATC | TTG | 1039 |
| Val | Gln | Thr | Gly | Pro | Leu | Pro | Thr | Leu | Val | Ser | Gly | Gly | Thr | Ile | Leu | |
| | | | | 280 | | | | | 285 | | | | | 290 | | |
| GCA | ACA | GTC | CCA | CTG | GTC | GTA | GAT | GCG | GAG | AAG | CTG | CCT | ATC | AAC | CGG | 1087 |
| Ala | Thr | Val | Pro | Leu | Val | Val | Asp | Ala | Glu | Lys | Leu | Pro | Ile | Asn | Arg | |
| | | | 295 | | | | | 300 | | | | | 305 | | | |
| CTC | GCA | GCT | GGC | AGC | AAG | GCC | CCG | GCC | TCT | GCC | CAG | AGC | CGT | GGA | GAG | 1135 |
| Leu | Ala | Ala | Gly | Ser | Lys | Ala | Pro | Ala | Ser | Ala | Gln | Ser | Arg | Gly | Glu | |
| | | 310 | | | | | 315 | | | | | 320 | | | | |
| AAG | CGC | ACA | GCC | CAC | AAC | GCC | ATT | GAG | AAG | CGC | TAC | CGC | TCC | TCC | ATC | 1183 |
| Lys | Arg | Thr | Ala | His | Asn | Ala | Ile | Glu | Lys | Arg | Tyr | Arg | Ser | Ser | Ile | |
| | 325 | | | | | 330 | | | | | 335 | | | | | |
| AAT | GAC | AAA | ATC | ATT | GAG | CTC | AAG | GAT | CTG | GTG | GTG | GGC | ACT | GAG | GCA | 1231 |
| Asn | Asp | Lys | Ile | Ile | Glu | Leu | Lys | Asp | Leu | Val | Val | Gly | Thr | Glu | Ala | |
| 340 | | | | | 345 | | | | | 350 | | | | | 355 | |
| AAG | CTG | AAT | AAA | TCT | GCT | GTC | TTG | CGC | AAG | GCC | ATC | GAC | TAC | ATT | CGC | 1279 |
| Lys | Leu | Asn | Lys | Ser | Ala | Val | Leu | Arg | Lys | Ala | Ile | Asp | Tyr | Ile | Arg | |
| | | | | 360 | | | | | 365 | | | | | 370 | | |
| TTT | CTG | CAA | CAC | AGC | AAC | CAG | AAA | CTC | AAG | CAG | GAG | AAC | CTA | AGT | CTG | 1327 |
| Phe | Leu | Gln | His | Ser | Asn | Gln | Lys | Leu | Lys | Gln | Glu | Asn | Leu | Ser | Leu | |
| | | | 375 | | | | | 380 | | | | | 385 | | | |

```
CGC  ACT  GCT  GTC  CAC  AAA  AGC  AAA  TCT  CTG  AAG  GAT  CTG  GTG  TCG  GCC    1375
Arg  Thr  Ala  Val  His  Lys  Ser  Lys  Ser  Leu  Lys  Asp  Leu  Val  Ser  Ala
          390                      395                      400

TGT  GGC  AGT  GGA  GGG  AAC  ACA  GAC  GTG  CTC  ATG  GAG  GGC  GTG  AAG  ACT    1423
Cys  Gly  Ser  Gly  Gly  Asn  Thr  Asp  Val  Leu  Met  Glu  Gly  Val  Lys  Thr
405                           410                      415

GAG  GTG  GAG  GAC  ACA  CTG  ACC  CCA  CCC  CCC  TCG  GAT  GCT  GGC  TCA  CCT    1471
Glu  Val  Glu  Asp  Thr  Leu  Thr  Pro  Pro  Pro  Ser  Asp  Ala  Gly  Ser  Pro
420                      425                      430                      435

TTC  CAG  AGC  AGC  CCC  TTG  TCC  CTT  GGC  AGC  AGG  GGC  AGT  GGC  AGC  GGT    1519
Phe  Gln  Ser  Ser  Pro  Leu  Ser  Leu  Gly  Ser  Arg  Gly  Ser  Gly  Ser  Gly
               440                      445                      450

GGC  AGT  GGC  AGT  GAC  TCG  GAG  CCT  GAC  AGC  CCA  GTC  TTT  GAG  GAC  AGC    1567
Gly  Ser  Gly  Ser  Asp  Ser  Glu  Pro  Asp  Ser  Pro  Val  Phe  Glu  Asp  Ser
               455                      460                      465

AAG  GCA  AAG  CCA  GAG  CAG  CGG  CCG  TCT  CTG  CAC  AGC  CGG  GGC  ATG  CTG    1615
Lys  Ala  Lys  Pro  Glu  Gln  Arg  Pro  Ser  Leu  His  Ser  Arg  Gly  Met  Leu
          470                      475                      480

GAC  CGC  TCC  CGC  CTG  GCC  CTG  TGC  ACG  CTC  GTC  TTC  CTC  TGC  CTG  TCC    1663
Asp  Arg  Ser  Arg  Leu  Ala  Leu  Cys  Thr  Leu  Val  Phe  Leu  Cys  Leu  Ser
     485                      490                      495

TGC  AAC  CCC  TTG  GCC  TCC  TTG  CTG  GGG  GCC  CGG  GGG  CTT  CCC  AGC  CCC    1711
Cys  Asn  Pro  Leu  Ala  Ser  Leu  Leu  Gly  Ala  Arg  Gly  Leu  Pro  Ser  Pro
500                      505                      510                      515

TCA  GAT  ACC  ACC  AGC  GTC  TAC  CAT  AGC  CCT  GGG  CGC  AAC  GTG  CTG  GGC    1759
Ser  Asp  Thr  Thr  Ser  Val  Tyr  His  Ser  Pro  Gly  Arg  Asn  Val  Leu  Gly
                    520                      525                      530

ACC  GAG  AGC  AGA  GAT  GGC  CCT  GGC  TGG  GCC  CAG  TGG  CTG  CTG  CCC  CCA    1807
Thr  Glu  Ser  Arg  Asp  Gly  Pro  Gly  Trp  Ala  Gln  Trp  Leu  Leu  Pro  Pro
               535                      540                      545

GTG  GTC  TGG  CTG  CTC  AAT  GGG  CTG  TTG  GTG  CTC  GTC  TCC  TTG  GTG  CTT    1855
Val  Val  Trp  Leu  Leu  Asn  Gly  Leu  Leu  Val  Leu  Val  Ser  Leu  Val  Leu
          550                      555                      560

CTC  TTT  GTC  TAC  GGT  GAG  CCA  GTC  ACA  CGG  CCC  CAC  TCA  GGC  CCC  GCC    1903
Leu  Phe  Val  Tyr  Gly  Glu  Pro  Val  Thr  Arg  Pro  His  Ser  Gly  Pro  Ala
     565                      570                      575

GTG  TAC  TTC  TGG  AGG  CAT  CGC  AAG  CAG  GCT  GAC  CTG  GAC  CTG  GCC  CGG    1951
Val  Tyr  Phe  Trp  Arg  His  Arg  Lys  Gln  Ala  Asp  Leu  Asp  Leu  Ala  Arg
580                      585                      590                      595

GGA  GAC  TTT  GCC  CAG  GCT  GCC  CAG  CAG  CTG  TGG  CTG  GCC  CTG  CGG  GCA    1999
Gly  Asp  Phe  Ala  Gln  Ala  Ala  Gln  Gln  Leu  Trp  Leu  Ala  Leu  Arg  Ala
                    600                      605                      610

CTG  GGC  CGG  CCC  CTG  CCC  ACC  TCC  CAC  CTG  GAC  CTG  GCT  TGT  AGC  CTC    2047
Leu  Gly  Arg  Pro  Leu  Pro  Thr  Ser  His  Leu  Asp  Leu  Ala  Cys  Ser  Leu
               615                      620                      625

CTC  TGG  AAC  CTC  ATC  CGT  CAC  CTG  CTG  CAG  CGT  CTC  TGG  GTG  GGC  CGC    2095
Leu  Trp  Asn  Leu  Ile  Arg  His  Leu  Leu  Gln  Arg  Leu  Trp  Val  Gly  Arg
          630                      635                      640

TGG  CTG  GCA  GGC  CGG  GCA  GGG  GGC  TTG  CAG  CAG  GAC  TGT  GCT  CTG  CGA    2143
Trp  Leu  Ala  Gly  Arg  Ala  Gly  Gly  Leu  Gln  Gln  Asp  Cys  Ala  Leu  Arg
     645                      650                      655

GTG  GAT  GCT  AGC  GCC  AGC  GCC  CGA  GAC  GCA  GCC  CTG  GTC  TAC  CAT  AAG    2191
Val  Asp  Ala  Ser  Ala  Ser  Ala  Arg  Asp  Ala  Ala  Leu  Val  Tyr  His  Lys
660                      665                      670                      675

CTG  CAC  CAG  CTG  CAC  ACC  ATG  GGG  AAG  CAC  ACA  GGC  GGG  CAC  CTC  ACT    2239
Leu  His  Gln  Leu  His  Thr  Met  Gly  Lys  His  Thr  Gly  Gly  His  Leu  Thr
                    680                      685                      690

GCC  ACC  AAC  CTG  GCG  CTG  AGT  GCC  CTG  AAC  CTG  GCA  GAG  TGT  GCA  GGG    2287
Ala  Thr  Asn  Leu  Ala  Leu  Ser  Ala  Leu  Asn  Leu  Ala  Glu  Cys  Ala  Gly
               695                      700                      705
```

| | | | | | | | | | | | | | | | |
|---|---|---|---|---|---|---|---|---|---|---|---|---|---|---|---|
| GAT | GCC | GTG | TCT | GTG | GCG | ACG | CTG | GCC | GAG | ATC | TAT | GTG | GCG | GCT | GCA | 2335
| Asp | Ala | Val | Ser | Val | Ala | Thr | Leu | Ala | Glu | Ile | Tyr | Val | Ala | Ala | Ala |
| | | 710 | | | | 715 | | | | | 720 | | | | |
| TTG | AGA | GTG | AAG | ACC | AGT | CTC | CCA | CGG | GCC | TTG | CAT | TTT | CTG | ACA | CGC | 2383
| Leu | Arg | Val | Lys | Thr | Ser | Leu | Pro | Arg | Ala | Leu | His | Phe | Leu | Thr | Arg |
| | 725 | | | | | 730 | | | | | 735 | | | | |
| TTC | TTC | CTG | AGC | AGT | GCC | CGC | CAG | GCC | TGC | CTG | GCA | CAG | AGT | GGC | TCA | 2431
| Phe | Phe | Leu | Ser | Ser | Ala | Arg | Gln | Ala | Cys | Leu | Ala | Gln | Ser | Gly | Ser |
| 740 | | | | | 745 | | | | | 750 | | | | | 755 |
| GTG | CCT | CCT | GCC | ATG | CAG | TGG | CTC | TGC | CAC | CCC | GTG | GGC | CAC | CGT | TTC | 2479
| Val | Pro | Pro | Ala | Met | Gln | Trp | Leu | Cys | His | Pro | Val | Gly | His | Arg | Phe |
| | | | | 760 | | | | 765 | | | | | 770 | | |
| TTC | GTG | GAT | GGG | GAC | TGG | TCC | GTG | CTC | AGT | ACC | CCA | TGG | GAG | AGC | CTG | 2527
| Phe | Val | Asp | Gly | Asp | Trp | Ser | Val | Leu | Ser | Thr | Pro | Trp | Glu | Ser | Leu |
| | | 775 | | | | | 780 | | | | | 785 | | | |
| TAC | AGC | TTG | GCC | GGG | AAC | CCA | GTG | GAC | CCC | CTG | GCC | CAG | GTG | ACT | CAG | 2575
| Tyr | Ser | Leu | Ala | Gly | Asn | Pro | Val | Asp | Pro | Leu | Ala | Gln | Val | Thr | Gln |
| | | 790 | | | | | 795 | | | | | 800 | | | |
| CTA | TTC | CGG | GAA | CAT | CTC | TTA | GAG | CGA | GCA | CTG | AAC | TGT | GTG | ACC | CAG | 2623
| Leu | Phe | Arg | Glu | His | Leu | Leu | Glu | Arg | Ala | Leu | Asn | Cys | Val | Thr | Gln |
| 805 | | | | | 810 | | | | | 815 | | | | | |
| CCC | AAC | CCC | AGC | CCT | GGG | TCA | GCT | GAT | GGG | GAC | AAG | GAA | TTC | TCG | GAT | 2671
| Pro | Asn | Pro | Ser | Pro | Gly | Ser | Ala | Asp | Gly | Asp | Lys | Glu | Phe | Ser | Asp |
| 820 | | | | | 825 | | | | | 830 | | | | | 835 |
| GCC | CTC | GGG | TAC | CTG | CAG | CTG | CTG | AAC | AGC | TGT | TCT | GAT | GCT | GCG | GGG | 2719
| Ala | Leu | Gly | Tyr | Leu | Gln | Leu | Leu | Asn | Ser | Cys | Ser | Asp | Ala | Ala | Gly |
| | | | | 840 | | | | | 845 | | | | | 850 | |
| GCT | CCT | GCC | TAC | AGC | TTC | TCC | ATC | AGT | TCC | AGC | ATG | GCC | ACC | ACC | ACC | 2767
| Ala | Pro | Ala | Tyr | Ser | Phe | Ser | Ile | Ser | Ser | Ser | Met | Ala | Thr | Thr | Thr |
| | | | 855 | | | | | 860 | | | | | 865 | | |
| GGC | GTA | GAC | CCG | GTG | GCC | AAG | TGG | TGG | GCC | TCT | CTG | ACA | GCT | GTG | GTG | 2815
| Gly | Val | Asp | Pro | Val | Ala | Lys | Trp | Trp | Ala | Ser | Leu | Thr | Ala | Val | Val |
| | | 870 | | | | | 875 | | | | | 880 | | | |
| ATC | CAC | TGG | CTG | CGG | CGG | GAT | GAG | GAG | GCG | GCT | GAG | CGG | CTG | TGC | CCG | 2863
| Ile | His | Trp | Leu | Arg | Arg | Asp | Glu | Glu | Ala | Ala | Glu | Arg | Leu | Cys | Pro |
| | 885 | | | | | 890 | | | | | 895 | | | | |
| CTG | GTG | GAG | CAC | CTG | CCC | CGG | GTG | CTG | CAG | GAG | TCT | GAG | AGA | CCC | CTG | 2911
| Leu | Val | Glu | His | Leu | Pro | Arg | Val | Leu | Gln | Glu | Ser | Glu | Arg | Pro | Leu |
| 900 | | | | | 905 | | | | | 910 | | | | | 915 |
| CCC | AGG | GCA | GCT | CTG | CAC | TCC | TTC | AAG | GCT | GCC | CGG | GCC | CTG | CTG | GGC | 2959
| Pro | Arg | Ala | Ala | Leu | His | Ser | Phe | Lys | Ala | Ala | Arg | Ala | Leu | Leu | Gly |
| | | | | 920 | | | | | 925 | | | | | 930 | |
| TGT | GCC | AAG | GCA | GAG | TCT | GGT | CCA | GCC | AGC | CTG | ACC | ATC | TGT | GAG | AAG | 3007
| Cys | Ala | Lys | Ala | Glu | Ser | Gly | Pro | Ala | Ser | Leu | Thr | Ile | Cys | Glu | Lys |
| | | | 935 | | | | | 940 | | | | | 945 | | |
| GCC | AGT | GGG | TAC | CTG | CAG | GAC | AGC | CTG | GCT | ACC | ACA | CCA | GCC | AGC | AGC | 3055
| Ala | Ser | Gly | Tyr | Leu | Gln | Asp | Ser | Leu | Ala | Thr | Thr | Pro | Ala | Ser | Ser |
| | | 950 | | | | | 955 | | | | | 960 | | | |
| TCC | ATT | GAC | AAG | GCC | GTG | CAG | CTG | TTC | CTG | TGT | GAC | CTG | CTT | CTT | GTG | 3103
| Ser | Ile | Asp | Lys | Ala | Val | Gln | Leu | Phe | Leu | Cys | Asp | Leu | Leu | Leu | Val |
| | 965 | | | | | 970 | | | | | 975 | | | | |
| GTG | CGC | ACC | AGC | CTG | TGG | CGG | CAG | CAG | CAG | CCC | CCG | GCC | CCG | GCC | CCA | 3151
| Val | Arg | Thr | Ser | Leu | Trp | Arg | Gln | Gln | Gln | Pro | Pro | Ala | Pro | Ala | Pro |
| 980 | | | | | 985 | | | | | 990 | | | | | 995 |
| GCA | GCC | CAG | GGC | ACC | AGC | AGC | AGG | CCC | CAG | GCT | TCC | GCC | CTT | GAG | CTG | 3199
| Ala | Ala | Gln | Gly | Thr | Ser | Ser | Arg | Pro | Gln | Ala | Ser | Ala | Leu | Glu | Leu |
| | | | | 1000 | | | | | 1005 | | | | | 1010 | |
| CGT | GGC | TTC | CAA | CGG | GAC | CTG | AGC | AGC | CTG | AGG | CGG | CTG | GCA | CAG | AGC | 3247
| Arg | Gly | Phe | Gln | Arg | Asp | Leu | Ser | Ser | Leu | Arg | Arg | Leu | Ala | Gln | Ser |
| | | | 1015 | | | | | 1020 | | | | | 1025 | | |

| | | | | | | | | | | | | | | | |
|---|---|---|---|---|---|---|---|---|---|---|---|---|---|---|---|
| TTC | CGG | CCC | GCC | ATG | CGG | AGG | GTG | TTC | CTA | CAT | GAG | GCC | ACG | GCC | CGG | 3295
| Phe | Arg | Pro | Ala | Met | Arg | Arg | Val | Phe | Leu | His | Glu | Ala | Thr | Ala | Arg |
| | | 1030 | | | | | 1035 | | | | | 1040 | | | |
| CTG | ATG | GCG | GGG | GCC | AGC | CCC | ACA | CGG | ACA | CAC | CAG | CTC | CTC | GAC | CGC | 3343
| Leu | Met | Ala | Gly | Ala | Ser | Pro | Thr | Arg | Thr | His | Gln | Leu | Leu | Asp | Arg |
| | | 1045 | | | | | 1050 | | | | | 1055 | | | |
| AGT | CTG | AGG | CGG | CGG | GCA | GGC | CCC | GGT | GGC | AAA | GGA | GGC | GCG | GTG | GCG | 3391
| Ser | Leu | Arg | Arg | Arg | Ala | Gly | Pro | Gly | Gly | Lys | Gly | Gly | Ala | Val | Ala |
| 1060 | | | | | 1065 | | | | | 1070 | | | | | 1075 |
| GAG | CTG | GAG | CCG | CGG | CCC | ACG | CGG | CGG | GAG | CAC | GCG | GAG | GCC | TTG | CTG | 3439
| Glu | Leu | Glu | Pro | Arg | Pro | Thr | Arg | Arg | Glu | His | Ala | Glu | Ala | Leu | Leu |
| | | | | 1080 | | | | | 1085 | | | | | 1090 | |
| CTG | GCC | TCC | TGC | TAC | CTG | CCC | CCC | GGC | TTC | CTG | TCG | GCG | CCC | GGG | CAG | 3487
| Leu | Ala | Ser | Cys | Tyr | Leu | Pro | Pro | Gly | Phe | Leu | Ser | Ala | Pro | Gly | Gln |
| | | | | 1095 | | | | | 1100 | | | | | 1105 | |
| CGC | GTG | GGC | ATG | CTG | GCT | GAG | GCG | GCG | CGC | ACA | CTC | GAG | AAG | CTT | GGC | 3535
| Arg | Val | Gly | Met | Leu | Ala | Glu | Ala | Ala | Arg | Thr | Leu | Glu | Lys | Leu | Gly |
| | | | 1110 | | | | | 1115 | | | | | 1120 | | |
| GAT | CGC | CGG | CTG | CTG | CAC | GAC | TGT | CAG | CAG | ATG | CTC | ATG | CGC | CTG | GGC | 3583
| Asp | Arg | Arg | Leu | Leu | His | Asp | Cys | Gln | Gln | Met | Leu | Met | Arg | Leu | Gly |
| | | 1125 | | | | | 1130 | | | | | 1135 | | | |
| GGT | GGG | ACC | ACT | GTC | ACT | TCC | AGC | TAGACCCGT | | GTCCCCGGCC | | TCAGCACCCC | | | | 3637
| Gly | Gly | Thr | Thr | Val | Thr | Ser | Ser | | | | | | | | |
| 1140 | | | | | 1145 | | | | | | | | | | |

| | | | | |
|---|---|---|---|---|
| TGTCTCTAGC | CACTTTGGTC | CCGTGCAGCT | TCTGTCCTGC | GTCGAAGCTT | TGAAGGCCGA | 3697
| AGGCAGTGCA | AGAGACTCTG | GCCTCCACAG | TTCGACCTGC | GGCTGCTGTG | TGCCTTCGCG | 3757
| GTGGAAGGCC | CGAGGGGCGC | GATCTTGACC | CTAAGACCGG | CGGCCATGAT | GGTGCTGACC | 3817
| TCTGGTGGCC | GATCGGGGCA | CTGCAGGGGC | CGAGCCATTT | TGGGGGGCCC | CCCTCCTTGC | 3877
| TCTGCAGGCA | CCTTAGTGGC | TTTTTCCTC | CTGTGTACAG | GGAAGAGAGG | GGTACATTTC | 3937
| CCTGTGCTGA | CGGAAGCCAA | CTTGGCTTTC | CCGGACTGCA | AGCAGGGCTC | TGCCCCAGAG | 3997
| GCCTCTCTCT | CCGTCGTGGG | AGAGAGACGT | GTACATAGTG | TAGGTCAGCG | TGCTTAGCCT | 4057
| CCTGACCTGA | GGCTCCTGTG | CTACTTTGCC | TTTTGCAAAC | TTTATTTTCA | TAGATTGAGA | 4117
| AGTTTTGTAC | AGAGAATTAA | AAATGAAATT | ATTTATA | | | 4154

( 2 ) INFORMATION FOR SEQ ID NO:38:

( i ) SEQUENCE CHARACTERISTICS:
        ( A ) LENGTH: 1147 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

| | | | | | | | | | | | | | | |
|---|---|---|---|---|---|---|---|---|---|---|---|---|---|---|
| Met | Asp | Glu | Pro | Pro | Phe | Ser | Glu | Ala | Ala | Leu | Glu | Gln | Ala | Leu | Gly |
| 1 | | | | 5 | | | | | 10 | | | | | 15 | |
| Glu | Pro | Cys | Asp | Leu | Asp | Ala | Ala | Leu | Leu | Thr | Asp | Ile | Glu | Asp | Met |
| | | | 20 | | | | | 25 | | | | | 30 | | |
| Leu | Gln | Leu | Ile | Asn | Asn | Gln | Asp | Ser | Asp | Phe | Pro | Gly | Leu | Phe | Asp |
| | | 35 | | | | | 40 | | | | | 45 | | | |
| Pro | Pro | Tyr | Ala | Gly | Ser | Gly | Ala | Gly | Gly | Thr | Asp | Pro | Ala | Ser | Pro |
| | 50 | | | | | 55 | | | | | 60 | | | | |
| Asp | Thr | Ser | Ser | Pro | Gly | Ser | Leu | Ser | Pro | Pro | Ala | Thr | Leu | Ser |
| 65 | | | | | 70 | | | | | 75 | | | | | 80 |
| Ser | Ser | Leu | Glu | Ala | Phe | Leu | Ser | Gly | Pro | Gln | Ala | Ala | Pro | Ser | Pro |
| | | | | 85 | | | | | 90 | | | | | 95 | |

-continued

```
Leu  Ser  Pro  Pro  Gln  Pro  Ala  Pro  Thr  Pro  Leu  Lys  Met  Tyr  Pro  Ser
               100                 105                      110

Met  Pro  Ala  Phe  Ser  Pro  Gly  Pro  Gly  Ile  Lys  Glu  Glu  Ser  Val  Pro
               115                 120                      125

Leu  Ser  Ile  Leu  Gln  Thr  Pro  Thr  Pro  Gln  Pro  Leu  Pro  Gly  Ala  Leu
               130                 135                      140

Leu  Pro  Gln  Ser  Phe  Pro  Ala  Pro  Ala  Pro  Gln  Phe  Ser  Ser  Thr
145                      150                      155                      160

Pro  Val  Leu  Gly  Tyr  Pro  Ser  Pro  Pro  Gly  Gly  Phe  Ser  Thr  Gly  Ser
               165                 170                      175

Pro  Pro  Gly  Asn  Thr  Gln  Gln  Pro  Leu  Pro  Gly  Leu  Pro  Leu  Ala  Ser
               180                 185                      190

Pro  Pro  Gly  Val  Pro  Pro  Val  Ser  Leu  His  Thr  Gln  Val  Gln  Ser  Val
               195                 200                      205

Val  Pro  Gln  Gln  Leu  Leu  Thr  Val  Thr  Ala  Ala  Pro  Thr  Ala  Ala  Pro
     210                 215                      220

Val  Thr  Thr  Thr  Val  Thr  Ser  Gln  Ile  Gln  Gln  Val  Pro  Val  Leu  Leu
225                      230                      235                      240

Gln  Pro  His  Phe  Ile  Lys  Ala  Asp  Ser  Leu  Leu  Leu  Thr  Ala  Met  Lys
               245                      250                      255

Thr  Asp  Gly  Ala  Thr  Val  Lys  Ala  Ala  Gly  Leu  Ser  Pro  Leu  Val  Ser
               260                 265                      270

Gly  Thr  Thr  Val  Gln  Thr  Gly  Pro  Leu  Pro  Thr  Leu  Val  Ser  Gly  Gly
               275                 280                      285

Thr  Ile  Leu  Ala  Thr  Val  Pro  Leu  Val  Val  Asp  Ala  Glu  Lys  Leu  Pro
     290                 295                      300

Ile  Asn  Arg  Leu  Ala  Ala  Gly  Ser  Lys  Ala  Pro  Ala  Ser  Ala  Gln  Ser
305                      310                      315                      320

Arg  Gly  Glu  Lys  Arg  Thr  Ala  His  Asn  Ala  Ile  Glu  Lys  Arg  Tyr  Arg
               325                 330                      335

Ser  Ser  Ile  Asn  Asp  Lys  Ile  Ile  Glu  Leu  Lys  Asp  Leu  Val  Val  Gly
               340                 345                      350

Thr  Glu  Ala  Lys  Leu  Asn  Lys  Ser  Ala  Val  Leu  Arg  Lys  Ala  Ile  Asp
               355                 360                      365

Tyr  Ile  Arg  Phe  Leu  Gln  His  Ser  Asn  Gln  Lys  Leu  Lys  Gln  Glu  Asn
     370                 375                      380

Leu  Ser  Leu  Arg  Thr  Ala  Val  His  Lys  Ser  Lys  Ser  Leu  Lys  Asp  Leu
385                      390                      395                      400

Val  Ser  Ala  Cys  Gly  Ser  Gly  Gly  Asn  Thr  Asp  Val  Leu  Met  Glu  Gly
               405                 410                      415

Val  Lys  Thr  Glu  Val  Glu  Asp  Thr  Leu  Thr  Pro  Pro  Pro  Ser  Asp  Ala
               420                 425                      430

Gly  Ser  Pro  Phe  Gln  Ser  Ser  Pro  Leu  Ser  Leu  Gly  Ser  Arg  Gly  Ser
               435                 440                      445

Gly  Ser  Gly  Gly  Ser  Gly  Ser  Asp  Ser  Glu  Pro  Asp  Ser  Pro  Val  Phe
               450                 455                      460

Glu  Asp  Ser  Lys  Ala  Lys  Pro  Glu  Gln  Arg  Pro  Ser  Leu  His  Ser  Arg
465                      470                      475                      480

Gly  Met  Leu  Asp  Arg  Ser  Arg  Leu  Ala  Leu  Cys  Thr  Leu  Val  Phe  Leu
               485                 490                      495

Cys  Leu  Ser  Cys  Asn  Pro  Leu  Ala  Ser  Leu  Leu  Gly  Ala  Arg  Gly  Leu
               500                 505                      510

Pro  Ser  Pro  Ser  Asp  Thr  Thr  Ser  Val  Tyr  His  Ser  Pro  Gly  Arg  Asn
```

-continued

|  |  | 515 |  |  |  | 520 |  |  |  | 525 |  |  |  |  |
|---|---|---|---|---|---|---|---|---|---|---|---|---|---|---|
| Val | Leu | Gly | Thr | Glu | Ser | Arg | Asp | Gly | Pro | Gly | Trp | Ala | Gln | Trp | Leu |
|  | 530 |  |  |  | 535 |  |  |  |  | 540 |  |  |  |  |
| Leu | Pro | Pro | Val | Val | Trp | Leu | Leu | Asn | Gly | Leu | Leu | Val | Leu | Val | Ser |
| 545 |  |  |  |  | 550 |  |  |  |  | 555 |  |  |  |  | 560 |
| Leu | Val | Leu | Leu | Phe | Val | Tyr | Gly | Glu | Pro | Val | Thr | Arg | Pro | His | Ser |
|  |  |  |  | 565 |  |  |  |  | 570 |  |  |  |  | 575 |  |
| Gly | Pro | Ala | Val | Tyr | Phe | Trp | Arg | His | Arg | Lys | Gln | Ala | Asp | Leu | Asp |
|  |  |  | 580 |  |  |  |  | 585 |  |  |  |  | 590 |  |  |
| Leu | Ala | Arg | Gly | Asp | Phe | Ala | Gln | Ala | Ala | Gln | Leu | Trp | Leu | Ala |
|  |  | 595 |  |  |  |  | 600 |  |  |  |  | 605 |  |  |
| Leu | Arg | Ala | Leu | Gly | Arg | Pro | Leu | Pro | Thr | Ser | His | Leu | Asp | Leu | Ala |
|  | 610 |  |  |  |  | 615 |  |  |  |  | 620 |  |  |  |  |
| Cys | Ser | Leu | Leu | Trp | Asn | Leu | Ile | Arg | His | Leu | Leu | Gln | Arg | Leu | Trp |
| 625 |  |  |  |  | 630 |  |  |  |  | 635 |  |  |  |  | 640 |
| Val | Gly | Arg | Trp | Leu | Ala | Gly | Arg | Ala | Gly | Gly | Leu | Gln | Gln | Asp | Cys |
|  |  |  |  | 645 |  |  |  |  | 650 |  |  |  |  | 655 |  |
| Ala | Leu | Arg | Val | Asp | Ala | Ser | Ala | Ser | Ala | Arg | Asp | Ala | Ala | Leu | Val |
|  |  |  | 660 |  |  |  |  | 665 |  |  |  |  | 670 |  |  |
| Tyr | His | Lys | Leu | His | Gln | Leu | His | Thr | Met | Gly | Lys | His | Thr | Gly | Gly |
|  |  | 675 |  |  |  |  | 680 |  |  |  |  | 685 |  |  |  |
| His | Leu | Thr | Ala | Thr | Asn | Leu | Ala | Leu | Ser | Ala | Leu | Asn | Leu | Ala | Glu |
|  | 690 |  |  |  |  | 695 |  |  |  |  | 700 |  |  |  |  |
| Cys | Ala | Gly | Asp | Ala | Val | Ser | Val | Ala | Thr | Leu | Ala | Glu | Ile | Tyr | Val |
| 705 |  |  |  |  | 710 |  |  |  |  | 715 |  |  |  |  | 720 |
| Ala | Ala | Ala | Leu | Arg | Val | Lys | Thr | Ser | Leu | Pro | Arg | Ala | Leu | His | Phe |
|  |  |  |  | 725 |  |  |  |  | 730 |  |  |  |  | 735 |  |
| Leu | Thr | Arg | Phe | Phe | Leu | Ser | Ser | Ala | Arg | Gln | Ala | Cys | Leu | Ala | Gln |
|  |  |  | 740 |  |  |  |  | 745 |  |  |  |  | 750 |  |  |
| Ser | Gly | Ser | Val | Pro | Pro | Ala | Met | Gln | Trp | Leu | Cys | His | Pro | Val | Gly |
|  |  | 755 |  |  |  |  | 760 |  |  |  |  | 765 |  |  |  |
| His | Arg | Phe | Phe | Val | Asp | Gly | Asp | Trp | Ser | Val | Leu | Ser | Thr | Pro | Trp |
|  | 770 |  |  |  |  | 775 |  |  |  |  | 780 |  |  |  |  |
| Glu | Ser | Leu | Tyr | Ser | Leu | Ala | Gly | Asn | Pro | Val | Asp | Pro | Leu | Ala | Gln |
| 785 |  |  |  |  | 790 |  |  |  |  | 795 |  |  |  |  | 800 |
| Val | Thr | Gln | Leu | Phe | Arg | Glu | His | Leu | Leu | Glu | Arg | Ala | Leu | Asn | Cys |
|  |  |  |  | 805 |  |  |  |  | 810 |  |  |  |  | 815 |  |
| Val | Thr | Gln | Pro | Asn | Pro | Ser | Pro | Gly | Ser | Ala | Asp | Gly | Asp | Lys | Glu |
|  |  |  | 820 |  |  |  |  | 825 |  |  |  |  | 830 |  |  |
| Phe | Ser | Asp | Ala | Leu | Gly | Tyr | Leu | Gln | Leu | Leu | Asn | Ser | Cys | Ser | Asp |
|  |  | 835 |  |  |  |  | 840 |  |  |  |  | 845 |  |  |  |
| Ala | Ala | Gly | Ala | Pro | Ala | Tyr | Ser | Phe | Ser | Ile | Ser | Ser | Ser | Met | Ala |
|  | 850 |  |  |  |  | 855 |  |  |  |  | 860 |  |  |  |  |
| Thr | Thr | Thr | Gly | Val | Asp | Pro | Val | Ala | Lys | Trp | Trp | Ala | Ser | Leu | Thr |
| 865 |  |  |  |  | 870 |  |  |  |  | 875 |  |  |  |  | 880 |
| Ala | Val | Val | Ile | His | Trp | Leu | Arg | Arg | Asp | Glu | Ala | Ala | Glu | Arg |
|  |  |  |  | 885 |  |  |  |  | 890 |  |  |  |  | 895 |  |
| Leu | Cys | Pro | Leu | Val | Glu | His | Leu | Pro | Arg | Val | Leu | Gln | Glu | Ser | Glu |
|  |  |  | 900 |  |  |  |  | 905 |  |  |  |  | 910 |  |  |
| Arg | Pro | Leu | Pro | Arg | Ala | Ala | Leu | His | Ser | Phe | Lys | Ala | Ala | Arg | Ala |
|  |  | 915 |  |  |  |  | 920 |  |  |  |  | 925 |  |  |  |
| Leu | Leu | Gly | Cys | Ala | Lys | Ala | Glu | Ser | Gly | Pro | Ala | Ser | Leu | Thr | Ile |
|  | 930 |  |  |  |  | 935 |  |  |  |  | 940 |  |  |  |  |

```
Cys  Glu  Lys  Ala  Ser  Gly  Tyr  Leu  Gln  Asp  Ser  Leu  Ala  Thr  Thr  Pro
945                 950                      955                           960

Ala  Ser  Ser  Ser  Ile  Asp  Lys  Ala  Val  Gln  Leu  Phe  Leu  Cys  Asp  Leu
                    965                      970                     975

Leu  Leu  Val  Val  Arg  Thr  Ser  Leu  Trp  Arg  Gln  Gln  Pro  Pro  Ala
               980                      985                     990

Pro  Ala  Pro  Ala  Ala  Gln  Gly  Thr  Ser  Ser  Arg  Pro  Gln  Ala  Ser  Ala
          995                      1000                     1005

Leu  Glu  Leu  Arg  Gly  Phe  Gln  Arg  Asp  Leu  Ser  Ser  Leu  Arg  Arg  Leu
          1010                     1015                     1020

Ala  Gln  Ser  Phe  Arg  Pro  Ala  Met  Arg  Arg  Val  Phe  Leu  His  Glu  Ala
1025                      1030                     1035                     1040

Thr  Ala  Arg  Leu  Met  Ala  Gly  Ala  Ser  Pro  Thr  Arg  Thr  His  Gln  Leu
                    1045                     1050                     1055

Leu  Asp  Arg  Ser  Leu  Arg  Arg  Arg  Ala  Gly  Pro  Gly  Gly  Lys  Gly  Gly
                    1060                     1065                     1070

Ala  Val  Ala  Glu  Leu  Glu  Pro  Arg  Pro  Thr  Arg  Arg  Glu  His  Ala  Glu
               1075                     1080                     1085

Ala  Leu  Leu  Ala  Ser  Cys  Tyr  Leu  Pro  Pro  Gly  Phe  Leu  Ser  Ala
          1090                     1095                     1100

Pro  Gly  Gln  Arg  Val  Gly  Met  Leu  Ala  Glu  Ala  Ala  Arg  Thr  Leu  Glu
1105                      1110                     1115                     1120

Lys  Leu  Gly  Asp  Arg  Arg  Leu  Leu  His  Asp  Cys  Gln  Gln  Met  Leu  Met
                    1125                     1130                     1135

Arg  Leu  Gly  Gly  Gly  Thr  Thr  Val  Thr  Ser  Ser
                    1140                     1145
```

(2) INFORMATION FOR SEQ ID NO:39:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 3..71

(xi) SEQUENCE DESCRIPTION: SEQ ID NO:39:

```
GG  AGG  GGT  AGG  GCC  AAC  GGC  CTG  GAC  GCC  CCA  AGG  GCG  GGC  GCA  GAT      47
    Arg  Gly  Arg  Ala  Asn  Gly  Leu  Asp  Ala  Pro  Arg  Ala  Gly  Ala  Asp
     1              5                        10                      15

CGC  GGA  GCC  ATG  GAT  TGC  ACT  TTC                                             71
Arg  Gly  Ala  Met  Asp  Cys  Thr  Phe
                    20
```

(2) INFORMATION FOR SEQ ID NO:40:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:40:

```
Arg  Gly  Arg  Ala  Asn  Gly  Leu  Asp  Ala  Pro  Arg  Ala  Gly  Ala  Asp  Arg
 1              5                        10                      15
```

```
Gly  Ala  Met  Asp  Cys  Thr  Phe
               20
```

( 2 ) INFORMATION FOR SEQ ID NO:41:

( i ) SEQUENCE CHARACTERISTICS:
        ( A ) LENGTH: 547 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( i x ) FEATURE:
        ( A ) NAME/KEY: CDS
        ( B ) LOCATION: 1..111

( x i ) SEQUENCE DESCRIPTION: SEQ ID NO:41:

```
CTG  ATG  GAT  GTG  CTG  ACT  AGT  GAG  AGT  GCT  TGG  GCC  CTC  CCC  CAG  CAC        48
Leu  Met  Asp  Val  Leu  Thr  Ser  Glu  Ser  Ala  Trp  Ala  Leu  Pro  Gln  His
 1                   5                        10                       15

CTA  GGC  AAA  GGC  TTC  CCC  TCC  CCC  TCC  GGA  CAC  AAG  GTC  CCT  GGG  TGG        96
Leu  Gly  Lys  Gly  Phe  Pro  Ser  Pro  Ser  Gly  His  Lys  Val  Pro  Gly  Trp
                20                       25                       30

CAC  GGG  AGG  ATG  GAC  TGACTTCAG   GACCTGTTGT  GTGACAGGAG  CTACAGCTTG             151
His  Gly  Arg  Met  Asp
                35

GGTCTCCCTG  CAAGAAGTCT  GGCACGTCTC  ACCTCCCCCA  TCCCGGCCCC  TGGTCATTTC              211

ACAGCAAAGA  AGCCTCCTCC  CTCCCGACCT  GCCGCCACAC  TGGAGAGGGG  GCACAGGGGC              271

GGGGGAGGTT  TCCTGTTCTG  TGAAAGGCCG  ACTCCCTGAC  TCCATTCATG  CCCCCCCCC               331

CAGCCCCTCC  CTTCATTCCC  ATTCCCCAAC  CTAAAGCCTG  GCCCGGCTCC  CAGCTGAATC              391

TGGTCGGAAT  CCACGGGCTG  CAGATTTTCC  AAAACAATCG  TTGTATCTTT  ATTGACTTTT              451

TTTTTTTTTT  TTTCTGAATG  CAATGACTGT  TTTTTACTCT  TAAGGAAAAT  AAACATCTTT              511

TAGAAACAAA  AAAAAAAAA   AAAAAAAAA   AAAAAA                                         547
```

( 2 ) INFORMATION FOR SEQ ID NO:42:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( x i ) SEQUENCE DESCRIPTION: SEQ ID NO:42:

```
Leu  Met  Asp  Val  Leu  Thr  Ser  Glu  Ser  Ala  Trp  Ala  Leu  Pro  Gln  His
 1                   5                        10                       15

Leu  Gly  Lys  Gly  Phe  Pro  Ser  Pro  Ser  Gly  His  Lys  Val  Pro  Gly  Trp
                20                       25                       30

His  Gly  Arg  Met  Asp
                35
```

( 2 ) INFORMATION FOR SEQ ID NO:43:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:43:

TAGTGGGGTG 10

( 2 ) INFORMATION FOR SEQ ID NO:44:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:44:

Ser Phe Thr Gln Val Thr Leu Pro Ser Phe Ser Pro Ser Ala Ala Ser
1               5                   10                  15

Pro Gln Ala ( 2 ) INFORMATION FOR SEQ ID NO:45:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( i x ) FEATURE:
        ( A ) NAME/KEY: wherein N=I (inosine)
        ( B ) LOCATION: 12

( x i ) SEQUENCE DESCRIPTION: SEQ ID NO:45:

TTYTCYTGYT TNAGYTTYTG 20

( 2 ) INFORMATION FOR SEQ ID NO:46:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:46:

GGCTTATGAG TATTTCTTCC AGGG 24

( 2 ) INFORMATION FOR SEQ ID NO:47:

( i ) SEQUENCE CHARACTERISTICS:
        ( A ) LENGTH: 17 nucleic acid
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( i x ) FEATURE:
        ( A ) NAME/KEY: wherein N=I (inosine)
        ( B ) LOCATION: 9

( x i ) SEQUENCE DESCRIPTION: SEQ ID NO:47:

TTYTGRTTNG ARTGYTG 17

( 2 ) INFORMATION FOR SEQ ID NO:48:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:48:

His His His His His His
1               5

( 2 ) INFORMATION FOR SEQ ID NO:49:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:49:

Asp Asp Asp Asp Lys
1               5

( 2 ) INFORMATION FOR SEQ ID NO:50:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:50:

Arg Arg Ala Ser Val
1               5

( 2 ) INFORMATION FOR SEQ ID NO:51:

( i ) SEQUENCE CHARACTERISTICS:
  ( A ) LENGTH: 60 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:51:

CGCGGATCCG ATGACGATGA CAAACGTCGT GCATCTGTTG AGAAGCTGCC TATCAACCGG    60

( 2 ) INFORMATION FOR SEQ ID NO:52:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA"

( x i ) SEQUENCE DESCRIPTION: SEQ ID NO:52:

CTAATTAAGC TTACTATCCA CTGCCACAGG CCGACAC    37

( 2 ) INFORMATION FOR SEQ ID NO:53:

(i) SEQUENCE CHARACTERISTICS:
    (A) LENGTH: 5197 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA"

(xi) SEQUENCE DESCRIPTION: SEQ ID NO:53:

| | | | | | | |
|---|---|---|---|---|---|---|
| CCGTCGGTGA | GGCGGTGCCG | GGCGGGGGTT | GTCGGGTGTC | ATGGGCGGTG | GCGACGGCAC | 60 |
| CGCCCCCGCG | TCTCCCTGAG | CGGGACGGCA | GGGGGGGCTT | CTGCGCTGAG | CCGGGCGATG | 120 |
| GACGACAGCG | GCGAGCTGGG | TGGTCTGGAG | ACCATGGAGA | CCCTCACGGA | GCTGGGCGAC | 180 |
| GAGCTGACCC | TGGGAGACAT | CGACGAGATG | CTGCAATTTG | TCAGTAATCA | AGTGGGAGAG | 240 |
| TTCCCTGACT | TGTTTTCAGA | ACAGCTGTGT | AGCTCCTTTC | CTGGCAGTGG | TGGTAGTGGT | 300 |
| AGCAGCAGCG | GCAGCAGTGG | CAGCAGCAGC | AGCAGCAGCA | ATGGCAGGGG | CAGCAGCAGC | 360 |
| GGAGCTGTGG | ACCCTTCAGT | GCAACGGTCA | TTCACCCAGG | TCACATTACC | TTCCTTCTCT | 420 |
| CCCTCGGCGG | CCTCCCCACA | GGCTCCAACT | CTGCAAGTCA | AGGTTTCTCC | CACCTCAGTT | 480 |
| CCCACCACAC | CCAGGGCAAC | TCCTATTCTT | CAGCCCCGCC | CCCAGCCCCA | GCCTCAACCT | 540 |
| CAAACTCAGC | TGCAACAACA | GACGGTAATG | ATCACGCCAA | CATTCAGCAC | CACTCCGCAG | 600 |
| ACGAGGATCA | TCCAGCAGCC | TTTGATATAC | CAGAATGCAG | CTACTAGCTT | TCAAGTCCTT | 660 |
| CAGCCTCAAG | TCCAAAGCCT | GGTGACATCC | TCCCAGGTAC | AGCCGGTCAC | CATTCAGCAG | 720 |
| CAGGTGCAGA | CAGTACAGGC | CCAGCGGGTG | CTGACACAAA | CGGCCAATGG | CACGCTGCAG | 780 |
| ACCCTTGCCC | CGGCTACGGT | GCAGACAGTT | GCTGCGCCAC | AGGTGCAGCA | GGTCCCGGTC | 840 |
| CTGGTCCAGC | CTCAGATCAT | CAAGACAGAT | TCCCTTGTTT | TGACCACACT | GAAGACAGAT | 900 |
| GGCAGCCCTG | TTATGGCTGC | GGTCCAGAAC | CCGGCCCTCA | CCGCCCTCAC | CACCCCTATC | 960 |
| CAGACGGCTG | CCCTTCAAGT | ACCAACCCTG | GTGGGCAGCA | GTGGGACCAT | TCTGACCACA | 1020 |
| ATGCCTGTAA | TGATGGGGCA | AGAGAAAGTG | CCCATTAAGC | AGGTACCTGG | GGGAGTCAAG | 1080 |
| CAGCTTGAGC | CCCCCAAAGA | AGGAGAAAGG | CGGACAACCC | ATAATATCAT | TGAGAAACGA | 1140 |
| TATCGCTCCT | CCATCAATGA | CAAAATCATC | GAATTGAAAG | ACCTGGTCAT | GGGGACAGAC | 1200 |
| GCCAAGATGC | ACAAGTCTGG | CGTTCTGAGG | AAGGCCATTG | ATTACATCAA | ATACTTGCAG | 1260 |
| CAGGTCAATC | ATAAACTGCG | CCAGGAGAAC | ATGGTGCTGA | AGCTGGCAAA | TCAAAAGAAC | 1320 |
| AAGCTTCTAA | AGGGCATCGA | CCTAGGCAGT | CTGGTGGACA | ATGAGGTGGA | CCTGAAGATC | 1380 |
| GAGGACTTTA | ATCAGAATGT | CCTTCTGATG | TCCCCCCCAG | CCTCTGACTC | AGGGTCCCAG | 1440 |
| GCTGGCTTCT | CTCCCTACTC | CATTGACTCT | GAGCCAGGAA | GCCCTCTATT | GGATGATGCA | 1500 |
| AAGGTCAAAG | ATGAGCCAGA | CTCTCCTCCT | GTGGCGCTGG | GCATGGTAGA | CCGCTCACGG | 1560 |
| ATTCTTCTGT | GTGTCCTCAC | CTTCCTGTGC | CTCTCCTTTA | ACCCCCTGAC | TTCCCTGCTG | 1620 |
| CAGTGGGGAG | GGGCCCACGA | CTCTGACCAG | CACCCACACT | CAGGCTCTGG | CCGCAGTGTC | 1680 |
| CTGTCATTCG | AGTCAGGTTC | TGGGGGCTGG | TTTGACTGGA | TGATGCCTAC | TCTTCTCTTA | 1740 |
| TGGCTGGTAA | ATGGTGTGAT | TGTCCTGAGC | GTCTTTGTGA | AGCTGCTGGT | TCATGGGGAG | 1800 |
| CCAGTGATCC | GGCCACACTC | GCGCTCCTCG | GTCACCTTCT | GGAGGCACCG | GAAACAGGCA | 1860 |
| GATCTGGATC | TCGCCAGAGG | AGATTTTGCA | GCTGCTGCCG | CCAACCTACA | AACCTGCCTG | 1920 |
| GCAGTTTTGG | GCCGGGCACT | GCCCACCTCC | CGCCTGGACC | TGGCCTGCAG | CCTCTCCTGG | 1980 |
| AACGTGATCC | GCTACAGCCT | GCAGAAGCTA | CGCCTGGTGC | GCTGGCTGCT | CAAGAAAGTC | 2040 |

| | | | | | | |
|---|---|---|---|---|---|---|
|TTCCAGTGCC|GGCGGGCCAC|GCCAGCCACT|GAGGCAGGCT|TTGAAGACGA|AGCTAAGACC|2100|
|AGCGCCCGGG|ATGCGGCTCT|GGCCTATCAC|CGGCTGCACC|AGCTGCACAT|CACAGGGAAG|2160|
|CTTCCTGCAG|GATCCGCCTG|TTCCGATGTA|CACATGGCGT|TGTGTGCCGT|GAACCTGGCT|2220|
|GAATGTGCAG|AGGAGAAGAT|CCCACCGAGC|ACACTGGTTG|AGATCCATCT|GACTGCTGCC|2280|
|ATGGGGCTCA|AGACCCGGTG|TGGAGGCAAG|CTGGGCTTCC|TGGCCAGCTA|CTTCCTCAGC|2340|
|CGAGCCCAGA|GCCTGTGTGG|CCCCGAGCAC|AGTGCTGTTC|CTGACTCCCT|GCGCTGGCTC|2400|
|TGCCACCCCC|TGGGCCAGAA|GTTTTCATG|GAGCGGAGCT|GGTCTGTGAA|GTCAGCTGCC|2460|
|AAGGAGAGTC|TATACTGTGC|CCAGAGGAAC|CCAGCTGACC|CCATTGCGCA|GGTCCACCAG|2520|
|GCCTTCTGCA|AGAACCTGCT|GGAGCGAGCT|ATAGAGTCCT|TGGTGAAACC|TCAGGCCAAG|2580|
|AAGAAGGCTG|GAGACCAGGA|AGAAGAGAGC|TGTGAATTCT|CCAGTGCTCT|GGAGTACTTG|2640|
|AAATTACTTC|ATTCTTTTGT|GGACTCTGTG|GGGGTTATGA|GCCCCCACT|CTCCAGGAGC|2700|
|TCCGTGCTCA|AGTCCGCCCT|GGGTCCAGAC|ATCATCTGTC|GGTGGTGGAC|GTCTGCAATC|2760|
|ACTGTGGCCA|TCAGCTGGCT|CCAGGGAGAC|GATGCAGCTG|TGCGCTCTCA|TTTTACCAAA|2820|
|GTGGAACGCA|TCCCCAAGGC|CCTGGAAGTG|ACAGAGAGCC|CCCTGGTGAA|GGCCATCTTC|2880|
|CATGCCTGCA|GAGCCATGCA|TGCCTCACTC|CCTGGGAAAG|CAGATGGGCA|GCAGAGTTCC|2940|
|TTCTGCCATT|GCGAGAGGGC|CAGTGGCCAC|CTATGGAGCA|GCCTCAACGT|CAGTGGGGGC|3000|
|ACCTCTGACC|CTGCCCTCAA|CCACGTGGTC|CAGCTGCTCA|CCTGTGACCT|GCTACTGTCG|3060|
|CTACGGACAG|CGCTCTGGCA|AAAACAGGCC|AGTGCCAGCC|AGGCTGTGGG|GGAGACCTAC|3120|
|CACGCGTCAG|GCGCTGAACT|GGCGGGCTTC|CAACGGGACC|TGGGCAGCCT|GCGCAGGCTG|3180|
|GCACACAGCT|TCCGCCCAGC|ATACCGCAAG|GTGTTCCTGC|ATGAAGCCAC|CGTGCGCCTG|3240|
|ATGGCAGGAG|GCAGCCCCAC|CCGCACCCAC|CAGCTGCTGG|AACACAGCCT|GCGGCGGCGC|3300|
|ACCACGCAGA|GCACCAAGCA|CGGAGAGGTG|GATGCCTGGC|CCGGCCAGCG|AGAGCGGGCC|3360|
|ACCGCCATCC|TGCTGGCCTG|CCGCCACCTG|CCCCTCTCCT|TCCTCTCCTC|CCCGGGCCAG|3420|
|CGGGCAGTGC|TGCTGGCCGA|AGCTGCCCGC|ACCCTGGAGA|AGGTGGGCGA|CCGGCGCTCC|3480|
|TGCAACGACT|GCCAGCAGAT|GATTGTTAAG|CTGGGTGGTG|GCACTGCCAT|TGCCGCCTCC|3540|
|TGACCACCAG|GCTCAGCCCA|CCCCTCCACC|TCTCTCTCGA|TTTCTCTCTC|TCCCCCTCAG|3600|
|CATCTTCCCG|CTGAGAGTGG|TGGGAAGAG|CCTTGTCTTC|TTAGCTGTCA|CCTGCCGAGG|3660|
|CTTCTGGGCC|ACTCAGGCCA|GTGCACCCCT|GGGCAGAGCC|CCTTAAAGCT|GCTGTCACTA|3720|
|GATGCCCATG|GTCCAGGGCC|TGGTGGGCGT|GAGAGGATAG|GTGGCAGGGC|AGAAACTGGG|3780|
|CAGCCCTGAC|TTGATAGCAG|CAGGGGGAGC|TCCCAAGCTG|CCAAGCCCT|GCCTCCAGCC|3840|
|TTCCTGAGTT|TCTCTCTCCT|GAACCCTACT|CTCTCCTTTT|TGCTTCCTCA|GTTTTATCA|3900|
|GGCTTTCTCT|GGGGACAGC|AGTCTCTGAG|CACCAGGGAG|CAGTTGCCCT|CAGGCCTGTG|3960|
|CCCAGCATGC|CCTCCCCTTT|TTATACGAAT|GTTTCTACC|AGTGTGCTTG|GGTTTGCCAT|4020|
|GATGCGAGGC|TGAGTTGCTG|TAGCGTCTTG|ATTCTCTCCC|TGGGTCTGCG|TTCCCTCCCC|4080|
|TGGGCCTGAC|TGAGCCTGCT|CATTGTTTTT|CCCTTTATTA|CACAGGACAG|CCAGGGAGG|4140|
|AGGGGGCCC|AGCCCTGGGA|GGCTGGTGGG|AGGCAGGGG|CAGGCCTGCG|GATGCATGAA|4200|
|ATAATGTTGG|CATTATTTTT|TAATTTTTA|AAAAATAAAT|GGTATCTTAT|TTAATTGTCC|4260|
|TGTTCCTTCC|CACTCCCCGC|CTCCTAGGAT|GTTAGCCCAA|GCTCAGGGTA|GGCCCAGGGG|4320|
|GCTGGGAGAA|ATGAAGCCAC|CCATGGGGAC|TGGGGACCAG|GGGCCTTCAG|CATGGCTTCT|4380|
|AGGTTCCCTC|CTCCCCCTAC|CCCATCTCCT|ACCTCCACAG|TACAGACTGT|CCCCAACTTA|4440|

-continued

```
ACAGTGGTTC AACTTAAACC ATGTTTCAAC TTTACAATTG GTCTGTTGGG GTATTAAATG        4500

AATTTGTGAC TTAGGATATT TTCATTTATG ATGGGTTTAT CAAGAAGTAA CCCCATGGTA        4560

AGTTGAGGCA TATCTGTATA TATTTAAACC TAATTAATTC TTGAGCTGAA AATAAATAAA        4620

CCAGGATGGC AGGGACCAAC CCCTAATCCC TCCCCAGCGG CAAGCCCCTC TTTTCAGAGT        4680

GGGCAGAGGG TTGCCTATGG TGGGCACTAG GAATGAGGTC CCCTGCCTCG ATGCGGGTCC        4740

TAGGAGAAAA AGTCCTACTT TTCTGGGTCC CCAGGTGCAG CACCTCCCGG AGACTGTTTC        4800

TCCCATGGCC TCCTGAGTGA TGGGCCCTGC CTCCCTGTGC CTCATCCTCA GGCTGGTTGG        4860

AGCAGAGGGT GGGCAGGAGC CCCAGCACAG ACTGGGGGGT GCTCACAGCA GGGCCACCTT        4920

GATGCAGGCT GGAATGTTAT CCCTGGGGTG TGCTTGGACC CCACCTGCTT TCTTTCTCTC        4980

CTGCCCCTCC CCTACTCTCA CTGTAATTTA TGGACCCTGC CCGCCTGCGT GTTGTGTGTA        5040

TGTCCTGTGC CTTTTCTCAC TATTGTTTGG GTGTGGGAGG GGGTGGTTTT TCACTGAAAA        5100

GGGGGGTACA CCTATAGCTT TCTTGATGTT CAATCAATCA GTCACTGTGT CCCAGACATA        5160

TTCAATAAAC ACAGATTGGT ACCACCCAAA AAAAAA                                  5197
```

( 2 ) INFORMATION FOR SEQ ID NO:54:

( i ) SEQUENCE CHARACTERISTICS:
        ( A ) LENGTH: 1141
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:54:

```
Met Asp Asp Ser Gly Glu Leu Gly Gly Leu Glu Thr Met Glu Thr Leu
 1               5                  10                  15

Thr Glu Leu Gly Asp Glu Leu Thr Leu Gly Asp Ile Asp Glu Met Leu
            20                  25                  30

Gln Phe Val Ser Asn Gln Val Gly Glu Phe Pro Asp Leu Phe Ser Glu
        35                  40                  45

Gln Leu Cys Ser Ser Phe Pro Gly Ser Gly Gly Ser Gly Ser Ser Ser
    50                  55                  60

Gly Ser Ser Gly Ser Ser Ser Ser Ser Asn Gly Arg Gly Ser Ser
65                  70                  75                  80

Ser Gly Ala Val Asp Pro Ser Val Gln Arg Ser Phe Thr Gln Val Thr
                85                  90                  95

Leu Pro Ser Phe Ser Pro Ser Ala Ala Ser Pro Gln Ala Pro Thr Leu
            100                 105                 110

Gln Val Lys Val Ser Pro Thr Ser Val Pro Thr Thr Pro Arg Ala Thr
        115                 120                 125

Pro Ile Leu Gln Pro Arg Pro Gln Pro Gln Pro Gln Pro Gln Thr Gln
    130                 135                 140

Leu Gln Gln Gln Thr Val Met Ile Thr Pro Thr Phe Ser Thr Thr Pro
145                 150                 155                 160

Gln Thr Arg Ile Ile Gln Gln Pro Leu Ile Tyr Gln Asn Ala Ala Thr
                165                 170                 175

Ser Phe Gln Val Leu Gln Pro Gln Val Gln Ser Leu Val Thr Ser Ser
            180                 185                 190

Gln Val Gln Pro Val Thr Ile Gln Gln Val Gln Thr Val Gln Ala
        195                 200                 205

Gln Arg Val Leu Thr Gln Thr Ala Asn Gly Thr Leu Gln Thr Leu Ala
    210                 215                 220
```

```
Pro  Ala  Thr  Val  Gln  Thr  Val  Ala  Ala  Pro  Gln  Val  Gln  Gln  Val  Pro
225            230                      235                           240

Val  Leu  Val  Gln  Pro  Gln  Ile  Ile  Lys  Thr  Asp  Ser  Leu  Val  Leu  Thr
               245                250                          255

Thr  Leu  Lys  Thr  Asp  Gly  Ser  Pro  Met  Ala  Ala  Val  Gln  Asn  Pro
               260                265                     270

Ala  Leu  Thr  Ala  Leu  Thr  Thr  Pro  Ile  Gln  Thr  Ala  Ala  Leu  Gln  Val
               275                280                      285

Pro  Thr  Leu  Val  Gly  Ser  Ser  Gly  Thr  Ile  Leu  Thr  Thr  Met  Pro  Val
          290                295                      300

Met  Met  Gly  Gln  Glu  Lys  Val  Pro  Ile  Lys  Gln  Val  Pro  Gly  Gly  Val
305                      310                315                           320

Lys  Gln  Leu  Glu  Pro  Pro  Lys  Glu  Gly  Arg  Arg  Thr  Thr  His  Asn
                    325                330                           335

Ile  Ile  Glu  Lys  Arg  Tyr  Arg  Ser  Ser  Ile  Asn  Asp  Lys  Ile  Ile  Glu
               340                     345                      350

Leu  Lys  Asp  Leu  Val  Met  Gly  Thr  Asp  Ala  Lys  Met  His  Lys  Ser  Gly
          355                     360                365

Val  Leu  Arg  Lys  Ala  Ile  Asp  Tyr  Ile  Lys  Tyr  Leu  Gln  Gln  Val  Asn
          370                     375                     380

His  Lys  Leu  Arg  Gln  Glu  Asn  Met  Val  Leu  Lys  Leu  Ala  Asn  Gln  Lys
385                      390                     395                      400

Asn  Lys  Leu  Leu  Lys  Gly  Ile  Asp  Leu  Gly  Ser  Leu  Val  Asp  Asn  Glu
                    405                     410                      415

Val  Asp  Leu  Lys  Ile  Glu  Asp  Phe  Asn  Gln  Asn  Val  Leu  Leu  Met  Ser
               420                     425                      430

Pro  Pro  Ala  Ser  Asp  Ser  Gly  Ser  Gln  Ala  Gly  Phe  Ser  Pro  Tyr  Ser
          435                     440                     445

Ile  Asp  Ser  Glu  Pro  Gly  Ser  Pro  Leu  Leu  Asp  Ala  Lys  Val  Lys
450                      455                     460

Asp  Glu  Pro  Asp  Ser  Pro  Pro  Val  Ala  Leu  Gly  Met  Val  Asp  Arg  Ser
465                      470                     475                      480

Arg  Ile  Leu  Leu  Cys  Val  Leu  Thr  Phe  Leu  Cys  Leu  Ser  Phe  Asn  Pro
               485                     490                      495

Leu  Thr  Ser  Leu  Leu  Gln  Trp  Gly  Gly  Ala  His  Asp  Ser  Asp  Gln  His
               500                     505                      510

Pro  His  Ser  Gly  Ser  Gly  Arg  Ser  Val  Leu  Ser  Phe  Glu  Ser  Gly  Ser
          515                     520                     525

Gly  Gly  Trp  Phe  Asp  Trp  Met  Met  Pro  Thr  Leu  Leu  Leu  Trp  Leu  Val
     530                     535                     540

Asn  Gly  Val  Ile  Val  Leu  Ser  Val  Phe  Val  Lys  Leu  Leu  Val  His  Gly
545                      550                     555                      560

Glu  Pro  Val  Ile  Arg  Pro  His  Ser  Arg  Ser  Ser  Val  Thr  Phe  Trp  Arg
               565                     570                     575

His  Arg  Lys  Gln  Ala  Asp  Leu  Asp  Leu  Ala  Arg  Gly  Asp  Phe  Ala  Ala
               580                     585                     590

Ala  Ala  Ala  Asn  Leu  Gln  Thr  Cys  Leu  Ala  Val  Leu  Gly  Arg  Ala  Leu
          595                     600                     605

Pro  Thr  Ser  Arg  Leu  Asp  Leu  Ala  Cys  Ser  Leu  Ser  Trp  Asn  Val  Ile
     610                     615                     620

Arg  Tyr  Ser  Leu  Gln  Lys  Leu  Arg  Leu  Val  Arg  Trp  Leu  Leu  Lys  Lys
625                      630                     635                      640

Val  Phe  Gln  Cys  Arg  Arg  Ala  Thr  Pro  Ala  Thr  Glu  Ala  Gly  Phe  Glu
               645                     650                     655
```

```
Asp Glu Ala Lys Thr Ser Ala Arg Asp Ala Ala Leu Ala Tyr His Arg
            660                 665                 670

Leu His Gln Leu His Ile Thr Gly Lys Leu Pro Ala Gly Ser Ala Cys
        675                 680                 685

Ser Asp Val His Met Ala Leu Cys Ala Val Asn Leu Ala Glu Cys Ala
    690                 695                 700

Glu Glu Lys Ile Pro Pro Ser Thr Leu Val Glu Ile His Leu Thr Ala
705                 710                 715                 720

Ala Met Gly Leu Lys Thr Arg Cys Gly Gly Lys Leu Gly Phe Leu Ala
                725                 730                 735

Ser Tyr Phe Leu Ser Arg Ala Gln Ser Leu Cys Gly Pro Glu His Ser
            740                 745                 750

Ala Val Pro Asp Ser Leu Arg Trp Leu Cys His Pro Leu Gly Gln Lys
        755                 760                 765

Phe Phe Met Glu Arg Ser Trp Ser Val Lys Ser Ala Ala Lys Glu Ser
    770                 775                 780

Leu Tyr Cys Ala Gln Arg Asn Pro Ala Asp Pro Ile Ala Gln Val His
785                 790                 795                 800

Gln Ala Phe Cys Lys Asn Leu Leu Glu Arg Ala Ile Glu Ser Leu Val
                805                 810                 815

Lys Pro Gln Ala Lys Lys Lys Ala Gly Asp Gln Glu Glu Ser Cys
            820                 825                 830

Glu Phe Ser Ser Ala Leu Glu Tyr Leu Lys Leu Leu His Ser Phe Val
        835                 840                 845

Asp Ser Val Gly Val Met Ser Pro Pro Leu Ser Arg Ser Ser Val Leu
    850                 855                 860

Lys Ser Ala Leu Gly Pro Asp Ile Ile Cys Arg Trp Trp Thr Ser Ala
865                 870                 875                 880

Ile Thr Val Ala Ile Ser Trp Leu Gln Gly Asp Asp Ala Ala Val Arg
                885                 890                 895

Ser His Phe Thr Lys Val Glu Arg Ile Pro Lys Ala Leu Glu Val Thr
        900                 905                 910

Glu Ser Pro Leu Val Lys Ala Ile Phe His Ala Cys Arg Ala Met His
    915                 920                 925

Ala Ser Leu Pro Gly Lys Ala Asp Gly Gln Gln Ser Phe Cys His
930                 935                 940

Cys Glu Arg Ala Ser Gly His Leu Trp Ser Ser Leu Asn Val Ser Gly
945                 950                 955                 960

Gly Thr Ser Asp Pro Ala Leu Asn His Val Val Gln Leu Leu Thr Cys
                965                 970                 975

Asp Leu Leu Leu Ser Leu Arg Thr Ala Leu Trp Gln Lys Gln Ala Ser
            980                 985                 990

Ala Ser Gln Ala Val Gly Glu Thr Tyr His Ala Ser Gly Ala Glu Leu
        995                 1000                1005

Ala Gly Phe Gln Arg Asp Leu Gly Ser Leu Arg Arg Leu Ala His Ser
    1010                1015                1020

Phe Arg Pro Ala Tyr Arg Lys Val Phe Leu His Glu Ala Thr Val Arg
1025                1030                1035                1040

Leu Met Ala Gly Gly Ser Pro Thr Arg Thr His Gln Leu Leu Glu His
                1045                1050                1055

Ser Leu Arg Arg Arg Thr Thr Gln Ser Thr Lys His Gly Glu Val Asp
            1060                1065                1070

Ala Trp Pro Gly Gln Arg Glu Arg Ala Thr Ala Ile Leu Leu Ala Cys
```

```
                    1075                        1080                        1085
Arg  His  Leu  Pro  Leu  Ser  Phe  Leu  Ser  Ser  Pro  Gly  Gln  Arg  Ala  Val
               1090                   1095                  1100

Leu  Leu  Ala  Glu  Ala  Ala  Arg  Thr  Leu  Glu  Lys  Val  Gly  Asp  Arg  Arg
1105                      1110                  1115                       1120

Ser  Cys  Asn  Asp  Cys  Gln  Gln  Met  Ile  Val  Lys  Leu  Gly  Gly  Gly  Thr
                    1125                  1130                       1135

Ala  Ile  Ala  Ala  Ser
               1140
```

( 2 ) INFORMATION FOR SEQ ID NO:55:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( i x ) FEATURE:
        ( A ) NAME/KEY: modified_base
        ( B ) LOCATION: 12
        ( D ) OTHER INFORMATION: /mod_base=OTHER
            / note= "N = Inosine"

( x i ) SEQUENCE DESCRIPTION: SEQ ID NO:55:

TTYTCYTGYT TNAGYTTYTG        20

( 2 ) INFORMATION FOR SEQ ID NO:56:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( i x ) FEATURE:
        ( A ) NAME/KEY: modified_base
        ( B ) LOCATION: 9
        ( D ) OTHER INFORMATION: /mod_base=OTHER
            / note= "N = Inosine"

( x i ) SEQUENCE DESCRIPTION: SEQ ID NO:56:

TTYTGRTTNG ARTGYTG        17

( 2 ) INFORMATION FOR SEQ ID NO:57:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( i x ) FEATURE:
        ( A ) NAME/KEY: modified_base
        ( B ) LOCATION: 6
        ( D ) OTHER INFORMATION: /mod_base=OTHER
            / note= "N = Inosine"

( x i ) SEQUENCE DESCRIPTION: SEQ ID NO:57:

TTYACNCARG TNACNYT        17

( 2 ) INFORMATION FOR SEQ ID NO:58:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( i x ) FEATURE:
        ( A ) NAME/KEY: modified_base
        ( B ) LOCATION: 6
        ( D ) OTHER INFORMATION: /mod_base=OTHER
          / note= "N = Inosine"

( x i ) SEQUENCE DESCRIPTION: SEQ ID NO:58:

GCYTGNGGNS WNGC                                  14

( 2 ) INFORMATION FOR SEQ ID NO:59:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( i x ) FEATURE:
        ( A ) NAME/KEY: modified_base
        ( B ) LOCATION: 6
        ( D ) OTHER INFORMATION: /mod_base=OTHER
          / note= "N = Inosine"

( x i ) SEQUENCE DESCRIPTION: SEQ ID NO:59:

TTYACNCARG TSACWYT                                17

( 2 ) INFORMATION FOR SEQ ID NO:60:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( i x ) FEATURE:
        ( A ) NAME/KEY: modified_base
        ( B ) LOCATION: 6
        ( D ) OTHER INFORMATION: /mod_base=OTHER
          / note= "N = Inosine"

( x i ) SEQUENCE DESCRIPTION: SEQ ID NO:60:

GCYTGNGGNG ASGC                                  14

( 2 ) INFORMATION FOR SEQ ID NO:61:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:61:

```
GGTCACATTA CCTTCCTTCT C                                                                    21
```

(2) INFORMATION FOR SEQ ID NO:62:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:62:

```
TTCCTTCTCT CCCTCGGC                                                                        18
```

(2) INFORMATION FOR SEQ ID NO:63:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:63:

```
GGAGGCCGCC GAGGGAG                                                                         17
```

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:64:

```
CGAGGGAGAG AAGGAAGGTA                                                                      20
```